United States Patent
Carpino et al.

(12)

(10) Patent No.: US 9,873,673 B2
(45) Date of Patent: *Jan. 23, 2018

(54) 2-THIOPYRIMIDINONES

(71) Applicant: Pfizer Inc., New York, NY (US)

(72) Inventors: Philip A. Carpino, Newton, MA (US); Edward L. Conn, Griswold, CT (US); Robert L. Dow, Groton, CT (US); Matthew S. Dowling, Old Lyme, CT (US); David Hepworth, Concord, MA (US); Daniel Wei-Shung Kung, Salem, CT (US); Suvi Orr, San Diego, CA (US); Benjamin N. Rocke, Manchester, CT (US); Roger B. Ruggeri, Waterford, CT (US); Matthew F. Sammons, Quincy, MA (US); Joseph S. Warmus, Ledyard, CT (US); Yan Zhang, Falmouth, ME (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/191,943

(22) Filed: Jun. 24, 2016

(65) Prior Publication Data

US 2016/0304469 A1 Oct. 20, 2016

Related U.S. Application Data

(63) Continuation of application No. 14/299,497, filed on Jun. 9, 2014, now Pat. No. 9,399,626, which is a continuation of application No. 13/875,604, filed on May 2, 2014, now Pat. No. 8,841,314, which is a continuation of application No. 13/670,852, filed on Nov. 7, 2012, now Pat. No. 8,835,449.

(60) Provisional application No. 61/558,605, filed on Nov. 11, 2011.

(51) Int. Cl.

| C07D 239/56 | (2006.01) |
|---|---|
| A61K 31/513 | (2006.01) |
| A61K 31/352 | (2006.01) |
| A61K 31/5377 | (2006.01) |
| A61K 45/06 | (2006.01) |
| C07D 401/04 | (2006.01) |
| C07D 401/06 | (2006.01) |
| C07D 401/10 | (2006.01) |
| C07D 403/04 | (2006.01) |
| C07D 403/06 | (2006.01) |
| C07D 403/10 | (2006.01) |
| C07D 403/12 | (2006.01) |
| C07D 405/04 | (2006.01) |
| C07D 405/10 | (2006.01) |
| C07D 409/04 | (2006.01) |
| C07D 409/10 | (2006.01) |
| C07D 413/06 | (2006.01) |
| C07D 417/10 | (2006.01) |
| C07D 487/04 | (2006.01) |
| C07D 417/04 | (2006.01) |
| C07D 471/04 | (2006.01) |
| A61K 31/37 | (2006.01) |
| C07D 405/06 | (2006.01) |

(52) U.S. Cl.
CPC .......... *C07D 239/56* (2013.01); *A61K 31/352* (2013.01); *A61K 31/37* (2013.01); *A61K 31/513* (2013.01); *A61K 31/5377* (2013.01); *A61K 45/06* (2013.01); *C07D 401/04* (2013.01); *C07D 401/06* (2013.01); *C07D 401/10* (2013.01); *C07D 403/04* (2013.01); *C07D 403/06* (2013.01); *C07D 403/10* (2013.01); *C07D 403/12* (2013.01); *C07D 405/04* (2013.01); *C07D 405/06* (2013.01); *C07D 405/10* (2013.01); *C07D 409/04* (2013.01); *C07D 409/10* (2013.01); *C07D 413/06* (2013.01); *C07D 417/04* (2013.01); *C07D 417/10* (2013.01); *C07D 471/04* (2013.01); *C07D 487/04* (2013.01)

(58) Field of Classification Search
CPC ............................ C07D 239/56; A61K 31/513
USPC .................... 544/309, 311, 312; 514/274
See application file for complete search history.

(56) References Cited

U.S. PATENT DOCUMENTS

| 4,088,751 A | 5/1978 | Kenkare et al. |
|---|---|---|
| 4,171,429 A | 10/1979 | Watanabe et al. |
| 4,411,699 A | 10/1983 | Iwakura et al. |
| 5,461,060 A | 10/1995 | Miyasaka et al. |
| 5,534,534 A | 7/1996 | Makino et al. |
| 5,612,359 A | 3/1997 | Murugesan |
| 5,719,190 A | 2/1998 | MacLean et al. |
| 5,747,500 A | 5/1998 | Son et al. |
| 6,043,265 A | 3/2000 | Murugesan et al. |

(Continued)

FOREIGN PATENT DOCUMENTS

| AU | 2005284098 | 3/2006 |
|---|---|---|
| CA | 2252144 | 4/2000 |

(Continued)

OTHER PUBLICATIONS

Berger et al., Peripheral artery disease, biomarkers, and darapladib, American Heart Journal, vol. 161, No. 5, pp. 972-978 (2011).*
Bundgaard, Design of Prodrugs, p. 1, 1985.*
Banker et al., Prodrugs, Modern Pharmaceutics, Third Edition, Revised and Expanded, pp. 451 and 596 (1996).*
Wolff, Some consideration for prodrug design, Burger's Medicinal Chemistry and Drug Discovery, 5th Edition, vol. 1: Principles and Practice, pp. 975-977, 1995.*
Medda et al., N1-Benzyl substituted cambinol analogues as isozyme selective inhibitors of the sirtuin family of protein deacetylases, Med. Chem. Commun., 2, pp. 611-615, 2011.*

(Continued)

*Primary Examiner* — Deepak Rao
(74) *Attorney, Agent, or Firm* — A. Dean Olson

(57) ABSTRACT

Myeloperoxidase inhibitors, pharmaceutical compositions containing such inhibitors and the use of such inhibitors to treat, for example, cardiovascular conditions.

11 Claims, 2 Drawing Sheets

(56) References Cited

U.S. PATENT DOCUMENTS

| | | | |
|---|---|---|---|
| 6,096,753 A | 8/2000 | Spohr et al. | |
| 6,130,340 A | 10/2000 | Jacobsen et al. | |
| 6,172,066 B1 | 1/2001 | Nagarathnam et al. | |
| 6,211,370 B1 | 4/2001 | Jacobsen et al. | |
| 6,228,861 B1 | 5/2001 | Nagarathnam et al. | |
| 6,245,773 B1 | 6/2001 | Wong et al. | |
| 6,268,369 B1 | 7/2001 | Nagarathnam et al. | |
| 6,444,656 B1 | 9/2002 | Nguyen-Ba et al. | |
| 6,562,966 B2 | 5/2003 | Deng et al. | |
| 6,562,967 B2 | 5/2003 | Deng et al. | |
| 6,720,324 B2 | 4/2004 | Marzabadi et al. | |
| 6,727,257 B1 | 4/2004 | Nagarathnam et al. | |
| 7,105,559 B2 | 9/2006 | South et al. | |
| 7,485,604 B2 | 2/2009 | Negoro et al. | |
| 7,485,729 B2 | 2/2009 | Hsieh et al. | |
| 7,781,584 B2 | 8/2010 | Feng et al. | |
| 7,795,428 B2 | 9/2010 | Feng et al. | |
| 7,807,689 B2 | 10/2010 | Zhang et al. | |
| 8,088,846 B2 | 1/2012 | Hsieh et al. | |
| 8,173,633 B2 | 5/2012 | Feng et al. | |
| 8,236,446 B2 | 8/2012 | Lu | |
| 8,277,691 B2 | 10/2012 | Lu | |
| 8,288,539 B2 | 10/2012 | Feng et al. | |
| 8,835,449 B2 | 9/2014 | Conn et al. | |
| 8,841,314 B2 | 9/2014 | Hepworth et al. | |
| 9,399,626 B2 * | 7/2016 | Carpino | A61K 31/352 |
| 2002/0151744 A1 | 10/2002 | Deng et al. | |
| 2003/0069261 A1 | 4/2003 | Marzabadi et al. | |
| 2004/0029742 A1 | 2/2004 | Mukkamala | |
| 2004/0029743 A1 | 2/2004 | Mukkamala | |
| 2004/0220148 A1 | 11/2004 | Stilz et al. | |
| 2004/0242609 A1 | 12/2004 | Marzabadi et al. | |
| 2004/0259864 A1 | 12/2004 | Geneste et al. | |
| 2005/0014657 A1 | 1/2005 | Negoro et al. | |
| 2005/0020533 A1 | 1/2005 | Macchia et al. | |
| 2005/0222180 A1 | 10/2005 | Fardis et al. | |
| 2006/0183748 A1 | 8/2006 | Balzarini et al. | |
| 2007/0154914 A1 | 7/2007 | Gelfand et al. | |
| 2007/0213323 A1 | 9/2007 | Imogai et al. | |
| 2008/0003283 A1 | 1/2008 | Feng et al. | |
| 2008/0113993 A1 | 5/2008 | DeBelin et al. | |
| 2009/0012059 A1 | 1/2009 | Feng et al. | |
| 2009/0042863 A1 | 2/2009 | Takeuchi et al. | |
| 2009/0130689 A1 | 5/2009 | Verdier et al. | |
| 2010/0324001 A1 | 12/2010 | Morand et al. | |
| 2011/0003828 A1 | 1/2011 | Blumberg et al. | |
| 2011/0076276 A1 | 3/2011 | Guo et al. | |
| 2011/0224155 A1 | 9/2011 | Tachdjian et al. | |
| 2011/0245282 A1 | 10/2011 | Westwood et al. | |
| 2012/0292565 A1 | 11/2012 | Delfort et al. | |
| 2013/0123230 A1 | 5/2013 | Carpino et al. | |
| 2013/0296351 A1 | 11/2013 | Carpino et al. | |
| 2016/0326121 A1 * | 11/2016 | Ruggeri | A61K 45/06 |

FOREIGN PATENT DOCUMENTS

| | | |
|---|---|---|
| DE | 19918725 | 10/2000 |
| DE | 102009037300 | 2/2011 |
| EP | 842943 | 5/1998 |
| EP | 1586571 | 10/2005 |
| EP | 1616874 | 1/2006 |
| EP | 2181985 | 5/2010 |
| ES | 2352926 | 2/2011 |
| GB | 2090850 | 7/1982 |
| GB | 2263639 | 8/1993 |
| JP | 3261641 | 11/1991 |
| JP | 5025142 | 2/1993 |
| JP | 5025144 | 2/1993 |
| JP | 5043555 | 2/1993 |
| JP | 6003761 | 1/1994 |
| JP | 7295165 | 11/1995 |
| JP | 7295166 | 11/1995 |
| JP | 2001131133 | 5/2001 |
| JP | 3781200 | 5/2006 |
| JP | 2009167179 | 7/2009 |
| JP | 2010126479 | 11/2010 |
| WO | 198910701 | 11/1989 |
| WO | 1995018109 | 7/1995 |
| WO | 199614846 | 5/1996 |
| WO | 199717969 | 5/1997 |
| WO | 199741097 | 11/1997 |
| WO | 199742956 | 11/1997 |
| WO | 199824780 | 6/1998 |
| WO | 199824782 | 6/1998 |
| WO | 199851311 | 11/1998 |
| WO | 1999005125 | 2/1999 |
| WO | 199936375 | 7/1999 |
| WO | 199959561 | 11/1999 |
| WO | 200001389 | 1/2000 |
| WO | 200075136 | 12/2000 |
| WO | 200140231 | 6/2001 |
| WO | 2001085146 | 11/2001 |
| WO | 200193841 | 12/2001 |
| WO | 200198306 | 12/2001 |
| WO | 200206244 | 1/2002 |
| WO | 200206277 | 1/2002 |
| WO | 200206389 | 1/2002 |
| WO | 2002006245 | 1/2002 |
| WO | 200210096 | 2/2002 |
| WO | 200232920 | 4/2002 |
| WO | 200233128 | 4/2002 |
| WO | 200269903 | 9/2002 |
| WO | 2002068410 | 9/2002 |
| WO | 2002090575 | 11/2002 |
| WO | 2003011799 | 2/2003 |
| WO | 2003016275 | 2/2003 |
| WO | 2006030323 | 3/2003 |
| WO | 2003028729 | 4/2003 |
| WO | 2003029216 | 4/2003 |
| WO | 2003029224 | 4/2003 |
| WO | 2003057677 | 7/2003 |
| WO | 2003072197 | 9/2003 |
| WO | 200384935 | 10/2003 |
| WO | 200384936 | 10/2003 |
| WO | 200384937 | 10/2003 |
| WO | 200384938 | 10/2003 |
| WO | 2003089430 | 10/2003 |
| WO | 2003093242 | 11/2003 |
| WO | 2003097604 | 11/2003 |
| WO | 2004037159 | 5/2004 |
| WO | 200473703 | 9/2004 |
| WO | 2004089927 | 10/2004 |
| WO | 2005005667 | 1/2005 |
| WO | 2005026184 | 3/2005 |
| WO | 200563751 | 7/2005 |
| WO | 200595381 | 10/2005 |
| WO | 2005116014 | 12/2005 |
| WO | 2006005142 | 1/2006 |
| WO | 2006022899 | 3/2006 |
| WO | 2006030032 | 3/2006 |
| WO | 2006046910 | 5/2006 |
| WO | 2006062465 | 6/2006 |
| WO | 2006070292 | 7/2006 |
| WO | 2006089221 | 8/2006 |
| WO | 2006131676 | 12/2006 |
| WO | 2007005774 | 1/2007 |
| WO | 2007015168 | 2/2007 |
| WO | 2007021803 | 2/2007 |
| WO | 2007023390 | 3/2007 |
| WO | 2007026252 | 3/2007 |
| WO | 2007031874 | 3/2007 |
| WO | 2007045998 | 4/2007 |
| WO | 2007064797 | 6/2007 |
| WO | 2007074884 | 7/2007 |
| WO | 2007077048 | 7/2007 |
| WO | 2007077057 | 7/2007 |
| WO | 2007120098 | 10/2007 |
| WO | 2007122482 | 11/2007 |
| WO | 2007142576 | 12/2007 |
| WO | 2007142577 | 12/2007 |
| WO | 2007143055 | 12/2007 |
| WO | 2008023249 | 2/2008 |
| WO | 2008046602 | 4/2008 |
| WO | 2008046609 | 4/2008 |

(56) References Cited

FOREIGN PATENT DOCUMENTS

| WO | 2008065508 | 6/2008 |
|---|---|---|
| WO | 2008070447 | 6/2008 |
| WO | 2008082561 | 7/2008 |
| WO | 2008154221 | 12/2008 |
| WO | 2009005674 | 1/2009 |
| WO | 2009005693 | 1/2009 |
| WO | 2009016462 | 2/2009 |
| WO | 2009025617 | 2/2009 |
| WO | 2009025618 | 2/2009 |
| WO | 2009055917 | 5/2009 |
| WO | 2009066060 | 5/2009 |
| WO | 2009114950 | 9/2009 |
| WO | 2009120872 | 10/2009 |
| WO | 2009129120 | 10/2009 |
| WO | 2009137508 | 11/2009 |
| WO | 2009144554 | 12/2009 |
| WO | 2009144555 | 12/2009 |
| WO | 2010013161 | 2/2010 |
| WO | 2010023594 | 3/2010 |
| WO | 2010038043 | 4/2010 |
| WO | 2010086820 | 8/2010 |
| WO | 2010103437 | 9/2010 |
| WO | 2010103438 | 9/2010 |
| WO | 2010106457 | 9/2010 |
| WO | 2010124201 | 10/2010 |
| WO | 2010124237 | 10/2010 |
| WO | 2010128414 | 11/2010 |
| WO | 2010128425 | 11/2010 |
| WO | 2010136546 | 12/2010 |
| WO | 2010138901 | 12/2010 |
| WO | 2010140092 | 12/2010 |
| WO | 2010151689 | 12/2010 |
| WO | 2010151711 | 12/2010 |
| WO | 2011003018 | 1/2011 |
| WO | 2011005611 | 1/2011 |
| WO | 2011045415 | 4/2011 |
| WO | 2011057220 | 5/2011 |
| WO | 2011064470 | 6/2011 |
| WO | 2011094890 | 8/2011 |
| WO | 2011097300 | 8/2011 |
| WO | 2011097607 | 8/2011 |
| WO | 2011109799 | 9/2011 |
| WO | 2011163594 | 12/2011 |
| WO | 2012016133 | 2/2012 |
| WO | 2012076736 | 6/2012 |

OTHER PUBLICATIONS

Zhang, et al., "PTP1B as a drug target: recent developments in PTP1B inhibitor discovery", Drug Discovery Today, vol. 12(9/10), pp. 373-381 (2007).

Jones, et al., "The Emergence of GPR119 Agonists as Anti-Diabetic Agents", Annual Reports in Medicinal Chemistry, vol. 44, pp. 149-170 (2009).

Kharitonenkov, et al., "FGF21: A novel prospect for the treatment of metabolic diseases", Current Opinion in Investigational Drugs, vol. 10(4), pp. 359-364 (2009).

Zhong, "TGR5 as a Therapeutic Target for Treating Obesity", Current Topics in Medicinal Chemistry, vol. 10, pp. 386-396 (2010).

Medina, "GPR40 (FFAR1) Modulators", Annual Reports in Medicinal Chemistry, vol. 43, pp. 75-85 (2008).

Carpino, et al., "Diabetes area participation analysis: a review of companies and targets described in 2008-2010 patent literature", Expert Opinion of Therapeutic Patents, vol. 20(12), pp. 1627-1651 (2010).

Gomes, et al., "Fluorescence probes used for detection of reactive oxygen species", Journal of Biochem. Biophys. Methods, vol. 65(2-3), pp. 45-80 (2005).

Neidlein, et al., "Synthesis of 3,4-and 4-Substituted Uracils and Sulfa-uracils", Archiv der Pharmazie, vol. 305(8), pp. 596-601 (1972).

Aldib, et al., "Evaluation of New Scaffolds of Myeloperoxidase Inhibitors by rational Design Combined with High-Throughput Virtual Screening", Journal of Medicinal Chemistry, vol. 55(16), pp. 7208-7218 (2012).

Tiden, et al., "2-Thioxanthines Are Mechanism-based Inactivators of Myeloperoxidase That Block Oxdative Stress during Inflammation", The Journal of Biological Chemistry, vol. 286(43), pp. 37578-37589 (2011).

Malvezzi, et al., "MPO Inhibitors Selected by Virtual Screening", Molecular Informatics, vol. 30(6-7), pp. 605-613 (2011).

Diaz-Ruiz, et al., "Delayed administration of dapsone protects from tissue damage and improves recovery after spinal cord injury", Journal of Neuroscience Research, vol. 89(3), pp. 373-380 (2011).

Soubhye, et al., "Structure-Based Design, Synthesis, and Pharmacological Evaluation of 3-(Aminoalkyl)-5-fluroindoles as Myeloperoxidase Inhibitors", Journal of Medicinal Chemistry, vol. 53(24), pp. 8747-8759 (2010).

Van Antwerpen, et al., "Conception of myeloperoxidase inhibitors derived from flufenamic acid by computational docking and structure modification", Bioorganic & Medicinal Chemistry, vol. 16(4), pp. 1702-1720 (2008).

Van Antwerpen, et al., "Inhibition of the myeloperoxidase chlorinating activity by non-steroidal anti-inflammatory drugs: Flufenamic acid and its 5-chloro-derivative directly interact with a recombinant human myeloperoxidase to inhibit the synthesis of hypochlorous acid", European Journal of Pharmacology, vol. 570(1-3), pp. 235-243 (2007).

Soyer, et al., "Synthesis of some 2(3H)-Benzoxazolone Derivatives and their in-vitro Effects on Human Leukocyte Myeloperoxidase Activity", Archiv der Pharmazie, vol. 338(9), pp. 405-410 (2005).

Choi et al., "Ablation of the inflammatory enzyme myeloperoxidase mitigates features of Parkinson's disease in mice", The Journal of Neuroscience, vol. 25(28), pp. 6594-6600 (2005).

Bekesi, et al., "Effect of inhibitors of myeloperoxidase on the development of aortic atherosclerosis in an animal model", Experimental Gerontology, vol. 40(3), pp. 199-208 (2005).

Yea, et al., "Identification of a myeloperoxidase inhibitor", Clinical and Experimental Immunology, vol. 84(2), pp. 347-352 (1991).

Egan, et al., "Naphthalenes as inhibitors of myeloperoxidase: direct and indirect mechanisms of inhibition", Agents and Actions, vol. 29(3-4), pp. 266-276 (1990).

Humphreys, et al., "Role of myeloperoxidase in the killing of *Staphylococcus aureus* by human neutrophils: studies with the myeloperoxidase inhibitor salicylhydroxamic acid", Journal of General Microbiology, vol. 135(5), pp. 1187-1193 (1989).

Pincemail, et al., "Human myeloperoxidase activity is inhibited in vitro by quercetin. Comparison with three related compounds", Experientia, vol. 44(5); pp. 450-453 (1988).

Medda, et al., "N1-Benzyl substituted cambinol analogues as isozyme selective inhibitors of the sirtuin family of protein deacetylases", Med. Chem. Commun., vol. 2, pp. 611-615 (2011).

Neidlein, et al., "Synthesis of 2-amino-4-alkylmercapto-6-aryl-1,3,5-s-triazines and 4-amino-6-alkyl-mercapto-2-aryl-5-cyano-pyrimidine", Archiv Der Pharmazie, vol. 305(9), pp. 689-691 (1972) (English Translation provided).

Neidlein, et al., "Synthesis and properties of various 1,2,4-thiadiazolyl-sulfenyl chlorides", Archly Der Pharmazie, vol. 305(5), pp. 373-379 (1972) (English Translation provided).

Neidlein, et al., "Reaction behavior of sulfenylchloride derivatives" Archiv Der Pharmazie, vol. 305(3), pp. 183-187 (1972) (English Translation provided).

Gomez, La modernizacion del derecho espanol de patentes, Montecorvo, Madrid, 1984, p. 7.

Ruggeri, et al. "Discovery of 2-(6-(5-Chloro-2-methoxyphenyl)-4-oxo-2-thioxo-3,4-dihydropyrimidin-1(2H)-yl) acetamide (PF-06282999): A Highly Selective Mechanism-Based Myeloperoxidase Inhibitor for the Treatment of Cardiovascular Disease", Journal of Medicinal Chemistry, vol. 58, pp. 8513-8528 (2015).

Zheng, et al., "PF-1355, a Mechanism-Based Myeloperoxidase Inhibitor, Prevents Immune Complex Vasculitis and Anti-Glomerular Basement Membrane Glomerulonephritis", JPET, vol. 353(2), pp. 288-298 (2015).

(56) References Cited

OTHER PUBLICATIONS

Hruba, et al., "Simultaneious Inhibition of Fatty Acid Amide Hydrolase and Monoacylglycerol Lipase Shares Discriminitive Stimulus Effects with Delta9-Tetrahydrocannabinol in Mice" JPET, vol. 353(2), pp. 261-268 (2015).

Kashiwagi, et al. "The Novel Prostaglandin I2 Mimetic ONO-1301 Escapes Desensitization in an Antiplatelet Effect Due to its Inhibitory Action on Thromboxane A2 Synthesis in Mice", JPET, vol. 353(2), pp. 269-278 (2015).

Schiebl, et al., "In vivo Visualization of the Antialbuminuric Effects of the Angiotensin-Converting Enzyme Inhibitor Enalapril", JPET, vol. 353(2), pp. 299-306 (2015).

Dong, et al., "Pharmacokinetics and Disposition of the Thiouracil Derivative PF-06282999, an Orall Bioavailable, Irreversible Inactivator of Myeloperoxidase Enzyme, Across Animals and Humans", Drug Metabolism and Disposition, vol. 44(2), pp. 209-219 (2016).

Eng, et al., "Species Differences in the Oxidative Desulfurization of a Thiouracil-Based Irreversible Myeloperoxidase Inactivator by Flavin-Containing Monooxygenase Enzymes", Drug Metabolism and Disposition, vol. 44(8), pp. 1262-1269 (2016).

Ruggeri, U.S. Appl. No. 15/618,498, filed Jun. 9, 2017.

\* cited by examiner

X-Ray Powder Diffraction Pattern For Example 1

X-Ray Powder Diffraction Pattern For Example 2

2-THIOPYRIMIDINONES

BACKGROUND OF THE INVENTION

This invention relates to compounds that are myeloperoxidase inhibitors, pharmaceutical compositions containing such inhibitors and the use of such inhibitors to treat for example, cardiovascular conditions including acute coronary syndrome.

Myeloperoxidase (MPO) is a heme-containing enzyme belonging to the peroxidase superfamily. Examples of animal peroxidases are lactoperoxidase, thyroid peroxidase, eosinophile peroxidase and myeloperoxidase. Myeloperoxidase is present in primary granules of neutrophils and to a lesser extent in monocytes. It catalyzes the synthesis of hypochlorous acid from chloride and hydrogen peroxide. The hypochlorous acid formed is a powerful oxidant that reacts with a variety of cellular substrates including heme proteins, porphyrins, thiols, iron sulfur centers, nucleotides, DNA, unsaturated lipids, amines and amino acids.

In addition, MPO-catalyzed reactions and their products have been found to exhibit pro-atherogenic biological activity during the development of atherosclerosis and cardiovascular disease. For example, the myeloperoxidase plasma content is correlated with the appearance of cardiovascular disorders in patients suffering unstable angina pectoris. Myeloperoxidase has been reported to contribute to the development of atherosclerosis by the oxidation of lipid and protein in LDL and HDL.

Furthermore, it has been observed that MPO-generated oxidants reduce the bioavailability of nitric oxide, an important vasodilator. Accordingly, high MPO plasma levels are inversely correlated with the success of therapy to establish reperfusion of occluded arteries. High MPO levels are also associated with decreased survival from congestive heart failure. Additionally, it has been shown that MPO plays a role in plaque destabilization which leads to plaque rupture and myocardial infarction.

Therefore, MPO is thought to play a role in several processes that lead to cardiovascular disease including 1) impaired cholesterol trafficking and progession of the atherosclerotic plaque towards an unstable state, 2) destabilization of the atherosclerotic plaque and plaque rupture, 3) consumption of nitric oxide leading to impaired endothelial function and flow, and 4) pathological tissue damage post ischemia contributing to atrial fibrillation and adverse cardiac remodeling with left ventricular hypertrophy leading to congestive heart failure. As such inhibitors of MPO activity are proposed to offer significant therapeutic benefit in the prevention and treatment of cardiovascular disease.

Nevertheless, although MPO has been implicated extensively in the etiology and progression of cardiovascular disease, a biologically safe and non-toxic inhibitor of MPO has yet to be developed. Accordingly, there remains a need for pharmaceutical agents that have myeloperoxidase inhibiting activity and are useful in the treatment, prevention or diminution of the manifestations of the maladies described herein.

SUMMARY OF THE INVENTION

The present invention is directed to a compound of the Formula I,

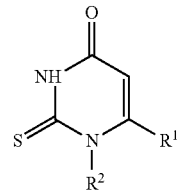

Formula I or a pharmaceutically acceptable salt or prodrug thereof wherein
$R^1$ is a five to six membered aromatic ring optionally having one to three heteroatoms selected independently from nitrogen, sulfur and oxygen or a bicyclic ring consisting of two fused partially saturated, fully saturated or fully unsaturated five to six membered rings, taken independently, optionally having one to four heteroatoms selected independently from nitrogen, sulfur and oxygen; and
said $R^1$ is optionally mono-, di-, or tri-substituted independently with cyano, halo, hydroxyl, amino, $(C_1-C_4)$alkyl, $(C_1-C_4)$alkoxy, $(C_1-C_4)$alkoxy$(C_1-C_4)$alkyl, hydroxy$(C_2-C_4)$alkoxy, carbamoyl$(C_1-C_4)$alkoxy, amino$(C_2-C_4)$alkoxy, cyano$(C_1-C_4)$alkyl, mono-N— or di-N,N—$(C_1-C_4)$alkylamino, am inocarbonyl, mono-N— or di-N,N$(C_1-C_4)$alkylaminocarbonyl, $(C_1-C_4)$alkylthio, am inosulfonyl, $(C_1-C_4)$alkylsulfinyl, $(C_1-C_4)$alkylsulfonyl, or mono-N— or di-N,N$(C_1-C_4)$alkylaminosulfonyl, wherein any of the $(C_1-C_4)$alkyl or $(C_1-C_4)$alkoxy may be optionally mono-, di- or tri-substituted with fluoro; or wherein $R^1$ is optionally substituted with a five to six membered aromatic ring optionally having one to three heteroatoms selected independently from nitrogen, sulfur and oxygen;
$R^2$ is a fully saturated, partially unsaturated or fully unsaturated one to fourteen membered straight carbon chain wherein the carbons, other than the connecting carbon,
  a. may be branched
  b. may optionally be replaced with one or two heteroatoms selected independently from oxygen, sulfur and nitrogen, wherein said sulfur is optionally mono- or di-substituted with oxo,
  c. may optionally be mono-, di- or tri-substituted independently with halo,
  d. may optionally be mono-substituted with hydroxy, and
  e. may optionally be mono-substituted with oxo,
and wherein the carbon chain is optionally mono-substituted with Z;
  wherein Z is a partially saturated, fully saturated or fully unsaturated three to seven membered ring optionally having one to three heteroatoms selected independently from oxygen, sulfur and nitrogen, or a bicyclic ring consisting of two fused partially saturated, fully saturated or fully unsaturated five to six membered rings, taken independently, optionally having one to four heteroatoms selected independently from nitrogen, sulfur and oxygen;
  wherein said Z is optionally mono-, di- or tri-substituted independently with halo, $(C_1-C_6)$alkyl, $(C_1-C_6)$alkylcarbonyl, aminothioxo, amino$(C_1-C_6)$alkylcarbonyl, hydroxyl, diaminomethylene, carbamoyl or $(C_1-C_6)$alkoxy and wherein said $(C_1-C_6)$alkyl or $(C_1-C_6)$alkoxy substituent is also optionally substituted with one to three halo, and wherein said (C$_1$-C$_6$)alkyl or (C$_2$-C$_6$)alkoxy substituent is also optionally substituted with one to three hydroxy;
with the proviso that R$^1$ is not phenyl, and R$^2$ is not (C$_1$-C$_6$)alkyl.

Yet another aspect of this invention is directed to a method for treating cardiovascular conditions in a mammal (including a human being either male or female) by administering to a mammal in need of such treatment a therapeutically effective amount of a compound of Formula I, a prodrug thereof, or a pharmaceutically acceptable salt of said compound or of said prodrug.

Also provided herein are compositions comprising a pharmaceutically effective amount of one or more of the compounds described herein and a pharmaceutically acceptable carrier, vehicle, or diluent.

This invention is also directed to pharmaceutical combination compositions comprising: a therapeutically effective amount of a composition comprising
a first compound, said first compound being a Formula I compound, a prodrug thereof, or a pharmaceutically acceptable salt of said compound or of said prodrug;
a second compound, said second compound being an angiotensin converting enzyme inhibitor, a HMG-CoA reductase inhibitor, a non-steroidal anti-inflammatory agent, a Factor Xa inhibitor or warfarin; and/or optionally
a pharmaceutical carrier, vehicle, or diluent.

The present invention is directed to a compound of the Formula IA,

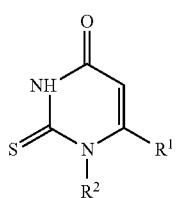

Formula IA or a pharmaceutically acceptable salt or prodrug thereof wherein
R$^1$ is a five to six membered aromatic ring optionally having one to three heteroatoms selected independently from nitrogen, sulfur and oxygen or a bicyclic ring consisting of two fused partially saturated, fully saturated or fully unsaturated five to six membered rings, taken independently, optionally having one to four heteroatoms selected independently from nitrogen, sulfur and oxygen; and
said R$^1$ is optionally mono-, di-, or tri-substituted independently with cyano, halo, hydroxyl, amino, (C$_1$-C$_4$)alkyl, (C$_1$-C$_4$)alkoxy, (C$_1$-C$_4$)alkoxy(C$_1$-C$_4$)alkyl, hydroxy(C$_2$-C$_4$)alkoxy, carbamoyl(C$_1$-C$_4$)alkoxy, amino(C$_2$-C$_4$)alkoxy, cyano(C$_1$-C$_4$)alkyl, (C$_1$-C$_4$)alkylcarbonyloxy(C$_1$-C$_4$)alkyl, amino(C$_1$-C$_4$)alkylcarbonyloxy(C$_1$-C$_4$)alkyl, (C$_1$-C$_4$)alkylcarbonyloxy(C$_1$-C$_4$)alkoxy, amino(C$_1$-C$_4$)alkylcarbonyloxy (C$_1$-C$_4$)alkoxy, mono-N— or di-N,N—(C$_1$-C$_4$)alkylamino, aminocarbonyl, mono-N— or di-N,N(C$_1$-C$_4$)alkylaminocarbonyl, (C$_1$-C$_4$)alkylthio, am inosulfonyl, (C$_1$-C$_4$)alkylsulfinyl, (C$_1$-C$_4$)alkylsulfonyl, or mono-N— or di-N,N(C$_1$-C$_4$) alkylaminosulfonyl, wherein any of the (C$_1$-C$_4$)alkyl or (C$_1$-C$_4$)alkoxy may be optionally mono-, di- or tri-substituted with fluoro; or
wherein R$^1$ is optionally substituted with a five to six membered aromatic ring optionally having one to three heteroatoms selected independently from nitrogen, sulfur and oxygen;

R$^2$ is a fully saturated, partially unsaturated or fully unsaturated one to fourteen membered straight carbon chain wherein the carbons, other than the connecting carbon,
a. may be branched
b. may optionally be replaced with one or two heteroatoms selected independently from oxygen and sulfur and may optionally be replaced with one to four nitrogens, wherein said sulfur is optionally mono- or di-substituted with oxo,
c. may optionally be mono-, di- or tri-substituted independently with halo,
d. may optionally be mono-substituted with hydroxy, and
e. may optionally be mono-substituted with oxo,
and wherein the carbon chain is optionally mono-substituted with Z;
wherein Z is a partially saturated, fully saturated or fully unsaturated three to seven membered ring optionally having one to three heteroatoms selected independently from oxygen, sulfur and nitrogen, or a bicyclic ring consisting of two fused partially saturated, fully saturated or fully unsaturated five to six membered rings, taken independently, optionally having one to four heteroatoms selected independently from nitrogen, sulfur and oxygen;
wherein said Z is optionally mono-, di- or tri-substituted independently with amino, halo, (C$_1$-C$_6$)alkyl, (C$_1$-C$_6$)alkylcarbonyl, aminothioxo, amino(C$_1$-C$_6$)alkylcarbonyl, hydroxyl, diaminomethylene, carbamoyl or (C$_1$-C$_6$)alkoxy and wherein said (C$_1$-C$_6$)alkyl or (C$_1$-C$_6$)alkoxy substituent is also optionally substituted with one to three halo, and wherein said (C$_1$-C$_6$)alkyl or (C$_2$-C$_6$)alkoxy substituent is also optionally substituted with one to three hydroxy;
with the proviso that R$^1$ is not unsubstituted phenyl, and R$^2$ is not unsubstituted(C$_1$-C$_6$)alkyl.

This invention is also directed to a method for treating cardiovascular events and conditions comprising administering to a mammal in need of such treatment a therapeutically effective amount of a compound of Formula IA or a prodrug thereof or a pharmaceutically acceptable salt of said compound or of said prodrug wherein the cardiovascular condition or event is heart failure, congestive heart failure, peripheral arterial disease, pulmonary hypertension, vasculitis, a primary or secondary myocardial infarction, ischemia, ischemia reperfusion injury, atrial fibrillation or coronary artery bypass graft surgery (CABG).

This invention is also directed to a method for treating a condition comprising administering to a mammal in need of such treatment a therapeutically effective amount of a compound of Formula IA or a prodrug thereof or a pharmaceutically acceptable salt of said compound or of said prodrug wherein the condition is diabetes, renal insufficiency, dialysis, delayed graft function, transplant organ rejection or nephropathy caused by contrasting agents.

Also provided herein are compositions comprising a pharmaceutically effective amount of one or more of the Formula IA compounds described herein and a pharmaceutically acceptable carrier, vehicle, or diluent.

This invention is also directed to pharmaceutical combination compositions comprising: a therapeutically effective amount of a composition comprising
a first compound, said first compound being a Formula IA compound, a prodrug thereof, or a pharmaceutically acceptable salt of said compound or of said prodrug;
a second compound, said second compound being an angiotensin converting enzyme inhibitor, a HMG-CoA reductase inhibitor, a non-steroidal anti-inflammatory agent, a Factor Xa inhibitor or warfarin; and/or optionally a pharmaceutical carrier, vehicle, or diluent.

All patents and patent applications referred to herein are hereby incorporated by reference.

Other features and advantages of this invention will be apparent from this specification and the appendant claims which describe the invention.

DETAILED DESCRIPTION OF THE INVENTION

Figure 1:
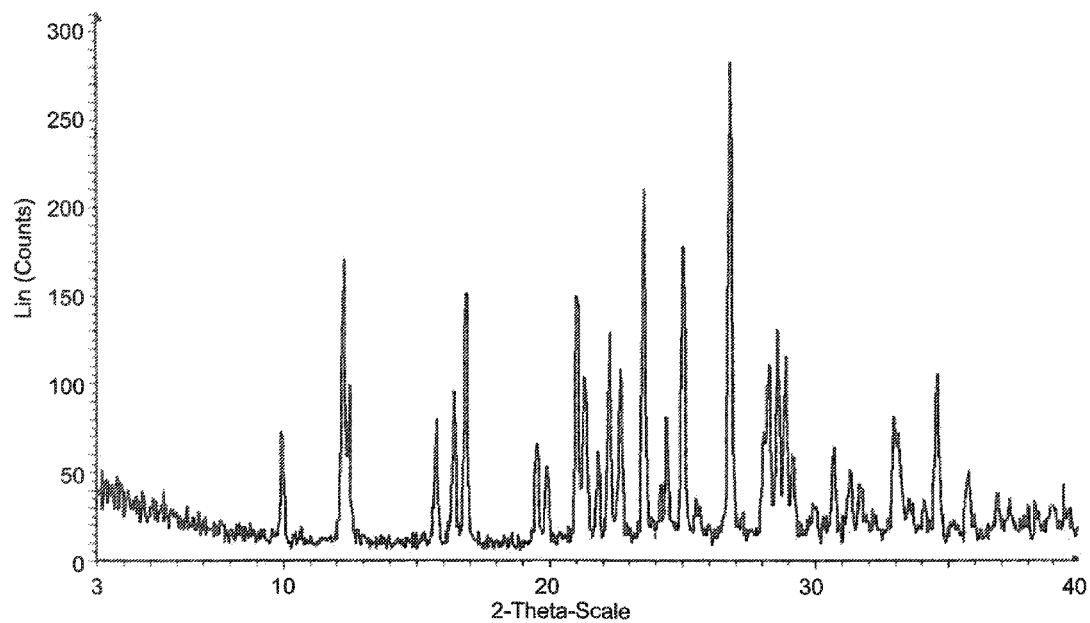
FIG. 1 is a characteristic x-ray powder diffraction pattern showing a crystalline form of Example 1(Vertical Axis: Intensity (CPS); Horizontal Axis: Two theta (degrees)).
Figure 2:
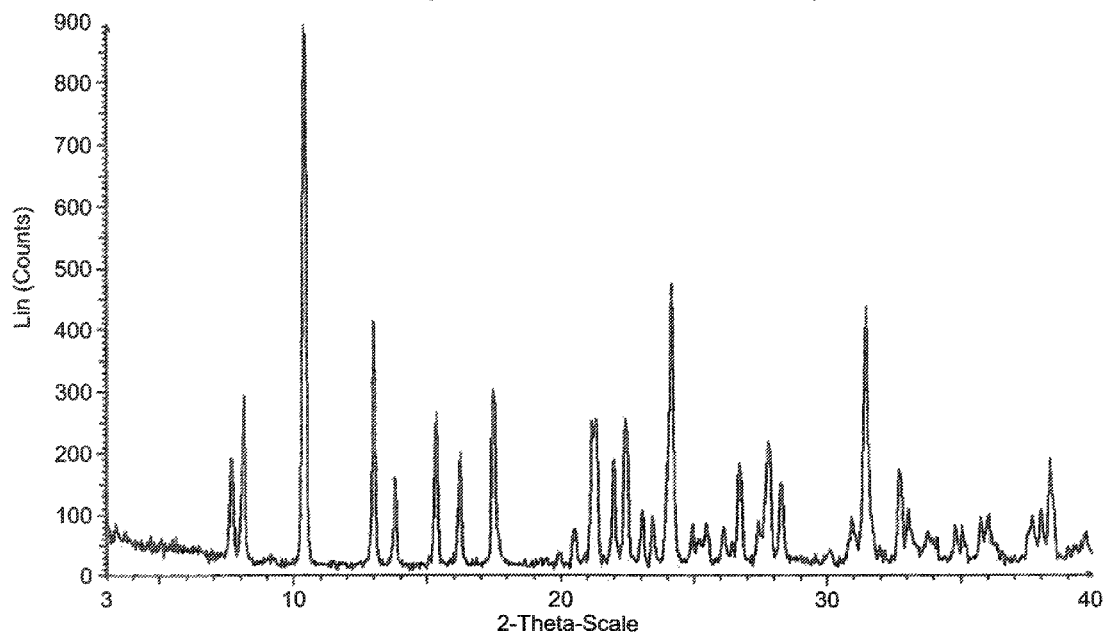
FIG. 2 is a characteristic x-ray powder diffraction pattern showing a crystalline form of Example 2(Vertical Axis: Intensity (CPS); Horizontal Axis: Two theta (degrees)).

A preferred group of compounds, designated the A Group, contains those compounds having the Formula I as shown above wherein $R^1$ is phenyl, naphthyl, furanyl, pyridinyl, pyrimidinyl, pyridazinyl, pyrazinyl, quinolinyl, isoquinolinyl, pyrazolyl, imidazolinyl, cyclopentyl, cyclohexyl, pyrrolyl, indolyl, benzo[b]thiophenyl, benzothiazolyl, benzo[b]furanyl or thiophenyl; and wherein said $R^1$ is mono-, di-, or tri-substituted independently with cyano, $(C_1-C_4)$alkyl, $(C_1-C_4)$alkoxy, hydroxy$(C_2-C_4)$alkoxy, trifluoro$(C_1-C_4)$alkyl, trifluoro$(C_1-C_4)$alkoxy or halo.

A group of compounds which is preferred among the A Group of compounds designated the B Group, contains those compounds wherein $R^2$ is a fully saturated, partially unsaturated or fully unsaturated one to fourteen membered straight carbon chain wherein the carbons, other than the connecting carbon,
a. may be branched
b. may optionally be replaced with one or two heteroatoms selected independently from oxygen, sulfur and nitrogen, wherein said sulfur is optionally mono- or di-substituted with oxo,
c. may optionally be mono-, di- or tri-substituted independently with halo,
d. may optionally be mono-substituted with hydroxy, and
e. may optionally be mono-substituted with oxo; or
$R^2$ is furanyl$(C_1-C_4)$alkyl, triazolyl$(C_1-C_4)$alkyl, pyridinyl$(C_1-C_4)$alkyl, pyrizinyl$(C_1-C_4)$alkyl, pyridazinyl$(C_1-C_4)$alkyl, pyrimidinyl$(C_1-C_4)$alkyl, imidazolyl$(C_1-C_4)$alkyl or pyrrolidinyl$(C_1-C_4)$alkyl, said $R^2$ rings optionally mono-, di- or tri-substituted independently with $(C_1-C_4)$alkyl, $(C_1-C_4)$alkoxy or halo.

A group of compounds which is preferred among the B Group of compounds designated the C Group, contains those compounds wherein $R^1$ is phenyl, naphthyl, pyridinyl, quinolinyl, isoquinolinyl, pyrazolyl, pyrimidinyl, pyridazinyl, pyrazinyl, imidazolinyl, furanyl, cyclopentyl, cyclohexyl, pyrrolyl, indolyl, benzo[b]thiophenyl, benzothiazolyl, benzo[b]furanyl or thiophenyl; wherein said $R^1$ is mono-, di-, or tri-substituted independently with $(C_1-C_4)$alkyl, $(C_1-C_4)$alkoxy, hydroxy$(C_2-C_4)$alkoxy, cyano, trifluoromethyl, trifluoromethoxy or halo; and
$R^2$ is $(C_1-C_4)$alkoxy$(C_1-C_4)$alkyl, carboxy$(C_1-C_4)$alkyl, mono- or di-hydroxy$(C_2-C_6)$alkyl, amino$(C_2-C_4)$alkyl, diaminomethyleneamino$(C_2-C_4)$alkyl, mono-N— or di-N,N $(C_1-C_4)$alkylamino$(C_2-C_4)$alkyl, $(C_1-C_4)$alkylcarbonyloxy $(C_1-C_4)$alkyl, $(C_1-C_4)$alkoxycarbonyl$(C_1-C_4)$alkyl, carbamoyl$(C_1-C_4)$alkyl, carbamoylamino$(C_2-C_4)$alkyl, mono-N— or di-N,N$(C_1-C_4)$alkylcarbamoyl$(C_1-C_4)$alkyl, amino$(C_2-C_4)$alkylcarbamoyl$(C_1-C_4)$alkyl, $(C_1-C_4)$alkylcarbonylamino$(C_2-C_4)$alkyl, amino$(C_1-C_4)$alkylcarbonylamino $(C_2-C_4)$alkyl, $(C_1-C_4)$alkoxycarbonylamino$(C_2-C_4)$alkyl, $(C_1-C_4)$alkylsulfonylamino$(C_2-C_4)$alkyl, $(C_1-C_4)$alkylaminosulfonyl$(C_1-C_4)$alkyl, am inosulfonyl$(C_1-C_4)$alkyl, amino$(C_3-C_4)$hydroxyalkyl or $(C_1-C_4)$alkylthioalkyl$(C_1-C_4)$.

A group of compounds which is preferred among the C Group of compounds designated the D Group, contains those compounds wherein $R^1$ is phenyl and said $R^1$ is mono-, di-, or tri-substituted independently with hydroxyethoxy, methyl, methoxy, fluoro or chloro; and
$R^2$ is diaminomethyleneamino$(C_2-C_4)$alkyl, carbamoyl$(C_1-C_4)$alkyl, hydroxy$(C_2-C_4)$alkyl, amino$(C_2-C_4)$alkylcarbamoyl$(C_1-C_4)$alkyl, $(C_1-C_4)$alkylcarbonylamino$(C_2-C_4)$alkyl, amino$(C_1-C_4)$alkylcarbonylamino$(C_2-C_4)$alkyl, amino$(C_3-C_4)$hydroxyalkyl or amino$(C_2-C_4)$alkyl.

A group of compounds which is preferred among the B Group of compounds designated the E Group, contains those compounds wherein $R^1$ is phenyl, naphthyl, pyridinyl, quinolinyl, isoquinolinyl, pyrazolyl, pyrimidinyl, pyridazinyl, pyrazinyl, imidazolinyl, furanyl, cyclopentyl, cyclohexyl, pyrrolyl, indolyl, benzo[b]thiophenyl, benzothiazolyl, benzo[b]furanyl or thiophenyl; wherein said $R^1$ is mono-, di-, or tri-substituted independently with $(C_1-C_4)$alkyl, $(C_1-C_4)$alkoxy, hydroxy$(C_2-C_4)$alkoxy, cyano, trifluoromethyl, trifluoromethoxy or halo; and
$R^2$ is triazolyl$(C_1-C_4)$alkyl, pyridinyl$(C_1-C_4)$alkyl, pyrizinyl $(C_1-C_4)$alkyl, pyridazinyl$(C_1-C_4)$alkyl, pyrimidinyl$(C_1-C_4)$alkyl, imidazolyl$(C_1-C_4)$alkyl or pyrrolidinyl$(C_1-C_4)$alkyl, said $R^2$ rings optionally mono-, di- or tri-substituted independently with $(C_1-C_4)$alkyl, $(C_1-C_4)$alkoxy or halo.

A preferred group of compounds, designated the F Group, contains those compounds having the Formula I as shown above wherein wherein $R^1$ is phenyl and said $R^1$ is mono-, di-, tri-substituted independently with hydroxyethoxy, methyl, methoxy, fluoro or chloro.

A preferred group of compounds, designated the G Group, contains those compounds having the Formula I as shown above wherein $R^2$ is hydroxy$(C_2-C_4)$alkyl, diaminomethyleneamino$(C_2-C_4)$alkyl, carbamoyl$(C_1-C_4)$alkyl, amino$(C_3-C_4)$hydroxyalkyl, amino$(C_2-C_4)$alkylcarbamoyl$(C_1-C_4)$ alkyl, $(C_1-C_4)$alkylcarbonylamino$(C_2-C_4)$alkyl, amino$(C_1-C_4)$alkylcarbonylamino$(C_2-C_4)$alkyl or amino$(C_2-C_4)$alkyl.

A preferred group of compounds, designated the H Group, contains those compounds having the Formula I as shown above wherein $R^2$ is $(C_1-C_4)$alkyl mono- or di-substituted independently with amino, carbamoyl, hydroxyl, $(C_1-C_4)$ alkoxy, amino$(C_1-C_4)$alkylcarbonylamino, amino$(C_2-C_4)$ alkylcarbamoyl, $(C_1-C_4)$alkylcarbonylamino or diaminomethyleneamino.

A preferred group of compounds, designated the I Group, contains those compounds wherein the compound is
6-(2,4-dimethoxyphenyl)-1-(2-hydroxyethyl)-2-thioxo-2,3-dihydropyrimidin-4(1H)-one;
1-(2-aminoethyl)-6-(2,4-dimethoxyphenyl)-2-thioxo-2,3-dihydropyrimidin-4(1H)-one;
2-[6-(2,5-dimethoxyphenyl)-4-oxo-2-thioxo-3,4-dihydropyrimidin-1(2H)-yl]acetamide;
2-[6-(5-chloro-2-methoxyphenyl)-4-oxo-2-thioxo-3,4-dihydropyrimidin-1(2H)-yl]acetamide;
1-(2-aminoethyl)-2-thioxo-6-(2,4,5-trimethoxyphenyl)-2,3-dihydropyrimidin-4(1H)-one;
1-(3-aminopropyl)-6-(2-methoxy-5-methylphenyl)-2-thioxo-2,3-dihydropyrimidin-4(1H)-one;
N-{2-[6-(2,4-dimethoxyphenyl)-4-oxo-2-thioxo-3,4-dihydropyrimidin-1(2H)-yl]ethyl}glycinamide;

2-{3-[6-(2-methoxyphenyl)-4-oxo-2-thioxo-3,4-dihydropyrimidin-1(2H)-yl]propyl}guanidine;

1-[(2S)-3-amino-2-hydroxypropyl]-6-(5-chloro-2-methoxyphenyl)-2-thioxo-2,3-dihydropyrimidin-4(1H)-one;

1-[(2R)-3-amino-2-hydroxypropyl]-6-(5-chloro-2-methoxyphenyl)-2-thioxo-2,3-dihydropyrimidin-4(1H)-one;

N-(2-aminoethyl)-2-[6-(2,4-dimethoxyphenyl)-4-oxo-2-thioxo-3,4-dihydropyrimidin-1(2H)-yl]acetamide; or 1-(2-aminoethyl)-6-[2-(2-hydroxyethoxy)phenyl]-2-thioxo-2,3-dihydropyrimidin-4(1H)-one or a pharmaceutically acceptable salt thereof.

An especially preferred compound is 2-(6-(2,5-dimethoxyphenyl)-4-oxo-2-thioxo-3,4-dihydropyrimidin-1(2H)-yl)acetamide or a pharmaceutically acceptable salt thereof.

It is especially preferred that the compound is

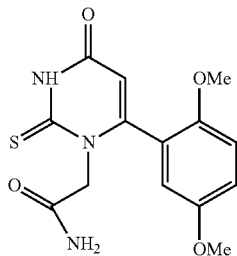 [SMILES: COc1ccc(OC)c(-c2cc(=O)[nH]c(=S)n2CC(N)=O)c1]

Another especially preferred compound is 2-(6-(5-chloro-2-methoxyphenyl)-4-oxo-2-thioxo-3,4-dihydropyrimidin-1(2H)-yl)acetamide or a pharmaceutically acceptable salt thereof.

It is especially preferred that the compound is

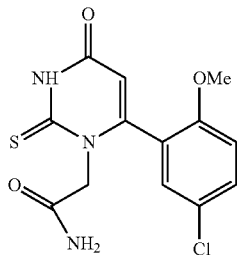 [SMILES: COc1ccc(Cl)cc1-c1cc(=O)[nH]c(=S)n1CC(N)=O]

A group of compounds which is preferred among the C Group of compounds designated the J Group contains those compounds wherein
$R^1$ is naphthyl, quinolinyl, isoquinolinyl, indolyl, benzo[b]thiophenyl, benzothiazolyl, benzo[b]furanyl or thiophenyl and said $R^1$ is mono-, di-, or tri-substituted independently with hydroxyethoxy, methyl, methoxy, fluoro or chloro; and
$R^2$ is diaminomethyleneamino($C_2$-$C_4$)alkyl, carbamoyl($C_1$-$C_4$)alkyl, hydroxy($C_2$-$C_4$)alkyl, amino($C_2$-$C_4$)alkylcarbamoyl($C_1$-$C_4$)alkyl, ($C_1$-$C_4$)alkylcarbonylamino($C_2$-$C_4$)alkyl, amino($C_1$-$C_4$)alkylcarbonylamino($C_2$-$C_4$)alkyl, amino($C_3$-$C_4$)hydroxyalkyl or amino($C_2$-$C_4$)alkyl.

A preferred group of compounds, designated the K Group, contains those compounds wherein the compound is
2-[6-(2,4-dimethoxyphenyl)-4-oxo-2-thioxo-3,4-dihydropyrimidin-1(2H)-yl]acetamide;

2-[6-(2-methoxy-5-methylphenyl)-4-oxo-2-thioxo-3,4-dihydropyrimidin-1(2H)-yl]acetamide;

1-[(2R)-2-aminopropyl]-6-(2,4-dimethoxyphenyl)-2-thioxo-2,3-dihydropyrimidin-4(1H)-one;

2-[6-(3-methoxy-2-naphthyl)-4-oxo-2-thioxo-3,4-dihydropyrimidin-1(2H)-yl]acetamide; or 2-[6-(1H-indol-4-yl)-4-oxo-2-thioxo-3,4-dihydropyrimidin-1(2H)-yl]acetamide or a pharmaceutically acceptable salt thereof.

A preferred group of compounds, designated the L Group, contains those compounds wherein the compound is
2-{6-[2-(2-hydroxyethoxy)-5-methoxyphenyl]-4-oxo-2-thioxo-3,4-dihydropyrimidin-1 (2H)-yl}acetamide;

N-(2-aminoethyl)-2-{6-[2-(2-hydroxyethoxy)-4-methoxyphenyl]-4-oxo-2-thioxo-3,4-dihydropyrimidin-1 (2H)-yl}acetamide;

6-[2-(2-hydroxyethoxy)-4-methoxyphenyl]-1-(2-hydroxyethyl)-2-thioxo-2,3-dihydropyrimidin-4(1H)-one;

6-[5-fluoro-2-(2-hydroxyethoxy)phenyl]-1-(2-hydroxyethyl)-2-thioxo-2,3-dihydropyrimidin-4(1H)-one; or 2-{6-[2-(2-hydroxyethoxy)-4-methoxyphenyl]-4-oxo-2-thioxo-3,4-dihydropyrimidin-1 (2H)-yl}acetamide or a pharmaceutically acceptable salt thereof.

An especially preferred compound is N-(2-aminoethyl)-2-[6-(2,4-dimethoxyphenyl)-4-oxo-2-thioxo-3,4-dihydropyrimidin-1(2H)-yl]acetamide or a pharmaceutically acceptable salt thereof.

It is especially preferred that the compound is

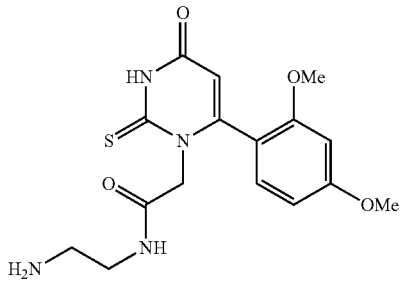 [SMILES: COc1ccc(-c2cc(=O)[nH]c(=S)n2CC(=O)NCCN)c(OC)c1]

Preferred cardiovascular conditions include heart failure, congestive heart failure, peripheral arterial disease, pulmonary hypertension or vasculitis.

Other preferred cardiovascular conditions include unstable angina or a patient that has experienced a myocardial infarction.

Pharmaceutically acceptable salts of the compounds of Formula I or IA include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palm itate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, calcium, choline, diethylamine, glycine, lysine, magnesium, meglumine, olamine, potassium, sodium, trimethamine and zinc salts. Hemisalts of acids and bases may also be formed, for example, hemisulphate and hemicalcium salts. For a review on suitable salts, see *Handbook of Pharmaceutical Salts: Properties, Selection, and Use* by Stahl and Wermuth (Wiley-VCH, 2002).

The compounds of the invention may exist in both unsolvated and solvated forms. The term 'solvate' is used herein to describe a molecular complex comprising the compound of the invention and one or more pharmaceutically acceptable solvent molecules, for example, ethanol. Such solvent molecules are those commonly used in the pharmaceutical art, which are known to be innocuous to the recipient, e.g., water, ethanol, and the like. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like. The term 'hydrate' is employed when said solvent is water. Pharmaceutically acceptable solvates include hydrates and other solvates wherein the solvent of crystallization may be isotopically substituted, e.g. $D_2O$, $d_6$-acetone, $d_6$-DMSO. The term "hydrate" refers to the complex where the solvent molecule is water. The solvates and/or hydrates preferably exist in crystalline form.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

The compounds of the invention include compounds of Formula I or IA as hereinbefore defined, polymorphs, and isomers thereof (including optical, geometric and tautomeric isomers) as hereinafter defined and isotopically-labelled compounds of Formula I or IA.

The compounds of the present invention may be administered as prodrugs. Thus certain derivatives of compounds of Formula I or IA which may have little or no pharmacological activity themselves can, when administered into or onto the body, be converted into compounds of Formula I or IA having the desired activity, for example, by hydrolytic cleavage. Such derivatives are referred to as 'prodrugs'. [Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).]

Prodrugs can, for example, be produced by replacing appropriate functionalities present in the compounds of Formula I or IA with certain moieties known to those skilled in the art as 'pro-moieties' as described, for example, in "Design of Prodrugs" by H Bundgaard (Elsevier, 1985).

Some examples of such prodrugs include:

(i) where the compound of Formula I or IA contains a carboxylic acid functionality (—COOH), an ester thereof, for example, replacement of the hydrogen with ($C_1$-$C_8$) alkyl;

(ii) where the compound of Formula I or IA contains an alcohol functionality (—OH), an ether thereof, for example, replacement of the hydrogen with ($C_1$-$C_6$) alkanoyloxymethyl; and (iii) where the compound of Formula I or IA contains a primary or secondary amino functionality (—$NH_2$ or —NHR where R≠H), an amide thereof, for example, replacement of one or both hydrogens with ($C_1$-$C_{10}$) alkanoyl.

In addition, certain compounds of Formula I or IA may themselves act as prodrugs of other compounds of Formula I or IA.

Compounds of Formula I or IA containing an asymmetric carbon atom can exist as two or more stereoisomers. Where a compound of Formula I or IA contains an alkenyl or alkenylene group or a cycloalkyl group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism. For example, the following is illustrative of tautomers of the compounds of Formula I or IA.

Thiouracil Tautomers

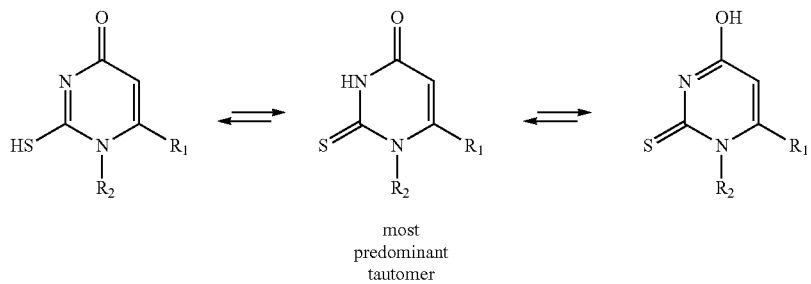

most predominant tautomer

Additional example of tautomerism within the scope of the claimed compounds is the following illustration of guanidine tautomers of the compounds.

Example of Guanidine Tautomers and Geometric Isomers

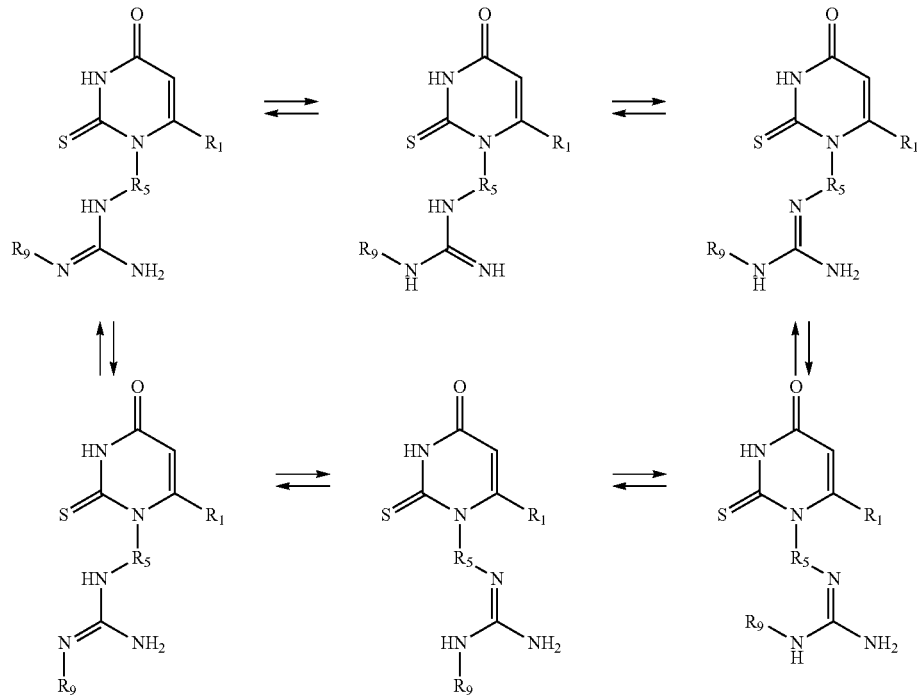

Included within the scope of the claimed compounds of the present invention are all stereoisomers, geometric isomers and tautomeric forms of the compounds of Formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

The present invention includes all pharmaceutically acceptable isotopically-labelled compounds of Formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of Formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Tomography (PET) studies for examining substrate receptor occupancy.

Isotopically-labelled compounds of Formula (I) can generally be prepared by conventional techniques known to those skilled in the art or by processes analogous to those described in the accompanying Examples and Preparations using an appropriate isotopically-labelled reagents in place of the non-labelled reagent previously employed. References herein to "treat", "treating", "treatment" and the like include curative, palliative and prophylactic treatment.

As used herein, the expressions "reaction-inert solvent" and "inert solvent" refer to a solvent or a mixture thereof which does not interact with starting materials, reagents, intermediates or products in a manner which adversely affects the yield of the desired product.

By "pharmaceutically acceptable" is meant the carrier, vehicle, or diluent and/or salt must be compatible with the other ingredients of the formulation, and not deleterious to the recipient thereof.

The term "pharmaceutically effective amount", as used herein, refers to an amount of the compound of Formula I or IA (or a combination agent or a Formula I or IA compound in combination with a combination agent) sufficient to treat, prevent onset of or delay or diminish the symptoms and physiological manifestations of the indications described herein.

The term "room temperature or ambient temperature" means a temperature between 18 to 25° C., "HPLC" refers to high pressure liquid chromatography, "MPLC" refers to medium pressure liquid chromatography, "TLC" refers to thin layer chromatography, "MS" refers to mass spectrum or mass spectroscopy or mass spectrometry, "NMR" refers to nuclear magnetic resonance spectroscopy, "DCM" refers to dichloromethane, "DMSO" refers to dimethyl sulfoxide, "DME" refers to dimethoxyethane, "EtOAc" refers to ethyl acetate, "MeOH" refers to methanol, "Ph" refers to the phenyl group, "Pr" refers to propyl, "trityl" refers to the triphenylmethyl group, "ACN" refers to acetonitrile, "DEAD" refers to diethylazodicarboxylate, and "DIAD" refers to diisopropylazodicarboxylate.

It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3-, or 4-pyridyl, the term "thienyl" means 2-, or 3-thienyl, and so forth. In general the compounds of this invention can be made by processes which include processes analogous to those known in the chemical arts, particularly in light of the description contained herein.

As used herein the term mono-N— or di-N,N—$(C_1$-$C_x)$ alkyl . . . refers to the $(C_1$-$C_x)$alkyl moiety taken independently when it is di-N,N—$(C_1$-$C_x)$alkyl . . . (x refers to integers).

By halo is meant chloro, bromo, iodo, or fluoro.

By alkyl is meant straight chain saturated hydrocarbon or branched chain saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, neopentyl, tertiary pentyl, 1-methylbutyl, 2-methylbutyl, 3-methylbutyl, hexyl, isohexyl, heptyl and octyl.

By alkoxy is meant straight chain saturated alkyl or branched chain saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy.

The following paragraphs describe exemplary ring(s) for the generic ring descriptions contained herein.

Exemplary five to six membered aromatic rings optionally having one to three heteroatoms selected independently from oxygen, nitrogen and sulfur include phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl and pyrazinyl.

Exemplary six membered rings include 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-oxathiazinyl, 1,4,2-oxadiazinyl and 1,3,5,2-oxadiazinyl.

Exemplary bicyclic rings consisting of two fused partially saturated, fully saturated or fully unsaturated five or six membered rings, taken independently, optionally having one to three heteroatoms selected independently from nitrogen, sulfur and oxygen include indolizinyl, indolyl, isoindolyl, 3H-indolyl, 1H-isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)-pyridinyl, pyrido(3,2-b)-pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

Certain processes for the manufacture of the compounds of this invention are provided as further features of the invention and are illustrated by the following reaction schemes. Other processes may be described in the experimental section. Specific synthetic schemes for preparation of the compounds of Formula I or IA are outlined below.

As an initial note, in the preparation of the Formula I or IA compounds it is noted that some of the preparation methods useful for the preparation of the compounds described herein may require protection of remote functionality (e.g., primary amine, secondary amine, carboxyl in Formula I or IA precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*, John Wiley & Sons, New York, 1991.

For example, certain compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as N-t-butoxycarbonyl, benzyloxycarbonyl, and 9-fluorenylmethylenoxycarbonyl for amines and lower alkyl or benzyl esters for carboxylic acids) which are generally not chemically reactive under the reaction conditions described and can typically be removed without chemically altering other functionality in the Formula I or IA compound.

SCHEME I

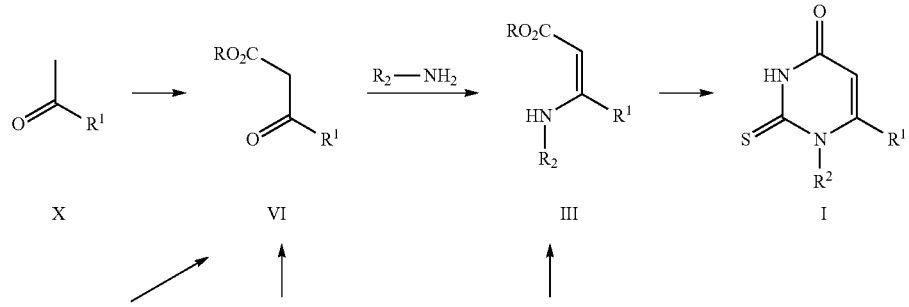

-continued

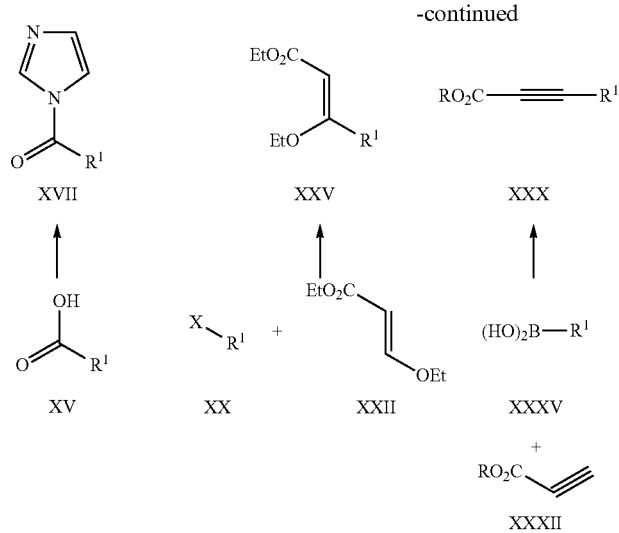

Those skilled in the art will recognize that there exists a variety of methods for preparing thiouracils, including the condensation of a thiourea with various carbonyl containing compounds, or by reaction of a uracil with a thiating agent such as phosphorous pentasulfide or Lawesson's reagent. In forming the thiouracils of the present invention it is useful to consider the method of construction in order to enhance the desired compounds over the variety of possible isomers in a regiospecific manner.

The Formula I or IA thiouracil compounds wherein $R^1$ and $R^2$ are as described above may be prepared from the Formula III enamine by a cyclization reaction. The Formula III enamine is cyclized to the corresponding Formula I or IA thiouracil, for example, by reaction with an isothiocyanate such as benzoyl, carboxyethyl or preferably (trimethylsilyl) isothiocyanate (TMSNCS). The reaction proceeds under reaction conditions such as a polar aprotic solvent (e.g., methyl tetrahydrofuran, tetrahydrofuran, dioxane, isobutylnitrile or neat in the isothiocyanate) at a temperature of about 20° C. to about 150° C., typically about 85° C. (via microwave or thermal heating), for about three hours to about forty-eight hours.

The Formula III enamine may be conveniently prepared from the Formula VI β-ketoester by reaction with an appropriate $R^2$—$NH_2$ amine (wherein $R^2$ is as described above or wherein reactive functionality in $R^2$, such as a primary amine, is in a suitably a protected form, such as an O-tert-butyl carbamate). For example, the Formula VI β-ketoester is reacted with the $R^2$—$NH_2$ amine in the presence of a weak acid such as acetic acid in a polar solvent (e.g., methanol, ethanol, isopropanol, toluene or neat in the amine) at a temperature of about 20° C. to about 120° C., for about four hours to about seventy-two hours, typically about 80° C. for about 12 hours.

As described above, the Formula VI β-ketoester may be prepared, for example, from a Formula X methyl ketone, a Formula XV carboxylic acid, a Formula XX aryl halide or other precursors known to those skilled in the art.

The Formula VI β-ketoester is prepared from the Formula X methyl ketone by carboalkoxylation. For example, the Formula X methyl ketone is reacted with a dialkylcarbonate, preferably dimethyl carbonate, in the presence of an alkoxide base such as potassium tert-butoxide, in a polar solvent such as methyl tert-butyl ether or the corresponding alcohol for the dialkylcarbonate, at a temperature of about 15° C. to about 100° C., typically ambient temperature, for about four hours to about forty-eight hours, typically twelve hours.

The Formula VI β-ketoester may also be prepared for example from a carboxylic acid. For example, the Formula VI β-ketoester may be prepared from an activated carboxylic acid. The Formula XV acid is conveniently converted to a corresponding XVII acyl imidazole by reaction with 1,1'-carbonyldiimidazole in a polar solvent, typically tetrahydrofuran at a temperature between 0° C. and 100° C., preferably ambient temperature, for between 1 hour and twenty-four hours, preferably three hours. A solution of the resulting acyl imidazole XVII in a polar aprotic solvent such as tetrahydrofuran is converted to the corresponding Formula VI β-ketoester by reaction with a solution of an activated acetate species, such as the enolate of an acetate ester or preferably ethyl magnesium malonate in a polar aprotic solvent such as tetrahydrofuran, at a temperature between −80° C. and 100° C., preferably ambient temperature, for between one and fourty-eight hours, preferably twelve hours to prepare the corresponding Formula VI β-ketoester.

Those skilled in the art will recognize that a variety of other methods can be used to prepare the β-ketoester from an acid.

Those skilled in the art will recognize that the Formula VI β-ketoesters may also be prepared from esters of Formula XV carboxylic acids, such as methyl, ethyl, isopropyl, or tert-butyl, preferably the isopropyl ester of Formula XV carboxylic acid by a condensation reaction with an activated acetate species, such as the enolate of an acetate ester, preferably the enolate of isopropyl acetate, in a polar aprotic solvent such as tetrahydrofuran, dioxane, or toluene, preferably tetrahydrofuran, at a temperature between −80° C. and 40° C., preferably ambient temperature, for between one and twenty-four hours, preferably twelve hours to prepare the corresponding Formula VI β-ketoester.

In addition, those skilled in the art will recognize that there are a variety of methods for converting an aryl halide into a β-ketoester including the following exemplary procedures. A Formula XX aryl halide (e.g., an aryl bromide) is combined via a palladium-mediated coupling with a Formula)(XII β-alkoxyacrylate, such as ethyl 3-ethoxyacrylate employing a palladium catalyst, typically bis(tri-tert-butylphosphine) palladium (optionally with lithium chloride), in the presence of an amine such as N,N-dicyclohexylmethyl-amine under an inert atmosphere such as nitrogen at a temperature of about 90° C. to about 140° C., typically at about 110° C., for about four hours to about forty-eight hours, typically 12 hours. The resulting)(XV enolether is converted to the corresponding Formula VI β-ketoester by treatment with an acid such as aqueous HCl in a polar solvent (e.g., dichloromethane, methanol, acetic acid) at a temperature of about 15° C. to about 40° C., typically at about ambient, for about thirty minutes to about six hours.

Alternatively, the Formula III enamine may be prepared from the Formula XXX propiolate via the following two-step reaction.

A Formula XXXII alkyne is coupled with a Formula XXXV boronic acid wherein $R^1$ is as described above, to prepare the Formula XXX propiolate via a transition metal mediated coupling. For example, the appropriate $R^1$-boronic acid in a polar aprotic solvent such as dichloromethane is reacted with cesium carbonate, copper iodide, silver (I) oxide and tert-butyl propiolate at a temperature of about 60° C. to about 100° C., typically about 80° C., for about 30 minutes to about six hours.

The resulting Formula XXX propiolate is transformed to the corresponding Formula III enamine by amination with the appropriate $R^2$—$NH_2$ amine (wherein $R^2$ is as defined above) in the presence of a weak acid such as acetic acid. The reaction proceeds in a polar solvent such as ethanol or isopropanol at a temperature of about 60° C. to about 100° C. typically, about 80° C. for about 24 hours to about 72 hours.

solvent (e.g., acetonitrile) at a temperature of about 15° C. to about 40° C., typically ambient temperature, for about eight hours to about twenty-four hours. The resulting Formula LVII halide undergoes a transition metal mediated coupling with the appropriate $R^1$-metal species (wherein $R^1$ is as defined above) by for example reaction with [1,1'-bis(diphenylphosphino)ferrocene]dichloropalladium(II) and $R^1$ boronic acid (wherein $R^1$ is as described above) with 1,4 dioxane and aqueous sodium carbonate. The mixture is heated at a temperature of about 90° C. to about 150° C., typically by subjecting to microwave irradiation at 120° C. for about fifteen minutes to about one hour. The resulting Formula LVIII compound is deprotected by reaction with a nucleophile, typically by reaction with ammonium sulfide in a polar solvent such as pyridine at a temperature of about 60° C. to about 150° C., typically by microwave irradiation at 75° C. for about fifteen minutes to about one hour to prepare the Formula I or IA thiouracil.

The Formula LVI halothiouracils may be prepared from the corresponding Formula LV thiouracils by for example, a two-step deprotonation/lithium-halogen-exchange with iodine. Typically the thiouracil is treated with a base such as lithium diisopropylamide in a polar aprotic solvent such as tetrahydrofuran at a temperature of about −20° C. to about −100° C., typically −78° C. Then the solution is allowed to warm to a temperature of about 0° C. to about −25° C., typically −10° C. for about fifteen minutes to about one hour to prepare the corresponding lithium intermediate followed by cooling to a temperature of about −60° C. to about −80° C., typically −78° C. whereupon the lithium intermediate is reacted with iodine in an appropriate polar aprotic solvent for about 5 minutes to about forty-eight hours, typically eight hours.

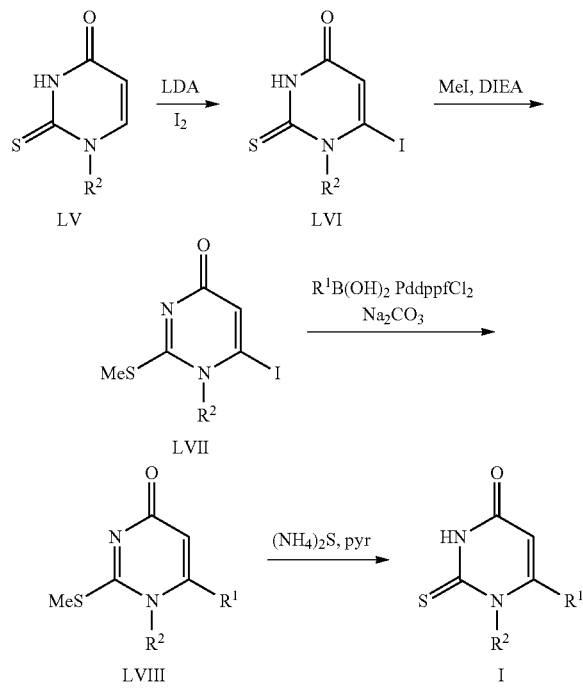

SCHEME II

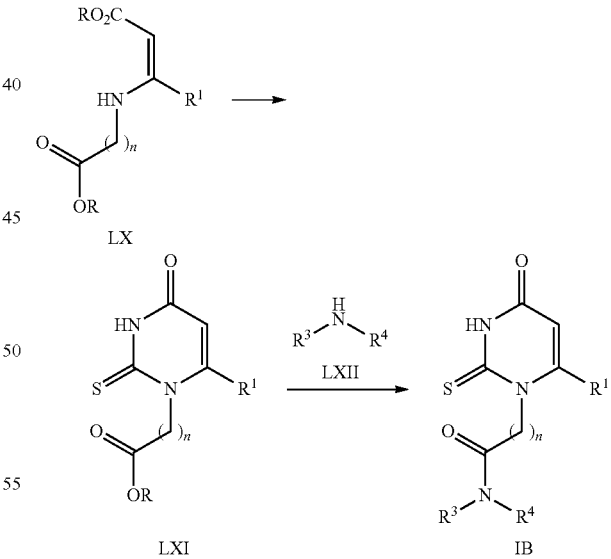

SCHEME III

The Formula I or IA thiouracil may also be prepared from a Formula LVI 6-halothiouracil as shown in Scheme II.

The thiocarbonyl of a Formula LVI halothiouracil is protected, for example, by reaction with iodomethane in the presence of a base such as diisopropylethylamine in a polar The Formula IB and LXI thiouracil compounds (wherein $R^1$ is described above, and while $R^3$ and $R^4$ are not specifically denoted above, refer to substituents that are generally described above) may be prepared from the Formula LX enamines as shown in Scheme III. Formula LXI thiouracils, wherein R is an alkyl group such as methyl, ethyl, isopropyl or tert-butyl, preferentially methyl or ethyl, may be converted into the corresponding carboxylic acid, wherein R=H, by a variety of methods known to those skilled in the art such as acid or base hydrolysis, preferably treatment with 5 equivalents of sodium or lithium hydroxide, in a polar solvent such as water, methanol, ethanol, tetrahydrofuran, or a mixture of such solvents, preferably water and ethanol, at a temperature between 0° C. to about 100° C., preferably ambient temperature, for a period between one hour and twenty-four hours, preferably four hours. The resulting Formula LXI carboxylic acid may be converted into the Formula IB amide by use of amide coupling reagents known to those skilled in the art, such as propane phosphonic acid anhydride (T3P) or (CDI), preferably propane phosphonic acid anhydride, in the presence of an organic base, such as pyridine, triethylamine, imidazole or diisopropylethylamine, preferably diisopropylethylamine, in a polar solvent, such as N,N'-dimethylformamide, methylene chloride or ethyl acetate, preferably methylene chloride, at a temperature between 0° C. and solvent reflux, preferably ambient temperature, for a period between 15 minutes and forty-eight hours, preferably eighteen hours.

The Formula LXI thiouracil compounds may be prepared from Formula LX enamines by reaction with an isothiocyanate, such as N-benzoyl-, N-carboxyethyl- or preferably (trimethylsilyl)isothiocyanate (TMSNCS) optionally in the presence of a polar aprotic solvent, such as, methyl tetrahydrofuran, tetrahydrofuran, dioxane, isobutylnitrile, n-butylacetate, N,N'-dimethylformamide, preferably neat in the isothiocyanate at a temperature between 20° C. and 150° C., typically about 85° C., heating with amicrowave reactor or a conventional heat source, for between 15 minutes and forty-eight hours, preferably three hours.

The Formula IC, LXXI and LXXII thiouracils may be prepared from the Formula LXX thiouracils as shown in Scheme IV.

The Formula IC (thiouracils (wherein $R^1$ is described above, and while $R^3$-$R^9$ are not specifically denoted above, refer to substituents that are generally described above and wherein at least one of $R^6$ through $R^9$ is bonded to the corresponding guanidine nitrogen through a carbonyl moiety) may be prepared from Formula LXXII thiouracils, which may exist in a variety of tautomeric forms such as these shown, by reaction of LXXII guanidines with an acylating reagent known to those skilled in the art such as an acyl chloride or alkyl chloroformate in the presence of an aqueous base such as sodium carbonate or sodium bicarbonate in polar aprotic solvent, such as tetrahydrofuran, at a temperature between 0° C. and solvent reflux, preferably ambient temperature, to provide the corresponding Formula ICguanidines. Alternatively, reaction of LXXII thiouracils with a dialkyl carbonate, in the presence of an alkoxide base such as sodium ethoxide, in a polar solvent such as the corresponding alcohol for the dialkylcarbonate, at a temperature of between 15° C. to about 100° C., preferably at 50° C., for between four hours and forty-eight hours, preferably fifteen hours provides the corresponding Formula IC thiouracils.

The Formula LXXII thiouracils may be prepared from the corresponding Formula LXX thiouracils by reaction with $R^7R^8$NCN-containing guanylating reagent, such as benzotriazole-$R^7R^8$N-methanimine, imidazole-$R^7R^8$N-methanimine, or pyrazole-$R^7R^8$N-methanimine in a polar aprotic solvent, preferably N,N'-dimethylformamide, in the pres-

SCHEME IV

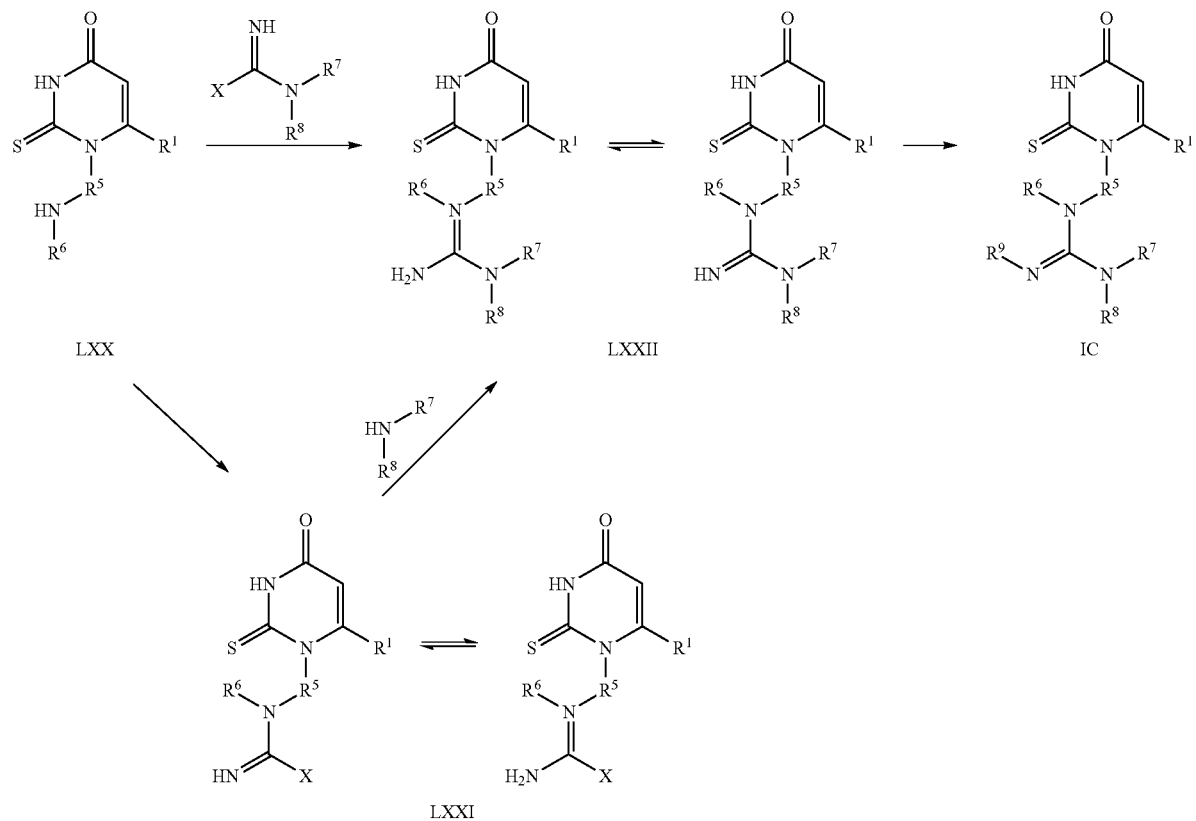

ence of a base, preferably diisopropylethylamine, at a temperature between 15° C. to 60° C., preferably ambient temperature, for between four to seventy-two hours, preferably eighteen hours. Alternatively, Formula LXX amines may be converted to an activated thiouracil LXXI wherein X is a leaving group, such as benzotriazole, imidazole, pyrrazole, by reaction with a methanimine reagent, such as 1,1-di(1H-benzotriazol-1-yl)methanimine, 1,1-di(1H-imidazol-1-yl)methanimine or 1,1-di(1H-pyrazol-1yl-) methanimine, in the presence of a base, such as diisopropylamine, in a polar aprotic solvent, such as N,N'-dimethylformamide, at a temperature between 15° C. and 100° C., preferably ambient temperature, for between four hours and forty-eight hours, preferably eighteen hours. The resulting Formula LXXI activated thiouracils can then be treated with $R^7R^8NH$ in the presence of a base, such as diisopropylethylamine, in a polar aprotic solvent, such as N,N'-dimethylformamide, at a temperature between 20° C. and 120° C., preferably 60° C., for between one hour and 24 hours, preferably three hours to obtain Formula LXXII guanidine thiouracils.

The starting materials and reagents for the above described Formula I or IA compounds, are also readily available or can be easily synthesized by those skilled in the art using conventional methods of organic synthesis. For example, many of the compounds used herein, are related to, or are derived from compounds in which there is a large scientific interest and commercial need, and accordingly many such compounds are commercially available or are reported in the literature or are easily prepared from other commonly available substances by methods which are reported in the literature.

Cis/trans isomers may be separated by conventional techniques well known to those skilled in the art, for example, chromatography and fractional crystallization.

Mixtures of stereoisomers may be separated by conventional techniques known to those skilled in the art. [see, for example, "Stereochemistry of Organic Compounds" by E L Eliel (Wiley, New York, 1994).]

Conventional techniques for the preparation/isolation of individual enantiomers include chiral synthesis from a suitable optically pure precursor.

Alternatively, the racemate (or a racemic precursor) may be reacted with a suitable optically active compound, for example, an alcohol, or, in the case where the compound of Formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Pharmaceutically acceptable salts of compounds of Formula I or IA may be prepared by one or more of three exemplary methods:
(i) by reacting the compound of Formula I or IA with the desired acid or base;
(ii) by removing an acid- or base-labile protecting group from a suitable precursor of the compound of Formula I or IA or by ring-opening a suitable cyclic precursor, for example, a lactone or lactam, using the desired acid or base; or
(iii) by converting one salt of the compound of Formula I or IA to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

The compounds of this invention may also be used in conjunction with other pharmaceutical agents (e.g., antiatherosclerotic and antithrombotic agents) for the treatment of the disease/conditions described herein.

Combination Agents

The compounds of the present invention can be administered alone or in combination with one or more additional therapeutic agents. By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Thus, the methods of prevention and treatment described herein include use of combination agents.

The combination agents are administered to a mammal in a therapeutically effective amount. By "therapeutically effective amount" it is meant an amount of a compound of the present invention that, when administered alone or in combination with an additional therapeutic agent to a mammal, is effective to treat the desired disease/condition e.g., cardiovascular condition such as acute coronary syndrome.

Additional therapeutic agents include anti-coagulant or coagulation inhibitory agents, anti-platelet or platelet inhibitory agents, thrombin inhibitors, thrombolytic or fibrinolytic agents, anti-arrythmic agents, anti-hypertensive agents, calcium channel blockers (L-type and T-type), cardiac glycosides, diruetics, mineralocorticoid receptor antagonists, NO donating agents such as organonitrates, NO promoting agents such as phosphodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid hormone receptor antagonist), anti-infective agents, anti-viral agents, anti-bacterial agents, and anti-fungal agents.

Agents used in an ICU setting are included, for example, dobutamine, dopamine, dpinephrine, nitroglycerin, nitroprusside etc.

Combination agents useful for treating vasculitis are included, for example, azathioprine, cyclophosphamide, mycophenolate, mofetil, rituximab etc.

In another embodiment, the present invention provides a combination wherein the second agent is at least one agent selected from a factor Xa inhibitor, an anti-coagulant agent, an anti-platelet agent, a thrombin inhibiting agent, a thrombolytic agent, and a fibrinolytic agent.

Exemplary factor Xa inhibitors include apixaban and rivaroxaban.

Examples of suitable anti-coagulants for use in combination with the compounds of the present invention include heparins (e.g., unfractioned and low molecular weight heparins such as enoxaparin and dalteparin).

In another preferred embodiment the second agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

A preferred second agent is is at least one anti-platelet agent. Especially preferred anti-platelet agents are aspirin and clopidogrel.

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and COX-2 inhibitors such as CELEBREX or piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., Pletal, dipyridamole), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the puringergic receptors $P_2Y_1$ and $P_2Y_{12}$, with $P_2Y_{12}$ being even more preferred. Preferred $P_2Y_{12}$ receptor antagonists include ticagrelor, prasugrel, ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastrointestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents include: Class I agents (such as propafenone); Class II agents (such as metoprolol, atenolol, carvadiol and propranolol); Class III agents (such as sotalol, dofetilide, amiodarone, azimilide and ibutilide); Class IV agents (such as ditiazem and verapamil); K$^+$ channel openers such as $I_{Ach}$ inhibitors, and $I_{Kur}$ inhibitors (e.g., compounds such as those disclosed in WO01/40231).

The compounds of the present invention may be used in combination with antihypertensive agents and such antihypertensive activity is readily determined by those skilled in the art according to standard assays (e.g., blood pressure measurements). Examples of suitable anti-hypertensive agents include: alpha adrenergic blockers; beta adrenergic blockers; calcium channel blockers (e.g., diltiazem, verapamil, nifedipine and amlodipine); vasodilators (e.g., hydralazine), diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, torsemide, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., gemopatrilat and nitrates). An exemplary antianginal agent is ivabradine.

Examples of suitable calcium channel blockers (L-type or T-type) include diltiazem, verapamil, nifedipine and amlodipine and mybefradil.

Examples of suitable cardiac glycosides include digitalis and ouabain.

In one embodiment, a Formulae I or IA compound may be co-administered with one or more diuretics. Examples of suitable diuretics include (a) loop diuretics such as furosemide (such as LASIX™), torsemide (such as DEMADEX™), bemetanide (such as BUMEX™), and ethacrynic acid (such as EDECRIN™); (b) thiazide-type diuretics such as chlorothiazide (such as DIURIL™, ESIDRIX™ or HYDRODIURIL™) hydrochlorothiazide (such as MICROZIDE™ or ORETIC™), benzthiazide, hydroflumethiazide (such as SALURON™), bendroflumethiazide, methychlorthiazide, polythiazide, trichlormethiazide, and indapamide (such as LOZOL™); (c) phthalimidine-type diuretics such as chlorthalidone (such as HYGROTON™), and metolazone (such as ZAROXOLYN™); (d) quinazoline-type diuretics such as quinethazone; and (e) potassium-sparing diuretics such as triamterene (such as DYRENIUM™), and amiloride (such as MIDAMOR™ or MODURETIC™).

In another embodiment, a compound of Formula I or IA may be co-administered with a loop diuretic. In still another embodiment, the loop diuretic is selected from furosemide and torsemide. In still another embodiment, one or more compounds of Formulae I or IA may be co-administered with furosemide. In still another embodiment, one or more compounds of Formulae I or IA may be co-administered with torsemide which may optionally be a controlled or modified release form of torsemide.

In another embodiment, a compound of Formulae I or IA may be co-administered with a thiazide-type diuretic. In still another embodiment, the thiazide-type diuretic is selected from the group consisting of chlorothiazide and hydrochlorothiazide. In still another embodiment, one or more compounds of Formulae I or IA may be co-administered with chlorothiazide. In still another embodiment, one or more compounds of Formulae I or IA may be co-administered with hydrochlorothiazide.

In another embodiment, one or more compounds of Formulae I or IA may be co-administered with a phthalimidine-type diuretic. In still another embodiment, the phthalimidine-type diuretic is chlorthalidone.

Examples of suitable combination mineralocorticoid receptor antagonists include sprionolactone and eplerenone.

Examples of suitable combination phosphodiesterase inhibitors include: PDE III inhibitors (such as cilostazol); and PDE V inhibitors (such as sildenafil).

The compounds of the present invention may be used in combination with cholesterol modulating agents (including cholesterol lowering agents) such as a lipase inhibitor, an HMG-CoA reductase inhibitor, an HMG-CoA synthase inhibitor, an HMG-CoA reductase gene expression inhibitor, an HMG-CoA synthase gene expression inhibitor, an MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, an ion-exchange resin, an antioxidant, an ACAT inhibitor or a bile acid sequestrant or an agent such as mipomersen.

Examples of suitable cholesterol/lipid lowering agents and lipid profile therapies include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesteryl ester transfer protein inhibitors.

Anti-inflammatory agents also include sPLA2 and IpPLA2 inhibitors (such as darapladib), 5 LO inhibitors (such as atrelueton) and IL-1 and IL-1 r antagonists (such as canakinurnab).

Other atherosclerotic agents include agents that modulate the action of PCSK9.

Cardiovascular complications of type 2 diabetes are associated with deleterious levels of MPO, accordingly, the compounds of the present invention may be used in combination with anti-diabetic agents, particularly type 2 anti-diabetic agents. Examples of suitable anti-diabetic agents include (e.g. insulins, metfomin, DPPIV inhibitors, GLP-1 agonists, analogues and mimetics, SGLT1 and SGLT2 inhibitors) Suitable anti-diabetic agents include an acetyl-CoA carboxylase-(ACC) inhibitor such as those described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, diacylglycerol O-acyltransferase 2 (DGAT-2) inhibitor, monoacylglycerol O-acyltransferase inhibitors, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone and rosiglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, lixisenatide, dulaglutide, semaglutide, NN-9924, TTP-054, a protein tyrosine phosphatase-1B (PTP-1B) inhibitor (e.g., trodusquemine, hyrtiosal extract, and compounds disclosed by Zhang, S., et al., *Drug Discovery Today*, 12(9/10), 373-381 (2007)), SIRT-1 inhibitor (e.g., resveratrol, GSK2245840 or GSK184072), a dipeptidyl peptidease IV (DPP-IV) inhibitor (e.g., those in WO2005116014, sitagliptin, vildagliptin, alogliptin, dutogliptin, linagliptin and saxagliptin), an insulin secreatagogue, a fatty acid oxidation inhibitor, an A2 antagonist, a c-jun amino-terminal kinase (JNK) inhibitor, glucokinase activators (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g. GSK1362885), a VPAC2 receptor agonist, SGLT2 inhibitors, such as those described in E. C. Chao et al. Nature Reviews Drug Discovery 9, 551-559 (July 2010) including dapagliflozin, canagliflozin, empagliflozin, tofogliflozin (CSG452), ASP-1941, THR1474, TS-071, ISIS388626 and LX4211 as well as those in WO2010023594, a glucagon receptor modulator such as those described in Demong, D. E. et al. Annual Reports in Medicinal Chemistry 2008, 43, 119-137, GPR119 modulators, particularly agonists, such as those described in WO2010140092, WO2010128425, WO2010128414, WO2010106457, Jones, R. M. et al. in Medicinal Chemistry 2009, 44, 149-170 (e.g. MBX-2982, GSK1292263, APD597 and PSN821), FGF21 derivatives or analogs such as those described in Kharitonenkov, A. et al. et al., Current Opinion in Investigational Drugs 2009, 10(4)359-364, TGR5 (also termed GPBAR1) receptor modulators, particularly agonists, such as those described in Zhong, M., Current Topics in Medicinal Chemistry, 2010, 10(4), 386-396 and INT777, GPR40 agonists, such as those described in Medina, J. C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235. A further representative listing of anti-diabetic agents that can be combined with the compounds of the present invention can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g. SSTR1, SSTR2, SSTR3 and SSTR5), inhibitors or modulators of PDHK2 or PDHK4, inhibitors of MAP4K4, modulators of IL1 family including IL1 beta, modulators of RXRalpha. In addition suitable anti-diabetic agents include mechanisms listed by Carpino, P. A., Goodwin, B. Expert Opin. Ther. Pat, 2010, 20(12), 1627-51.

Those skilled in the art will recognize that the compounds of this invention may also be used in conjunction with other cardiovascular or cerebrovascular treatments including PCI, stenting, drug eluting stents, stem cell therapy and medical devices such as implanted pacemakers, defibrillators, or cardiac resynchronization therapy.

Myeloperoxidase activity has been demonstrated in neuroinflammatory conditions, accordingly, the compounds of the present invention may be used in combination with neuroinflammatory and neurodegenerative agents in mammals. Examples of additional neuroinflammatory and neurodegenerative agents include antidepressants, antipsychotics, anti-pain agents, anti-Alzheimer's agents, and anti-anxiety agents. Examples of particular classes of antidepressants that can be used in combination with the compounds of the invention include norepinephrine reuptake inhibitors, selective serotonin reuptake inhibitors (SSRIs), NK-1 receptor antagonists, monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, and atypical antidepressants. Suitable norepinephrine reuptake inhibitors include tertiary amine tricyclics and secondary amine tricyclics. Examples of suitable tertiary amine tricyclics and secondary amine tricyclics include amitriptyline, clomipramine, doxepin, imipramine, trimipramine, dothiepin, butriptyline, nortriptyline, protriptyline, amoxapine, desipramine and maprotiline. Examples of suitable SSRIs include fluoxetine, fluvoxamine, paroxetine, and sertraline. Examples of monoamine oxidase inhibitors include isocarboxazid, phenelzine, and tranylcyclopramine. Examples of suitable reversible inhibitors of monoamine oxidase include moclobemide. Examples of suitable SNRIs of use in the present invention include venlafaxine. Examples of suitable atypical anti-depressants include bupropion, lithium, trazodone and viloxazine. Examples of anti-Alzheimer's agents include NMDA receptor antagonists such as memantine; and cholinesterase inhibitors such as donepezil and galantamine. Examples of suitable classes of anti-anxiety agents that can be used in combination with the compounds of the invention include benzodiazepines and serotonin 1A receptor (5-HT1A) agonists, and CRF antagonists. Suitable benzodiazepines include alprazolam, chlordiazepoxide, clonazepam, chlorazepate, diazepam, lorazepam, oxazepam, and prazepam. Suitable 5-HT1A receptor agonists include buspirone and ipsapirone. Suitable CRF antagonists include verucerfont. Suitable atypical antipsychotics include paliperidone, ziprasidone, risperidone, aripiprazole, olanzapine, and quetiapine. Suitable nicotine acetylcholine agonists include CP-601927 and varenicline. Anti-pain agents include pregabalin, gabapentin, clonidine, neostigmine, baclofen, midazolam, ketamine and ziconotide.

Particularly when provided as a single dosage unit, the potential exists for a chemical interaction between the combined active ingredients. For this reason, when a Formula I or IA compound and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In combination therapy treatment, both the compounds of this invention and the other drug therapies are administered to mammals (e.g., humans, male or female) by conventional methods.

The Formula I or IA compounds of this invention, their prodrugs and the salts of such compounds and prodrugs are all adapted to therapeutic use as agents that inhibit myeloperoxidase in mammals, particularly humans and thus are useful for the treatment of the various conditions (e.g., those described herein) in which such action is implicated.

It is believed that myeloperoxidase is involved in the pathologic oxidation of proteins, lipids and nucleic acids and contributes to dysfunctional cholesterol metabolism, tissue damage, and organ dysfunction and can induce or contribute to the development of cardiovascular diseases and associated adverse outcomes.

The disease/conditions that can be treated in accordance with the present invention include, but are not limited to, cardiovascular conditions, diabetes (e.g., type II) and diabetic complications, vascular conditions, neuroinflammatory conditions, neurodegenerative conditions, pain, cancer, sepsis, NASH (non-alcoholic steatatohepatitis), pulmonary injury and hypertension, renal diseases, and vasculitis syndromes especially those related to ANCA (anti-neutrophil cytoplasmic antibodies) and the like.

Given the positive correlation between activation of the myeloperoxidase with the development of cardiovascular and associated disease/conditions, Formula I or IA compounds of this invention, their prodrugs and the salts of such compounds and prodrugs, by virtue of their pharmacologic action, are useful for the prevention, arrestment and/or regression of atherosclerosis and its associated disease states.

It is believed that MPO exhibits pro-atherogenic biological activity during the evolution of cardiovascular disease. Furthermore, it has been observed that MPO-generated oxidants reduce the bioavailability of nitric oxide, an important vasodilator. Additionally, it has been shown that MPO plays a role in plaque destabilization by causing the activation of metalloproteinases, leading to a weakening of the fibrous cap of the plaques and subsequent plaque destabilization and rupture. Given these wide-ranging effects of MPO, MPO has thus been implicated in a wide variety of cardiovascular diseases.

Cardiovascular conditions include, but are not limited to coronary heart disease, acute coronary syndrome, ischaemic heart disease, first or recurrent myocardial infarction, secondary myocardial infarction, non-ST segment elevation myocardial infarction, or ST segment elevation myocardial infarction, ischemic sudden death, transient ischemic attack, peripheral occlusive arterial disease, angina, atherosclerosis, hypertension, heart failure (such as congestive heart failure), diastolic dysfunction (such as left ventricular diastolic dysfunction, diastolic heart failure, and impaired diastolic filling), systolic dysfunction (such as systolic heart failure with reduced ejection fraction), atrial fibrillation, arrhythmia (ventricular), ischemia, hypertrophic cardiomyopathy, sudden cardiac death, myocardial and vascular fibrosis, impaired arterial compliance, myocardial necrotic lesions, vascular damage, left ventricular hypertrophy, decreased ejection fraction, cardiac lesions, vascular wall hypertrophy, endothelial thickening, fibrinoid necrosis of coronary arteries, adverse remodeling, stroke, and the like. Also, included are venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g., after a bypass) and reocclusion (e.g., during or after percutaneous transluminal coronary angioplasty).

Cardiovascular complications of type 2 diabetes are associated with deleterious levels of MPO, accordingly, the compounds of the present invention may be used to treat diabetes and diabetic complications such as macrovascular disease, hyperglycemia, metabolic syndrome, impaired glucose tolerance, hyperuricemia, glucosuria, cataracts, diabetic neuropathy, diabetic nephropathy, diabetic retinopathy, obesity, dyslididemia, hypertension, hyperinsulinemia, and insulin resistance syndrome.

In addition, linkage of myeloperoxidase activity to disease has been demonstrated in neuroinflammatory and neurodegenerative conditions. Therefore, the compounds of the present invention are particularly indicated for use in the treatment of neuroinflammatory and neurodegenerative conditions (i.e., disorders or diseases) in mammals including humans such as multiple sclerosis, migraine; epilepsy; Alzheimer's disease; Parkinson's disease; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV associated dementia, Alzheimer's associated dementia, Huntington's associated dementia, Lewy body dementia, vascular dementia, drug related dementia, delirium, and mild cognitive impairment); mental deficiency (including Down syndrome and fragile X syndrome); sleep disorders (including hypersomnia, circadian rhythm sleep disorder, insomnia, parasomnia, and sleep deprivation) and psychiatric disorders (such as anxiety (including acute stress disorder, generalized anxiety disorder, social anxiety disorder, panic disorder, post-traumatic stress disorder and obsessive-compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, and postpartum depression); psychomotor disorder; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, and pagophagia); and pediatric psychiatric disorders (including attention deficit disorder, attention deficit/hyperactive disorder, conduct disorder, and autism) in a mammal, preferably a human, comprising administering to said mammal a therapeutically effective amount of a compound of Formula I or IA or pharmaceutically acceptable salt thereof.

Other inflammatory diseases or disorders such as asthma, chronic obstructive pulmonary disease, cystic fibrosis, idiopathic pulmonaryfibrosis, acute respiratory distress syndrome, sinusitis, rhinitis, psoriasis, dermatitis, uveitis, gingivitis, atherosclerosis, inflammatory bowel disease, renal glomerular damage, liver fibrosis, sepsis, proctitis, rheumatoid arthritis, and inflammation associated with reperfusion injury, spinal cord injury and tissue damage/scarring/adhesion/rejection.

The term "nephropathy caused by contrasting agents" includes contrasting induced nephropathy following procedures that utilize imaging agents including cardiac surgery, non-cardiac surgery and transplant surgery. Nephropathy caused by contrasting agents also includes nephropathy caused by the use of enhanced imaging contrasting agents in patients including those at risk of a primary MI or secondary MI.

The utility of the Formula I or IA compounds of the invention, their prodrugs and the salts of such compounds and prodrugs as medical agents in the treatment of the above described disease/conditions in mammals (e.g. humans, male or female) is demonstrated by the activity of the compounds of this invention in conventional in vitro and in vivo assays described below. The in vivo assays (with appropriate modifications within the skill in the art) may be used to determine the activity of other agents as well as the compounds of this invention. Such assays also provide a means whereby the activities of the Formula I or IA compounds of this invention, their prodrugs and the salts of such compounds and prodrugs (or the other agents described herein) can be compared to each other and with the activities of other known compounds. The results of these comparisons are useful for determining dosage levels in mammals, including humans, for the treatment of such diseases.

The following protocols may of course be varied by those skilled in the art.

MPO Amplex Red Activity Assay.

MPO peroxidase activity was measured by monitoring the formation of resorufin generated from the oxidation of Amplex Red (10-Acetyl-3,7-dihydroxyphenoxazine) (Invitrogen, Carlsbad, Calif.) by MPO (Gomes, Fernandes et al. 2005). Assay mixtures (100 μL total volume) contained 50 mM NaPi pH 7.4, 150 mM NaCl, 1 mM DTPA (diethylenetriaminepentaacetic acid), 2% DMSO, 2 μM $H_2O_2$, 30 μM Amplex Red and the reaction was initiated by the addition of 100 pM MPO (purified from human polynuclear leukocytes and purchased from Calbiochem/EMD Biosciences, Gibbstown, N.J.). All assays were performed in 96-well, half-area, black, nonbinding surface, polystyrene plates (Corning) and the production of resorufin (excitation 530 nm, emission 580 nm) was monitored every 20 sec on a Spectramax M2 Microplate Spectrophotometer (Molecular Devices, Palo Alto, Calif.) equipped with Softmax Pro software (Molecular Devices, Palo Alto, Calif.). Reactions to determine the background reaction rate consisted of all assay components and 4 μL of 500 unit/mL bovine catalase (Sigma) in 50 mM KPi pH 7.0. The background rate was subtracted from each reaction progress curve. All data was analyzed using non-linear regression analysis in Microsoft Excel and Kaleidagraph (Synergy Software).

To determine inhibitor potency ($k_{inact}/K_I$) against MPO, the first 600 sec of the reaction progress curves were fit to equation 1, where $V_o$ is the initial rate in RFU/sec and t is time in seconds, to obtain the first order rate constant for enzyme inactivation ($k_{obs}$) at each inhibitor concentration.

$$\text{Product} = \frac{V_0}{k_{obs}} [1 - \exp(-k_{obs}t)] \quad (1)$$

Equation 1 is a variation of the standard equation for slow binding inhibition where the steady state velocity ($V_s$) is set to zero. Each $k_{obs}$ value was corrected for auto-inactivation of the enzyme by subtracting the $k_{obs}$ value for the uninhibited reaction. The corrected $k_{obs}$ values were then plotted versus inhibitor concentration ([I]) and fit to equation 2

$$k_{obs} = \frac{k_{inact}[I]}{K_I + [I]} \quad (2)$$

where $k_{inact}$ is the maximal rate of inactivation and $K_I$ is the inhibitor concentration that yields half the rate of maximal inactivation (Copeland 2005).

Table 1 and (1A) below provides the myeloperoxidase inhibitory activity for the Examples below in accordance with the above-described assay.

TABLE 1

MPO $k_{inact}/K_i$ for Examples

| Example # | MPO $k_{inact}/K_i$ (1/s per M) |
|---|---|
| 1 | 11600 |
| 2 | 12500 |
| 3 | 29300 |
| 4 | 8790 |
| 5 | 1280 |
| 6 | 12900 |
| 7 | 10900 |
| 8 | 12100 |
| 9 | 15000 |
| 10 | 619 |
| 11 | 6880 |
| 12 | 5010 |
| 13 | 745 |
| 14 | 5310 |
| 15 | 5420 |
| 16 | 6510 |
| 17 | 4460 |
| 18 | 8280 |
| 19 | 1960 |
| 20 | 1330 |
| 21 | 4530 |
| 22 | 6340 |
| 23 | 991 |
| 24 | 7640 |
| 25 | 9210 |
| 26 | 3180 |
| 27 | 15800 |
| 28 | 13700 |
| 29 | 14900 |
| 30 | 5870 |
| 31 | 7680 |
| 32 | 2120 |
| 33 | 4520 |
| 34 | 13100 |
| 35 | 4110 |
| 36 | 5980 |
| 37 | 6460 |
| 38 | 5240 |
| 39 | 4520 |
| 40 | 6430 |
| 41 | 5000 |
| 42 | 6070 |
| 43 | 34600 |
| 44 | 3440 |
| 45 | 4000 |
| 46 | 1110 |
| 47 | 2340 |
| 48 | 6570 |
| 49 | 2230 |
| 50 | 2610 |
| 51 | 6180 |
| 52 | 33.4 |
| 53 | 3290 |
| 54 | 7070 |
| 55 | 7740 |
| 56 | 4770 |
| 57 | 13100 |
| 58 | 11700 |
| 59 | 8480 |
| 60 | 3470 |
| 61 | 3530 |
| 62 | 6930 |
| 63 | 12200 |
| 64 | 22500 |
| 65 | 7940 |
| 66 | 1580 |
| 67 | 7520 |
| 68 | 1160 |
| 69 | 4250 |
| 70 | 1590 |
| 71 | 3570 |
| 72 | 3580 |
| 73 | 9870 |
| 74 | 14400 |
| 75 | 2040 |
| 76 | 4190 |
| 77 | 6660 |
| 78 | 9730 |
| 79 | 1580 |
| 80 | 4130 |
| 81 | 24300 |

TABLE 1-continued

MPO $k_{inact}/K_i$ for Examples

| Example # | MPO $k_{inact}/K_i$ (1/s per M) |
|---|---|
| 82 | 3390 |
| 83 | 3510 |
| 84 | 6630 |
| 85 | 10700 |
| 86 | 3960 |
| 87 | 15400 |
| 88 | 898 |
| 89 | 276 |
| 90 | 11600 |
| 91 | 9360 |
| 92 | 22100 |
| 93 | 5120 |
| 94 | 6930 |
| 95 | 15400 |
| 96 | 2200 |
| 97 | 6310 |
| 98 | 1870 |
| 99 | 2920 |
| 100 | 16100 |
| 101 | 4140 |
| 102 | 4200 |
| 103 | 41800 |
| 104 | 1210 |
| 105 | 27300 |
| 106 | 10500 |
| 107 | 1280 |
| 108 | 5800 |
| 109 | 914 |
| 110 | 864 |
| 111 | 10300 |
| 112 | 14900 |
| 113 | 25900 |
| 114 | 9770 |
| 115 | 4380 |
| 116 | 9920 |
| 117 | 11400 |
| 118 | 5500 |
| 119 | 25600 |
| 120 | 9720 |
| 121 | 15800 |
| 122 | 9310 |
| 123 | 3780 |
| 124 | 4610 |
| 125 | 10600 |
| 126 | 18200 |
| 127 | 5810 |
| 128 | 7680 |
| 129 | 18700 |
| 130 | 4830 |
| 131 | 14500 |
| 132 | 3840 |
| 133 | 15300 |
| 134 | 5350 |
| 135 | 6750 |
| 136 | 1920 |
| 137 | 701 |
| 138 | 4530 |
| 139 | 2890 |
| 140 | 10400 |
| 141 | 10500 |
| 142 | 4210 |
| 143 | 8110 |
| 144 | 6010 |
| 145 | 5080 |
| 146 | 8950 |
| 147 | 6500 |
| 148 | 6690 |
| 149 | 9770 |
| 150 | 8970 |
| 151 | 3740 |
| 152 | 4770 |
| 153 | 2200 |
| 154 | 1070 |
| 155 | 8090 |
| 156 | 16800 |
| 157 | 7320 |
| 158 | 1750 |
| 159 | 11400 |
| 160 | 7540 |
| 161 | 29600 |
| 162 | 8950 |
| 163 | 8090 |
| 164 | 14900 |
| 165 | 1280 |
| 166 | 8920 |
| 167 | 20300 |
| 168 | 8890 |
| 169 | 17800 |
| 170 | 4030 |
| 171 | 8590 |
| 172 | 2950 |
| 173 | 2910 |
| 174 | 10500 |
| 175 | 459 |
| 176 | 2160 |
| 177 | 5130 |
| 178 | 11100 |
| 179 | 2790 |
| 180 | 6960 |
| 181 | 7160 |
| 182 | 8200 |
| 183 | 4830 |
| 184 | 5970 |
| 185 | 9740 |
| 186 | 3930 |
| 187 | 5640 |
| 188 | 2180 |
| 189 | 2210 |
| 190 | 4090 |
| 191 | 14100 |
| 192 | 10800 |
| 193 | 458 |
| 194 | 2560 |
| 195 | 5350 |
| 196 | 5640 |
| 197 | 5650 |
| 198 | 8460 |
| 199 | 9080 |
| 200 | 4930 |
| 201 | 4350 |
| 202 | 8280 |
| 203 | 3450 |
| 204 | 3900 |
| 205 | 4900 |
| 206 | 7690 |
| 207 | 2400 |
| 208 | 3760 |
| 209 | 4360 |
| 210 | 968 |
| 211 | 6090 |
| 212 | 7590 |
| 213 | 4690 |
| 214 | 10700 |
| 215 | 1920 |
| 216 | 3260 |
| 217 | 3940 |
| 218 | 14100 |
| 219 | 1970 |
| 220 | 2420 |
| 221 | 6230 |
| 222 | 9820 |
| 223 | 3000 |
| 224 | 3280 |
| 225 | 5490 |
| 226 | 6280 |
| 227 | 745 |
| 228 | 615 |
| 229 | 5900 |
| 230 | 1740 |
| 231 | 1910 |

TABLE 1-continued

MPO $k_{inact}/K_i$ for Examples

| Example # | MPO $k_{inact}/K_i$ (1/s per M) |
|---|---|
| 232 | 4520 |
| 233 | 2510 |
| 234 | 3060 |
| 235 | 2690 |
| 236 | 5740 |
| 237 | 2360 |
| 238 | 8740 |
| 239 | 1850 |
| 240 | 7070 |
| 241 | 7060 |
| 242 | 142 |
| 243 | 952 |
| 244 | 8970 |
| 245 | 1520 |
| 246 | 246 |
| 247 | 3060 |
| 248 | 3590 |
| 249 | 1050 |
| 250 | 7510 |
| 251 | 68 |
| 252 | 2480 |
| 253 | 12700 |
| 254 | 5630 |
| 255 | 3550 |
| 256 | 6520 |
| 257 | 3700 |
| 258 | 1460 |
| 259 | 4000 |
| 260 | 19700 |
| 261 | 2280 |
| 262 | 1730 |
| 263 | 4340 |
| 264 | 3620 |
| 265 | 3730 |
| 266 | 604 |
| 267 | 3840 |
| 268 | 6640 |
| 269 | 9510 |
| 270 | 20500 |
| 271 | 2010 |
| 272 | 3160 |
| 273 | 8180 |
| 274 | 22800 |
| 275 | 4730 |
| 276 | 6710 |
| 277 | 767 |
| 278 | 1560 |
| 279 | 386 |
| 280 | 430 |
| 281 | 1060 |
| 282 | 1180 |
| 283 | 2790 |
| 284 | 1470 |
| 285 | 1750 |
| 286 | 1500 |
| 287 | 2130 |
| 288 | 4230 |
| 289 | 1580 |
| 290 | 1890 |
| 291 | 2450 |
| 292 | 1070 |
| 293 | 1810 |
| 294 | 1910 |
| 295 | 793 |
| 296 | 1570 |
| 297 | 762 |
| 298 | 1080 |
| 299 | 2060 |
| 300 | 2460 |
| 301 | 3330 |
| 302 | 3630 |
| 303 | 5270 |
| 304 | 6290 |
| 305 | 6370 |
| 306 | 6740 |
| 307 | 14400 |
| 308 | 5340 |
| 309 | 3160 |
| 310 | 3110 |
| 311 | 2080 |
| 312 | 17100 |
| 313 | 973 |
| 314 | 429 |
| 315 | 1420 |
| 316 | 3060 |
| 317 | 7380 |
| 318 | 5240 |
| 319 | 7810 |
| 320 | 2390 |
| 321 | 2480 |
| 322 | 2800 |
| 323 | 10200 |
| 324 | 11300 |
| 325 | 1160 |
| 326 | 7480 |
| 327 | 1880 |
| 328 | 4370 |
| 329 | 963 |
| 330 | 5210 |
| 331 | 6330 |
| 332 | 3270 |
| 333 | 6100 |
| 334 | 6840 |
| 335 | 9820 |
| 336 | 589 |
| 337 | 13200 |
| 338 | 1280 |
| 339 | 10400 |
| 340 | 1450 |
| 341 | 14300 |
| 342 | 817 |
| 343 | 3570 |
| 344 | 8480 |
| 345 | 946 |
| 346 | 5890 |
| 347 | 378 |
| 348 | 1400 |

Table 1A below provides the myeloperoxidase inhibitory activity for the Examples below in accordance with the above-described assay.

TABLE 1A

MPO $k_{inact}/K_i$ for Examples

| Example # | MPO $k_{inact}/K_i$ (1/s per M) |
|---|---|
| 349 | 3630 |
| 350 | 8740 |
| 351 | 7870 |
| 352 | 6720 |
| 353 | 11000 |
| 354 | 1830 |
| 355 | 1540 |
| 356 | 2910 |
| 357 | 2940 |
| 358 | 1710 |
| 359 | 2660 |
| 360 | 2280 |
| 361 | 2060 |
| 362 | 2690 |
| 363 | 9680 |
| 364 | 6580 |
| 365 | 9290 |
| 366 | 13600 |
| 367 | 1340 |

TABLE 1A-continued

MPO $k_{inact}/K_i$ for Examples

| Example # | MPO $k_{inact}/K_i$ (1/s per M) |
|---|---|
| 368 | 3270 |
| 369 | 8040 |
| 370 | 9060 |
| 371 | 4570 |
| 372 | 6250 |
| 373 | 12800 |
| 374 | 4600 |
| 375 | 11300 |
| 376 | 7870 |
| 377 | 8770 |
| 378 | 5040 |
| 379 | 7370 |
| 380 | 4470 |
| 381 | 1970 |
| 382 | 2310 |
| 383 | 5230 |
| 384 | 2930 |
| 385 | 3530 |
| 386 | 4960 |
| 387 | 4720 |
| 388 | 8690 |
| 389 | 4910 |
| 390 | 6250 |
| 391 | 3480 |
| 392 | 5830 |
| 393 | 13600 |
| 394 | 4020 |
| 395 | 6980 |
| 396 | 10900 |
| 397 | 4050 |
| 398 | 4780 |
| 399 | 4860 |
| 400 | 2650 |
| 401 | 4060 |
| 402 | 4810 |
| 403 | 13300 |
| 404 | 6200 |
| 405 | 5970 |
| 406 | 4480 |
| 407 | 18700 |
| 408 | 9890 |
| 409 | 18000 |
| 410 | 3150 |
| 411 | 15000 |
| 412 | 3980 |
| 413 | 6560 |
| 414 | 1680 |
| 415 | 3910 |
| 416 | 4480 |
| 417 | 9280 |
| 418 | 11500 |
| 419 | 1200 |
| 420 | 5210 |
| 421 | 4950 |
| 422 | 4460 |
| 423 | 3290 |
| 424 | 6870 |
| 425 | 13400 |
| 426 | 4410 |
| 427 | 5360 |
| 428 | 5890 |
| 429 | 6620 |
| 430 | 9440 |
| 431 | 3440 |
| 432 | 1410 |
| 433 | 3490 |
| 434 | 4070 |
| 435 | 2420 |
| 436 | 3710 |
| 437 | 3400 |
| 438 | 7550 |
| 439 | 9200 |
| 440 | 3310 |
| 441 | 3260 |
| 442 | 12300 |
| 443 | 7330 |
| 444 | 17400 |
| 445 | 7350 |
| 446 | 14200 |
| 447 | 17200 |
| 448 | 6490 |
| 449 | 12000 |
| 450 | 7730 |
| 451 | 16000 |
| 452 | 11600 |
| 453 | 27800 |

TPO Amplex Red Activity Assay

TPO activity was measured using the same assay as MPO with 2 µM $H_2O_2$, 30 µM Amplex Red and the reactions were initiated with 1.3 µg of protein from HEK293 cell membranes expressing human TPO. The cDNA encoding 933 amino acids of the full length human TPO was cloned into the inducible expression vector pcDNA5/frt/to (InVitrogen), stable 293 clones were selected using 100 ug/ml of hygromycin and 15 ug/ml blasticidine in DMEM w/10% FBS. When cells reached 50-60% confluence, TPO expression was induced in medium containing all of above plus 10 ug/ml doxicycline and 5 ug/ml hemin (Sigma). Membranes were isolated from HEK293hTPO by harvesting the cells in PBS. The cells were pelleted at 1000×g for 5 minutes at 4° C., resuspended in homogenization buffer (1 mM sodium bicarbonate, pH 7.4) containing EDTA-Free protease inhibitor (Roche), and incubated on ice for 10 minutes followed by Dounce homogenization. Nuclei and unlysed cells were removed by pelleting at 1000×g for 10 minutes at 4° C. The supernatent was then centrifuged at 25,000×g for 20 minutes at 4° C. The pellet was resuspended in homogenization buffer and centrifuged again at 25,000×g for 20 minutes at 4° C. The final pellet was resuspended in storage buffer (50 mM Tris pH 7, 150 mM NaCl) containing protease inhibitors as described above. Membrane concentration was determined using the BCA Protein Assay (Pierce). TPO activity was measured using the Amplex Red assay as described above. Aliquots were made based on the activity accordingly and stored at −80° C.

The $IC_{50}$ values were determined by plotting the initial rates (from the first 200 sec of each reaction progress curve) as percentage of inhibition relative to the uninhibited (DMSO) reaction as a function of inhibitor concentration. The data were fit to equation 3

$$y = \frac{100}{1 + (x/IC_{50})^z} \quad (3)$$

where $IC_{50}$ is the inhibitor concentration at 50% inhibition and z is the Hill slope (the slope of the curve at its inflection point).

REFERENCES

Copeland, R. A. (2005). *Evaluation of Enzyme Inhibitors in Drug Discovery A Guide for Medicinal Chemists and Pharmacologists*. Hoboken, Wiley.

Gomes, A., E. Fernandes, et al. (2005). "Fluorescence probes used for detection of reactive oxygen species." *J Biochem Biophys Methods* 65(2-3): 45-80.

Human Whole Blood Assay for Irreversible Inhibition of MPO

To measure the inhibition of MPO activity in a biological system in the present invention, bioassays are performed with human whole blood that is collected from medication-free, human volunteers in heparin treated tubes (APP Pharmaceuticals, LLC, cat # NDC#63323-047-10, #4710). Blood is aliquoted and treated with different concentrations of the MPO inhibitor or vehicle control and co-treated with or without bacterial lipopolysaccharide (LPS, InVivogen, cat# tlrl-pelps) to stimulate blood leukocytes to simultaneously generate $H_2O_2$ (a required MPO substrate) and the release of MPO. After 4 hour incubation at room temperature the plasma fraction is collected following a 2000×g centrifugation at 4° C.

The plasma fraction is divided into two for analysis of total MPO and active MPO. The total MPO content is determined using a standard sandwich ELISA (capture and detection antibodies: Cell Sciences, Cat# HP9048, and Cell Sciences, Cat# HM2164, clone 266-6K1) and calculated relative to a standard curve of purified MPO (myeloperoxidase, Calbiochem, cat#475911) that is prepared by dilution in the autologous donor plasma. The MPO activity is determined by capturing the total MPO from plasma using the capture step as described for the ELISA method. After washing unbound plasma material including unreacted MPO inhibitor, MPO reaction substrates are added [$H_2O_2$ (2 uM) and Amplex Red (Invitrogen, Cat# A12222)] and the Vmax of the MPO-catalyzed conversion of the Amplex Red substrate to resorufin is determined by measuring the increase in fluorescence (excitation 530 nM, emission 580 nm) using a fluorescent plate reader in a kinetic analysis. The MPO activity of the captured material is compared to that obtained with a standard curve of purified MPO (myeloperoxidase, Calbiochem, cat#475911) that was prepared in autologous donor plasma. The percent of 'active' myeloperoxidase for each sample is calculated from the ratio of the active myeloperoxidase in the Amplex Red assay and the total myeloperoxidase from the ELISA for each sample. A dose response curve of the MPOi concentration versus MPO activity is then plotted to determine the IC50 value.

Administration of the compounds of this invention can be via any method which delivers a compound of this invention systemically and/or locally. These methods include oral routes, parenteral, intraduodenal routes, buccal, intranasal etc. Generally, the compounds of this invention are administered orally, but parenteral administration (e.g., intravenous, intramuscular, subcutaneous or intramedullary) may be utilized, for example, where oral administration is inappropriate for the target or where the patient is unable to ingest the drug.

For administration to human patients, an oral daily dose of the compounds herein may be in the range 1 mg to 5000 mg depending, of course, on the mode of and frequency of administration, the disease state, and the age and condition of the patient, etc. An oral daily dose is in the range of 3 mg to 2000 mg may be used. A further oral daily dose is in the range of 5 mg to 1000 mg. For convenience, the compounds of the present invention can be administered in a unit dosage form. If desired, multiple doses per day of the unit dosage form can be used to increase the total daily dose. The unit dosage form, for example, may be a tablet or capsule containing about 0.1, 0.5, 1, 5, 10, 15, 20, 25, 30, 35, 40, 45, 50, 55, 60, 65, 70, 75, 80, 85, 90, 95, 100, 125, 150, 175, 200, 250, 500, or 1000 mg of the compound of the present invention. The total daily dose may be administered in single or divided doses and may, at the physician's discretion, fall outside of the typical ranges given herein.

For administration to human patients, an infusion daily dose of the compounds herein may be in the range 1 mg to 2000 mg depending, of course, on the mode of and frequency of administration, the disease state, and the age and condition of the patient, etc. A further infusion daily dose is in the range of 5 mg to 1000 mg. The total daily dose may be administered in single or divided doses and may, at the physician's discretion, fall outside of the typical ranges given herein.

These compounds may also be administered to animals other than humans, for example, for the indications detailed above. The precise dosage administered of each active ingredient will vary depending upon any number of factors, including but not limited to, the type of animal and type of disease state being treated, the age of the animal, and the route(s) of administration.

A dosage of the combination pharmaceutical agents to be used in conjuction with the Formula I or IA compounds is used that is effective for the indication being treated. Such dosages can be determined by standard assays such as those referenced above and provided herein. The combination agents may be administered simultaneously or sequentially in any order.

These dosages are based on an average human subject having a weight of about 60 kg to 70 kg. The physician will readily be able to determine doses for subjects whose weight falls outside this range, such as infants and the elderly.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regiments for administration of the chemotherapeutic agent are well-known in the relevant art and would be understood to be encompassed by the skilled artisan once provided the teachings disclosed herein.

The present invention further comprises use of a compound of Formula I or IA for use as a medicament (such as a unit dosage tablet or unit dosage capsule). In another embodiment, the present invention comprises the use of a compound of Formula I or IA for the manufacture of a medicament (such as a unit dosage tablet or unit dosage capsule) to treat one or more of the conditions previously identified in the above sections discussing methods of treatment.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The compounds described herein may be administered as a formulation comprising a pharmaceutically effective amount of a compound of Formula I or IA, in association with one or more pharmaceutically acceptable excipients including carriers, vehicles and diluents. The term "excipient" herein means any substance, not itself a therapeutic agent, used as a diluent, adjuvant, or vehicle for delivery of a therapeutic agent to a subject or added to a pharmaceutical composition to improve its handling or storage properties or to permit or facilitate formation of a solid dosage form such as a tablet, capsule, or a solution or suspension suitable for oral, parenteral, intradermal, subcutaneous, or topical application. Excipients can include, by way of illustration and not limitation, diluents, disintegrants, binding agents, adhesives, wetting agents, polymers, lubricants, glidants, stabilizers, substances added to mask or counteract a disagreeable taste or odor, flavors, dyes, fragrances, and substances added to improve appearance of the composition. Acceptable excipients include (but are not limited to) stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials, such as cellulose esters of alkanoic acids and cellulose alkyl esters, low melting wax, cocoa butter or powder, polymers such as polyvinyl-pyrrolidone, polyvinyl alcohol, and polyethylene glycols, and other pharmaceutically acceptable materials. Examples of excipients and their use may be found in *Remington's Pharmaceutical Sciences,* 20th Edition (Lippincott Williams & Wilkins, 2000). The choice of excipient will to a large extent depend on factors such as the particular mode of administration, the effect of the excipient on solubility and stability, and the nature of the dosage form.

The compounds herein may be formulated for oral, buccal, intranasal, parenteral (e.g., intravenous, intramuscular or subcutaneous) or rectal administration or in a form suitable for administration by inhalation. The compounds of the invention may also be formulated for sustained delivery.

Methods of preparing various pharmaceutical compositions with a certain amount of active ingredient are known, or will be apparent in light of this disclosure, to those skilled in this art. For examples of methods of preparing pharmaceutical compositions see *Remington's Pharmaceutical Sciences,* 20th Edition (Lippincott Williams & Wilkins, 2000).

Pharmaceutical compositions according to the invention may contain 0.1%-95% of the compound(s) of this invention, preferably 1%-70%. In any event, the composition to be administered will contain a quantity of a compound(s) according to the invention in an amount effective to treat the disease/condition of the subject being treated.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I or IA a prodrug thereof or a salt of such compound or prodrug and a second compound as described above. The kit comprises a means for containing the separate compositions such as a container, a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, etc. . . . Second Week, Monday, Tuesday, . . . " etc. Other variations of memory aids will be readily apparent. A "daily dose" can be a single tablet or capsule or several pills or capsules to be taken on a given day. Also, a daily dose of Formula I or IA compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Also, as the present invention has an aspect that relates to the treatment of the disease/conditions described herein with a combination of active ingredients which may be administered jointly, the invention also relates to combining separate pharmaceutical compositions in a single dosage form, such as (but not limited to) a single tablet or capsule, a bilayer or multilayer tablet or capsule, or through the use of segregated components or compartments within a tablet or capsule.

The active ingredient may be delivered as a solution in an aqueous or non-aqueous vehicle, with or without additional solvents, co-solvents, excipients, or complexation agents selected from pharmaceutically acceptable diluents, excipients, vehicles, or carriers.

An exemplary intravenous formulation is prepared as follows:
Formulation: Intravenous Solution

| Ingredient | Quantity |
| --- | --- |
| Active ingredient dissolved in 5% Dextrose Injection, USP | 150 mg |
| 5% Dextrose Injection, USP | 1.0 mL |

The solution of the above ingredients is intravenously administered to a patient at a rate of about 1 mL per minute.

The active ingredient may be formulated as a solid dispersion or as a self emulsified drug delivery system (SEDDS) with pharmaceutically acceptable excipients.

The active ingredient may be formulated as an immediate release or modified release tablet or capsule. Alternatively, the active ingredient may be delivered as the active ingredient alone within a capsule shell, without additional excipients.

General Experimental Procedures

All chemicals, reagents and solvents were purchased from commercial sources when available and used without further purification. Proton nuclear magnetic spectroscopy ($^1$H NMR) was recorded with 400 and 500 MHz Varian spectrometers. Chemical shifts are expressed in parts per million downfield from tetramethylsilane. The peak shapes are denoted as follows: s, singlet; d, doublet; t, triplet; q, quartet; m, multiplet; br s, broad singlet. Mass spectrometry (MS) was performed via atmospheric pressure chemical ionization (APCI) or electron scatter (ES) ionization sources. Observed mass (Obs Mass) reported in the Tables correspond to the exact mass of the parent molecule plus one, unless otherwise noted. Silica gel chromatography was performed primarily using a medium pressure Biotage or ISCO systems using columns pre-packaged by various commercial vendors including Biotage and ISCO. Microanalyses were performed by Quantitative Technologies Inc. and were within 0.4% of the calculated values. The terms "concentrated" and "evaporated" refer to the removal of solvent at reduced pressure on a rotary evaporator with a bath temperature less than 60° C. The abbreviation "min" and "h" stand for "minutes" and "hours" respectively.

Powder X-Ray Diffraction

Powder diffraction analysis was conducted using a Bruker D8 diffractometer equipped with a Cu radiation source, fixed slits (divergence=1.0 mm, anti-scatter=0.6 mm, and receiving=0.6 mm) and a scintillation counter detector. Data was collected in the Theta-Theta goniometer at the Cu wavelength $K\alpha_1$=1.54056 Å from 3.0 to 40.0 degrees 2-Theta using a step size of 0.040 degrees and a step time of 2.0 second. X-ray tube voltage and amperage were set at 40 kV and 40 mA respectively. Samples were prepared by placement in a Nickel Disk (Gasser & Sons, Inc. Commack, N.Y.) and rotated during data collection. Data were collected and analyzed using Bruker DIFFRAC Plus software (Version 2.6).

I. Beta Keto Ester Route Section
   A. Carboxylic Acid Route Section

Preparation 1

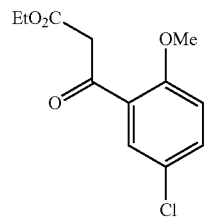 [SMILES: CCOC(=O)CC(=O)c1cc(Cl)ccc1OC]

Ethyl 3-(5-chloro-2-methoxyphenyl)-3-oxopropanoate

A 3000 mL 3-necked round-bottomed flask flushed with nitrogen was charged with magnesium ethoxide (67.46 g, 589.51 mmoles) and THF (1100 mL), and the resulting mixture was stirred as ethyl hydrogen malonate (162.26 g, 1.18 moles; 145.00 mL diluted in 100 ml of THF) was added and the mixture was heated at 45° C. for 4 hours. Meanwhile, a 2000 mL 3-necked round-bottomed flask flushed with nitrogen was charged with 5-chloro-2-methoxybenzoic acid (100 g, 536 mmoles) and THF (600 mL). To this mixture stirring at room temperature was added 1,1'-carbonyldiimidazole (95.59 g, 589.5 mmoles) in portions to avoid excess foaming. After stirring for 3 hours at room temperature the second solution was added gradually to the first solution. After addition the reaction mixture was heated to 45° C. After 20 hours, the reaction mixture was concentrated under reduced pressure before adding ethyl acetate (1 L) followed by 2 N HCl (500 mL). After mixing, the layers were separated and the organic phase was washed sequentially with 2 N HCl (500 mL), saturated sodium bicarbonate (500 mL), and water (500 mL). The organic phase was concentrated under reduced pressure, the residue taken up in ethyl acetate (1000 mL) and concentrated again to afford the title compound (104.94 g).

MS (ES+) 257.2 [M+1]+. 1H NMR showed product as a 7.5:1 keto:enol mixture. For the keto tautomer: 1H NMR (500 MHz, CDCl$_3$) δ ppm 7.85 (d, J=2.93 Hz, 1H) 7.45 (dd, J=8.90, 2.81 Hz, 1H) 6.92 (d, J=8.78 Hz, 1H) 4.18 (q, J=7.16 Hz, 2H) 3.95 (s, 2H) 3.90 (s, 3H) 1.24 (t, J=7.07 Hz, 3H).

Preparation 2

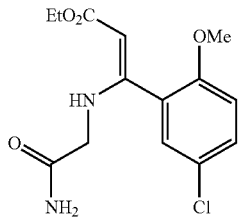 [SMILES: CCOC(=O)/C=C(\NCC(N)=O)c1cc(Cl)ccc1OC]

(Z)-Ethyl 3-((2-amino-2-oxoethyl)amino)-3-(5-chloro-2-methoxyphenyl)acrylate

A 5-L reaction vessel was charged with methanol (3.3 L), sodium methoxide (102.4 g, 1.8 moles), and glycinamide hydrochloride (202 g, 1.8 moles). The mixture was heated at 65° C. for 1 hour before cooling to 50° C. and adding acetic acid (514.25 mmoles, 30.88 g, 29.47 mL) and ethyl 3-(5-chloro-2-methoxyphenyl)-3-oxopropanoate (300 g, 1.03 mole). After heating to reflux for 16 hours, the reaction mixture was stirred as it was cooled to 10° C. After 30 min the resulting solid was collected by vacuum filtration, pulling dry to form a cake that was dried in a vacuum oven (20 mm Hg, 65° C.) for 14 hours to afford the title compound (339.4 g).

MS (ES+) 313.2 [M+1]+. 1H NMR (500 MHz, DMSO-d$_6$) δ ppm 8.80 (t, J=5.00 Hz, 1H) 7.47 (dd, J=8.90, 2.81 Hz, 1H) 7.27 (br. s., 1H) 7.22 (d, J=2.68 Hz, 1H) 7.14 (d, J=8.78 Hz, 1H) 7.09 (br. s., 1H) 4.30 (s, 1H) 4.03 (q, J=7.07 Hz, 2H) 3.80 (s, 3H) 3.56 (br. s., 1H) 3.45 (br. s., 1H) 1.18 (t, J=7.07 Hz, 3H).

Example 1

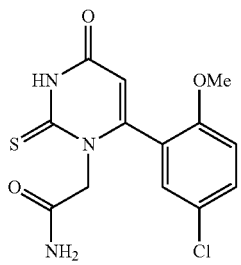

2-(6-(5-Chloro-2-methoxyphenyl)-4-oxo-2-thioxo-3,4-dihydropyrimidin-1(2H)-yl) acetamide A reaction vessel equipped with an efficient stirrer was charged with (Z)-ethyl 3-((2-amino-2-oxoethyl)amino)-3-(5-chloro-2-methoxyphenyl)acrylate (15 g, 50.2 mmol), butyl acetate (150 mL) and trimethylsilyl isothiocyanate (160.7 mmole, 21.1 g, 22.7 mL) and the mixture was heated to reflux. After 15 hours, the mixture was cooled to 30° C. and treated with 1 N aqueous sodium hydroxide (112.5 mL, 112.5 mmoles). After 30 min, the organic layer was separated and extracted with another portion of 1 N sodium hydroxide (37.5 mL, 37.5 mmoles). The combined aqueous phases were extracted twice with dichloromethane (2×45 mL), filtered, and treated with 6N HCl until a pH of 2.5 was achieved. After stirring for 1 hour, the resulting solid was isolated by vacuum filtration, resuspended in 100 mL of a 1:1 methanol-water solution, heated with stirring at 50° C. for 2 hours, and cooled to room temperature before collecting the solid by vacuum filtration, pulling dry and drying in a vacuum oven (20 mm Hg, 50° C.) for 12 hours to afford 8.7 g of the desired product as a tan solid.

MS (ES+) 326.0 [M+1]+. 1H NMR (500 MHz, DMSO-d$_6$) δ ppm 12.85 (s, 1H) 7.57 (dd, J=9.03, 2.68 Hz, 1H) 7.33 (s, 1H) 7.17-7.23 (m, 2H) 7.10 (s, 1H) 5.89 (d, J=1.71 Hz, 1H) 5.41 (br. s, 1H) 3.89 (br. s, 1H) 3.84 (s, 3H).

Alternative Preparation of Example 1

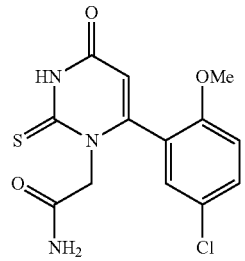

2-(6-(5-Chloro-2-methoxyphenyl)-4-oxo-2-thioxo-3,4-dihydropyrimidin-1(2H)-yl) acetamide A slurry of (Z)-ethyl 3-((2-amino-2-oxoethyl)amino)-3-(5-chloro-2-methoxyphenyl)acrylate (20 g, 63 mmol) in a mixture of butyl acetate (140 mL) and DMF (38 mL) was treated with trimethylsilyl isothiocyanate (16.8 g, 125 mmol) and the mixture was heated at 115-120° C. for 5-6 hours. The mixture was cooled to 0-5° C., butyl acetate (100 mL) was added and the mixture was slurried for 8 hours. The formed solids were filtered, and the filter cake was washed with butyl acetate (2×100 mL). The solid was dried in a vacuum oven at 50° C. for 12 hours to a tan solid. The solid was dissolved in a 5:1 mixture of DMF and water at room temperature and additional water was added slowly to crystallize the material. The slurry was cooled to 10° C. and stirred for 8 hours, followed by filtration and washing with water. The filter cake was dried in a vacuum oven at 50° C. for 8 hours. The solid was dissolved in a 1:1 mixture of methanol and water and the slurry was heated to 50° C. and held at this temperature for 2 hours. After cooling to 10° C. over 30 minutes, the slurry was held at this temperature for 1 hour, filtered and washed with water and dried in a vacuum oven at 50° C. for 8 hours to give the title compound as a white solid.

MS (ES+) 326.0 [M+1]+. 1H NMR (500 MHz, DMSO-d$_6$) δ ppm 12.85 (s, 1H) 7.57 (dd, J=9.03, 2.68 Hz, 1H) 7.33 (s, 1H) 7.17-7.23 (m, 2H) 7.10 (s, 1H) 5.89 (d, J=1.71 Hz, 1H) 5.41 (br. s, 1H) 3.89 (br. s, 1H) 3.84 (s, 3H).

Preparation 3

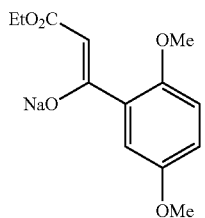

Sodium 1-(2,5-dimethoxyphenyl)-3-ethoxy-3-oxo-prop-1-en-1-olate

A 20-L reaction vessel was charged with magnesium ethoxide (3.61 moles; 413.52 g) and THF (6.6 L), and the resulting mixture was stirred as ethyl hydrogen malonate (7.23 moles; 888.89 mL; 994.67 g; diluted with 20 mL of THF) was added and the mixture was heated at 45° C. for 4 hours. Meanwhile, a 20 L reactor was charged with 2,5-dimethoxybenzoic acid (3.29 moles; 600.00 g) and THF (3.6 L). To this mixture stirring at room temperature was added 1,1'-carbonyldiimidazole (3.61 moles; 585.98 g) in portions to avoid excess foaming. After stirring for 3 hours at room temperature the second solution was added gradually to the first solution. After addition the reaction mixture was heated to 45° C. After 20 hours, the reaction mixture was concentrated under reduced pressure before adding ethyl acetate (6 L) followed by 2 N HCl (3 L). After mixing, the layers were separated and the organic phase was washed sequentially with 2 N HCl (3 L), saturated sodium bicarbonate (3 L), and water (3 L). The organic phase was concentrated under reduced pressure, the residue taken up in ethyl acetate (6 L) and concentrated again to afford an oil, which was transferred to a 20 L reaction vessel with 5 L of ethyl acetate and treated with sodium methoxide (3.45 moles; 793.00 mL of a 4.35 M solution in methanol). After stirring at room temperature for 3 hours, an additional 6 L of ethyl acetate was added and the solid collected by vacuum filtration and dried overnight in a vacuum oven at 40° C. to give 661 grams of the title product.

MS (ES+) 253.1[M+1]$^+$. $^1$H NMR (400 MHz, DMSO-d$_6$) δ ppm 6.92 (d, J=3.0 Hz, 1H) 6.84 (d, J=8.8 Hz, 1H) 6.73 (dd, J=8.8, 3.0 Hz, 1H) 4.67 (s, 1H) 3.88 (q, J=7.0 Hz, 2H) 3.67 (s, 6H) 1.12 (t, J=7.0 Hz, 3H).

Preparation 4

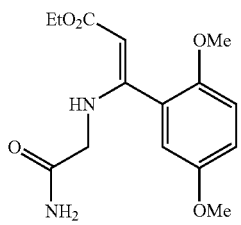 [SMILES: CCOC(=O)/C=C(\NCC(N)=O)c1cc(OC)ccc1OC]

(Z)-Ethyl 3-((2-amino-2-oxoethyl)amino)-3-(2,5-dimethoxyphenyl)acrylate

A 5-L reaction vessel was charged with methanol (3.3 L), sodium methoxide (102.4 g, 1.8 moles), and glycinamide hydrochloride (202 g, 1.8 moles). The mixture was heated at 65° C. for 1 hour before cooling to 50° C. and adding acetic acid (514.25 mmoles, 30.88 g, 29.47 mL) and ethyl 3-(2,5-dimethoxyphenyl)-3-oxopropanoate (300 g, 1.03 mole). After heating at reflux for 16 hours, the reaction mixture was stirred as it was cooled to 10° C. After 30 min the resulting solid was collected by vacuum filtration, pulling dry to form a cake that was dried in a vacuum oven (20 mm Hg, 65° C.) for 14 hours to afford the title compound (339.4 g).

MS (ES+) 309.1[M+1]$^+$. $^1$H NMR (400 MHz, DMSO-d$_6$) δ ppm 8.84 (t, J=4.7 Hz, 1H) 7.36 (s, 1H) 7.09 (s, 1H) 7.02 (d, J=8.9 Hz, 1H) 6.97 (dd, J=8.9, 2.8 Hz, 1H) 6.74 (d, J=2.8 Hz, 1H) 4.31 (s, 1H) 4.03 (q, J=7.1 Hz, 2H) 3.74 (s, 6H) 3.58 (br. s., 1H) 3.47 (br. s., 1H) 1.18 (t, J=7.1 Hz, 3H).

Example 2

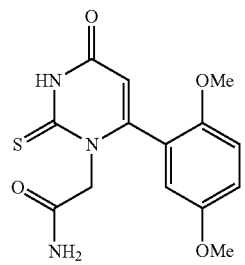

2-(6-(2,5-Dimethoxyphenyl)-4-oxo-2-thioxo-3,4-dihydropyrimidin-1(2H)-yl)acetamide A 5-L reaction vessel equipped with an efficient stirrer was charged with (Z)-ethyl 3-((2-amino-2-oxoethyl)amino)-3-(2,5-dimethoxyphenyl)acrylate (1.30 moles; 400.00 g), butyl acetate (3.4 L) and trimethylsilyl isothiocyanate (4.15 moles; 585.67 mL; 544.96 g) and the mixture was heated to reflux. After 16 hours, the mixture was cooled to 40° C. and treated with 2 N aqueous sodium hydroxide (1.95 L). The organic layer was separated and extracted with another portion of 2 N sodium hydroxide (0.325 L). The combined aqueous phases were filtered, extracted twice with dichloromethane (2×1.6 L), and added slowly to a well-stirred 3N aqueous HCl solution (1.3 L) at room temperature. After stirring for 30 min, the resulting solid was isolated by vacuum filtration, rinsing with water, and pulled dry to afford a water wet cake (640 g). The cake was dissolved in dimethylformamide (2.4 L) at 90° C. and stirred as water (2 L) was added slowly to the solution. The mixture was cooled gradually to room temperature and the resulting solid isolated by vacuum filtration, rinsing with water and pulling dry to afford 245 g of solid. This solid was then suspended in 1.25 L of methanol and stirred as 1.25 L of water was added. The mixture was heated with stirring at 50° C. for 2 hours, and then cooled to 10° C. for 2 hours before collecting the solid by vacuum filtration, pulling dry before drying in a vacuum oven (20 mm Hg, 60 C) to afford the desired product.

MS (ES+) 322.2[M+1]$^+$. $^1$H NMR (500 MHz, DMSO-d6) δ ppm 12.80 (s, 1H) 7.32 (br. s., 1H) 7.06-7.11 (m, 2H) 7.06 (br. s., 1H) 6.74-6.77 (m, 1H) 5.82 (d, J=2.20 Hz, 1H) 5.37 (br. s., 1H) 3.88 (br. s., 1H) 3.78 (s, 3H) 3.70 (s, 3H).

B. Methyl Ketone Route Section

Preparation 5

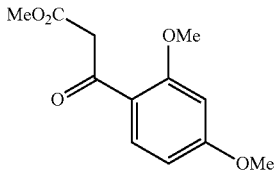 [SMILES: COC(=O)CC(=O)c1ccc(OC)cc1OC]

Methyl 3-(2,4-dimethoxyphenyl)-3-oxopropanoate

To a three-necked round-bottomed flask equipped with a mechanical stirrer under $N_2$ was added potassium tert-butoxide (1M in THF, 108.77 mL, 108.77 mmol), followed by a solution of 2,4-dimethoxyacetophenone (10.00 g, 54.38 mmol) and dimethyl carbonate (13.93 mL, 163.15 mmol) in methyl tert-butyl ether (50 mL) dropwise via an addition funnel over 1.5 hours. During addition, reaction turned from a initial cloudy yellow mixture to a thick red-orange slurry. Reaction mixture was stirred at room temperature overnight. Aqueous citric acid solution (0.5 N, 110.95 mL, 54.39 mmol) was added via addition funnel to quench the reaction. Exotherm was observed during quenching and solids dissolved to give an orange mixture. The layers were separated and the aqueous layer was extracted with methyl tert-butyl ether (2×25 mL). The combined organic extracts were concentrated to low volume. Heptane (50 mL) was added and brown solids precipitated. The resulting slurry was stirred under $N_2$ overnight at room temperature. Solids were filtered and dried under $N_2$ to give the title compound (11.05 g, 85% yield) as a beige colored powder.

MS (ES+) 239.1 [M+1]$^+$. $^1$H NMR (500 MHz, CDCl$_3$) δ 7.95 (d, J=8.78 Hz, 1H) 6.57 (dd, J=8.78, 2.20 Hz, 1H) 6.45 (d, J=2.20 Hz, 1H) 3.94 (s, 2H) 3.88 (s, 3H) 3.87 (s, 3H) 3.73 (s, 3H).

Preparation 6

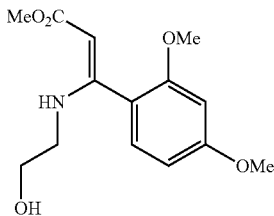

(Z)-Methyl 3-(2,4-dimethoxyphenyl)-3-(2-hydroxyethyl)amino)acrylate

To a mixture of methyl 3-(2,4-dimethoxyphenyl)-3-oxopropanoate (3.50 g, 14.69 mmol) and acetic acid (0.17 mL, 2.94 mmol) in i-PrOH (70 mL) was added ethanolamine (0.88 mL, 14.69 mmol) and the reaction mixture was heated to 83° C. Additional ethanolamine (0.88 mL, 14.69 mmol) was added to the reaction mixture at two, four and six hours. After stirring at 80° C. for 48 hours, the reaction mixture was cooled and concentrated under reduced pressure before the residue was suspended in equal parts of a saturated sodium bicarbonate solution and water under $N_2$. After stirring overnight, the solids were collected by vacuum filtration and dried in a vacuum oven at 30° C. overnight to afford the title compound (2.72 g, 63%) as a beige colored power.

$^1$H NMR (400 MHz, CDCl$_3$) δ 8.77 (t, J=5.37 Hz, 1H) 7.13 (d, J=8.29 Hz, 1H) 6.47-6.52 (m, 2H) 4.53 (s, 1H) 3.84 (s, 3H) 3.82 (s, 3H) 3.66 (s, 3H) 3.61 (td, J=5.45, 5.45 Hz, 2H) 3.15 (td, J=5.53, 5.53 Hz, 2H).

Example 3

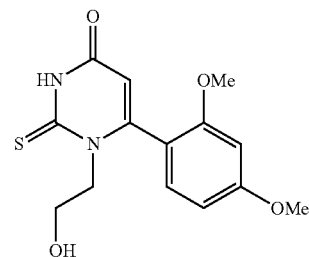 [SMILES: COc1ccc(-c2cc(=O)[nH]c(=S)n2CCO)c(OC)c1]

6-(2,4-Dimethoxyphenyl)-1-(2-hydroxyethyl)-2-thioxo-2,3-dihydropyrimidin-4(1H)-one To a solution of (Z)-methyl 3-(2,4-dimethoxyphenyl)-3-((2-hydroxyethyl)amino)acrylate (9.50 g, 33.77 mmol) in 2-MeTHF (100 mL) was added (trimethylsilyl)isothiocyanate (23.80 mL, 168.79 mmol), and the reaction mixture was heated at 85° C. After stirring overnight, the reaction mixture was cooled, extracted with an aqueous 1N NaOH solution (1×250 mL, then 1×50 mL), the combined aqueous layers were washed with CH$_2$Cl$_2$ (2×50 mL) and the aqueous phase acidified to pH 4 with concentrated HCl. The resulting solids were filtered, washed with water (2×50 mL) and dried under $N_2$ overnight to give a light yellow powder. The product was dissolved in DMF (70 mL) at 90° C., and then water (80 mL) was added to this hot solution. After allowing to cool to room temperature and stirring overnight, the solids were collected by vacuum filtration, washed with water and dried under high vacuum to provide the title compound (6.7 g, 61%) as an off-white powder.

MS (ES+) 309.1 [M+1]$^+$. $^1$H NMR (500 MHz, DMSO-d$_6$) δ ppm 12.68 (s, 1H) 7.24 (d, J=8.29 Hz, 1H) 6.69 (d, J=2.44 Hz, 1H) 6.65 (dd, J=8.42, 2.32 Hz, 1H) 5.70 (d, J=2.20 Hz, 1H) 4.69 (t, J=4.88 Hz, 1H) 4.50 (ddd, J=13.42, 7.07, 4.15 Hz, 1H) 3.83 (s, 3H) 3.82 (s, 3H) 3.59 (dt, J=13.42, 7.32 Hz, 1H) 3.46-3.55 (m, 1H) 3.38-3.46 (m, 1H).

C. Aryl Halide Route Section

Preparation 7

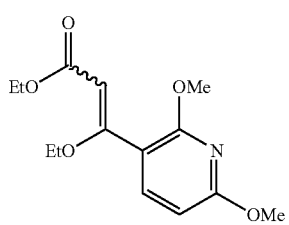 [SMILES: CCOC(=O)C=C(OCC)c1ccc(OC)nc1OC]

(Z,E)-Ethyl 3-(2, 6-dimethoxypyridin-3-yl)-3-ethoxyacrylate

Bis(tri-t-butylphosphine)palladium (47 mg, 0.092 mmol)) and lithium chloride (292 mg, 0.27 mmol) were added to a flask equipped with reflux condenser, and the apparatus was evacuated under vacuum and refilled with $N_2$ several times. To this flask was added via cannula a degassed solution of anhydrous 1,4-dioxane (8 mL) under $N_2$, followed by 3-bromo-2,6-dimethoxypyridine (500 mg, 2.29 mmol), N,N-dicyclohexylmethylamine (540 uL, 2.52 mmol) and ethyl 3-ethoxyacrylate (1.0 mL, 6.88 mmol), and the resulting orange solution was heated to 110° C. After 20 hours, the reaction mixture was cooled to room temperature, quenched with water and diluted with EtOAc. The layers were separated and the aqueous layer was extracted with EtOAc. The combined organic extracts were washed with brine, dried over $Na_2SO_4$ and concentrated in vacuo. The residue was purified by chromatography on silica eluting with 0-50% EtOAc/heptane to yield the title compound (604 mg, 94%) as an amber oil. $^1$H NMR showed the product to be composed of a 2.5:1 mixture of E/Z isomers.

Preparation 8

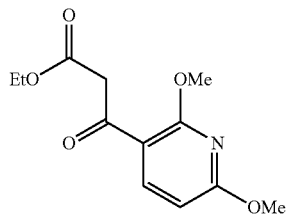 [SMILES: CCOC(=O)CC(=O)c1ccc(OC)nc1OC]

Ethyl 3-(2, 6-dimethoxypyridin-3-yl)-3-oxopropanoate

To a solution of ethyl 3-(2,6-dimethoxypyridin-3-yl)-3-ethoxyacrylate (600 mg, 2.13 mmol) in $CH_2Cl_2$ (18 mL) was gradually added 3N aqueous HCl (3.5 mL). The reaction mixture was stirred at room temperature for 2 hours, then carefully added to a saturated sodium bicarbonate solution (30 mL). The layers were separated and the aqueous layer was extracted with $CH_2Cl_2$. The combined organic extracts were passed though a plug of cotton to dry and concentrated in vacuo. The resulting oil was purified by flash chromatography (0-60% EtOAc/heptanes) to provide the title compound (515 mg, 95% yield) as a white solid.

$^1$H NMR (400 MHz, CDCl$_3$) δ ppm 8.22 (d, J=8.59 Hz, 1H) 6.40 (d, J=8.39 Hz, 1H) 4.20 (q, J=7.03 Hz, 2H) 4.03 (s, 3H) 3.99 (s, 3H) 3.94 (s, 2H) 1.26 (t, J=7.13 Hz, 3H).

D. Amine Deprotection Route and Derivatization

Preparation 9

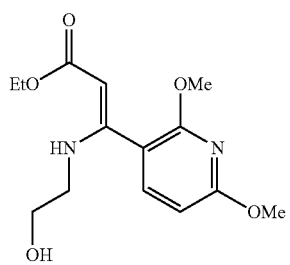 [SMILES: CCOC(=O)/C=C(\NCCO)c1ccc(OC)nc1OC]

(Z)-Ethyl 3-(2, 6-dimethoxypyridin-3-yl)-3-((2-hydroxyethyl)amino)acrylate

To a solution of ethyl 3-(2,6-dimethoxypyridin-3-yl)-3-oxopropanoate (500 mg, 1.97 mmol) in EtOH (4 mL) was added 2-aminoethanol (0.60 mL, 9.9 mmol) followed by acetic acid (0.63 mL, 9.9 mmol). The reaction mixture was heated to 90° C. for 16 hours, cooled to room temperature and concentrated in vacuo. The residue was partitioned between EtOAc and water. The organic layer was concentrated in vacuo and the crude material was purified by chromatography on silica eluting with 20-80% EtOAc/heptane to provide the title compound (573 mg, 98%) as a clear gum.

MS (ES+) 297.3 [M+1]$^+$. $^1$H NMR (500 MHz, CDCl$_3$) δ 8.75 (br. s., 1H) 7.44 (d, J=8.05 Hz, 1H) 6.34 (d, J=8.05 Hz, 1H) 4.51 (s, 1H) 4.14 (q, J=7.16 Hz, 2H) 3.97 (s, 3H) 3.95 (s, 3H) 3.64 (td, J=5.53, 5.53 Hz, 2H) 3.17 (td, J=5.53, 5.53 Hz, 2H) 1.96 (br. s., 1H) 1.27 (t, J=7.07 Hz, 3H).

Example 4

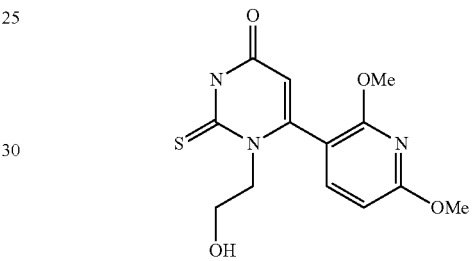

6-(2,6-Dimethoxypyridin-3-yl)-1-(2-hydroxyethyl)-2-thioxo-2,3-dihydropyrimidin-4(1H)-one To a solution of (Z)-ethyl 3-(2,6-dimethoxypyridin-3-yl)-3-((2-hydroxyethyl)amino)acrylate (100 mg, 0.34 mmol) in 2-MeTHF (1.0 mL) was added (trimethylsilyl)isothiocyanate (0.30 mL, 2.0 mmol) and the reaction mixture was heated to 80° C. for 4 hours. The cooled reaction mixture was diluted with EtOAc and washed with a saturated aqueous sodium bicarbonate solution. The layers were separated and the organic layer was concentrated in vacuo. The residue was triturated with MeOH and the resulting solids were collected by vacuum filtration to give the title compound (16 mg, 16%) as a white solid.

MS (ES+) 310.2 [M+1]$^+$. $^1$H NMR (500 MHz, CD$_3$OD) δ 7.60 (d, J=8.29 Hz, 1H) 6.47 (d, J=8.05 Hz, 1H) 5.76 (s, 1H) 4.66-4.75 (m, 1H) 4.01 (s, 3H) 3.98 (s, 3H) 3.77-3.85 (m, 2H) 3.57-3.63 (m, 1H)

Preparation 10

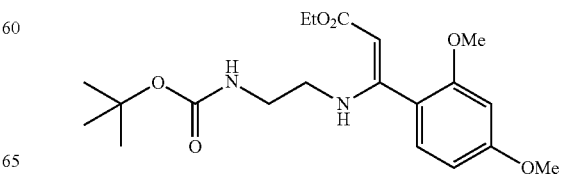

(Z)-ethyl 3-(2-(tert-butoxycarbonylamino)ethylamino)-3-(2,4-dimethoxyphenyl)acrylate A solution of ethyl 3-(2,4-dimethoxyphenyl)-3-oxopropanoate (41.91 g, 166 mmol), tert-butyl 2-aminoethylcarbamate (54.7 g, 342 mmol), and acetic acid (16.14 g, 269 mmol) in ethanol (180 mL) was heated at reflux for 5.3 h. After removal of most of the solvent by rotary evaporation, the resulting oil was partitioned between EtOAc (ca. 300 mL) and 10% (w/v) aq. ammonium chloride. The EtOAc layer was separated and then washed with water, 10% (w/v) aq. ammonium chloride (3 mL), and brine (10 mL). The EtOAc layer was washed with sat. aq. sodium bicarbonate, brine (6 mL) was added, and the emulsion was allowed to settle. The EtOAc layer was finally washed with brine and dried over sodium sulfate. Evaporation of the EtOAc layer's volatile components afforded a viscous, amber taffy (62.3 g, 95%). This crude product was used without further purification.

LCMS (ESI) m/z: 395.4 [M+H] (100%). $^1$H NMR (500 MHz, CDCl$_3$) δ 1.27 (t, J=7.1 Hz, 3H), 1.43 (s, 9H), 3.03-3.21 (m, 4H), 3.83 (s, 6H), 4.14 (q, J=7.1 Hz, 2H), 4.51 (s, 1H), 4.88 (br. s., 1H), 6.47 (d, J=1.7 Hz, 1H), 6.50 (dd, J=8.4, 1.8 Hz, 1H), 7.12 (d, J=8.3 Hz, 1H), 8.65 (br. s., 1H).

Example 5

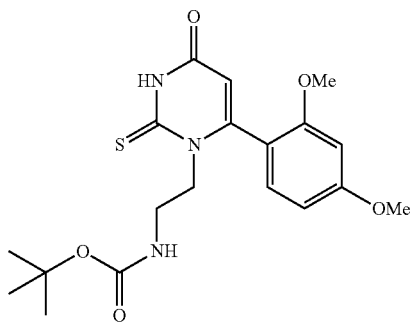 [SMILES: COc1ccc(-c2cc(=O)[nH]c(=S)n2CCNC(=O)OC(C)(C)C)c(OC)c1]

tert-butyl 2-(6-(2,4-dimethoxyphenyl)-4-oxo-2-thioxo-3,4-dihydropyrimidin-1(2H)-yl)ethylcarbamate (Trimethylsilyl)isothocyanate (66 mL, 470 mmol) was added to a solution of (Z)-ethyl 3-(2-(tert-butoxycarbonylamino)ethylamino)-3-(2,4-dimethoxyphenyl)acrylate (62.3 g, 158 mmol) in 2-MeTHF (160 mL). After heating at reflux under nitrogen for 15 h, the reaction mixture was cooled to ambient temperature and quenched by cautious addition of sat. aq. sodium bicarbonate (470 mL). The rxn. mixture was extracted with dichloromethane, and the aq. layer was twice more extracted with dichloromethane. The combined organic layers were dried over sodium sulfate and evaporated to afford a yellow-amber foam, which was purified by chromatography on silica eluting with 0-80% ethyl acetate in heptanes to afford 49.2 g of solid. These solids were re-suspended in 1:1 EtOAc/heptane at 70° C. for 1 h and then at r.t. for another 1 h. The resulting solids were isolated by vacuum filtration, rinsing with additional 1:1 EtOAc/heptane, and pulled dry on the filter. The title compound was obtained as a white, microcrystalline solid (38.3 g, 59.5% yield).

LCMS (ESI) m/z: 408.3 [M+H] (100%). $^1$H NMR (500 MHz, CDCl$_3$, major rotamer) δ 1.40 (s, 9H), 3.23-3.45 (m, 2H), 3.74 (dt, J=14.4, 5.4 Hz, 1H), 3.84 (s, 3H), 3.87 (s, 3H), 4.68-4.81 (m, 2H), 5.81 (d, J=2.2 Hz, 1H), 6.51 (d, J=2.2 Hz, 1H), 6.59 (dd, J=8.4, 2.1 Hz, 1H), 7.26 (d, J=8.4 Hz, 1H), 9.58 (br. s., 1H).

Example 6

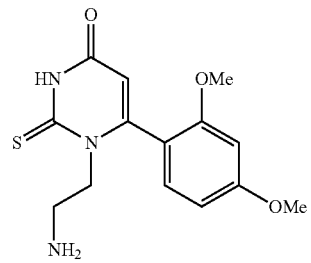 [SMILES: COc1ccc(-c2cc(=O)[nH]c(=S)n2CCN)c(OC)c1]

1-(2-aminoethyl)-6-(2,4-dimethoxyphenyl)-2-thioxo-2,3-dihydropyrimidin-4(1H)-one hydrochloride To a solution of EtOH (50 mL, 860 mmol) in EtOAc (390 mL), cooled in an ice/water bath, was slowly added acetyl chloride (55 mL, 770 mmol) over 3 minutes. After 5 minutes the cooling bath was removed, and after stirring for 45 min, the solution was added to tert-butyl 2-(6-(2,4-dimethoxyphenyl)-4-oxo-2-thioxo-3,4-dihydropyrimidin-1(2H)-yl)ethylcarbamate (31.7 g, 77.8 mmol). A suspension formed over time, and after stirring for 5 h, the solid was collected by vacuum filtration, rinsing with EtOAc. The solid was pulled dry and dried further under vacuum to afford 26.6 g (99.3%) of the desired product as a colorless solid.

LCMS (ESI) m/z: 291.3 [M-NH3+H] (100%), 308.3 [M+H] (33%), 615.5 [2M+H] (2.3%). $^1$H NMR (500 MHz, CD3OD) δ 3.06 (ddd, J=12.9, 7.8, 5.9 Hz, 1H), 3.12 (ddd, J=12.9, 7.7, 6.4 Hz, 1H), 3.87 (s, 3H), 3.89 (s, 3H), 4.14 (ddd, J=14.0, 7.8, 5.9 Hz, 1H), 4.82 (ddd, J=14.0, 7.7, 6.4 Hz, 1H), 5.80 (s, 1H), 6.70 (dd, J=8.3, 2.2 Hz, 1H), 6.73 (d, J=2.2 Hz, 1H), 7.27 (d, J=8.3 Hz, 1H).

Example 7

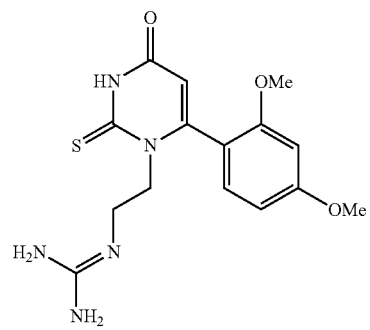 [SMILES: COc1ccc(-c2cc(=O)[nH]c(=S)n2CCN=C(N)N)c(OC)c1]

2-(2-(6-(2, 4-dimethoxyphenyl)-4-oxo-2-thioxo-3, 4-dihydropyrimidin-1 (2H)-yl) ethyl)guanidine Diisopropylethylamine (0.22 mL, 1.3 mmol) was added to a suspension of 1-(2-aminoethyl)-6-(2,4-dimethoxyphenyl)-2-thioxo-2,3-dihydropyrimidin-4(1H)-one hydrochloride (181.6 mg, 0.528 mmol) (the product of Example 6) and 1H-pyrazole-1-carboxamidine hydrochloride (90.6 mg, 0.618 mmol) in DMF (0.55 mL). After heating for 1 h at 55° C., the reaction mixture was cooled to ambient temperature, diluted with EtOH (1.6 mL), and the solid product collected by vacuum filtration, rinsing with additional EtOH. The isolated solid was re-suspended in EtOH (2.1 mL) for 3 h at r.t. before being collected again by vacuum filtration and rinsing with additional EtOH. The desired product was obtained, after drying, as a colorless solid. Solubility data for this product is consistent with it being in its zwitterionic form.

1H NMR (500 MHz, CD3OD+2 drops 20. % DCl in D2O) δ 3.31-3.37 (m, 1H), 3.67 (ddd, J=14.8, 8.6, 5.9 Hz, 1H), 3.88-3.99 (m, 1H), 3.90 (s, 6H), 4.66-4.77 (m, 1H), 5.80 (s, 1H), 6.69 (d, J=2.2 Hz, 1H), 6.71 (dd, J=8.3, 2.2 Hz, 1H), 7.28 (d, J=8.3 Hz, 1H).

2-(2-(6-(2, 4-dimethoxyphenyl)-4-oxo-2-thioxo-3, 4-dihydropyrimidin-1 (2H)-yl)ethyl)guanidine hydrochloride The product from the above reaction (116.3 mg, 0.333 mmol) was suspended in dioxane and treated with a 4.0 M HCl/dioxane solution (0.30 mL, 1.2 mmol). After thorough vortexing, the volatile components of the mixture were removed to afford a white solid (130.6 mg, 0.338 mmol). LCMS (ESI) m/z: 350.1 [M+H] (100%).

Preparation 11

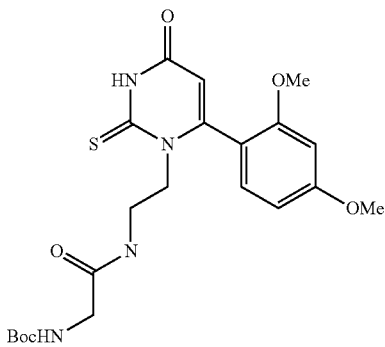 [SMILES: COc1ccc(-c2cc(=O)[nH]c(=S)n2CCNC(=O)CNC(=O)OC(C)(C)C)c(OC)c1]

tert-butyl 2-(2-(6-(2, 4-dimethoxyphenyl)-4-oxo-2-thioxo-3,4-dihydropyrimidin-1 (2H)-yl)ethylamino)-2-oxoethylcarbamate To a solution of 1-(2-aminoethyl)-6-(2,4-dimethoxyphenyl)-2-thioxo-2,3-dihydropyrimidin-4(1H)-one hydrochloride (123 mg, 0.4 mmol)(the product of Example 6) in dry methylene chloride (4 mL) was added O-(7-azabenzotriazol-1-yl)-N,N,N',N'-tetramethyluronium hexafluorophosphate (182 mg, 0.48 mmol) and tert-butoxycarbonylamino-acetic acid (70 mg, 0.4 mmol) and diisoproplyethylamine (336 mg, 1.6 mmol). After stirring overnight at RT the reaction mixture was concentrated under reduced pressure and the residue purified by preparative thin layer chromatography (1:1 petroleum ether: ethyl acetate) to provide tert-butyl 2-(2-(6-(2,4-dimethoxyphenyl)-4-oxo-2-thioxo-3,4-dihydropyrimidin-1(2H)-yl)ethylamino)-2-oxoethylcarbamate (120 mg, 65%).

Example 8

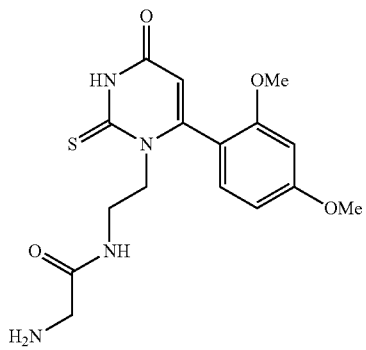 [SMILES: COc1ccc(-c2cc(=O)[nH]c(=S)n2CCNC(=O)CN)c(OC)c1]

2-amino-N-(2-(6-(2, 4-di methoxyphenyl)-4-oxo-2-thioxo-3,4-dihydropyrimidin-1 (2H)-yl)ethyl)acetamide hydrochloride To a solution of tert-butyl 2-(2-(6-(2,4-dimethoxyphenyl)-4-oxo-2-thioxo-3,4-dihydropyrimidin-1(2H)-yl)ethylamino)-2-oxoethylcarbamate (70 mg, 0.15 mmol) in ethyl acetate (2 mL) was added a solution of HCl in ethyl acetate (2 mL). After stirring at room temperature for 4 hours, the reaction mixture was concentrated under reduced pressure to afford the desired 2-amino-N-(2-(6-(2,4-dimethoxyphenyl)-4-oxo-2-thioxo-3,4-dihydropyrimidin-1(2H)-yl)ethyl)acetamide hydrochloride as a solid (65 mg, 100%).

II. 6-Iodo-Thiouracil Route Section

Preparation 12

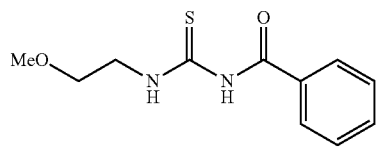 [SMILES: COCCNC(=S)NC(=O)c1ccccc1]

N-((2-Methoxyethyl)carbamothioyl)benzamide

2-Methoxyethylamine (17.7 mL, 202.2 mmol) was added dropwise over 30 minutes to a stirring solution of benzoylisothiocyanate (30.00 g, 183.8 mmol) in CH₂Cl₂ (300 mL) at room temperature under argon and the mixture was stirred at room temperature for 16 hours. The mixture was washed sequentially with 10% aqueous citric acid (75 mL), water (75 mL) and brine (75 mL), dried over MgSO₄ and concentrated in vacuo. The resulting yellow oil solidified on standing to give the title compound (41.85 g, 96%). The material was used directly in the next step without further purification.

Preparation 13

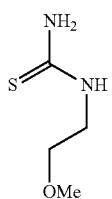

1-(2-Methoxyethyl)thiourea

A solution of N-((2-methoxyethyl)carbamothioyl)benzamide (41.82 g, 175.5 mmol), potassium carbonate (24.25 g, 175.5 mmol) in MeOH (200 mL) and water (200 mL) was stirred at room temperature for 16 hours. The mixture was concentrated in vacuo and the aqueous layer was extracted with EtOAc (5×100 mL). The combined organic layers were dried over Na$_2$SO$_4$ and concentrated in vacuo. The resulting yellow oil solidified on standing to provide the title compound (21.38 g, 91%). The material was used directly in the next step without further purification.

MS (ES+) 135.1 (M+1)$^+$. $^1$H NMR (500 MHz, CDCl$_3$) δ 6.66 (br. s., 1H) 6.46 (br. s., 1H) 5.81 (br. s., 1H) 3.80 (br. s., 2H) 3.48-3.65 (m, 2H) 3.40 (s, 3H).

Preparation 14

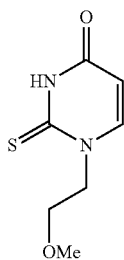 [SMILES: COCCn1ccc(=O)[nH]c1=S]

1-(2-Methoxyethyl)-2-thioxo-2,3-dihydropyrimidin-4(1H)-one

To a stirring solution of 1-(2-methoxyethyl)thiourea (21.38 g, 159.3 mmol) and ethyl 3,3-diethoxypropanoate (46.5 mL, 239.0 mmol) in MeOH (300 mL) was added a freshly prepared solution of 0.96N sodium methoxide in MeOH (250 mL, 239.0 mmol) dropwise over 30 minutes at room temperature under argon. The reaction mixture was heated to 60° C. for 45 minutes and cooled to room temperature. Solvent was removed under reduced pressure and toluene (250 mL) was added to the residue. The mixture was stirred at reflux for an additional 3 hours and then cooled to room temperature. Water (200 mL) was added and the layers were separated. The aqueous layer was washed with CH$_2$Cl$_2$ (50 mL), neutralized with 2N aqueous HCl and extracted with CH$_2$Cl$_2$ (3×200 mL). The combined organic layers were dried over Na$_2$SO$_4$ and concentrated in vacuo. The residue was recrystallized from i-PrOH (200 mL) to give the title compound (13.3 g, 45%) as a light yellow crystalline solid.

MS (ES+) 187.1 (M+1)$^+$. $^1$H NMR (400 MHz, CDCl$_3$) δ 9.81 (br. s., 1H) 7.39 (d, J=7.81 Hz, 1H) 5.94 (d, J=8.00 Hz, 1H) 4.39 (dd, J=5.27, 4.49 Hz, 2H) 3.73 (dd, J=5.07, 4.29 Hz, 2H) 3.36 (s, 3H).

Preparation 15

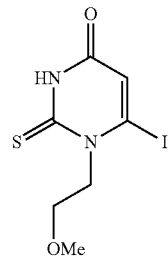 [SMILES: COCCn1c(I)cc(=O)[nH]c1=S]

6-Iodo-1-(2-methoxyethyl)-2-thioxo-2,3-dihydropyrimidin-4(1H)-one

To a stirring solution of diisopropylamine (8.3 mL, 59.10 mmol) in THF (50 mL) was added n-butyl lithium (2N in hexanes, 30.0 mL, 60.0 mmol) dropwise at −78° C. under argon. The reaction mixture was slowly warmed to −20° C. and then cooled to −78° C. A solution of 1-(2-methoxyethyl)-2-thioxo-2,3-dihydropyrimidin-4(1H)-one (5.0 g, 26.85 mmol) in THF (50 mL) was added dropwise at −78° C. The reaction mixture was slowly warmed to −10° C. over 1 hour and then cooled to −78° C. A solution of iodine (15.0 g, 59.07 mmol) in THF (50 mL) was added at −78° C. and the reaction mixture was stirred at room temperature for 20 hours. Reaction was diluted with saturated aqueous ammonium chloride (200 mL) and the organic solvents were removed under reduced pressure. The aqueous residue was acidified to pH 4 with 1N aqueous HCl and extracted with CH$_2$Cl$_2$ (3×300 mL, 1×200 mL). The combined organic layers were washed with 10% aqueous sodium thiosulfate solution (400 mL), brine (300 mL), dried over MgSO$_4$ and concentrated in vacuo. The resulting residue was stirred in CH$_2$Cl$_2$ at room temperature and solids were collected by filtration to give the title compound (9.05 g, 54%) as a pale brown solid. The filtrate was concentrated and purified by flash chromatography (0-25% CH$_2$Cl$_2$/EtOAc) to afford a second batch of the title compound (3.10 g, 18%) as a cream colored solid (72% combined yield).

MS (ES+) 313.0 [M+1]$^+$. $^1$H NMR (400 MHz, CDCl$_3$) δ 9.88 (br. s., 1H) 6.70 (s, 1H) 4.88 (br. s., 2H) 3.78 (t, J=6.05 Hz, 2H) 3.40 (s, 3H).

Preparation 16

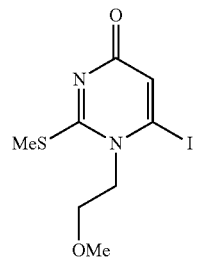 [SMILES: COCCn1c(I)cc(=O)nc1SC]

6-Iodo-1-(2-methoxyethyl)-2-(methylthio)pyrimidin-4(1H)-one

To a stirring solution of 6-iodo-1-(2-methoxyethyl)-2-thioxo-2,3-dihydropyrimidin-4(1H)-one (9.00 g, 28.83 mmol) in MeCN (200 mL) was added diisopropylethylamine (5.0 mL, 28.83 mmol) and iodomethane (9.0 mL, 144.17 mmol). The reaction mixture was stirred at room temperature for 18 hours, and concentrated in vacuo. The residue was partitioned ortioned between CH$_2$Cl$_2$ (200 mL) and 1N aqueous HCl (100 mL). The layers were separated and the organic layer was washed with brine (100 mL), dried over MgSO$_4$ and concentrated in vacuo. The resulting residue was purified by hot trituration with CH$_2$Cl$_2$/heptane to give the title compound (4.05 g, 43%) as a cream colored solid.

MS(ES+) 327.0 [M+1]$^+$. $^1$H NMR (500 MHz, CDCl$_3$) δ 6.77 (s, 1H) 4.42 (t, J=6.34 Hz, 2H) 3.69 (t, J=6.34 Hz, 2H) 3.40 (s, 3H) 2.58 (s, 3H).

IIA. Suzuki Route Section

Preparation 17

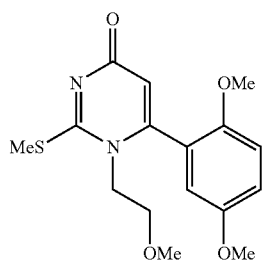 [SMILES: COCCn1c(-c2cc(OC)ccc2OC)cc(=O)nc1SC]

6-(2,5-dimethoxyphenyl)-1-(2-methoxyethyl)-2-(methylthio)pyrimidin-4(1H)-one To a mixture of 6-iodo-1-(2-methoxyethyl)-2-(methylthio)pyrimidin-4(1H)-one (100 mg, 0.31 mmol), (2,5-dimethoxyphenyl)boronic acid (0.37 mmol, 1.2 equiv.) and [1,1'-bis(diphenylphosphino)ferrocene]dichloropalladium(II) (14 mg, 0.017 mmol, 0.05 equiv) was added degassed 1,4-dioxane (2 mL), followed by a degassed solution of sodium carbonate (65 mg, 0.61 mmol) in water (0.7 mL). This reaction mixture was subjected to microwave irradiation at 120° C. for 30 minutes and the crude reaction mixture was used directly in the next step.

Example 9

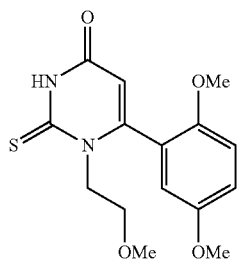 [SMILES: COCCn1c(-c2cc(OC)ccc2OC)cc(=O)[nH]c1=S]

6-(2,5-dimethoxyphenyl)-1-(2-methoxyethyl)-2-thioxo-2,3-dihydropyrimidin-4(1H)-one Ammonium sulfide (1 mL, 14.63 mmol) and pyridine (1 mL, 12.41 mmol) were added to the crude reaction mixture obtained from the previous Suzuki coupling reaction (0.31 mmol theoretical yield), and the mixture was subjected to microwave irradiation at 75° C. for 30 minutes. The reaction mixture was cooled to room temperature, taken up in CH$_2$Cl$_2$ (10 mL) and water (10 mL), then basified with 2N NaOH. The layers were separated and the aqueous layer was washed with CH$_2$Cl$_2$ (2×10 mL). The aqueous layer was then acidified to pH 6 with 2N aqueous HCl and extracted with EtOAc (3×10 mL). The combined organic extracts were dried over MgSO$_4$ and concentrated in vacuo. The crude reaction mixture was purified by flash chromatography to give the desired product (38 mg, 38% over two steps) as solid.

MS (ES+) 323.1 [M+1]$^+$. $^1$H NMR (400 MHz, CDCl$_3$) δ 10.14 (br. s., 1H), 7.01 (dd, J=8.90, 3.10 Hz, 1H), 6.89 (d, J=9.16 Hz, 1H), 6.80 (d, J=3.21 Hz, 1H), 5.84 (d, J=1.83 Hz, 1H), 4.70 (dt, J=13.74, 4.35 Hz, 1H), 3.83-3.92 (m, 1H), 3.78-3.82 (m, 6H), 3.73-3.79 (m, 1H), 3.44 (ddd, J=9.96, 5.84, 3.89 Hz, 1H), 3.16 (s, 3H)

II B. Negishi Route Section

Preparation 18

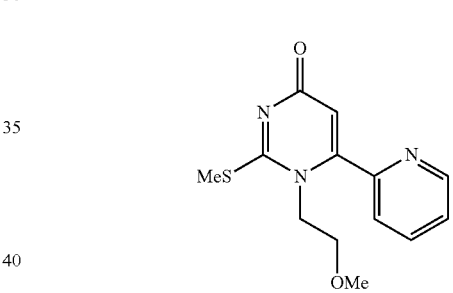

1-(2-Methoxyethyl)-2-(methylthio)-6-(pyridin-2-yl)pyrimidin-4(1H)-one n-Butyl lithium (2.0 M, 0.32 mL, 0.64 mmol) was slowly added to 2-bromopyridine (0.058 mL, 0.61 mmol) in dry THF (2 mL) at −78° C. After 30 minutes, anhydrous zinc chloride (92 mg, 0.67 mmol) was added and the reaction mixture was stirred for an additional 30 minutes as it warmed to room temperature. To the reaction mixture was added 6-iodo-1-(2-methoxyethyl)-2-(methylthio)pyrimidin-4(1H)-one (200 mg, 0.61 mmol), followed by tris(dibenzylideneacetone)dipalladium(0) (27 mg, 0.03 mmol), 2-dicyclohexylphosphino-2',6'-dimethoxybiphenyl (26 mg, 0.06 mmol) and DMF (2 mL), and the reaction mixture was then heated to 80° C. After stirring overnight, the product was extracted with EtOAc (3×10 mL) and washed with water (3×10 mL). The aqueous was then acidified with 2M HCl to pH 4 and the product was extracted with DCM (3×10 mL) and dried over MgSO$_4$. The solvent was removed in vacuo to give an orange oil (100 mg) as a mixture of 1-(2-methoxyethyl)-2-(methylthio)-6-(pyridin-2-yl)pyrimidin-4(1H)-one (37%) and 1-(2-methoxyethyl)-2-(methylthio)pyrimidin-4(1H)-one (32%).

Example 10

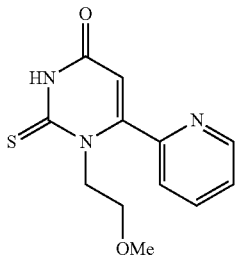 [SMILES: COCCn1c(-c2ccccn2)cc(=O)[nH]c1=S]

1-(2-Methoxyethyl)-6-(pyridin-2-yl)-2-thioxo-2,3-dihydropyrimidin-4(1H)-one

A mixture of crude 1-(2-methoxyethyl)-2-(methylthio)-6-(pyridin-2-yl)pyrimidin-4(1H)-one (100 mg, 0.36 mmol), ammonium sulfide solution (0.2 mL, 0.64 mmol) and pyridine (0.2 mL) was stirred in dioxane (2 mL) at 70° C. for 4 hours. The reaction mixture was diluted with water (10 mL), basified with 2M NaOH and washed with dichloromethane (3×10 mL). The aqueous layer was acidified to pH 6 with 2M HCl and extracted with ethyl acetate (3×10 mL). The combined organic layers were washed with water (3×10 mL), brine (3×10 mL), dried over MgSO$_4$ and concentrated in vacuo. The crude material was purified by mass directed automatic purification using an acidic method to give the product as a brown solid (3 mg, 3%).

MS(ES+) 264.07 [M+H]$^+$. 1H NMR (400 MHz, CDCl3) δ 8.76 (br s, 1H), 7.92 (br s, 1H), 7.48-7.54 (m, 2H), 7.32 (br d, 1H), 5.95 (br d, 1H), 4.65 (br s, 2H), 3.64 (br s, 2H).

The following Examples of Table 2 were prepared from the corresponding carboxylic acid to afford the intermediate beta-keto-ester as described for the Preparations in the Carboxylic Acid Route Section above followed by employing other methods described above in the I. Beta-Keto Ester Route Section as well as standard methods and techniques known to those skilled in the art.

TABLE 2

Examples from Carboxylic Acid Route

| Example # | Structure | Compound Name | Obs Mass | 1H NMR Spectral Data or HPLC Retention Time and Conditions |
|---|---|---|---|---|
| 11 | 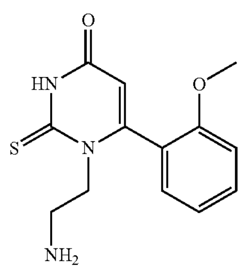 [SMILES: COc1ccccc1-c1cc(=O)[nH]c(=S)n1CCN] | 1-(2-aminoethyl)-6-(2-methoxyphenyl)-2-thioxo-2,3-dihydropyrimidin-4(1H)-one hydrochloride | 278.1 | 1H NMR (400 MHz, DMSO-d6) δ ppm 7.58-7.98 (m, 3 H), 7.54 (td, J = 8.20, 1.60 Hz, 1 H), 7.35 (dd, J = 7.56, 1.60 Hz, 1 H), 7.19 (d, J = 8.24 Hz, 1 H), 7.08 (t, J = 7.44 Hz, 1 H), 5.77 (s, 1 H), 4.60 (ddd, J = 13.51, 7.79, 6.41 Hz, 1 H), 3.82-3.87 (m, 1 H), 3.81 (s, 3 H), 2.76-2.91 (m, 2 H) |
| 12 | 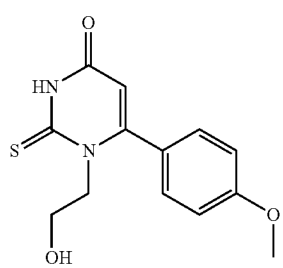 [SMILES: COc1ccc(-c2cc(=O)[nH]c(=S)n2CCO)cc1] | 1-(2-hydroxyethyl)-6-(4-methoxyphenyl)-2-thioxo-2,3-dihydropyrimidin-4(1H)-one | 279.0 | 1H NMR (500 MHz, METHANOL-d4) δ ppm 7.38 (d, J = 8.54 Hz, 2 H) 7.05 (d, J = 8.54 Hz, 2 H) 5.77 (s, 1 H) 4.37 (t, J = 6.22 Hz, 2 H) 3.86 (s, 3 H) 3.74 (t, J = 6.34 Hz, 2 H) |
| 13 | 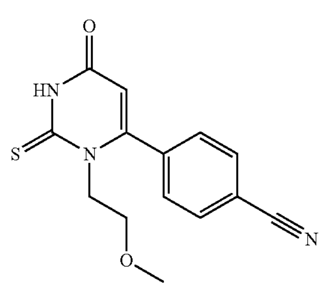 [SMILES: COCCn1c(-c2ccc(C#N)cc2)cc(=O)[nH]c1=S] | 4-[3-(2-methoxyethyl)-6-oxo-2-thioxo-1,2,3,6-tetrahydropyrimidin-4-yl]benzonitrile | 288.1 | 1H NMR (400 MHz, CHLOROFORM-d) δ ppm 9.53 (br. s, 1 H), 7.80 (d, J = 8.70 Hz, 2 H), 7.50 (d, J = 8.70 Hz, 2 H), 5.80 (s, 1 H), 4.30 (br. s., 2 H), 3.65 (t, J = 5.04 Hz, 2 H), 3.21 (s, 3 H) |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 14 | 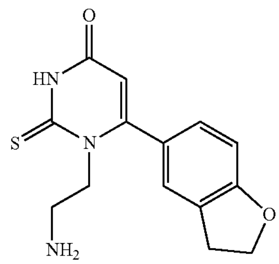 [SMILES: NCCn1c(-c2ccc3c(c2)CCO3)cc(=O)[nH]c1=S] | 1-(2-aminoethyl)-6-(2,3-dihydro-1-benzofuran-5-yl)-2-thioxo-2,3-dihydropyrimidin-4(1H)-one hydrochloride | 290.0 | 1H NMR (300 MHz, DMSO-d6) δ ppm 12.82 (br. s., 1 H), 7.79 (br. s., 3 H), 7.38 (s, 1 H), 7.24 (dd, J = 8.01, 1.74 Hz, 1 H), 6.90 (d, J = 8.36 Hz, 1 H), 5.76 (d, J = 2.09 Hz, 1 H), 4.61 (t, J = 8.71 Hz, 2 H), 4.34 (t, J = 8.01 Hz, 2 H), 3.24 (t, J = 8.71 Hz, 2 H), 2.89-3.02 (m, 2 H) |
| 15 | 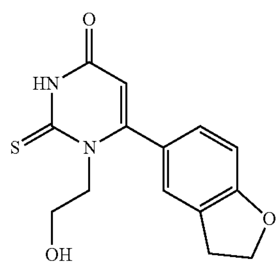 [SMILES: O=c1cc(-c2ccc3c(c2)CCO3)n(CCO)c(=S)[nH]1] | 6-(2,3-dihydro-1-benzofuran-5-yl)-1-(2-hydroxyethyl)-2-thioxo-2,3-dihydropyrimidin-4(1H)-one | 291.0 | 1H NMR (300 MHz, DMSO-d6) δ ppm 12.68 (br. s., 1 H), 7.34 (s, 1 H), 7.20 (d, J = 8.36 Hz, 1 H), 6.86 (d, J = 8.36 Hz, 1 H), 5.70 (d, J = 2.09 Hz, 1 H), 4.75 (t, J = 5.57 Hz, 1 H), 4.60 (t, J = 9.06 Hz, 2 H), 4.19 (t, J = 6.62 Hz, 2 H), 3.53 (td, J = 5.60 Hz, 2 H), 3.23 (t, J = 8.71 Hz, 2 H) |
| 16 | 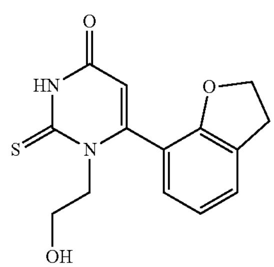 [SMILES: O=c1cc(-c2cccc3c2OCC3)n(CCO)c(=S)[nH]1] | 6-(2,3-dihydro-1-benzofuran-7-yl)-1-(2-hydroxyethyl)-2-thioxo-2,3-dihydropyrimidin-4(1H)-one | 291.1 | 1H NMR (400 MHz, CHLOROFORM-d) δ ppm 9.50 (br. s., 1 H), 7.33 (d, J = 7.10 Hz, 1 H), 7.04 (d, J = 7.56 Hz, 1 H), 6.95 (t, J = 7.56 Hz, 1 H), 5.86 (s, 1 H), 4.70-4.81 (m, 1 H), 4.64 (t, J = 8.70 Hz, 2 H), 3.98-4.10 (m, 1 H), 3.81-3.90 (m, 1 H), 3.65-3.78 (m, 2 H), 3.30 (t, J = 8.70 Hz, 1 H), 1.86 (t, J = 5.95 Hz, 1 H) |
| 17 | 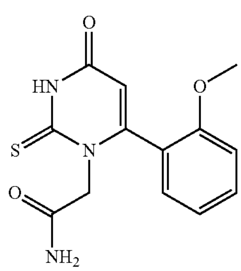 | 2-[6-(2-methoxyphenyl)-4-oxo-2-thioxo-3,4-dihydropyrimidin-1(2H)-yl]acetamide | 292.0 | 1H NMR (400 MHz, DMSO-d6) δ ppm 12.78 (br. s., 1 H), 7.48 (td, J = 7.90, 1.60 Hz, 1 H), 7.26 (br. s., 1 H), 7.08-7.17 (m, 2 H), 7.00 (t, J = 7.44 Hz, 1 H), 6.96 (br. s., 1 H), 5.76 (d, J = 2.06 Hz, 1 H), 5.22-5.48 (m, 2 H), 3.80 (s, 3 H) |
| 18 | 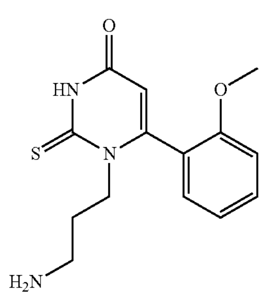 [SMILES: COc1ccccc1-c1cc(=O)[nH]c(=S)n1CCCN] | 1-(3-aminopropyl)-6-(2-methoxyphenyl)-2-thioxo-2,3-dihydropyrimidin-4(1H)-one hydrochloride | 292.0 | 1H NMR (400 MHz, METHANOL-d4) δ ppm 7.55 (ddd, J = 8.00, 8.00, 1.30 Hz, 1 H), 7.33 (dd, J = 7.42, 1.37 Hz, 1 H), 7.17 (d, J = 8.39 Hz, 1 H), 7.10 (dd, J = 7.40, 7.40 Hz, 1 H), 5.78 (s, 1 H), 4.58 (dt, J = 15.13, 7.66 Hz, 1 H), 3.88 (s, 3 H), 3.72-3.83 (m, 1 H), 2.73 (t, J = 7.81 Hz, 2 H), 1.94-2.07 (m, 1 H), 1.75-1.88 (m, 1 H) |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 19 | 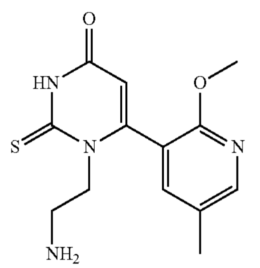 [SMILES: COc1ncc(C)cc1-c1cc(=O)[nH]c(=S)n1CCN] | 1-(2-aminoethyl)-6-(2-methoxy-5-methylpyridin-3-yl)-2-thioxo-2,3-dihydropyrimidin-4(1H)-one trifluoroacetate | 292.9 | 1H NMR (400 MHz, DMSO-d6): δ 12.99 (br, 1H), 8.27 (s, 1H), 7.81 (br, 3H), 7.74 (s, 1H), 5.96 (s, 1H), 3.96-4.02 (m, 5H), 3.00 (m, 2H), 2.38 (s, 3H). |
| 20 | 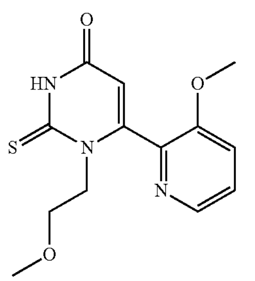 | 1-(2-methoxyethyl)-6-(3-methoxypyridin-2-yl)-2-thioxo-2,3-dihydropyrimidin-4(1H)-one | 294.0 | 1H NMR (400 MHz, CHLOROFORM-d) δ ppm 8.30 (dd, J = 4.81, 1.14 Hz, 1 H), 7.43 (dd, J = 8.70, 4.58 Hz, 1 H), 7.35 (dd, J = 8.70, 1.37 Hz, 1 H), 5.92 (s, 1 H), 4.33 (br. s., 2 H), 3.88 (s, 3 H), 3.55 (t, J = 6.41 Hz, 2 H), 3.13 (s, 3 H) |
| 21 | 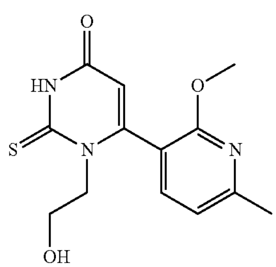 [SMILES: COc1nc(C)ccc1-c1cc(=O)[nH]c(=S)n1CCO] | 1-(2-hydroxyethyl)-6-(2-methoxy-6-methylpyridin-3-yl)-2-thioxo-2,3-dihydropyrimidin-4(1H)-one | 294.1 | 1H NMR (400 MHz, DMSO-d6) δ ppm 12.73 (br. s., 1 H), 7.62 (d, J = 7.56 Hz, 1 H), 6.97 (d, J = 7.33 Hz, 1 H), 5.76 (s, 1 H), 4.69 (t, J = 5.38 Hz, 1 H), 4.43-4.55 (m, 1 H), 3.86 (s, 3 H), 3.44-3.60 (m, 3 H), 2.43 (s, 3 H) |
| 22 | 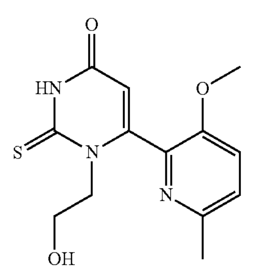 | 1-(2-hydroxyethyl)-6-(3-methoxy-6-methylpyridin-2-yl)-2-thioxo-2,3-dihydropyrimidin-4(1H)-one | 294.1 | 1H NMR (400 MHz, CHLOROFORM-d) δ ppm 7.33 (d, J = 8.47 Hz, 1 H), 7.29 (d, J = 8.47 Hz, 1 H), 5.93 (s, 1 H), 4.18-4.35 (m, 2 H), 3.91-3.98 (m, 2 H), 3.84 (s, 3 H), 2.54 (s, 3 H) |
| 23 | 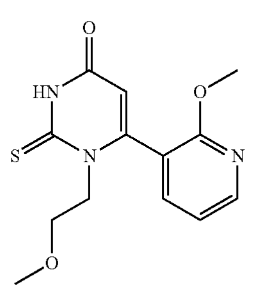 [SMILES: COCCn1c(-c2cccnc2OC)cc(=O)[nH]c1=S] | 1-(2-methoxyethyl)-6-(2-methoxypyridin-3-yl)-2-thioxo-2,3-dihydropyrimidin-4(1H)-one | 294.2 | 1H NMR (400 MHz, CHLOROFORM-d) δ ppm 9.76 (br. s, 1 H), 8.32 (dd, J = 5.04, 1.83 Hz, 1 H), 7.56 (dd, J = 7.33, 1.83 Hz, 1 H), 7.03 (dd, J = 7.33, 5.04 Hz, 1 H), 5.80 (s, 1 H), 4.76 (dt, J = 13.74, 3.43 Hz, 1 H), 3.99 (s, 3 H), 3.69-3.86 (m, 2 H), 3.40 (dt, J = 10.00, 4.20 Hz, 1 H), 3.15 (s, 3 H) |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 24 | 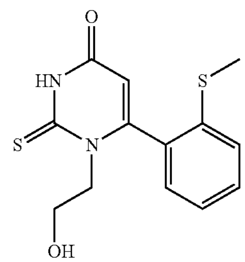 | 1-(2-hydroxyethyl)-6-[2-(methylthio)phenyl]-2-thioxo-2,3-dihydropyrimidin-4(1H)-one | 295.0 | 1H NMR (400 MHz, CHLOROFORM-d) δ ppm 9.54 (br. s, 1 H), 7.44-7.52 (m, 1 H), 7.30 (d, J = 8.01 Hz, 1 H), 7.25-7.27 (m, 2 H), 5.85 (s, 1 H), 4.71 (dt, J = 13.74, 5.38 Hz, 1 H), 3.88 (td, J = 11.28, 5.38 Hz, 1 H), 3.80 (dt, J = 13.74, 5.95 Hz, 1 H), 3.70 (td, J = 11.05, 5.15 Hz, 1 H), 2.49 (s, 3 H), 1.87 (t, J = 5.72 Hz, 1 H) |
| 25 | 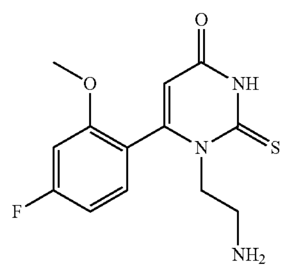 [SMILES: COc1cc(F)ccc1-c1cc(=O)[nH]c(=S)n1CCN] | 1-(2-aminoethyl)-6-(4-fluoro-2-methoxyphenyl)-2-thioxo-2,3-dihydropyrimidin-4(1H)-one hydrochloride | 296.0 | $^1$H NMR (400 MHz, DMSO-d6) δ ppm 12.89 (s, 1 H), 7.80 (br. s., 3 H), 7.44 (dd, J = 8.39, 6.64 Hz, 1 H), 7.18 (dd, J = 11.22, 2.24 Hz, 1 H), 6.97 (ddd, J = 8.40, 8.40, 2.20 Hz, 1 H), 5.82 (s, 1 H), 4.54-4.66 (m, 1 H), 3.86 (s, 3 H), 3.79-3.85 (m, 1 H), 2.88 (br. s, 2 H) |
| 26 | 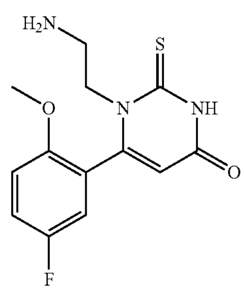 [SMILES: COc1ccc(F)cc1-c1cc(=O)[nH]c(=S)n1CCN] | 1-(2-aminoethyl)-6-(5-fluoro-2-methoxyphenyl)-2-thioxo-2,3-dihydropyrimidin-4(1H)-one hydrochloride | 296.2 | 1H NMR (400 MHz, DMSO-d6) δ ppm 12.91 (s, 1 H), 7.88 (br. s., 3 H), 7.42 (td, J = 8.78, 3.12 Hz, 1 H), 7.34 (dd, J = 8.20, 3.12 Hz, 1 H), 7.23 (dd, J = 9.27, 4.20 Hz, 1 H), 5.88 (d, J = 1.95 Hz, 1 H), 4.53-4.63 (m, 1 H), 3.85-3.93 (m, 1 H), 3.83 (s, 3 H), 2.85-2.99 (m, 2 H) |
| 27 | 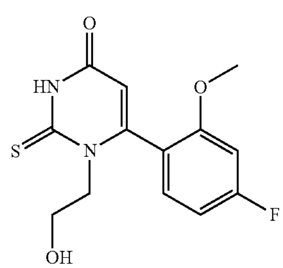 [SMILES: COc1cc(F)ccc1-c1cc(=O)[nH]c(=S)n1CCO] | 6-(4-fluoro-2-methoxyphenyl)-1-(2-hydroxyethyl)-2-thioxo-2,3-dihydropyrimidin-4(1H)-one | 297.0 | 1H NMR (400 MHz, METHANOL-d4) δ ppm 7.33 (dd, J = 8.39, 6.44 Hz, 1 H), 6.95 (dd, J = 10.83, 2.24 Hz, 1 H), 6.82 (ddd, J = 8.40, 8.40, 2.30 Hz, 1 H), 5.73 (s, 1 H), 4.57-4.69 (m, 1 H), 3.87 (s, 3 H), 3.67-3.83 (m, 2 H), 3.55-3.62 (m, 1 H) |
| 28 | 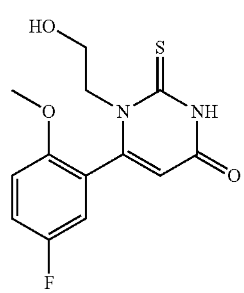 [SMILES: COc1ccc(F)cc1-c1cc(=O)[nH]c(=S)n1CCO] | 6-(5-fluoro-2-methoxyphenyl)-1-(2-hydroxyethyl)-2-thioxo-2,3-dihydropyrimidin-4(1H)-one | 297.3 | 1H NMR (500 MHz, DMSO-d6) δ ppm 12.77 (br. s., 1 H), 7.37 (ddd, J = 8.70, 8.70, 2.90 Hz, 1 H), 7.26 (dd, J = 8.42, 3.05 Hz, 1 H), 7.18 (dd, J = 9.03, 4.15 Hz, 1 H), 5.82 (d, J = 1.71 Hz, 1 H), 4.45-4.54 (m, 1 H), 3.82 (s, 3 H), 3.50-3.64 (m, 2 H), 3.40-3.47 (m, 1 H) |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 29 | 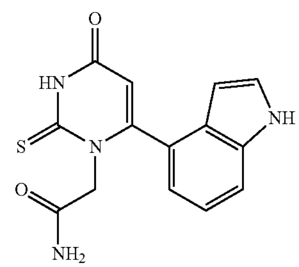 [SMILES: NC(=O)Cn1c(-c2cccc3[nH]ccc23)cc(=O)[nH]c1=S] | 2-[6-(1H-indol-4-yl)-4-oxo-2-thioxo-3,4-dihydropyrimidin-1(2H)-yl]acetamide | 301.0 | 1H NMR (400 MHz, DMSO-d6) δ ppm 12.81 (br. s., 1 H), 11.49 (br. s, 1 H), 7.54 (d, J = 8.31 Hz, 1 H), 7.49 (br. s., 1 H), 7.27 (br. s., 1 H), 7.17 (t, J = 7.83 Hz, 1 H), 6.99 (d, J = 7.34 Hz, 1 H), 6.96 (br. s., 1 H), 6.36 (br. s., 1 H), 5.84 (s, 1 H), 5.16-5.34 (m, 1 H), 3.77-3.96 (m, 1 H) |
| 30 | 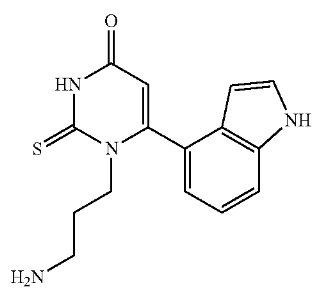 [SMILES: NCCCn1c(-c2cccc3[nH]ccc23)cc(=O)[nH]c1=S] | 1-(3-aminopropyl)-6-(1H-indol-4-yl)-2-thioxo-2,3-dihydropyrimidin-4(1H)-one trifluoroacetate | 301.1 | 1H NMR (300 MHz, METHANOL-d4) δ ppm 7.60 (d, J = 8.36 Hz, 1 H), 7.43 (d, J = 3.14 Hz, 1 H), 7.28 (t, J = 7.66 Hz, 1 H), 7.12 (d, J = 6.97 Hz, 1 H), 6.37 (d, J = 2.09 Hz, 1 H), 5.92 (s, 1 H), 4.49-4.63 (m, 1 H), 3.94-4.09 (m, 1 H), 2.63 (t, J = 7.84 Hz, 2 H), 1.79-2.05 (m, 2 H) |
| 31 | 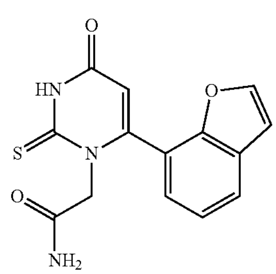 [SMILES: NC(=O)Cn1c(-c2cccc3ccoc23)cc(=O)[nH]c1=S] | 2-[6-(1-benzofuran-7-yl)-4-oxo-2-thioxo-3,4-dihydropyrimidin-1(2H)-yl]acetamide | 301.9 | 1H NMR (300 MHz, METHANOL-d4) δ ppm 7.88 (d, J = 2.09 Hz, 1 H), 7.80-7.84 (m, 1 H), 7.34-7.38 (m, 2 H), 6.99 (d, J = 2.26 Hz, 1 H), 5.98 (s, 1 H) |
| 32 | 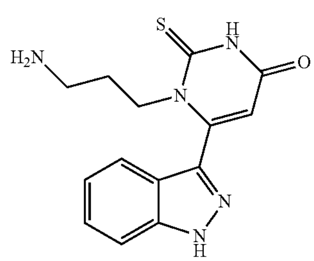 [SMILES: NCCCn1c(-c2n[nH]c3ccccc23)cc(=O)[nH]c1=S] | 1-(3-aminopropyl)-6-(1H-indazol-3-yl)-2-thioxo-2,3-dihydropyrimidin-4(1H)-one formate | 302.1 | 1.36 min Waters Atlantis dC18 5 um 4.6 × 50 mm, 95% H2O/5% MeCN linear to 5% H2O/95% MeCN over 4.0 min, HOLD at 5% H2O/95% MeCN to 5.0 min. (0.05% TFA). Flow rate: 2 mL/min |
| 33 | 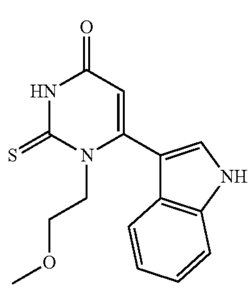 [SMILES: COCCn1c(-c2c[nH]c3ccccc23)cc(=O)[nH]c1=S] | 6-(1H-indol-3-yl)-1-(2-methoxyethyl)-2-thioxo-2,3-dihydropyrimidin-4(1H)-one | 302.1 | 1H NMR (400 MHz, METHANOL-d3) δ ppm 7.63 (s, 1 H), 7.45 (t, J = 8.01 Hz, 2 H), 7.22 (t, J = 7.79 Hz, 1 H), 7.16 (t, J = 7.33 Hz, 1 H), 5.92 (s, 1 H), 4.64 (br. s., 2 H), 3.60 (t, J = 5.72 Hz, 2 H), 3.03 (s, 3 H) |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 34 | 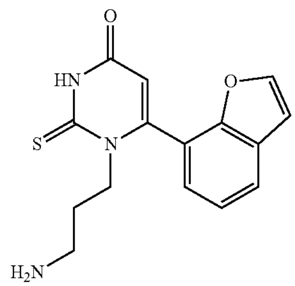 [SMILES: NCCCn1c(-c2cccc3ccoc23)cc(=O)[nH]c1=S] | 1-(3-aminopropyl)-6-(1-benzofuran-7-yl)-2-thioxo-2,3-dihydropyrimidin-4(1H)-one hydrochloride | 302.1 | 1H NMR (400 MHz, METHANOL-d4) δ ppm 7.91 (d, J = 1.96 Hz, 1 H), 7.88 (dd, J = 6.85, 2.45 Hz, 1 H), 7.41-7.46 (m, 2 H), 7.03 (d, J = 1.96 Hz, 1 H), 5.98 (s, 1 H), 4.48-4.60 (m, 1 H), 3.87-4.00 (m, 1 H), 2.67 (t, J = 7.83 Hz, 2 H), 1.83-1.98 (m, 2 H) |
| 35 | 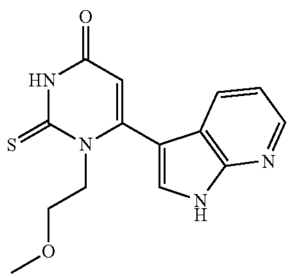 [SMILES: COCCn1c(-c2c[nH]c3ncccc23)cc(=O)[nH]c1=S] | 1-(2-methoxyethyl)-6-(1H-pyrrolo[2,3-b]pyridin-3-yl)-2-thioxo-2,3-dihydropyrimidin-4(1H)-one | 303.1 | 1H NMR (400 MHz, DMSO-d6) δ ppm 12.30 (br. s., 1 H), 8.30 (dd, J = 4.81, 1.60 Hz, 1 H), 7.94 (dd, J = 8.01, 1.60 Hz, 1 H), 7.89 (s, 1 H), 7.17 (dd, J = 7.79, 4.58 Hz, 1 H), 5.87 (s, 1 H), 4.44 (br. s., 2 H), 3.45 (t, J = 5.95 Hz, 2 H), 2.92 (s, 3 H) |
| 36 | 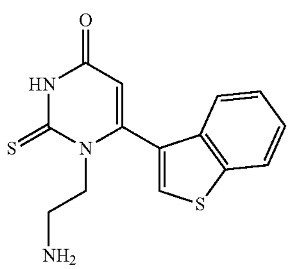 [SMILES: NCCn1c(-c2csc3ccccc23)cc(=O)[nH]c1=S] | 1-(2-aminoethyl)-6-(1-benzothien-3-yl)-2-thioxo-2,3-dihydropyrimidin-4(1H)-one hydrochloride | 304.0 | 1H NMR (400 MHz, D2O) δ ppm 7.92-7.94 (m, 1H), 7.82 (s, 1H), 7.51-7.48 (m, 1H), 7.39-7.37 (m, 2H), 5.99 (s, 1H), 4.72-4.71 (m, 1H), 4.05-3.99 (m, 1H), 3.01-2.94 (m, 2H) |
| 37 | 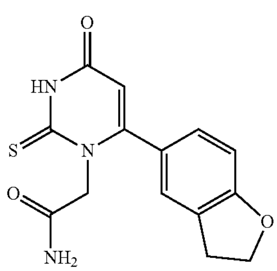 [SMILES: NC(=O)Cn1c(-c2ccc3c(c2)CCO3)cc(=O)[nH]c1=S] | 2-[6-(2,3-dihydro-1-benzofuran-5-yl)-4-oxo-2-thioxo-3,4-dihydropyrimidin-1(2H)-yl]acetamide | 304.0 | 1H NMR (300 MHz, DMSO-d6) δ ppm 12.74 (br. s., 1 H), 7.45 (br. s., 1 H), 7.29 (br. s, 1 H), 7.09-7.17 (m, 2 H), 6.85 (d, J = 8.36 Hz, 1 H), 5.75 (s, 1 H), 4.59 (t, J = 8.62 Hz, 1 H), 3.20 (t, J = 8.88 Hz, 2 H) |
| 38 | 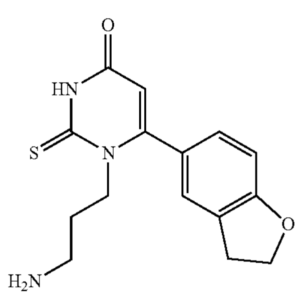 [SMILES: NCCCn1c(-c2ccc3c(c2)CCO3)cc(=O)[nH]c1=S] | 1-(3-aminopropyl)-6-(2,3-dihydro-1-benzofuran-5-yl)-2-thioxo-2,3-dihydropyrimidin-4(1H)-one hydrochloride | 304.1 | 1H NMR (300 MHz, DMSO-d6) δ ppm 12.74 (s, 1 H), 7.81 (br. s., 3 H), 7.37 (s, 1 H), 7.23 (dd, J = 8.36, 2.09 Hz, 1 H), 6.88 (d, J = 8.36 Hz, 1 H), 5.76 (d, J = 2.79 Hz, 1 H), 4.61 (t, J = 8.71 Hz, 2 H), 4.10 (t, J = 6.97 Hz, 2 H), 3.25 (t, J = 8.71 Hz, 2 H), 2.53-2.61 (m, 2 H), 1.79-1.93 (m, 2 H) |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 39 | 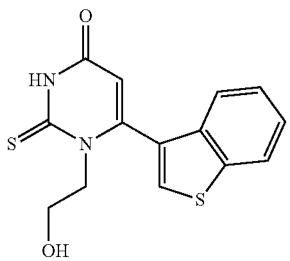 [SMILES: O=c1cc(-c2csc3ccccc23)n(CCO)c(=S)[nH]1] | 6-(1-benzothien-3-yl)-1-(2-hydroxyethyl)-2-thioxo-2,3-dihydropyrimidin-4(1H)-one | 305.0 | 1H NMR (400 MHz, METHANOL-d4) 7.97 (d, 1H), 7.92 (s, 1H), 7.61 (dd, 1H), 7.46-7.45 (m, 2H), 5.92 (s, 1H), 4.65-4.63 (m, 1H), 3.90-3.85 (m, 1H), 3.84-3.80 (m, 1H), 3.62-3.61 (m, 1H) |
| 40 | 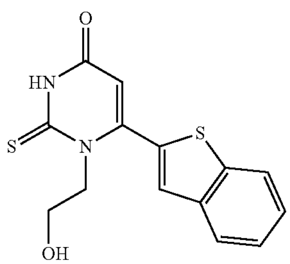 [SMILES: O=c1cc(-c2cc3ccccc3s2)n(CCO)c(=S)[nH]1] | 6-(1-benzothien-2-yl)-1-(2-hydroxyethyl)-2-thioxo-2,3-dihydropyrimidin-4(1H)-one | 305.0 | 1H NMR (400 MHz, DMSO-d6) δ ppm 12.82 (br. s., 1 H), 8.02-8.06 (m, 1 H), 7.89-7.94 (m, 1 H), 7.74 (s, 1 H), 7.41-7.47 (m, 2 H), 6.06 (d, J = 2.29 Hz, 1 H), 4.86 (t, J = 6.18 Hz, 1 H), 4.31 (t, J = 6.18 Hz, 2 H), 3.63 (td, J = 6.40, 6.40 Hz, 2 H) |
| 41 | 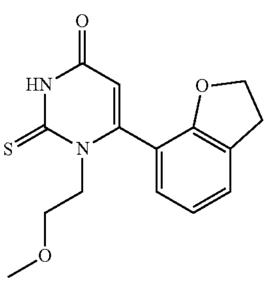 [SMILES: COCCn1c(-c2cccc3c2OCC3)cc(=O)[nH]c1=S] | 6-(2,3-dihydro-1-benzofuran-7-yl)-1-(2-methoxyethyl)-2-thioxo-2,3-dihydropyrimidin-4(1H)-one | 305.1 | 1H NMR (400 MHz, CHLOROFORM-d) δ ppm 9.89 (br. s., 1 H), 7.31 (d, J = 7.33 Hz, 1 H), 7.03 (d, J = 7.56 Hz, 1 H), 6.93 (t, J = 7.56 Hz, 1 H), 5.84 (s, 1 H), 4.68-4.81 (m, 1 H), 4.63 (t, J = 8.70 Hz, 2 H), 3.95-4.05 (m, 1 H), 3.67 (br. s., 1 H), 3.48 (br. s, 1 H), 3.28 (t, J = 8.70 Hz, 2 H), 3.14 (s, 3 H) |
| 42 | 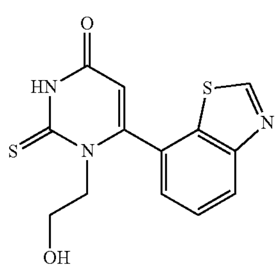 [SMILES: O=c1cc(-c2cccc3ncsc23)n(CCO)c(=S)[nH]1] | 6-(1,3-benzothiazol-7-yl)-1-(2-hydroxyethyl)-2-thioxo-2,3-dihydropyrimidin-4(1H)-one | 305.9 | 1H NMR (400 MHz, DMSO-d6) δ ppm 12.91 (s, 1 H) 9.50 (s, 1 H) 8.24 (d, J = 7.34 Hz, 1 H) 7.71 (dd, J = 7.83, 7.34 Hz, 1 H) 7.65 (d, J = 7.83 Hz, 1 H) 6.03 (s, 1 H) 4.72 (t, J = 5.62 Hz, 1 H) 4.22-4.31 (m, 1 H) 3.86-3.96 (m, 1 H) 3.43-3.56 (m, 2 H) |
| 43 | 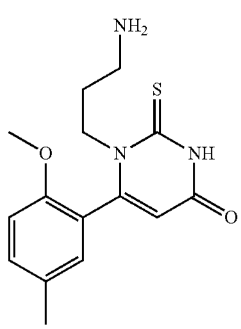 [SMILES: COc1ccc(C)cc1-c1cc(=O)[nH]c(=S)n1CCCN] | 1-(3-aminopropyl)-6-(2-methoxy-5-methylphenyl)-2-thioxo-2,3-dihydropyrimidin-4(1H)-one hydrochloride | 306.1 | $^1$H NMR (500 MHz, DMSO-d6) δ ppm 12.79 (s, 1 H), 7.92 (br. s., 3 H), 7.34 (dd, J = 8.29, 1.22 Hz, 1 H), 7.19 (d, J = 1.46 Hz, 1 H), 7.08 (d, J = 8.54 Hz, 1 H), 5.78 (d, J = 1.46 Hz, 1 H), 4.38 (br. s., 1 H), 3.62 (br. s., 1 H), 3.34 (s, 3 H), 2.47-2.56 (m, 2 H), 2.30 (s, 3 H), 1.84 (s, 1 H), 1.69-1.79 (m, 1 H) |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 44 | 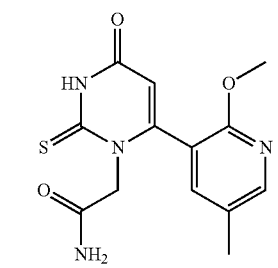 | 2-[6-(2-methoxy-5-methylpyridin-3-yl)-4-oxo-2-thioxo-3,4-dihydropyrimidin-1(2H)-yl]acetamide | 306.7 | 1H NMR (400 MHz, DMSO-d6): δ 12.82 (br.s., 1H), 8.14 (s, 1H), 7.71 (s, 1H), 7.44 (s, 1H), 7.31 (s, 1H), 7.02 (s, 1H), 5.86 (s, 1H), 5.50 (br.s., 1H), 3.87 (s, 4H), 2.20 (s, 3H). |
| 45 | 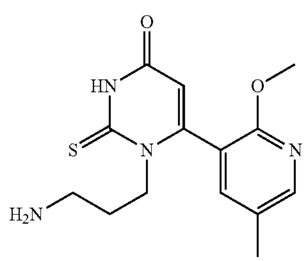 [SMILES: COc1ncc(C)cc1-c1cc(=O)[nH]c(=S)n1CCCN] | 1-(3-aminopropyl)-6-(2-methoxy-5-methylpyridin-3-yl)-2-thioxo-2,3-dihydropyrimidin-4(1H)-one trifluoroacetate | 306.9 | 1H NMR (400 MHz, DMSO-d6): δ 12.82 (s, 1H), 8.20 (s, 1H), 7.71 (s, 1H), 7.60 (br.s., 2H), 5.90 (s, 1H), 4.35-4.45 (m, 1H), 3.97 (s, 3H), 3.58-3.65 (m, 1H), 2.50-2.65 (m, 2H), 2.30 (s, 3H), 1.90-1.65 (m, 2H). |
| 46 | 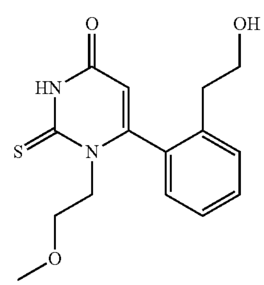 [SMILES: COCCn1c(-c2ccccc2CCO)cc(=O)[nH]c1=S] | 6-[2-(2-hydroxyethyl)phenyl]-1-(2-methoxyethyl)-2-thioxo-2,3-dihydropyrimidin-4(1H)-one | 307.1 | 1H NMR (400 MHz, CHLOROFORM-d) δ ppm 9.44 (br. s., 1 H), 7.44-7.52 (m, 1 H), 7.41 (d, J = 7.10 Hz, 1 H), 7.34 (dd, J = 7.79, 6.87 Hz, 1 H), 7.23-7.25 (m, 1 H), 5.84 (s, 1 H), 4.48 (dt, J = 13.68, 5.07 Hz, 1 H), 3.81-3.99 (m, 3 H), 3.65 (ddd, J = 10.25, 6.93, 5.27 Hz, 1 H), 3.58 (dt, J = 10.36, 5.24 Hz, 1 H), 3.16 (s, 3 H), 2.83 (dt, J = 14.25, 6.96 Hz, 1 H), 2.72 (dt, J = 14.20, 7.00 Hz, 1 H) |
| 47 | 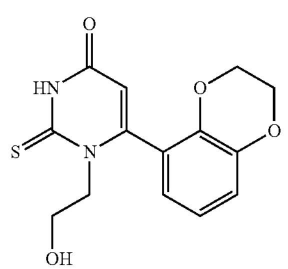 [SMILES: O=c1cc(-c2cccc3c2OCCO3)n(CCO)c(=S)[nH]1] | 6-(2,3-dihydro-1,4-benzodioxin-5-yl)-1-(2-hydroxyethyl)-2-thioxo-2,3-dihydropyrimidin-4(1H)-one | 307.1 | 1H NMR (400 MHz, CHLOROFORM-d) δ ppm 9.57 (br. s., 1 H), 7.02 (dd, J = 8.24, 1.37 Hz, 1 H), 6.94 (dd, J = 7.90, 7.90 Hz, 1 H), 6.80 (dd, J = 7.56, 1.37 Hz, 1 H), 5.87 (s, 1 H), 4.73 (dt, J = 14.14, 5.52 Hz, 1 H), 4.30 (s, 4 H), 3.97 (dt, J = 14.31, 5.78 Hz, 1 H), 3.83-3.92 (m, 1 H), 3.67-3.78 (m, 1 H) |
| 48 | 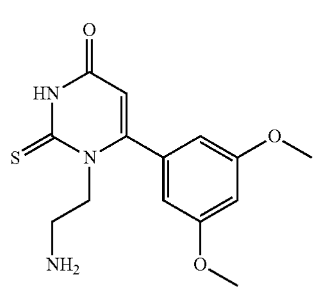 [SMILES: COc1cc(OC)cc(-c2cc(=O)[nH]c(=S)n2CCN)c1] | 1-(2-aminoethyl)-6-(3,5-dimethoxyphenyl)-2-thioxo-2,3-dihydropyrimidin-4(1H)-one hydrochloride | 308.0 | 3.442 min Column: XBRIDGE-C18 4.6 × 75 mm 3.5 μm; Mobile phase-A = 0.1% TFA IN ACN, B = 0.1% TFA IN WATER; Time(min)/% B = 0/90, 0.8/90, 1.8/55, 3/5, 6.5/5, 7/90; Flow: 0.8 mL/min, Column Temp = 40° C.; Diluent: CAN |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 49 | 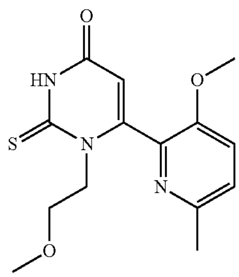 | 1-(2-methoxyethyl)-6-(3-methoxy-6-methylpyridin-2-yl)-2-thioxo-2,3-dihydropyrimidin-4(1H)-one | 308.1 | 1H NMR (400 MHz, CHLOROFORM-d) δ ppm 9.41 (br. s., 1 H), 7.25-7.27 (m, 2 H), 5.90 (s, 1 H), 4.22-4.38 (m, 2 H), 3.84 (s, 3 H), 3.57 (t, J = 6.41 Hz, 2 H), 3.15 (s, 3 H), 2.53 (s, 3 H) |
| 50 | 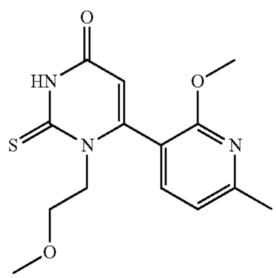 [SMILES: COCCn1c(-c2ccc(C)nc2OC)cc(=O)[nH]c1=S] | 1-(2-methoxyethyl)-6-(2-methoxy-6-methylpyridin-3-yl)-2-thioxo-2,3-dihydropyrimidin-4(1H)-one | 308.1 | 1H NMR (400 MHz, METHANOL-d3) δ ppm 7.56 (d, J = 7.56 Hz, 1 H), 6.94 (d, J = 7.33 Hz, 1 H), 5.74 (s, 1 H), 4.72 (dt, J = 13.57, 3.86 Hz, 1 H), 3.95 (s, 3 H), 3.67-3.83 (m, 2 H), 3.35-3.43 (m, 1 H), 3.11 (s, 3 H), 2.49 (s, 3 H) |
| 51 | 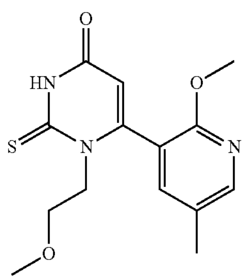 [SMILES: COCCn1c(-c2cc(C)cnc2OC)cc(=O)[nH]c1=S] | 1-(2-methoxyethyl)-6-(2-methoxy-5-methylpyridin-3-yl)-2-thioxo-2,3-dihydropyrimidin-4(1H)-one | 308.1 | 1H NMR (400 MHz, METHANOL-d3) δppm 8.11 (s, 1 H), 7.56 (d, J = 2.06 Hz, 1 H), 5.76 (s, 1 H), 4.64-4.76 (m, 1 H), 3.94 (s, 3 H), 3.68-3.82 (m, 2 H), 3.35-3.44 (m, 1 H), 3.10 (s, 3 H), 2.30 (s, 3 H) |
| 52 | 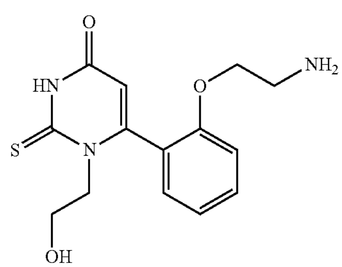 [SMILES: NCCOc1ccccc1-c1cc(=O)[nH]c(=S)n1CCO] | 6-[2-(2-aminoethoxy)phenyl]-1-(2-hydroxyethyl)-2-thioxo-2,3-dihydropyrimidin-4(1H)-one formate | 308.2 | 2.14 min Waters Atlantis dC18 5 um 4.6 × 50 mm, 95% H2O/5% MeCN linear to 5% H2O/95% MeCN over 4.0 min, HOLD at 5% H2O/95% MeCN to 5.0 min. (0.05% TFA). Flow rate: 2 mL/min |
| 53 | 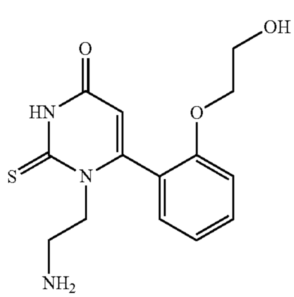 [SMILES: NCCn1c(-c2ccccc2OCCO)cc(=O)[nH]c1=S] | 1-(2-aminoethyl)-6-[2-(2-hydroxyethoxy)phenyl]-2-thioxo-2,3-dihydropyrimidin-4(1H)-one hydrochloride | 308.2 | 1H NMR (400 MHz, CD3OD) δ 3.09 (ddd, J = 12.9, 7.6, 6.1 Hz, 1 H), 3.19 (ddd, J = 12.9, 7.6, 6.5 Hz, 1 H), 3.81-3.91 (m, 2 H), 4.16 (ddd, J = 10.6, 4.7, 3.5 Hz, 1 H), 4.22 (ddd, J = 10.8, 6.1, 3.9 Hz, 1 H), 4.26-4.37 (m, 1 H), 4.60-4.74 (m, 1 H), 5.84 (s, 1 H), 7.15 (td, J = 7.5, 1.0 Hz, 1 H), 7.23 (dd, J = 8.4, 0.6 Hz, 1 H), 7.36 (dd, J = 7.4, 1.6 Hz, 1 H), 7.57 (ddd, J = 8.5, 7.5, 1.8 Hz, 1 H) |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 54 | 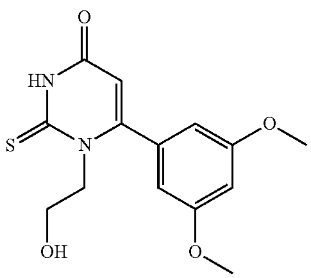 [SMILES: COc1cc(OC)cc(-c2cc(=O)[nH]c(=S)n2CCO)c1] | 6-(3,5-dimethoxyphenyl)-1-(2-hydroxyethyl)-2-thioxo-2,3-dihydropyrimidin-4(1H)-one | 309.1 | 1H NMR (300 MHz, DMSO-d6) δ ppm 12.72 (br. s, 1 H), 6.67 (d, J = 2.26 Hz, 2 H), 6.62 (t, J = 2.30 Hz, 1 H), 5.76 (d, J = 2.26 Hz, 1 H), 4.77 (t, J = 5.57 Hz, 1 H), 4.14 (t, J = 6.45 Hz, 2 H), 3.78 (s, 6 H), 3.57 (td, J = 5.90 Hz, 2 H) |
| 55 | 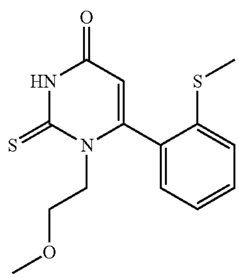 | 1-(2-methoxyethyl)-6-[2-(methylthio)phenyl]-2-thioxo-2,3-dihydropyrimidin-4(1H)-one | 309.1 | 1H NMR (400 MHz, CHLOROFORM-d) δ ppm 9.66 (br. s, 1 H), 7.40-7.50 (m, 1 H), 7.28 (d, J = 8.01 Hz, 1 H), 7.24 (d, J = 6.64 Hz, 2 H), 5.82 (s, 1 H), 4.59-4.71 (m, 1 H), 3.68-3.81 (m, 2 H), 3.41-3.51 (m, 1 H), 3.15 (s, 3 H), 2.48 (s, 3 H) |
| 56 | 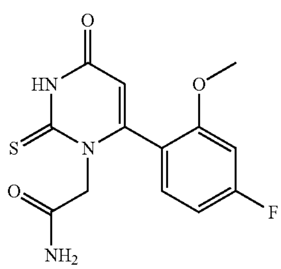 | 2-[6-(4-fluoro-2-methoxyphenyl)-4-oxo-2-thioxo-3,4-dihydropyrimidin-1(2H)-yl]acetamide | 310.0 | 1H NMR (400 MHz, DMSO-d6) δ ppm 12.78 (s, 1 H), 7.27 (br. s., 1 H), 7.17 (dd, J = 8.30, 6.93 Hz, 1 H), 7.08 (dd, J = 11.13, 2.15 Hz, 1 H), 6.97 (br. s., 1 H), 6.86 (td, J = 8.44, 2.24 Hz, 1 H), 5.78 (d, J = 2.15 Hz, 1 H), 5.36 (br. s., 2 H), 3.28 (s, 3 H) |
| 57 | 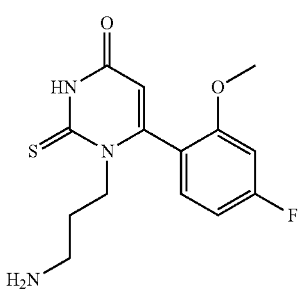 [SMILES: COc1cc(F)ccc1-c1cc(=O)[nH]c(=S)n1CCCN] | 1-(3-aminopropyl)-6-(4-fluoro-2-methoxyphenyl)-2-thioxo-2,3-dihydropyrimidin-4(1H)-one hydrochloride | 310.0 | 1H NMR (400 MHz, METHANOL-d4) δppm 7.36 (dd, J = 8.39, 6.44 Hz, 1 H), 7.01 (dd, J = 10.83, 2.24 Hz, 1 H), 6.85 (td, J = 8.30, 2.34 Hz, 1 H), 5.79 (s, 1 H), 4.51-4.63 (m, 1 H), 3.89 (s, 3 H), 3.69-3.81 (m, 1 H), 2.76 (t, J = 7.81 Hz, 2 H), 1.93-2.07 (m, 1 H), 1.74-1.88 (m, 1 H) |
| 58 | 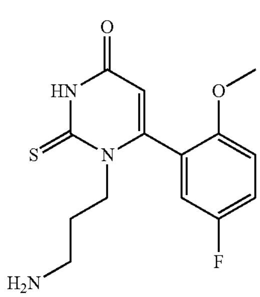 [SMILES: COc1ccc(F)cc1-c1cc(=O)[nH]c(=S)n1CCCN] | 1-(3-aminopropyl)-6-(5-fluoro-2-methoxyphenyl)-2-thioxo-2,3-dihydropyrimidin-4(1H)-one hydrochloride | 310.0 | 1H NMR (400 MHz, METHANOL-d4) δ ppm 7.31 (td, J = 8.59, 3.12 Hz, 1 H), 7.14-7.23 (m, 2 H), 5.81 (s, 1 H), 4.51-4.64 (m, 1 H), 3.87 (s, 3 H), 3.73-3.83 (m, 1 H), 2.77 (t, J = 7.71 Hz, 2 H), 1.95-2.09 (m, 1 H), 1.77-1.91 (m, 1 H) |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 59 | 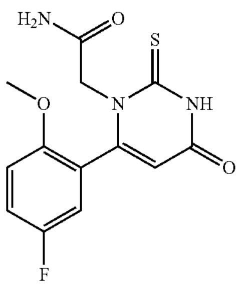 [SMILES: COc1ccc(F)cc1-c1cc(=O)[nH]c(=S)n1CC(N)=O] | 2-[6-(5-fluoro-2-methoxyphenyl)-4-oxo-2-thioxo-3,4-dihydropyrimidin-1(2H)-yl]acetamide | 310.0 | 1H NMR (500 MHz, DMSO-d6) δ ppm 3.35 (br. s., 2 H) 3.83 (s, 3 H) 5.85-5.90 (m, 1 H) 7.03 (d, J = 7.56 Hz, 1 H) 7.07 (br. s., 1 H) 7.19 (dd, J = 9.15, 4.27 Hz, 1 H) 7.33 (br. s., 1 H) 7.38 (td, J = 8.72, 3.05 Hz, 1 H) 12.85 (br. s., 1 H) |
| 60 | 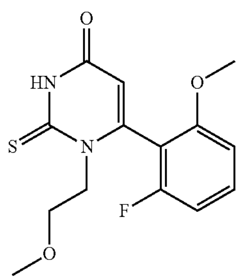 [SMILES: COCCn1c(-c2c(F)cccc2OC)cc(=O)[nH]c1=S] | 6-(2-fluoro-6-methoxyphenyl)-1-(2-methoxyethyl)-2-thioxo-2,3-dihydropyrimidin-4(1H)-one | 311.1 | 1H NMR (400 MHz, CHLOROFORM-d) δ ppm 10.08 (br. s., 1 H), 7.44 (ddd, J = 8.30, 8.30, 6.80 Hz, 1 H), 6.82 (t, J = 8.47 Hz, 1 H), 6.77 (d, J = 8.47 Hz, 1 H), 5.88 (s, 1 H), 4.49-4.65 (m, 1 H), 3.88-3.97 (m, 1 H), 3.85 (s, 3 H), 3.56-3.66 (m, 1 H), 3.45-3.54 (m, 1 H), 3.16 (s, 3 H) |
| 61 | 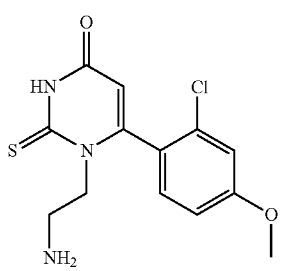 [SMILES: COc1ccc(-c2cc(=O)[nH]c(=S)n2CCN)c(Cl)c1] | 1-(2-aminoethyl)-6-(2-chloro-4-methoxyphenyl)-2-thioxo-2,3-dihydropyrimidin-4(1H)-one hydrochloride | 311.9 | 1H NMR (300 MHz, DMSO-d6) δ ppm 12.99 (br. s., 1 H), 7.74 (br. s., 3 H), 7.55 (d, J = 8.36 Hz, 1 H), 7.30 (d, J = 2.09 Hz, 1 H), 7.12 (dd, J = 8.36, 2.09 Hz, 1 H), 5.91 (d, J = 2.09 Hz, 1 H), 4.53-4.71 (m, 1 H), 3.85 (s, 3 H), 3.73-3.84 (m, 1 H), 2.92-3.08 (m, 1 H), 2.77-2.90 (m, 1 H) |
| 62 | 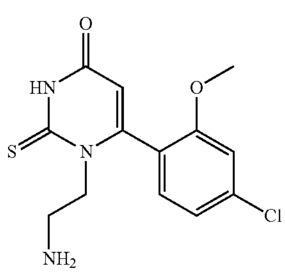 [SMILES: COc1cc(Cl)ccc1-c1cc(=O)[nH]c(=S)n1CCN] | 1-(2-aminoethyl)-6-(4-chloro-2-methoxyphenyl)-2-thioxo-2,3-dihydropyrimidin-4(1H)-one hydrochloride | 312.0 | 1H NMR (400 MHz, METHANOL-d3) δ ppm 7.34 (d, J = 8.24 Hz, 1 H), 7.27 (d, J = 1.60 Hz, 1 H), 7.16 (dd, J = 8.13, 1.72 Hz, 1 H), 5.83 (s, 1 H), 4.68-4.81 (m, 1 H), 4.01-4.12 (m, 1 H), 3.91 (s, 3 H), 2.97-3.16 (m, 2 H) |
| 63 | 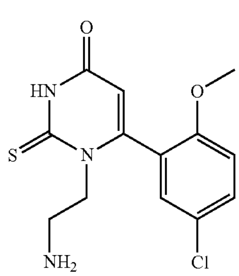 [SMILES: COc1ccc(Cl)cc1-c1cc(=O)[nH]c(=S)n1CCN] | 1-(2-aminoethyl)-6-(5-chloro-2-methoxyphenyl)-2-thioxo-2,3-dihydropyrimidin-4(1H)-one hydrochloride | 312.2 | 1.67 min Waters Atlantis dC18 5 um 4.6 × 50 mm, 95% H2O/5% MeCN linear to 5% H2O/95% MeCN over 4.0 min, HOLD at 5% H2O/95% MeCN to 5.0 min. (0.05% TFA). Flow rate: 2 mL/min |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 64 | 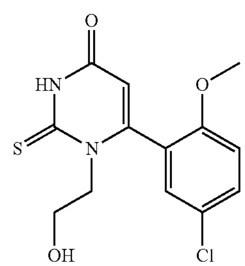 [SMILES: COc1ccc(Cl)cc1-c1cc(=O)[nH]c(=S)n1CCO] | 6-(5-chloro-2-methoxyphenyl)-1-(2-hydroxyethyl)-2-thioxo-2,3-dihydropyrimidin-4(1H)-one | 313.2 | 1H NMR (500 MHz, DMSO-d6) δ ppm 12.76 (br. s., 1 H) 7.57 (dd, J = 8.78, 2.68 Hz, 1 H) 7.42 (d, J = 2.68 Hz, 1 H) 7.19 (d, J = 9.03 Hz, 1 H) 5.83 (d, J = 2.20 Hz, 1 H) 5.18 (br. s., 1 H) 4.44-4.52 (m, 1 H) 3.83 (s, 3 H) 3.56-3.62 (m, 1 H) 3.53 (dt, J = 13.66, 6.83 Hz, 1 H) 3.42 (ddd, J = 10.12, 6.46, 3.90 Hz, 1 H) |
| 65 | 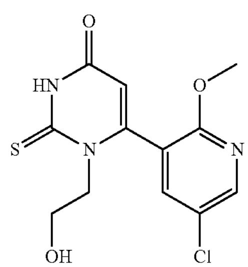 [SMILES: COc1ncc(Cl)cc1-c1cc(=O)[nH]c(=S)n1CCO] | 6-(5-chloro-2-methoxypyridin-3-yl)-1-(2-hydroxyethyl)-2-thioxo-2,3-dihydropyrimidin-4(1H)-one | 314.0 | 1H NMR (400 MHz, DMSO-d6) δ ppm 12.80 (br. s., 1 H), 8.38 (d, J = 2.75 Hz, 1 H), 7.89 (d, J = 2.75 Hz, 1 H), 5.93 (d, J = 2.06 Hz, 1 H), 4.45-4.54 (m, 1 H), 3.89 (s, 3 H), 3.55-3.65 (m, 1 H), 3.36-3.51 (m, 2 H) |
| 66 | 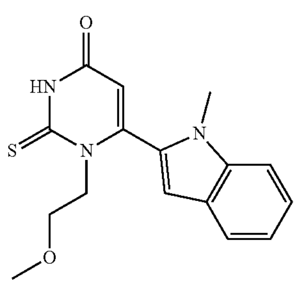 [SMILES: COCCn1c(-c2cc3ccccc3n2C)cc(=O)[nH]c1=S] | 1-(2-methoxyethyl)-6-(1-methyl-1H-indol-2-yl)-2-thioxo-2,3-dihydropyrimidin-4(1H)-one | 316.0 | 1H NMR (400 MHz, CHLOROFORM-d) d ppm 9.90 (br. s, 1 H), 7.67 (d, J = 7.79 Hz, 1 H), 7.31-7.42 (m, 2 H), 7.21 (dd, J = 7.10, 7.10 Hz, 1 H), 6.65 (s, 1 H), 5.98 (s, 1 H), 4.71 (br. s, 1 H), 4.34 (br. s, 1 H), 3.72-3.84 (m, 1 H), 3.69 (s, 3 H), 3.43-3.58 (m, 1 H), 3.11 (s, 3 H) |
| 67 | 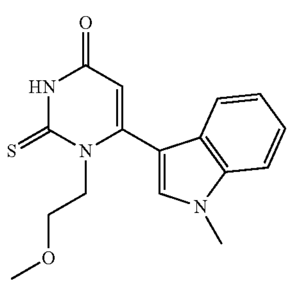 [SMILES: COCCn1c(-c2cn(C)c3ccccc23)cc(=O)[nH]c1=S] | 1-(2-methoxyethyl)-6-(1-methyl-1H-indol-3-yl)-2-thioxo-2,3-dihydropyrimidin-4(1H)-one | 316.1 | 1H NMR (400 MHz, CHLOROFORM-d) δ ppm 9.70 (br. s., 1 H), 7.50 (d, J = 7.79 Hz, 1 H), 7.36-7.43 (m, 2 H), 7.33 (t, J = 7.44 Hz, 1 H), 7.19-7.26 (m, 1 H), 5.99 (s, 1 H), 4.61 (br. s., 2 H), 3.88 (s, 3 H), 3.68 (t, J = 5.50 Hz, 2 H), 3.18 (s, 3 H) |
| 68 | 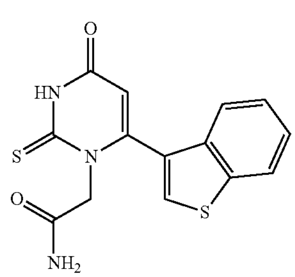 [SMILES: NC(=O)Cn1c(-c2csc3ccccc23)cc(=O)[nH]c1=S] | 2-[6-(1-benzothien-3-yl)-4-oxo-2-thioxo-3,4-dihydropyrimidin-1(2H)-yl]acetamide | 318.0 | 1H NMR (400 MHz, METHANOL-d3) δppm 7.99-8.12 (m, 1 H), 7.92 (s, 1 H), 7.77 (d, J = 6.18 Hz, 1 H), 7.42-7.57 (m, 2 H), 6.02 (s, 1 H), 5.17-5.68 (m, 1 H), 3.77-4.25 (m, 1 H) |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 69 | 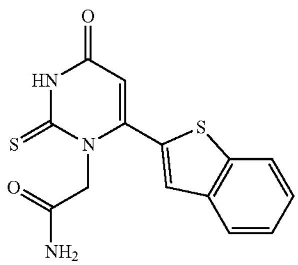 [SMILES: NC(=O)Cn1c(-c2cc3ccccc3s2)cc(=O)[nH]c1=S] | 2-[6-(1-benzothien-2-yl)-4-oxo-2-thioxo-3,4-dihydropyrimidin-1(2H)-yl]acetamide | 318.0 | 1H NMR (400 MHz, DMSO-d6) δ ppm 12.63 (br. s, 1 H), 7.97-8.04 (m, 1 H), 7.86-7.93 (m, 1 H), 7.61 (s, 1 H), 7.40-7.48 (m, 2 H), 7.34 (br. s, 1 H), 6.97 (br. s., 1 H), 6.03-6.11 (m, 1 H), 4.53-5.06 (m, 2 H) |
| 70 | 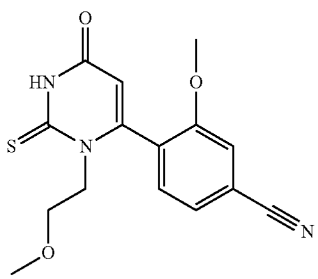 [SMILES: COCCn1c(-c2ccc(C#N)cc2OC)cc(=O)[nH]c1=S] | 3-methoxy-4-[3-(2-methoxyethyl)-6-oxo-2-thioxo-1,2,3,6-tetrahydropyrimidin-4-yl]benzonitrile | 318.1 | 1H NMR (400 MHz, CHLOROFORM-d) δ ppm 9.46 (br. s, 1 H), 7.32-7.42 (m, 2 H), 7.20 (s, 1 H), 5.75 (s, 1 H), 4.71 (dt, J = 14.20, 3.43 Hz, 1 H), 3.90 (s, 3 H), 3.80 (td, J = 9.79, 3.78 Hz, 1 H), 3.64 (ddd, J = 14.20, 9.39, 4.35 Hz, 1 H), 3.36 (ddd, J = 10.30, 4.35, 3.21 Hz, 1 H), 3.14 (s, 3 H) |
| 71 | 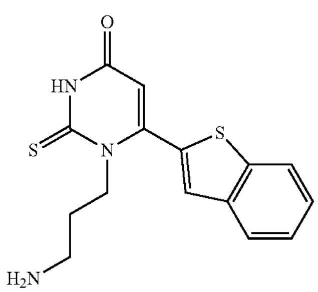 [SMILES: NCCCn1c(-c2cc3ccccc3s2)cc(=O)[nH]c1=S] | 1-(3-aminopropyl)-6-(1-benzothien-2-yl)-2-thioxo-2,3-dihydropyrimidin-4(1H)-one hydrochloride | 318.1 | 1H NMR (300 MHz, DMSO-d6) δ ppm 12.90 (br. s., 1 H), 8.06-8.11 (m, 1 H), 7.95-8.01 (m, 1 H), 7.80 (s, 1 H), 7.73 (br. s., 3 H), 7.47-7.54 (m, 2 H), 6.16 (s, 1 H), 4.22-4.33 (m, 2 H), 2.60-2.70 (m, 2 H), 1.94-2.06 (m, 2 H) |
| 72 | 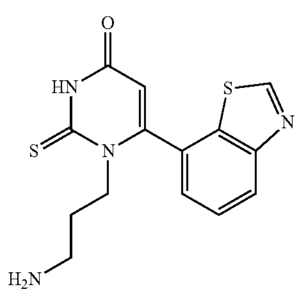 [SMILES: NCCCn1c(-c2cccc3ncsc23)cc(=O)[nH]c1=S] | 1-(3-aminopropyl)-6-(1,3-benzothiazol-7-yl)-2-thioxo-2,3-dihydropyrimidin-4(1H)-one trifluoroacetate | 319.2 | 1H NMR (400 MHz, DMSO-d6) δ ppm 12.98 (s, 1 H), 9.54 (s, 1 H), 8.29 (d, J = 7.34 Hz, 1 H), 7.72 (m, J = 9.78 Hz, 2 H), 7.52 (br. s., 3 H), 6.10 (d, J = 1.96 Hz, 1 H), 4.21-4.31 (m, 1 H), 3.49-3.82 (m, 3 H), 1.68-1.87 (m, 2 H) |
| 73 | 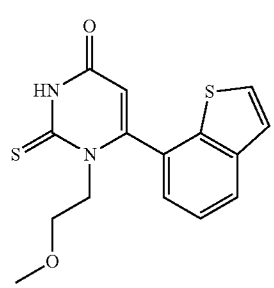 | 6-(1-benzothien-7-yl)-1-(2-methoxyethyl)-2-thioxo-2,3-dihydropyrimidin-4(1H)-one | 319.4 | 1H NMR (400 MHz, CHLOROFORM-d) δ ppm 9.72 (br. s, 1 H), 7.94 (dd, J = 8.01, 0.69 Hz, 1 H), 7.53 (d, J = 5.50 Hz, 1 H), 7.49 (t, J = 7.67 Hz, 1 H), 7.42 (d, J = 5.50 Hz, 1 H), 7.33 (d, J = 7.33 Hz, 1 H), 6.02 (s, 1 H), 4.55 (dt, J = 14.03, 4.89 Hz, 1 H), 4.06 (dt, J = 13.40, 6.58 Hz, 1 H), 3.65 (ddd, J = 10.42, 6.98, 5.04 Hz, 1 H), 3.47 (dt, J = 10.42, 5.09 Hz, 1 H), 3.07 (s, 3 H) |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 74 | 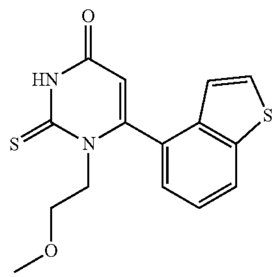 [SMILES: COCCn1c(-c2cccc3sccc23)cc(=O)[nH]c1=S] | 6-(1-benzothien-4-yl)-1-(2-methoxyethyl)-2-thioxo-2,3-dihydropyrimidin-4(1H)-one | 319.4 | 1H NMR (301 MHz, DMSO-d6) δ ppm 12.85 (br. s., 1 H), 8.16 (t, J = 4.48 Hz, 1 H), 7.90 (d, J = 5.51 Hz, 1 H), 7.47 (d, J = 4.36 Hz, 2 H), 7.37 (d, J = 5.51 Hz, 1 H), 5.87 (s, 1 H), 4.31 (ddd, J = 13.31, 7.57, 5.74 Hz, 1 H), 3.84 (dt, J = 13.37, 6.74 Hz, 1 H), 3.32-3.45 (m, 2 H), 2.82 (s, 3 H) |
| 75 | 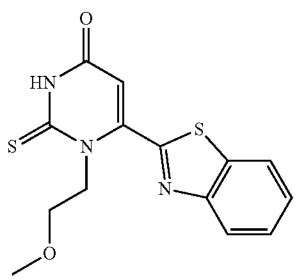 [SMILES: COCCn1c(-c2nc3ccccc3s2)cc(=O)[nH]c1=S] | 6-(1,3-benzothiazol-2-yl)-1-(2-methoxyethyl)-2-thioxo-2,3-dihydropyrimidin-4(1H)-one | 320.0 | 1H NMR (400 MHz, CHLOROFORM-d) δ ppm 9.91 (br. s., 1 H), 8.14 (d, J = 8.01 Hz, 1 H), 7.98 (d, J = 7.79 Hz, 1 H), 7.61 (ddd, J = 8.01, 7.10, 1.15 Hz, 1 H), 7.54 (ddd, J = 7.80, 7.80, 0.90 Hz, 1 H), 6.27 (s, 1 H), 5.04 (t, J = 5.27 Hz, 2 H), 3.63 (t, J = 5.27 Hz, 2 H), 3.09 (s, 3 H) |
| 76 | 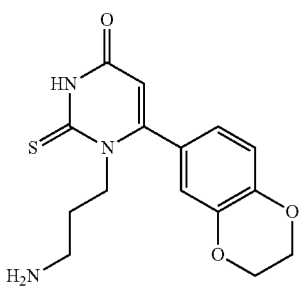 [SMILES: NCCCn1c(-c2ccc3c(c2)OCCO3)cc(=O)[nH]c1=S] | 1-(3-aminopropyl)-6-(2,3-dihydro-1,4-benzodioxin-6-yl)-2-thioxo-2,3-dihydropyrimidin-4(1H)-one hydrochloride | 320.0 | 1H NMR (300 MHz, DMSO-d6) δ ppm 12.76 (br. s., 1 H), 7.71 (br. s., 3 H), 7.07 (s, 1 H), 6.93-7.02 (m, 2 H), 5.77 (d, J = 2.09 Hz, 1 H), 4.30 (s, 4 H), 4.03-4.18 (m, 2 H), 2.53-2.66 (m, 2 H), 1.76-1.93 (m, 2 H) |
| 77 | 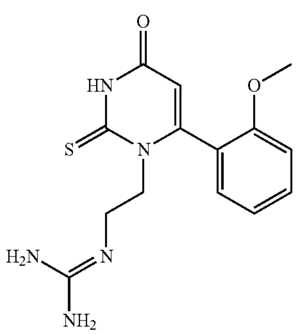 [SMILES: COc1ccccc1-c1cc(=O)[nH]c(=S)n1CCN=C(N)N] | 2-{2-[6-(2-methoxyphenyl)-4-oxo-2-thioxo-3,4-dihydropyrimidin-1(2H)-yl]ethyl}guanidine hydrochloride | 320.0 | 1H NMR (500 MHz, DMSO-d6) δ ppm 12.85 (s, 1 H), 7.65 (br. t, J = 6.10, 6.10 Hz, 1 H), 7.53 (td, J = 7.93, 1.46 Hz, 1 H), 7.32 (dd, J = 7.56, 1.46 Hz, 1 H), 7.17 (d, J = 8.29 Hz, 1 H), 7.07 (t, J = 7.44 Hz, 2 H), 6.97 (br. s., 4 H), 5.80 (d, J = 2.20 Hz, 1 H), 4.54 (br. d, J = 13.70 Hz, 1 H), 3.84 (s, 3 H), 3.63 (m, J = 9.03 Hz, 1 H), 3.53 (td, J = 9.33, 4.51 Hz, 1 H), 3.17-3.22 (m, 1 H) |
| 78 | 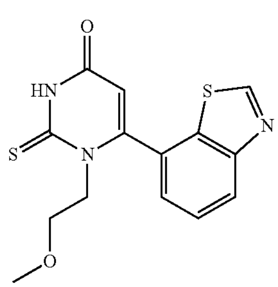 [SMILES: COCCn1c(-c2cccc3ncsc23)cc(=O)[nH]c1=S] | 6-(1,3-benzothiazol-7-yl)-1-(2-methoxyethyl)-2-thioxo-2,3-dihydropyrimidin-4(1H)-one | 320.4 | 1H NMR (301 MHz, CHLOROFORM-d) δ ppm 9.97 (br. s., 1 H), 9.10 (s, 1 H), 8.27 (d, J = 8.26 Hz, 1 H), 7.66 (t, J = 7.80 Hz, 1 H), 7.44 (d, J = 7.34 Hz, 1 H), 6.01 (s, 1 H), 4.48 (dt, J = 14.00, 4.82 Hz, 1 H), 4.11-4.32 (m, 1 H), 3.45-3.69 (m, 2 H), 3.06 (s, 3 H) |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 79 | 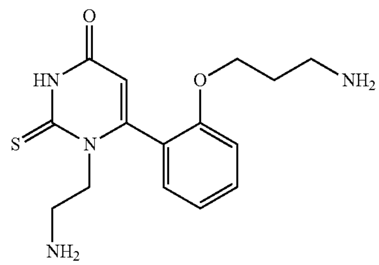 [SMILES: NCCCOc1ccccc1-c1cc(=O)[nH]c(=S)n1CCN] | 1-(2-aminoethyl)-6-[2-(3-aminopropoxy)phenyl]-2-thioxo-2,3-dihydropyrimidin-4(1H)-one hydrochloride | 321.0 | 1H NMR (400 MHz, METHANOL-d4) δppm 7.57 (t, J = 7.42 Hz, 1 H), 7.40 (d, J = 6.83 Hz, 1 H), 7.22 (d, J = 8.59 Hz, 1 H), 7.15 (t, J = 7.03 Hz, 1 H), 5.83 (s, 1 H), 4.90-5.00 (m, 1 H), 4.26-4.35 (m, 1 H), 4.17-4.25 (m, 1 H), 4.02-4.13 (m, 1 H), 2.97-3.18 (m, 4 H), 2.08-2.20 (m, 2 H) |
| 80 | 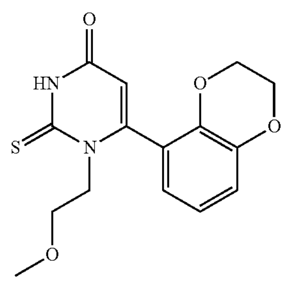 [SMILES: COCCn1c(-c2cccc3c2OCCO3)cc(=O)[nH]c1=S] | 6-(2,3-dihydro-1,4-benzodioxin-5-yl)-1-(2-methoxyethyl)-2-thioxo-2,3-dihydropyrimidin-4(1H)-one | 321.2 | 1H NMR (400 MHz, CHLOROFORM-d) δ ppm 9.79 (br. s., 1 H), 7.00 (dd, J = 8.24, 1.60 Hz, 1 H), 6.92 (t, J = 7.90 Hz, 1 H), 6.79 (dd, J = 7.56, 1.60 Hz, 1 H), 5.84 (s, 1 H), 4.70 (dt, J = 13.91, 4.84 Hz, 1 H), 4.29 (s, 4 H), 3.94 (dt, J = 14.08, 6.93 Hz, 1 H), 3.70 (ddd, J = 10.19, 7.67, 5.95 Hz, 1 H), 3.48 (ddd, J = 10.25, 6.13, 4.24 Hz, 1 H), 3.16 (s, 3 H) |
| 81 | 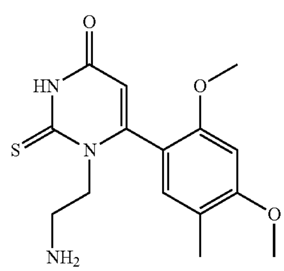 [SMILES: COc1cc(OC)c(-c2cc(=O)[nH]c(=S)n2CCN)cc1C] | 1-(2-aminoethyl)-6-(2,4-dimethoxy-5-methylphenyl)-2-thioxo-2,3-dihydropyrimidin-4(1H)-one hydrochloride | 321.8 | 1H NMR (400 MHz, DMSO-d6): δ 12.85 (s, 1 H), 7.80 (br.s., 3 H), 7.11 (s, 1 H), 6.76 (s, 1 H), 5.75 (s, 1 H), 4.58-4.69 (m, 1 H), 3.88-3.95 (m, 1H), 3.89 (s, 4 H), 3.86 (s, 3 H), 2.82-2.95 (m, 2 H), 2.10 (s, 3 H): |
| 82 | 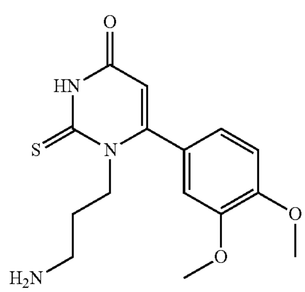 [SMILES: COc1ccc(-c2cc(=O)[nH]c(=S)n2CCCN)cc1OC] | 1-(3-aminopropyl)-6-(3,4-dimethoxyphenyl)-2-thioxo-2,3-dihydropyrimidin-4(1H)-one hydrochloride | 322.0 | 1H NMR (400 MHz, DMSO-d6) δ ppm 12.76 (br. s., 1 H), 7.71 (br. s., 3 H), 7.13 (d, J = 1.96 Hz, 1 H), 7.05 (d, J = 5.38 Hz, 2 H), 5.81 (d, J = 1.96 Hz, 1 H), 4.09-4.20 (m, 2 H), 3.82 (s, 3 H), 3.80 (s, 3 H), 2.53-2.62 (m, 2 H), 1.79-1.90 (m, 2 H) |
| 83 | 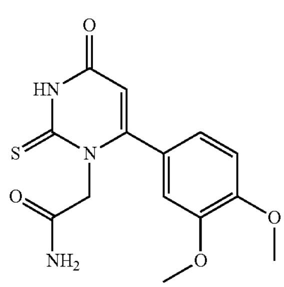 [SMILES: COc1ccc(-c2cc(=O)[nH]c(=S)n2CC(N)=O)cc1OC] | 2-[6-(3,4-dimethoxyphenyl)-4-oxo-2-thioxo-3,4-dihydropyrimidin-1(2H)-yl]acetamide | 322.0 | 1H NMR (300 MHz, DMSO-d6) δ ppm 12.75 (br. s., 1 H), 7.46 (br. s., 1 H), 7.16 (br. s., 1 H), 7.00-7.09 (m, 2 H), 6.91-6.99 (m, 1 H), 5.81 (s, 1 H), 4.98-5.44 (m, 1 H), 3.94-4.29 (m, 1 H), 3.80 (s, 3 H), 3.74 (s, 3 H) |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 84 | 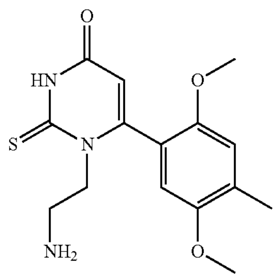 [SMILES: COc1cc(-c2cc(=O)[nH]c(=S)n2CCN)c(OC)cc1C] | 1-(2-aminoethyl)-6-(2,5-dimethoxy-4-methylphenyl)-2-thioxo-2,3-dihydropyrimidin-4(1H)-one hydrochloride | 322.0 | 1H NMR (400 MHz, METHANOL-d4): δ 6.95 (s, 1H), 6.81 (s, 1H), 5.75 (s, 1H), 4.58-4.47 (m, 1H), 4.11-4.20 (m, 1H), 3.75 (s, 3H), 3.30 (s, 3H), 2.95-3.08 (m, 2H), 2.18 (s, 3H). |
| 85 | 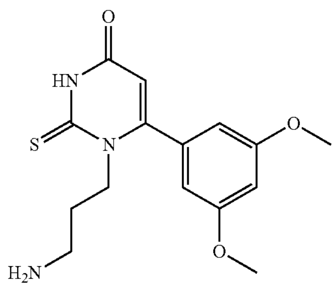 [SMILES: COc1cc(OC)cc(-c2cc(=O)[nH]c(=S)n2CCCN)c1] | 1-(3-aminopropyl)-6-(3,5-dimethoxyphenyl)-2-thioxo-2,3-dihydropyrimidin-4(1H)-one hydrochloride | 322.0 | 3.567 min (Column: XBRIDGE-C18 4.6 × 75 mm 3.5 μm; Mobile phase-A = 0.1% TFA IN ACN, B = 0.1% TFA IN WATER; Time(min)/% B = 0/90, 0.8/90, 1.8/55, 3/5, 6.5/5, 7/90 Flow: 0.8 mL/min, Column Temp = 40° C.; Diluent: CAN) |
| 86 | 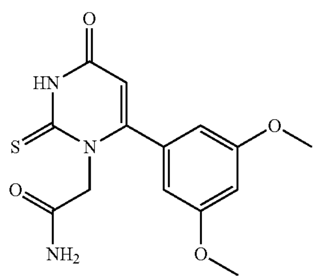 [SMILES: COc1cc(OC)cc(-c2cc(=O)[nH]c(=S)n2CC(N)=O)c1] | 2-[6-(3,5-dimethoxyphenyl)-4-oxo-2-thioxo-3,4-dihydropyrimidin-1(2H)-yl]acetamide | 322.1 | 1H NMR (300 MHz, DMSO-d6) δ ppm 12.79 (br. s., 1 H), 7.46 (br. s., 1 H), 7.17 (br. s., 1 H), 6.62 (d, J = 1.74 Hz, 1 H), 6.60 (s, 2 H), 5.83 (d, J = 1.92 Hz, 1 H), 5.17 (br. s, 1 H), 4.08 (br. s, 1 H), 3.75 (s, 6 H) |
| 87 | 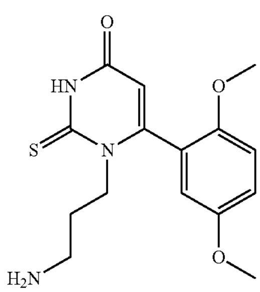 [SMILES: COc1ccc(OC)c(-c2cc(=O)[nH]c(=S)n2CCCN)c1] | 1-(3-aminopropyl)-6-(2,5-dimethoxyphenyl)-2-thioxo-2,3-dihydropyrimidin-4(1H)-one hydrochloride | 322.1 | 1H NMR (400 MHz, METHANOL-d4) δ ppm 7.08-7.12 (m, 2 H), 6.93 (s, 1 H), 5.79 (s, 1 H), 4.47-4.62 (m, 1 H), 3.84-3.87 (m, 1 H), 3.83 (s, 3 H), 3.78 (s, 3 H), 2.76 (t, J = 7.71 Hz, 2 H), 1.95-2.09 (m, 1 H), 1.78-1.93 (m, 1 H) |
| 88 | 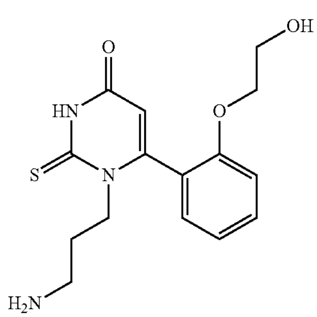 [SMILES: NCCCn1c(-c2ccccc2OCCO)cc(=O)[nH]c1=S] | 1-(3-aminopropyl)-6-[2-(2-hydroxyethoxy)phenyl]-2-thioxo-2,3-dihydropyrimidin-4(1H)-one hydrochloride | 322.2 | 1H NMR (500 MHz, CD$_3$OD) δ 1.81-1.92 (m, 1 H), 2.05 (dqd, J = 13.4, 8.1, 5.6 Hz, 1 H), 2.76 (t, J = 7.8 Hz, 2 H), 3.82-3.90 (m, 2 H), 3.90-4.02 (m, 1 H), 4.16 (ddd, J = 11.0, 4.6, 3.7 Hz, 1 H), 4.20 (ddd, J = 10.7, 5.9, 4.1 Hz, 1 H), 4.45-4.59 (m, 1 H), 5.82 (s, 1 H), 7.13 (t, J = 7.4 Hz, 1 H), 7.21 (d, J = 8.5 Hz, 1 H), 7.35 (dd, J = 7.4, 1.6 Hz, 1 H), 7.55 (ddd, J = 8.4, 7.6, 1.3 Hz, 1 H) |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 89 | 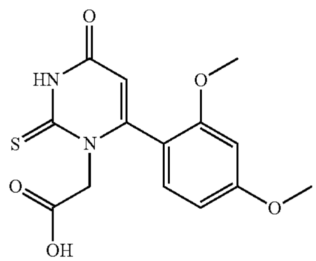 [SMILES: COc1ccc(-c2cc(=O)[nH]c(=S)n2CC(=O)O)c(OC)c1] | [6-(2,4-dimethoxyphenyl)-4-oxo-2-thioxo-3,4-dihydropyrimidin-1(2H)-yl]acetic acid | 323.1 | 2.09 min Waters Atlantis dC18 5 um 4.6 × 50 mm, 95% H2O/5% MeCN linear to 5% H2O/95% MeCN over 4.0 min, HOLD at 5% H2O/95% MeCN to 5.0 min. (0.05% TFA). Flow rate: 2 mL/min |
| 90 | 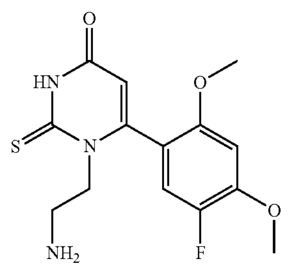 | 1-(2-aminoethyl)-6-(5-fluoro-2,4-dimethoxyphenyl)-2-thioxo-2,3-dihydropyrimidin-4(1H)-one hydrochloride | 325.9 | 1H NMR (400 MHz, DMSO-d6): δ 12.88 (s, 1 H), 7.87 (br.s., 3 H), 7.32 (d, 1 H), 6.97 (d, 1 H), 5.82 (s, 1 H), 4.55-4.66 (m, 1 H), 3.95 (s, 3 H), 3.87 (s, 3 H), 3.83-3.92 (m, 1H), 2.87-2.98 (m, 2 H). |
| 91 | 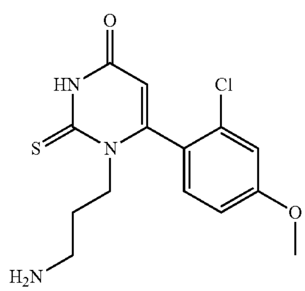 [SMILES: COc1ccc(-c2cc(=O)[nH]c(=S)n2CCCN)c(Cl)c1] | 1-(3-aminopropyl)-6-(2-chloro-4-methoxyphenyl)-2-thioxo-2,3-dihydropyrimidin-4(1H)-one hydrochloride | 326.0 | 1H NMR (400 MHz, DMSO-d6) δ ppm 12.88 (s, 1 H), 7.66 (br. s, 3 H), 7.55 (d, J = 8.80 Hz, 1 H), 7.27 (d, J = 2.45 Hz, 1 H), 7.09 (dd, J = 8.80, 2.45 Hz, 1 H), 5.89 (d, J = 1.96 Hz, 1 H), 4.36-4.46 (m, 1 H), 3.85 (s, 3 H), 3.57-3.63 (m, 1 H), 2.53-2.64 (m, 2 H), 1.86-1.95 (m, 1 H), 1.67-1.76 (m, 1 H) |
| 92 | 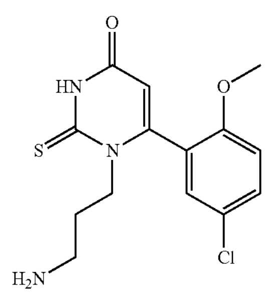 [SMILES: COc1ccc(Cl)cc1-c1cc(=O)[nH]c(=S)n1CCCN] | 1-(3-aminopropyl)-6-(5-chloro-2-methoxyphenyl)-2-thioxo-2,3-dihydropyrimidin-4(1H)-one hydrochloride | 326.3 | $^1$H NMR (500 MHz, METHANOL-d4) δ ppm 7.57 (dd, J = 9.03, 2.68 Hz, 1 H), 7.44 (d, J = 2.44 Hz, 1 H), 7.19 (d, J = 9.03 Hz, 1 H), 5.83 (s, 1 H), 4.53-4.63 (m, 1 H), 3.91 (s, 3 H), 3.75-3.84 (m, 1 H), 2.80 (t, J = 7.81 Hz, 2 H), 1.98-2.08 (m, 1 H), 1.80-1.90 (m, 1 H) |
| 93 | 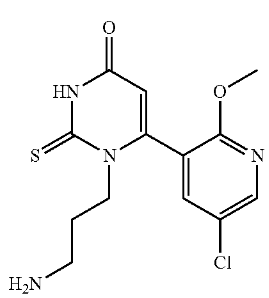 [SMILES: COc1ncc(Cl)cc1-c1cc(=O)[nH]c(=S)n1CCCN] | 1-(3-aminopropyl)-6-(5-chloro-2-methoxypyridin-3-yl)-2-thioxo-2,3-dihydropyrimidin-4(1H)-one hydrochloride | 326.9 | 1H NMR (400 MHz, METHANOL-d4) δ ppm 8.37 (d, J = 2.45 Hz, 1 H), 7.92 (d, J = 2.45 Hz, 1 H), 5.90 (s, 1 H), 4.52-4.62 (m, 1 H), 4.02 (s, 3 H), 3.74-3.85 (m, 1 H), 2.84 (t, J = 7.83 Hz, 2 H), 1.98-2.09 (m, 1 H), 1.81-1.94 (m, 1 H) |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 94 | 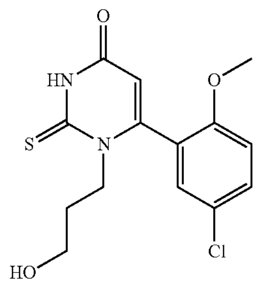 [SMILES: COc1ccc(Cl)cc1-c1cc(=O)[nH]c(=S)n1CCCO] | 6-(5-chloro-2-methoxyphenyl)-1-(3-hydroxypropyl)-2-thioxo-2,3-dihydropyrimidin-4(1H)-one | 327.0 | 1H NMR (400 MHz, METHANOL-d3) δ ppm 7.51 (dd, J = 8.93, 2.52 Hz, 1 H), 7.39 (d, J = 2.29 Hz, 1 H), 7.14 (d, J = 8.93 Hz, 1 H), 5.77 (s, 1 H), 4.52 (ddd, J = 13.91, 9.79, 4.69 Hz, 1 H), 3.88 (s, 3 H), 3.78 (ddd, J = 14.43, 10.08, 5.27 Hz, 1 H), 3.36 (t, J = 6.18 Hz, 2 H), 1.82-1.96 (m, 1 H), 1.62-1.76 (m, 1 H) |
| 95 | 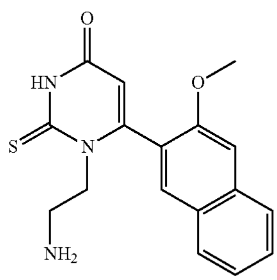 [SMILES: COc1cc2ccccc2cc1-c1cc(=O)[nH]c(=S)n1CCN] | 1-(2-aminoethyl)-6-(3-methoxy-2-naphthyl)-2-thioxo-2,3-dihydropyrimidin-4(1H)-one hydrochloride | 327.9 | 1H NMR (400 MHz, DMSO-d6) δ ppm 12.92 (d, J = 1.83 Hz, 1 H), 7.97 (s, 1 H), 7.90 (t, J = 7.33 Hz, 2 H), 7.73 (br. s., 3 H), 7.53-7.59 (m, 2 H), 7.40-7.46 (m, 1 H), 5.92 (d, J = 2.29 Hz, 1 H), 4.58-4.69 (m, 1 H), 3.92 (s, 3 H), 3.77-3.87 (m, 1 H), 2.79-2.99 (m, 2 H) |
| 96 | 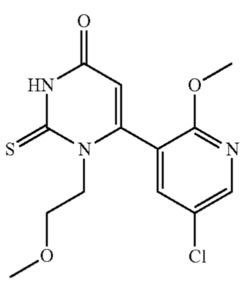 [SMILES: COCCn1c(-c2cc(Cl)cnc2OC)cc(=O)[nH]c1=S] | 6-(5-chloro-2-methoxypyridin-3-yl)-1-(2-methoxyethyl)-2-thioxo-2,3-dihydropyrimidin-4(1H)-one | 328.0 | 1H NMR (400 MHz, CHLOROFORM-d) δ ppm 9.79 (br. s., 1 H), 8.24 (d, J = 2.52 Hz, 1 H), 7.54 (d, J = 2.52 Hz, 1 H), 5.78 (d, J = 2.29 Hz, 1 H), 4.76 (dt, J = 14.37, 2.89 Hz, 1 H), 3.96 (s, 3 H), 3.86 (td, J = 9.96, 3.43 Hz, 1 H), 3.65 (ddd, J = 14.20, 9.85, 3.89 Hz, 1 H), 3.36 (dt, J = 10.36, 3.52 Hz, 1 H), 3.17 (s, 3 H) |
| 97 | 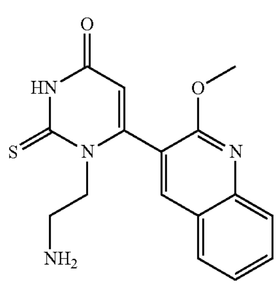 [SMILES: COc1nc2ccccc2cc1-c1cc(=O)[nH]c(=S)n1CCN] | 1-(2-aminoethyl)-6-(2-methoxyquinolin-3-yl)-2-thioxo-2,3-dihydropyrimidin-4(1H)-one trifluoroacetate | 328.8 | 1H NMR (400 MHz, DMSO-d6): δ 12.92 (br.s., 1 H), 8.20 (s, 1 H), 7.83-7.65 (m, 6 H), 7.38 (t, 1 H), 6.01 (s, 1 H), 4.52-4.61 (m, 1 H), 3.70-3.80 (m, 1H), 3.68 (s, 3 H), 2.98-3.18 (m, 2 H). |
| 98 | 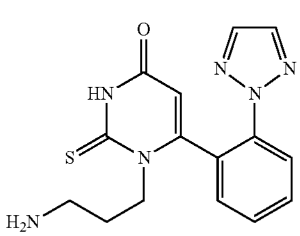 [SMILES: NCCCn1c(-c2ccccc2-n2nccn2)cc(=O)[nH]c1=S] | 1-(3-aminopropyl)-2-thioxo-6-[2-(2H-1,2,3-triazol-2-yl)phenyl]-2,3-dihydropyrimidin-4(1H)-one hydrochloride | 328.9 | 0.893 min Column: LCMS-Q Supelco 3 × 30 mm; Mobile phase: from 0% CH3CN (0.1% TFA) in water (0.1% TFA) to 60% CH3CN (0.1% TFA) in water (0.1% TFA) |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 99 | 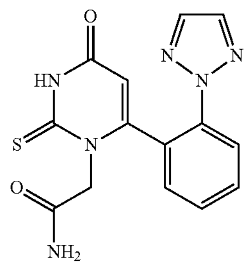 [SMILES: NC(=O)Cn1c(-c2ccccc2-n2nccn2)cc(=O)[nH]c1=S] | 2-{4-oxo-2-thioxo-6-[2-(2H-1,2,3-triazol-2-yl)phenyl]-3,4-dihydropyrimidin-1(2H)-yl}acetamide | 329.0 | 1H NMR (400 MHz, DMSO-d6): δ 12.76 (s, 1H), 8.11 (s, 2H), 7.98 (d, 1H), 7.72 (t, 1H), 7.55 (t, 1H), 7.45 (d, 1H), 7.35 (s, 1H), 7.04 (s, 1H), 5.68 (s, 1H), 5.22 (d, 1H), 3.79 (d, 1H).: |
| 100 | 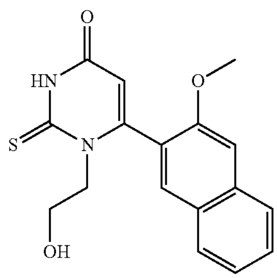 [SMILES: COc1cc2ccccc2cc1-c1cc(=O)[nH]c(=S)n1CCO] | 1-(2-hydroxyethyl)-6-(3-methoxy-2-naphthyl)-2-thioxo-2,3-dihydropyrimidin-4-(1H)-one | 329.4 | 1H NMR (400 MHz, DMSO-d6) δ ppm 12.80 (d, J = 1.37 Hz, 1 H), 7.92 (s, 1 H), 7.88 (d, J = 9.16 Hz, 2 H), 7.54 (ddd, J = 8.13, 6.98, 0.92 Hz, 1 H), 7.49 (s, 1 H), 7.41 (ddd, J = 8.24, 6.87, 0.92 Hz, 1 H), 5.87 (d, J = 2.29 Hz, 1 H), 4.68 (br. s., 1 H), 4.47-4.58 (m, 1 H), 3.91 (s, 3 H), 3.44-3.54 (m, 2 H) |
| 101 | 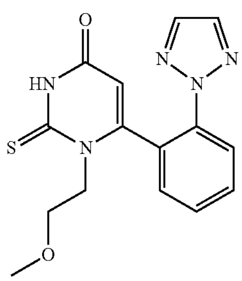 [SMILES: COCCn1c(-c2ccccc2-n2nccn2)cc(=O)[nH]c1=S] | 1-(2-methoxyethyl)-2-thioxo-6-[2-(2H-1,2,3-triazol-2-yl)phenyl]-2,3-dihydropyrimidin-4(1H)-one | | 1H NMR (300 MHz, DMSO-d6) δ ppm 12.77 (br. s., 1 H), 8.14 (s, 2 H), 8.05 (d, J = 7.67 Hz, 1 H), 7.77 (td, J = 7.67, 2.09 Hz, 1 H), 7.60-7.71 (m, 2 H), 5.79 (s, 1 H), 4.32-4.44 (m, 1 H), 3.47-3.62 (m, 1 H), 3.36-3.46 (m, 1 H), 2.99 (s, 3 H) |
| 102 | 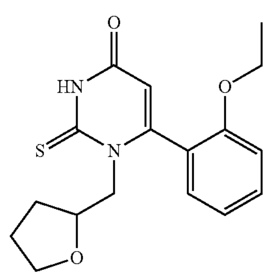 [SMILES: CCOc1ccccc1-c1cc(=O)[nH]c(=S)n1CC1CCCO1] | 6-(2-ethoxyphenyl)-1-(tetrahydrofuran-2-ylmethyl)-2-thioxo-2,3-dihydropyrimidin-4(1H)-one | 333.1 | 1H NMR (400 MHz, CHLOROFORM-d) δ ppm 10.25-10.39 (m, 1 H) 7.39-7.50 (m, 1 H) 7.30-7.36 (m, 1 H) 7.00-7.07 (m, 1 H) 6.88-6.99 (m, 1 H) 5.81-5.88 (m, 1 H) 4.68-4.77 (m, 1 H) 4.56-4.65 (m, 1 H) 4.05-4.14 (m, 2 H) 3.49-3.57 (m, 1 H) 3.34-3.44 (m, 1 H) 3.05-3.13 (m, 1 H) 1.90-2.01 (m, 1 H)1.63-1.78 (m, 1 H) 1.40-1.49 (m, 1 H) 1.32-1.38 (m, 3 H) 1.23-1.32 (m, 1 H) |
| 103 | 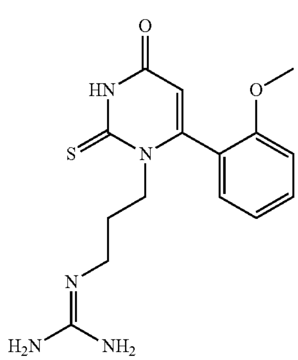 [SMILES: COc1ccccc1-c1cc(=O)[nH]c(=S)n1CCCN=C(N)N] | 2-{3-[6-(2-methoxyphenyl)-4-oxo-2-thioxo-3,4-dihydropyrimidin-1(2H)-yl]propyl}guanidine | 334.1 | 1.31 min Waters Atlantis dC18 5 um 4.6 × 50 mm, 95% H2O/5% MeCN linear to 5% H2O/95% MeCN over 4.0 min, HOLD at 5% H2O/95% MeCN to 5.0 min. (0.05% TFA). Flow rate: 2 mL/min |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 104 | 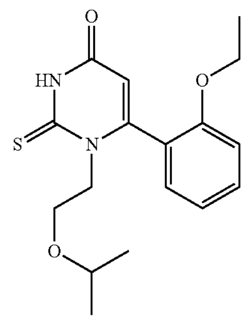 [SMILES: CCOc1ccccc1-c1cc(=O)[nH]c(=S)n1CCOC(C)C] | 6-(2-ethoxyphenyl)-1-(2-isopropoxyethyl)-2-thioxo-2,3-dihydropyrimidin-4(1H)-one | 335.1 | 1H NMR (400 MHz, CHLOROFORM-d) δ ppm 10.15 (br. s., 1 H) 7.45 (ddd, J = 8.29, 7.51, 1.76 Hz, 1 H) 7.24 (dd, J = 7.51, 1.66 Hz, 1 H) 7.03 (ddd, J = 7.41, 0.78 Hz, 1 H) 6.94 (d, J = 8.39 Hz, 1 H) 5.83 (d, J = 2.34 Hz, 1 H) 4.69 (ddd, J = 13.46, 5.66, 4.10 Hz, 1 H) 4.10 (q, J = 6.89 Hz, 2 H) 3.68-3.85 (m, 2 H) 3.50 (ddd, J = 9.71, 6.19, 3.61 Hz, 1 H) 3.43 (spt, J = 6.05 Hz, 1 H) 1.37 (t, J = 7.02 Hz, 3 H) 1.02 (dd, J = 6.05, 1.76 Hz, 6 H) |
| 105 | 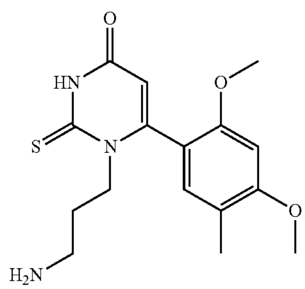 [SMILES: COc1cc(OC)c(-c2cc(=O)[nH]c(=S)n2CCCN)cc1C] | 1-(3-aminopropyl)-6-(2,4-dimethoxy-5-methylphenyl)-2-thioxo-2,3-dihydropyrimidin-4(1H)-one hydrochloride | 335.9 | 1H NMR (400 MHz, DMSO-d6): δ 12.76 (s, 1H), 7.68 (br.s., 3H), 7.11 (s, 1H), 6.74 (s, 1H), 5.73 (s, 1H), 4.35-4.45 (m, 1H), 3.88 (s, 3H), 3.85 (s, 3H), 3.59-3.68 (m, 1H), 2.52-2.51 (m, 2H), 2.09 (s, 3H), 1.81-1.71 (m, 2H).: |
| 106 | 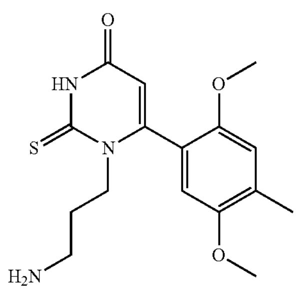 [SMILES: COc1cc(-c2cc(=O)[nH]c(=S)n2CCCN)c(OC)cc1C] | 1-(3-aminopropyl)-6-(2,5-dimethoxy-4-methylphenyl)-2-thioxo-2,3-dihydropyrimidin-4(1H)-one hydrochloride | 336.0 | 1H NMR (400 MHz, METHANOL-d4): δ 6.91 (s, 1H), 6.79 (s, 1H), 5.72 (s, 1H), 4.40-4.50 (m, 1H), 3.78-3.88 (m, 1H), 3.74 (s, 3H), 3.72 (s, 3H), 2.68 (t, 2H), 2.17 (s, 3H), 1.89-1.94 (m, 1H), 1.76-1.86 (m, 1H). |
| 107 | 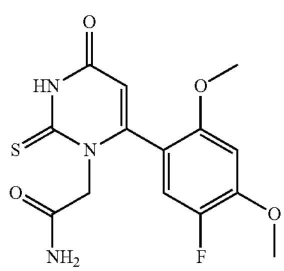 | 2-[6-(5-fluoro-2,4-dimethoxyphenyl)-4-oxo-2-thioxo-3,4-dihydropyrimidin-1(2H)-yl]acetamide | 339.9 | 1H NMR (400 MHz, DMSO-d6): δ 7.11 (br.s., 1 H), 6.94 (d, 1 H), 6.87 (d, 1 H), 6.83 (br.s., 1 H), 5.72 (br.s., 1 H), 5.41 (s, 1 H), 3.91 (s, 3 H), 3.83 (s, 3 H), 3.72-3.82 (m, 1 H). |
| 108 | 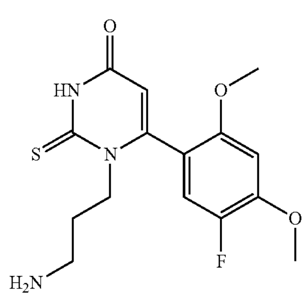 | 1-(3-aminopropyl)-6-(5-fluoro-2,4-dimethoxyphenyl)-2-thioxo-2,3-dihydropyrimidin-4(1H)-one hydrochloride | 339.9 | 1H NMR (400 MHz, DMSO-d6): δ 7.36 (d, 1H), 6.95 (d, 1H), 5.80 (s, 1H), 4.38-4.48 (m, 1H), 3.95 (s, 3H), 3.86 (s, 3H), 3.59-3.67 (m, 1H), 2.45-2.61 (m, 2H), 1.67-1.78 (m, 2H).: |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 109 | 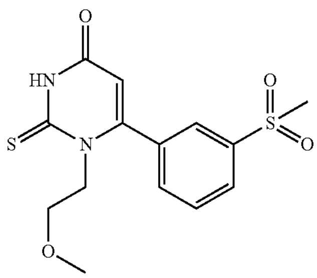 [SMILES: COCCn1c(-c2cccc(S(C)(=O)=O)c2)cc(=O)[nH]c1=S] | 1-(2-methoxyethyl)-6-[3-(methylsulfonyl)phenyl]-2-thioxo-2,3-dihydropyrimidin-4(1H)-one | 341.0 | 1H NMR (400 MHz, CHLOROFORM-d) d ppm 10.70 (br. s., 1 H), 8.08 (d, J = 7.79 Hz, 1 H), 8.03 (s, 1 H), 7.72 (dd, J = 7.80, 7.80 Hz, 1 H), 7.65 (d, J = 7.33 Hz, 1 H), 5.87 (s, 1 H), 4.30 (br. s., 2 H), 3.67 (br. s., 2 H), 3.22 (s, 3 H), 3.12 (s, 3 H) |
| 110 | 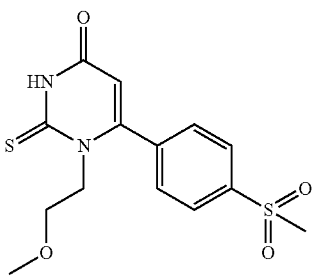 [SMILES: COCCn1c(-c2ccc(S(C)(=O)=O)cc2)cc(=O)[nH]c1=S] | 1-(2-methoxyethyl)-6-[4-(methylsulfonyl)phenyl]-2-thioxo-2,3-dihydropyrimidin-4(1H)-one | 341.1 | 1H NMR (400 MHz, CHLOROFORM-d) δ ppm 8.08 (d, J = 8.24 Hz, 2 H), 7.59 (d, J = 8.24 Hz, 2 H), 5.81 (s, 1 H), 4.31 (br. s., 2 H), 3.66 (t, J = 5.04 Hz, 2 H), 3.21 (s, 3 H), 3.14 (s, 3 H) |
| 111 | 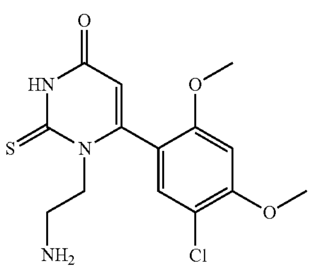 [SMILES: COc1cc(OC)c(-c2cc(=O)[nH]c(=S)n2CCN)cc1Cl] | 1-(2-aminoethyl)-6-(5-chloro-2,4-dimethoxyphenyl)-2-thioxo-2,3-dihydropyrimidin-4(1H)-one hydrochloride | 342.0 | 1H NMR (400 MHz, DMSO-d6) δ ppm 12.87 (br. s, 1 H), 7.80 (br. s, 3 H), 7.48 (s, 1 H), 6.94 (s, 1 H), 5.84 (d, J = 1.96 Hz, 1 H), 4.55-4.65 (m, 1 H), 3.97 (s, 3 H), 3.90 (s, 3 H), 3.71-3.80 (m, 1 H), 2.86-2.99 (m, 2 H) |
| 112 | 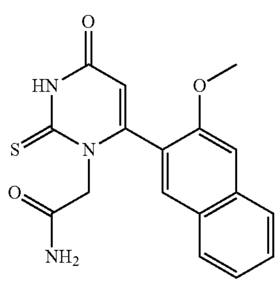 [SMILES: COc1cc2ccccc2cc1-c1cc(=O)[nH]c(=S)n1CC(N)=O] | 2-[6-(3-methoxy-2-naphthyl)-4-oxo-2-thioxo-3,4-dihydropyrimidin-1(2H)-yl]acetamide | 342.0 | 1H NMR (400 MHz, METHANOL-d3) δ ppm 7.84 (d, J = 8.24 Hz, 1 H), 7.81 (d, J = 7.79 Hz, 1 H), 7.79 (s, 1 H), 7.52 (ddd, J = 8.24, 7.10, 1.14 Hz, 1 H), 7.35-7.44 (m, 2 H), 5.89 (s, 1 H), 5.42-5.70 (m, 1 H), 4.05-4.26 (m, 1 H), 3.98 (s, 3 H) |
| 113 | ABS | 1-[(2S)-3-amino-2-hydroxypropyl]-6-(5-chloro-2-methoxyphenyl)-2-thioxo-2,3-dihydropyrimidin-4(1H)-one trifluoroacetate | 342.1 | 1H NMR (300 MHz, DMSO-d6) δ ppm 12.84 (s, 1 H), 7.69 (br. s, 3 H), 7.56 (dd, J = 9.06, 2.79 Hz, 1 H), 7.29 (d, J = 2.79 Hz, 1 H), 7.18 (d, J = 9.06 Hz, 1 H), 5.87 (d, J = 2.09 Hz, 1 H), 5.74 (d, J = 5.57 Hz, 1 H), 4.55-4.65 (m, 1 H), 4.21-4.34 (m, 1 H), 3.83 (s, 3 H), 3.13-3.23 (m, 1 H), 2.75-2.88 (m, 2 H) |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 114 | ABS | 1-[(2R)-3-amino-2-hydroxypropyl]-6-(5-chloro-2-methoxyphenyl)-2-thioxo-2,3-dihydropyrimidin-4(1H)-one trifluoroacetate | 342.2 | 1H NMR (300 MHz, DMSO-d6) δ ppm 12.84 (s, 1 H), 7.69 (br. s, 3 H), 7.56 (dd, J = 9.06, 2.79 Hz, 1 H), 7.29 (d, J = 2.79 Hz, 1 H), 7.18 (d, J = 9.06 Hz, 1 H), 5.87 (d, J = 2.09 Hz, 1 H), 5.74 (d, J = 5.57 Hz, 1 H), 4.55-4.65 (m, 1 H), 4.21-4.34 (m, 1 H), 3.83 (s, 3 H), 3.13-3.23 (m, 1 H), 2.75-2.88 (m, 2 H) |
| 115 | 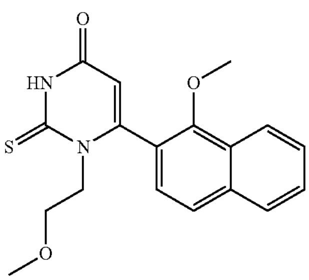 | 1-(2-methoxyethyl)-6-(1-methoxy-2-naphthyl)-2-thioxo-2,3-dihydropyrimidin-4(1H)-one | 343.0 | 1H NMR (400 MHz, CHLOROFORM-d) δ ppm 9.54 (br. s., 1 H), 8.11-8.19 (m, 1 H), 7.86-7.95 (m, 1 H), 7.71 (d, J = 8.47 Hz, 1 H), 7.61 (dd, J = 6.30, 3.09 Hz, 2 H), 7.28 (d, J = 8.47 Hz, 1 H), 5.96 (s, 1 H), 4.67-4.81 (m, 1 H), 4.02 (ddd, J = 14.03, 8.30, 5.38 Hz, 1 H), 3.90 (s, 3 H), 3.68-3.78 (m, 1 H), 3.36 (dt, J = 9.90, 4.78 Hz, 1 H), 3.06 (s, 3 H) |
| 116 | ABS | 6-(5-chloro-2-methoxyphenyl)-1-[(2R)-2,3-dihydroxypropyl]-2-thioxo-2,3-dihydropyrimidin-4(1H)-one | 343.0 | 1.942 min (Column: AQUITY BEH C-18, 2.1 × 50 mm, 1.7 μm; Mobile Phase: A-0.1% FA IN ACN, B-0.1% FA IN WATER; T/% B(min): 0/90, 0.7/90, 2/55, 3/55, 3.8/5, 5.8/5, 6/90; Flow: 0.5 mL/min, Diluent: CAN) |
| 117 | 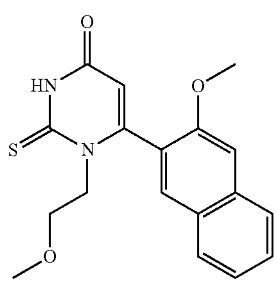 | 1-(2-methoxyethyl)-6-(3-methoxy-2-naphthyl)-2-thioxo-2,3-dihydropyrimidin-4(1H)-one | 343.4 | 1H NMR (400 MHz, CHLOROFORM-d) δ ppm 9.76 (br. s., 1 H), 7.80 (t, J = 8.36 Hz, 2 H), 7.74 (s, 1 H), 7.55 (ddd, J = 8.13, 7.10, 1.03 Hz, 1 H), 7.43 (ddd, J = 8.07, 6.93, 1.03 Hz, 1 H), 7.21 (s, 1 H), 5.90 (d, J = 2.06 Hz, 1 H), 4.67-4.77 (m, 1 H), 3.95 (s, 3 H), 3.70-3.86 (m, 2 H), 3.34-3.44 (m, 1 H), 3.07 (s, 3 H) |
| 118 | 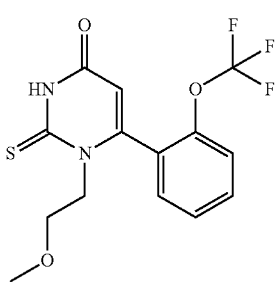 | 1-(2-methoxyethyl)-2-thioxo-6-[2-(trifluoromethoxy)phenyl]-2,3-dihydropyrimidin-4(1H)-one | 347.1 | 1H NMR (400 MHz, CHLOROFORM-d) δ ppm 9.79 (br. s., 1 H), 7.54-7.63 (m, 1 H), 7.35-7.48 (m, 3 H), 5.86 (s, 1 H), 4.57-4.73 (m, 1 H), 3.71-3.94 (m, 2 H), 3.38-3.49 (m, 1 H), 3.17 (s, 3 H) |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 119 | 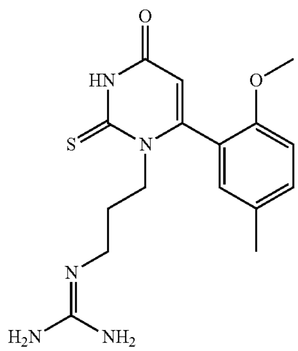 [SMILES: COc1ccc(C)cc1-c1cc(=O)[nH]c(=S)n1CCCN=C(N)N] | 2-{3-[6-(2-methoxy-5-methylphenyl)-4-oxo-2-thioxo-3,4-dihydropyrimidin-1(2H)-yl]propyl}guanidine | 348.2 | 1.37 min Waters XBridge C18 4.6 × 50 mm, 5 um 95% H20/5% MeCN linear to 5% H20/95% MeCN over 4.0 min, HOLD at 5% H20/95% MeCN to 5.0 min. Flow: 2.0 mL/min. NH4OH 0.03%. Flow rate: 2 mL/min |
| 120 | 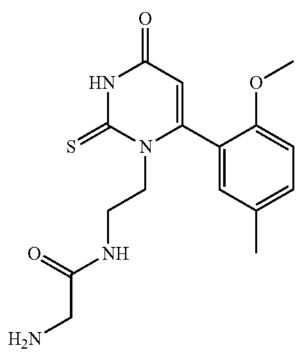 [SMILES: COc1ccc(C)cc1-c1cc(=O)[nH]c(=S)n1CCNC(=O)CN] | N-{2-[6-(2-methoxy-5-methylphenyl)-4-oxo-2-thioxo-3,4-dihydropyrimidin-1(2H)-yl]ethyl}glycinamide hydrochloride | 349.2 | 1H NMR (500 MHz, CD3OD) d ppm 7.37 (d, 1 H), 7.22 (s, 1 H), 7.06 (d, 1 H), 5.78 (s, 1 H), 4.81 (m, 1 H), 3.88 (s, 3 H), 3.86 (br. s., 0 H), 3.55 (m, 2 H), 3.45 (m, 2 H), 2.36 (s, 3 H) |
| 121 | 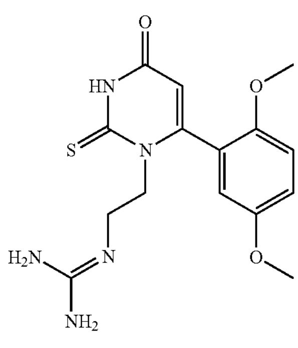 [SMILES: COc1ccc(OC)c(-c2cc(=O)[nH]c(=S)n2CCN=C(N)N)c1] | 2-{2-[6-(2,5-dimethoxyphenyl)-4-oxo-2-thioxo-3,4-dihydropyrimidin-1(2H)-yl]ethyl}guanidine hydrochloride | 350.1 | 1H NMR (400 MHz, DMSO-d6) δ ppm 12.85 (s, 1 H), 7.61 (br. t, J = 6.10, 6.10 Hz, 1 H), 7.07-7.12 (m, 2 H), 6.98 (br. s., 3 H), 6.93 (d, J = 1.56 Hz, 1 H), 5.85 (d, J = 2.15 Hz, 1 H), 4.54 (br. d, J = 14.30 Hz, 1 H), 3.78 (s, 3 H), 3.76 (s, 3 H), 3.66-3.75 (m, 1 H), 3.47-3.60 (m, 1 H), 3.15-3.26 (m, 1 H) |
| 122 | ABS | 6-(5-chloro-2-methoxyphenyl)-1-[(2R)-pyrrolidin-2-ylmethyl]-2-thioxo-2,3-dihydropyrimidin-4(1H)-one hydrochloride | 352 | 3.641 min Column: XBRIDGE-C18 4.6 × 75 mm 3.5 μm; Mobile phase-A = 0.1% FA IN ACN, B = 0.1% FA IN WATER; Time(min)/% B = 0/90, 0.8/90, 1.8/55, 3/5, 6.5/5, 7/90; Flow: 0.8 mL/min, Column Temp = 40° C.; Diluent: CAN |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 123 | ABS | 6-(5-chloro-2-methoxyphenyl)-1-[(2S)-pyrrolidin-2-ylmethyl]-2-thioxo-2,3-dihydropyrimidin-4(1H)-one hydrochloride | 352.1 | 1H NMR (400 MHz, DMSO-d6) δ ppm 12.99 (br. s., 1 H), 9.08 (br. s., 1 H), 8.14-8.52 (m, 1 H), 7.61-7.67 (m, 1 H), 7.50-7.58 (m, 1 H), 7.23-7.28 (m, 1 H), 5.92-6.00 (m, 1 H), 4.90-5.04 (m, 1 H), 3.83-3.88 (m, 3 H), 3.63-3.77 (m, 1 H), 2.98-3.20 (m, 3 H), 1.76-1.89 (m, 2 H), 1.62-1.75 (m, 2 H) |
| 124 | 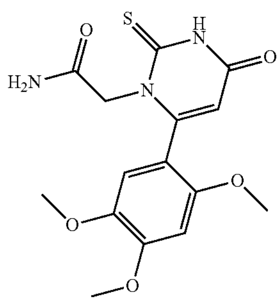 | 2-[4-oxo-2-thioxo-6-(2,4,5-trimethoxyphenyl)-3,4-dihydropyrimidin-1(2H)-yl]acetamide | 352.1 | 1.23 min Waters Atlantis dC18 5 um 4.6 × 50 mm, 95% H2O/5% MeCN linear to 5% H2O/95% MeCN over 4.0 min, HOLD at 5% H2O/95% MeCN to 5.0 min. (0.05% TFA). Flow rate: 2 mL/min |
| 125 | 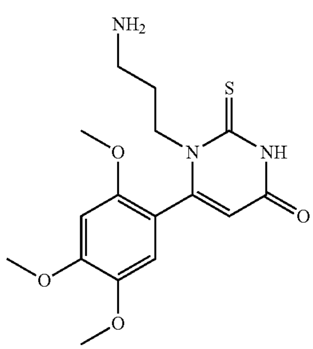 | 1-(3-aminopropyl)-2-thioxo-6-(2,4,5-trimethoxyphenyl)-2,3-dihydropyrimidin-4(1H)-one hydrochloride | 352.1 | 1H NMR (500 MHz, DMSO-d6) δ ppm 1.70-1.91 (m, 2 H) 2.53-2.60 (m, 2 H) 3.57 (s, 2 H) 3.69 (d, J = 7.07 Hz, 1 H) 3.75 (s, 3 H) 3.83 (s, 3 H) 3.87 (s, 3 H) 4.42 (br. s., 1 H) 5.79 (d, J = 1.95 Hz, 1 H) 6.82 (s, 1 H) 7.00 (s, 1 H) 7.86 (br. s., 2 H) 12.76 (s, 1 H) |
| 126 | 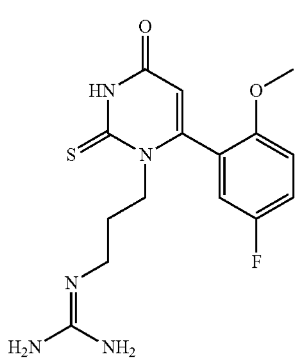 | 2-{3-[6-(5-fluoro-2-methoxyphenyl)-4-oxo-2-thioxo-3,4-dihydropyrimidin-1(2H)-yl]propyl}guanidine | 352.2 | 1.22 min Waters XBridge C18 4.6 × 50 mm, 5 um; 95% H20/5% MeCN linear to 5% H20/95% MeCN over 4.0 min, HOLD at 5% H20/95% MeCN to 5.0 min. Flow: 2.0 mL/min. NH4OH 0.03% Flow rate: 2 mL/min |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 127 | 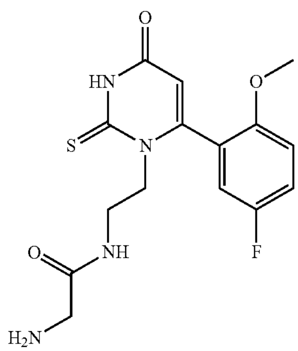 [SMILES: COc1ccc(F)cc1-c1cc(=O)[nH]c(=S)n1CCNC(=O)CN] | N-{2-[6-(5-fluoro-2-methoxyphenyl)-4-oxo-2-thioxo-3,4-dihydropyrimidin-1(2H)-yl]ethyl}glycinamide hydrochloride | 353.2 | 1H NMR (500 MHz, CD$_3$OD) d ppm 7.30 (td, 1 H), 7.25 (dd, 1 H), 7.16 (dd, 1 H), 5.81 (s, 1 H), 4.79 (m, 1 H), 3.89 (s, 3 H), 3.82 (m, 1 H), 3.54 (m, 2 H), 3.45 (m, 2 H) |
| 128 | 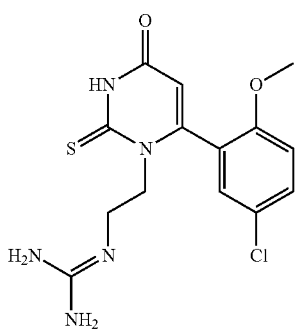 [SMILES: COc1ccc(Cl)cc1-c1cc(=O)[nH]c(=S)n1CCN=C(N)N] | 2-{2-[6-(5-chloro-2-methoxyphenyl)-4-oxo-2-thioxo-3,4-dihydropyrimidin-1(2H)-yl]ethyl}guanidine hydrochloride | 354.0 | 1H NMR (500 MHz, DMSO-d6) δ ppm 12.88 (s, 1 H), 7.63 (br. s., 1 H), 7.58 (dd, J = 9.03, 2.68 Hz, 1 H), 7.39-7.41 (m, 1 H), 7.20 (d, J = 9.03 Hz, 1 H), 7.00 (br. s., 4 H), 5.91 (d, J = 2.20 Hz, 1 H), 4.54 (br. d, J = 13.40 Hz, 1 H), 3.84 (s, 3 H), 3.59-3.67 (m, 1 H), 3.55 (dt, J = 9.33, 4.97 Hz, 1 H), 3.17-3.25 (m, 1 H) |
| 129 | 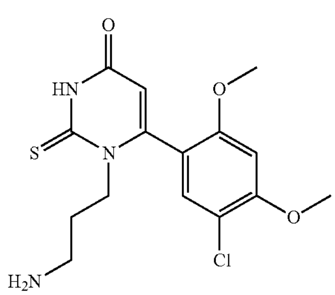 [SMILES: COc1cc(OC)c(-c2cc(=O)[nH]c(=S)n2CCCN)cc1Cl] | 1-(3-aminopropyl)-6-(5-chloro-2,4-dimethoxyphenyl)-2-thioxo-2,3-dihydropyrimidin-4(1H)-one hydrochloride | 356.0 | 1H NMR (400 MHz, DMSO-d6) δ ppm 12.78 (s, 1 H), 7.75 (br. s., 3 H), 7.49 (s, 1 H), 6.92 (s, 1 H), 5.83 (d, J = 2.45 Hz, 1 H), 4.32-4.45 (m, 1 H), 3.97 (s, 3 H), 3.90 (s, 3 H), 3.59-3.70 (m, 1 H), 2.53-2.65 (m, 2 H), 1.66-1.88 (m, 2 H) |
| 130 | 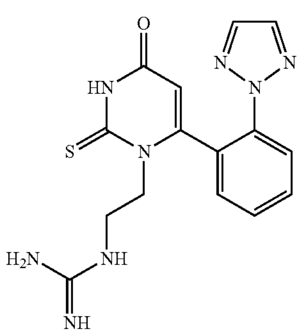 [SMILES: N=C(N)NCCn1c(-c2ccccc2-n2nccn2)cc(=O)[nH]c1=S] | 1-(2-{4-oxo-2-thioxo-6-[2-(2H-1,2,3-triazol-2-yl)phenyl]-3,4-dihydropyrimidin-1(2H)-yl}ethyl)guanidine hydrochloride | 357.1 | 1H NMR (400 MHz, METHANOL-d4): δ 8.12 (d, 1H), 7.91 (s, 2H), 7.75 (t, 1H), 7.55-7.59 (m, 2H), 5.74 (s, 1H), 4.40 (m, 1H), 3.75 (m, 1H), 3.55 (m, 1H), 3.35 (m, 1H). |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 131 | 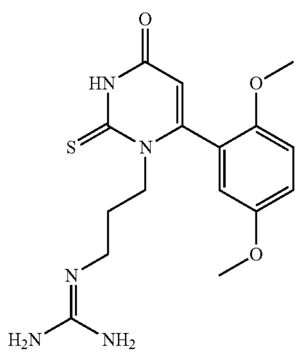 [SMILES: COc1ccc(OC)c(-c2cc(=O)[nH]c(=S)n2CCCN=C(N)N)c1] | 2-{3-[6-(2,5-dimethoxyphenyl)-4-oxo-2-thioxo-3,4-dihydropyrimidin-1(2H)-yl]propyl}guanidine trifluoroacetate | 364.1 | 2.44 min Waters Atlantis dC18 5 um 4.6 × 50 mm, 95% H2O/5% MeCN linear to 5% H2O/95% MeCN over 4.0 min, HOLD at 5% H2O/95% MeCN to 5.0 min. (0.05% TFA). Flow rate: 2 mL/min |
| 132 | 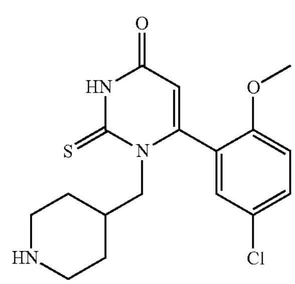 [SMILES: COc1ccc(Cl)cc1-c1cc(=O)[nH]c(=S)n1CC1CCNCC1] | 6-(5-chloro-2-methoxyphenyl)-1-(piperidin-4-ylmethyl)-2-thioxo-2,3-dihydropyrimidin-4(1H)-one hydrochloride | 366.0 | 3.639 min Column: XBRIDGE-C18 4.6 × 75 mm 3.5 μm Mobile phase-A = 0.1% FA IN ACN, B = 0.1% FA IN WATER Time(min)/% B = 0/90, 0.8/90, 1.8/55, 3/5, 6.5/5, 7/90 Flow: 0.8 mL/min, Column Temp = 40° C.; Diluent: MEOH |
| 133 | 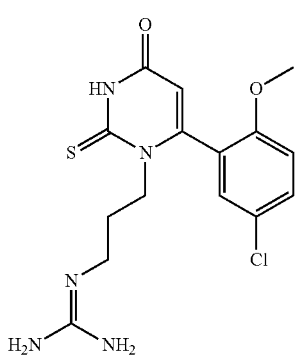 [SMILES: COc1ccc(Cl)cc1-c1cc(=O)[nH]c(=S)n1CCCN=C(N)N] | 2-{3-[6-(5-chloro-2-methoxyphenyl)-4-oxo-2-thioxo-3,4-dihydropyrimidin-1(2H)-yl]propyl}guanidine | 368.1 | 1.38 min Waters XBridge C18 4.6 × 50 mm, 5 um 95% H20/5% MeCN linear to 5% H20/95% MeCN over 4.0 min, HOLD at 5% H20/95% MeCN to 5.0 min. Flow: 2.0 mL/min. NH4OH 0.03% Flow rate: 2 mL/min |
| 134 | 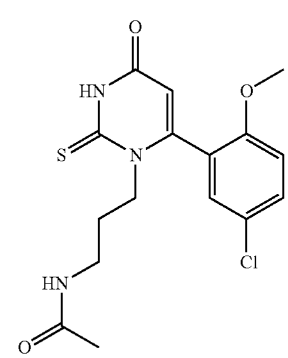 [SMILES: COc1ccc(Cl)cc1-c1cc(=O)[nH]c(=S)n1CCCNC(C)=O] | N-{3-[6-(5-chloro-2-methoxyphenyl)-4-oxo-2-thioxo-3,4-dihydropyrimidin-1(2H)-yl]propyl}acetamide | 368.1 | 1H NMR (400 MHz, DMSO-d6) d ppm 12.73 (s, 1 H), 7.62 (t, J = 6.0 Hz, 1 H), 7.58 (dd, J = 9.0, 2.7 Hz, 1 H), 7.50 (d, J = 2.7 Hz, 1 H), 7.21 (s, 0 H), 5.83 (d, J = 2.1 Hz, 1 H), 4.12-4.27 (m, 1 H), 3.85 (s, 3 H), 3.58-3.70 (m, 1 H), 2.78 (q, J = 6.2 Hz, 2 H), 1.65-1.75 (m, 0 H), 1.61 (s, 3 H), 1.46-1.58 (m, 1 H) |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 135 | 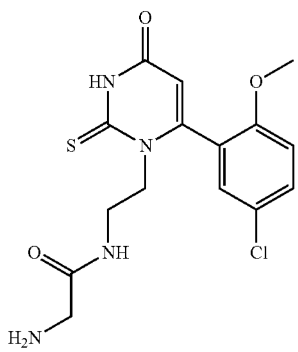 [SMILES: COc1ccc(Cl)cc1-c1cc(=O)[nH]c(=S)n1CCNC(=O)CN] | N-{2-[6-(5-chloro-2-methoxyphenyl)-4-oxo-2-thioxo-3,4-dihydropyrimidin-1(2H)-yl]ethyl}glycinamide hydrochloride | 369.2 | 1H NMR (400 MHz, CD$_3$OD) d ppm 7.54 (dd, 1 H), 7.46 (d, 1 H), 7.17 (d, 1 H), 5.81 (s, 1 H), 4.78 (m, 1 H), 3.91 (s, 3 H), 3.80 (m, 1 H), 3.55 (m, 2 H), 3.46 (t, 2 H) |
| 136 | 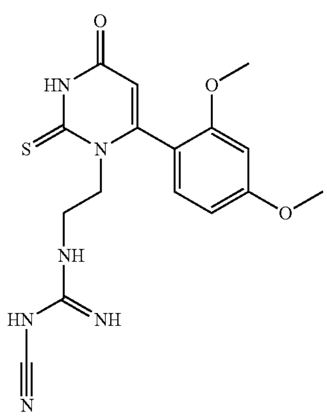 [SMILES: COc1ccc(-c2cc(=O)[nH]c(=S)n2CCNC(=N)NC#N)c(OC)c1] | 1-cyano-3-{2-[6-(2,4-dimethoxyphenyl)-4-oxo-2-thioxo-3,4-dihydropyrimidin-1(2H)-yl]ethyl}guanidine | 375.0 | 1H NMR (400 MHz, DMSO-d6): δ 7.17 (d, 1 H), 6.70-6.88 (br, 1 H), 6.55-6.65 (m, 4 H), 5.69 (s, 1 H), 4.43-4.45 (m, 1 H), 3.88 (s, 3 H), 3.84 (s, 3 H), 3.59-3.68 (m, 1 H), 3.30-3.40 (m, 1H), 3.16-3.17 (m, 1 H). |
| 137 | 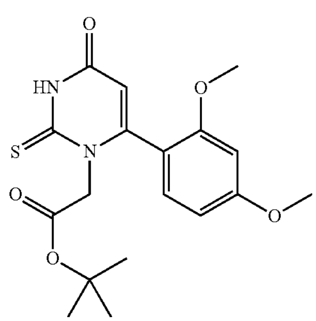 [SMILES: COc1ccc(-c2cc(=O)[nH]c(=S)n2CC(=O)OC(C)(C)C)c(OC)c1] | tert-butyl [6-(2,4-dimethoxyphenyl)-4-oxo-2-thioxo-3,4-dihydropyrimidin-1(2H)-yl]acetate | 379.1 | 2.59 min Waters XBridge C18 4.6 × 50 mm, 5 um 95% H20/5% MeCN linear to 5% H20/95% MeCN over 4.0 min, HOLD at 5% H20/95% MeCN to 5.0 min. Flow: 2.0 mL/min. NH4OH 0.03% Flow rate: 2 mL/min |
| 138 | 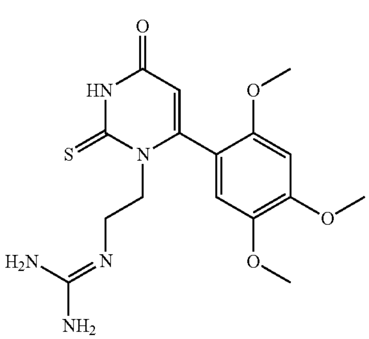 [SMILES: COc1cc(OC)c(-c2cc(=O)[nH]c(=S)n2CCN=C(N)N)cc1OC] | 2-{2-[4-oxo-2-thioxo-6-(2,4,5-trimethoxyphenyl)-3,4-dihydropyrimidin-1(2H)-yl]ethyl}guanidine hydrochloride | 380.1 | 1H NMR (500 MHz, DMSO-d6) δ ppm 12.80 (d, J = 1.71 Hz, 1 H), 7.59 (t, J = 6.10 Hz, 1 H), 6.98 (br. s., 4 H), 6.89 (s, 1 H), 6.80 (s, 1 H), 5.81 (d, J = 2.20 Hz, 1 H), 4.54 (br. d, J = 14.15 Hz, 1 H), 3.86 (s, 3 H), 3.82 (s, 3 H), 3.77-3.81 (m, 1 H), 3.75 (s, 3 H), 3.53 (ddt, J = 14.45, 8.72, 5.49, 5.49 Hz, 1 H), 3.15-3.25 (m, 1 H) |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 139 | 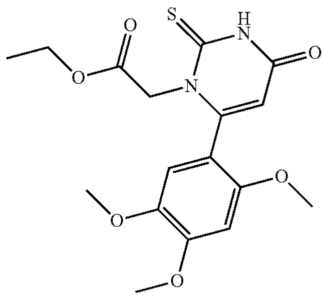 [SMILES: CCOC(=O)Cn1c(-c2cc(OC)c(OC)cc2OC)cc(=O)[nH]c1=S] | ethyl [4-oxo-2-thioxo-6-(2,4,5-trimethoxyphenyl)-3,4-dihydropyrimidin-1(2H)-yl]acetate | 381.1 | 1H NMR (400 MHz, CHLOROFORM-d) δ ppm 9.60 (br. s., 1 H), 6.71 (s, 1 H), 6.52 (s, 1 H), 5.86 (s, 1 H), 5.39 (br. d, J = 17.40 Hz, 1 H), 4.24 (br. d, J = 17.80 Hz, 1 H), 4.02-4.18 (m, 2 H), 3.93 (s, 3 H), 3.81 (s, 3 H), 3.79 (s, 3 H), 1.18 (t, J = 7.13 Hz, 3 H) |
| 140 | 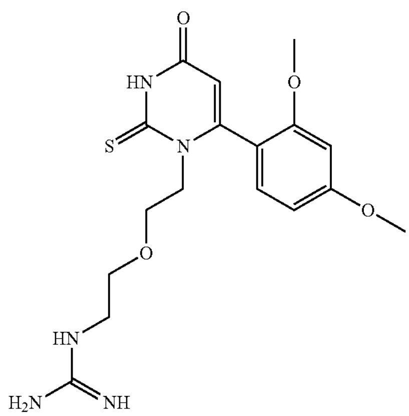 [SMILES: COc1ccc(-c2cc(=O)[nH]c(=S)n2CCOCCNC(=N)N)c(OC)c1] | 1-(2-{2-[6-(2,4-dimethoxyphenyl)-4-oxo-2-thioxo-3,4-dihydropyrimidin-1(2H)-yl]ethoxy}ethyl)guanidine formate | 393.8 | 1H NMR (400 MHz, METHANOL-d4): δ 8.38 (br.s., 1H), 7.21 (d, 1H), 6.66-6.62 (m, 2H), 5.73 (s, 1H), 4.82-4.76 (m, 1H), 3.93-3.81 (m, 7H), 3.77-3.71 (m, 1H), 3.57-3.51 (m, 1H), 3.44-3.40 (m, 2H), 3.27-3.22 (m, 2H). |
| 141 | 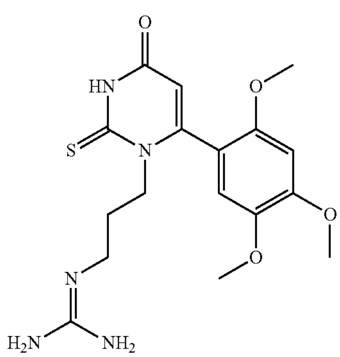 [SMILES: COc1cc(OC)c(-c2cc(=O)[nH]c(=S)n2CCCN=C(N)N)cc1OC] | 2-{3-[4-oxo-2-thioxo-6-(2,4,5-trimethoxyphenyl)-3,4-dihydropyrimidin-1(2H)-yl]propyl}guanidine trifluoroacetate | 394.1 | 1.60 min Waters Atlantis dC18 5 um 4.6 × 50 mm, 95% H2O/5% MeCN linear to 5% H2O/95% MeCN over 4.0 min, HOLD at 5% H2O/95% MeCN to 5.0 min. (0.05% TFA). Flow rate: 2 mL/min |
| 142 | 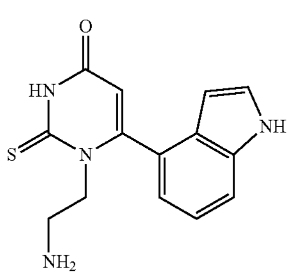 [SMILES: NCCn1c(-c2cccc3[nH]ccc23)cc(=O)[nH]c1=S] | 1-(2-aminoethyl)-6-(1H-indol-4-yl)-2-thioxo-2,3-dihydropyrimidin-4(1H)-one trifluoroacetate | 270.1 [M − NH3 + 1]+ | 1H NMR (300 MHz, METHANOL-d4) δ ppm 11.13 (br. s., 1 H), 7.62 (d, J = 8.01 Hz, 1 H), 7.44 (d, J = 3.14 Hz, 1 H), 7.29 (t, J = 7.66 Hz, 1 H), 7.13 (d, J = 7.32 Hz, 1 H), 6.40 (d, J = 2.44 Hz, 1 H), 5.93 (s, 1 H), 4.70-4.81 (m, 1 H), 4.32 (dt, J = 14.28, 7.14 Hz, 1 H), 2.91-3.11 (m, 2 H) |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 143 | 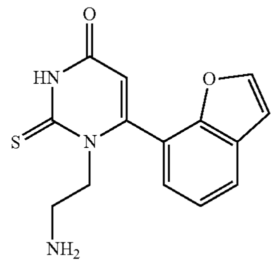 [SMILES: NCCn1c(-c2cccc3ccoc23)cc(=O)[nH]c1=S] | 1-(2-aminoethyl)-6-(1-benzofuran-7-yl)-2-thioxo-2,3-dihydropyrimidin-4(1H)-one hydrochloride | 270.9 [M − NH3 + 1]+ | 1H NMR (400 MHz, DMSO-d6) δ ppm 13.01 (br. s, 1 H), 8.13 (d, J = 1.96 Hz, 1 H), 7.90 (dd, J = 7.34, 1.96 Hz, 1 H), 7.67 (br. s, 3 H), 7.42-7.49 (m, 2 H), 7.14 (d, J = 2.45 Hz, 1 H), 6.04 (s, 1 H), 4.57-4.73 (m, 1 H), 3.85-4.02 (m, 1 H), 3.03-3.09 (m, 1 H), 2.83-2.91 (m, 1 H) |
| 144 | 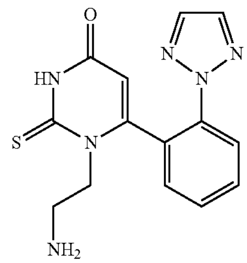 [SMILES: NCCn1c(-c2ccccc2-n2nccn2)cc(=O)[nH]c1=S] | 1-(2-aminoethyl)-2-thioxo-6-[2-(2H-1,2,3-triazol-2-yl)phenyl]-2,3-dihydropyrimidin-4(1H)-one hydrochloride | 297.9 [M − NH3 + 1]+ | 1H NMR (400 MHz, METHANOL-d4): δ 8.11 (d, 1H), 7.90 (s, 2H), 7.74 (t, 1H), 7.60 (d, 2H), 5.62 (s, 1H), 4.67 (m, 1H), 4.10 (m, 1H), 3.28 (m, 1H), 3.05 (s, 1H).: |
| 145 | 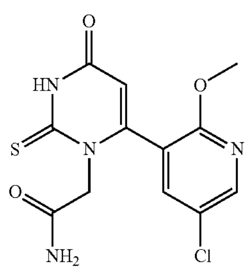 [SMILES: COc1ncc(Cl)cc1-c1cc(=O)[nH]c(=S)n1CC(N)=O] | 2-[6-(5-chloro-2-methoxypyridin-3-yl)-4-oxo-2-thioxo-3,4-dihydropyrimidin-1(2H)-yl]acetamide | 325.0 [M − H]− | 1H NMR (400 MHz, METHANOL-d4) δ ppm 8.31 (s, 1 H), 7.72 (s, 1 H), 5.88 (s, 1 H), 5.56-5.72 (m, 1 H), 4.06-4.21 (m, 1 H), 3.95 (s, 3 H) |
| 146 | 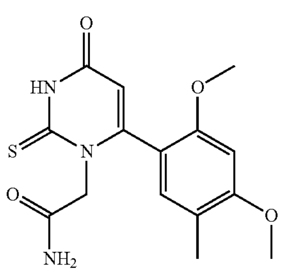 [SMILES: COc1cc(OC)c(-c2cc(=O)[nH]c(=S)n2CC(N)=O)cc1C] | 2-[6-(2,4-dimethoxy-5-methylphenyl)-4-oxo-2-thioxo-3,4-dihydropyrimidin-1(2H)-yl]acetamide | 358.0 [M + Na]+ | 1H NMR (400 MHz, DMSO-d6): δ 12.55 (br, 1 H), 7.31 (s, 1 H), 7.02 (s, 1 H), 6.92 (s, 1 H), 6.72 (s, 1 H), 5.72 (s, 1 H), 5.35 (br.s., 1 H), 3.93 (br.s., 1 H), 3.88 (s, 3 H), 3.85 (s, 3 H), 2.05 (s 3 H). |
| 147 | 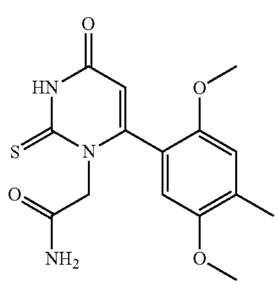 [SMILES: COc1cc(-c2cc(=O)[nH]c(=S)n2CC(N)=O)c(OC)cc1C] | 2-[6-(2,5-dimethoxy-4-methylphenyl)-4-oxo-2-thioxo-3,4-dihydropyrimidin-1(2H)-yl]acetamide | 358.0 [M + Na]+ | 1H NMR (400 MHz, METHANOL-d4): δ 6.86 (s, 1H), 6.69 (s, 1H), 5.72 (s, 1H), 4.57 (m, 1H), 4.10 (m, 1H), 3.74 (s, 3H), 3.68 (s, 3H), 2.16 (s, 3H). |

TABLE 2-continued

Examples from Carboxylic Acid Route

| Example # | Structure | Compound Name | Obs Mass | 1H NMR Spectral Data or HPLC Retention Time and Conditions |
|---|---|---|---|---|
| 148 | 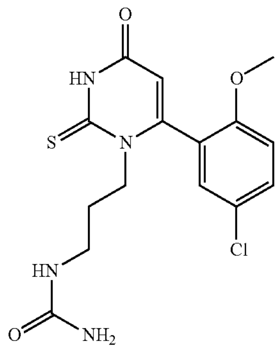 [SMILES: COc1ccc(Cl)cc1-c1cc(=O)[nH]c(=S)n1CCCNC(N)=O] | 1-{3-[6-(5-chloro-2-methoxyphenyl)-4-oxo-2-thioxo-3,4-dihydropyrimidin-1(2H)-yl]propyl}urea | 367.2 [M − 1]⁻ | 1H NMR (500 MHz, DMSO-d6) d ppm 12.72 (br. s, 1 H), 7.57 (dd, J = 9.0, 2.7 Hz, 1 H), 7.52 (d, J = 2.7 Hz, 1 H), 7.19 (d, J = 9.0 Hz, 1 H), 5.84 (s, 1 H), 5.75 (m, 1 H), 5.26 (s, 2 H), 4.26 (m, 1 H), 3.84 (s, 3 H), 3.61 (m, J = 10.0 Hz, 1 H), 2.72 (m, 2 H), 1.65 (m, 1 H), 1.49 (dd, J = 11.6, 5.7 Hz, 1 H) |
| 149 | 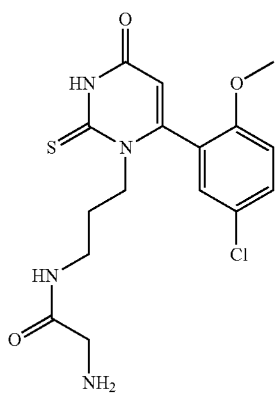 [SMILES: COc1ccc(Cl)cc1-c1cc(=O)[nH]c(=S)n1CCCNC(=O)CN] | N-{3-[6-(5-chloro-2-methoxyphenyl)-4-oxo-2-thioxo-3,4-dihydropyrimidin-1(2H)-yl]propyl}glycinamide hydrochloride | 381.2 [M − 1]⁻ | 1H NMR (500 MHz, DMSO-d6) d ppm 8.29 (t, J = 5.6 Hz, 1 H), 7.87-8.16 (m, 2 H), 7.60 (dd, J = 9.0, 2.7 Hz, 1 H), 7.53 (d, J = 2.7 Hz, 1 H), 7.23 (d, J = 9.0 Hz, 1 H), 5.87 (s, 1 H), 4.17-4.32 (m, 1 H), 3.84 (s, 3 H), 3.56-3.73 (m, 1 H), 3.34-3.42 (m, 2 H), 2.80-3.00 (m, 2 H), 1.74 (d, J = 6.6 Hz, 1 H), 1.55-1.64 (m, 1 H) |
| 150 | 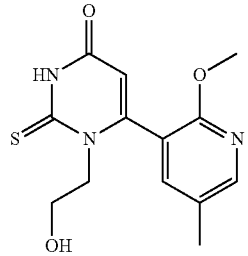 [SMILES: COc1ncc(C)cc1-c1cc(=O)[nH]c(=S)n1CCO] | 1-(2-hydroxyethyl)-6-(2-methoxy-5-methylpyridin-3-yl)-2-thioxo-2,3-dihydropyrimidin-4(1H)-one | 293.8 | 1H NMR (400 MHz, CD₃OD) d ppm 8.14 (m, 1 H), 7.59 (d, 1 H), 5.78 (d, 1 H), 4.71 (m, 1 H), 3.96 (d, 3 H), 3.85 (dt, 1 H), 3.70 (dt, 1 H), 3.59 (m, 1 H), 2.32 (s, 3 H) |

The following Examples of Table 3 were prepared from the corresponding methyl ketone to afford the intermediate beta-keto-ester as described above for the Preparations in the Methyl Ketone Route section followed by employing other methods described in the I. Beta Ketone Ester Route Section as well as standard methods and techniques known to those skilled in the art.

TABLE 3

Examples from Methyl Ketone Route

| Example # | Structure | Compound Name | Obs Mass | 1H NMR Spectral Data or HPLC Retention Time and Conditions |
|---|---|---|---|---|
| 151 | ABS | 6-(2,4-dimethoxyphenyl)-1-[(3R)-piperidin-3-ylmethyl]-2-thioxo-2,3-dihydropyrimidin-4(1H)-one hydrochloride | 362.0 | 3.653 min Column: XBRIDGE-C18 4.6 X 75 mm 3.5 μm Mobile phase- A = 0.1% FA IN ACN, B = 0.1% FA IN WATER Time(min)/% B = 0/90, 0.8/90, 1.8/55, 3/5, 6.5/5, 7/90 Flow: 0.8 mL/min, Column Temp = 40° C.; Diluent: CAN |
| 152 | 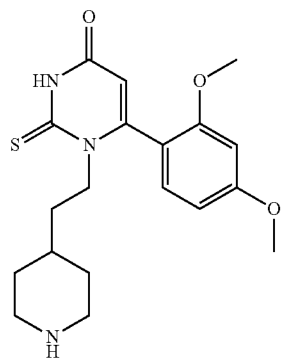 | 6-(2,4-dimethoxyphenyl)-1-(2-piperidin-4-ylethyl)-2-thioxo-2,3-dihydropyrimidin-4(1H)-one hydrochloride | 376.1 | 1H NMR (400 MHz, METHANOL-d4): δ 7.26 (d, 1H), 6.70 (d, 1H), 6.67 (dd, 1H), 5.76 (s, 1H), 4.56-4.67 (m, 1H), 3.88 (s, 3H), 3.8 (s, 3H), 3.72-3.80 (m, 1H), 3.22-3.25 (m, 2H), 2.82-2.89 (t, 2H), 1.63-1.75 (m, 3H), 1.341.48 (m, 2H), 1.08-1.29 (m, 2H). |
| 153 | 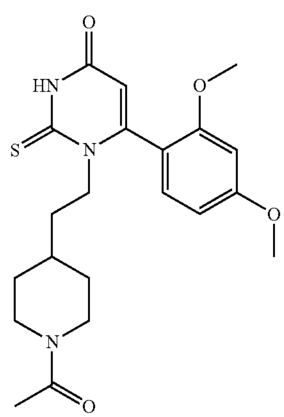 | 1-[2-(1-acetylpiperidin-4-yl)ethyl]-6-(2,4-dimethoxyphenyl)-2-thioxo-2,3-dihydropyrimidin-4(1H)-one | 440.1 [M + Na]+ | 1H NMR (400 MHz, METHANOL-d4): δ 7.25 (d, 1H), 6.71 (d, 1H), 6.68 (dd, 1H), 5.75 (s, 1H), 4.52-4.65 (m, 1H), 4.27-4.35 (m, 1H), 3.88 (s, 6H), 3.70-3.80 (m, 2H), 2.92-3.03 (m, 1H), 2.49-2.56 (m, 1H), 2.05 (s, 3H), 1.71-1.74 (m, 1H), 1.33-1.57 (m, 4H), 0.68-1.10 (m, 2H). |
| 154 | 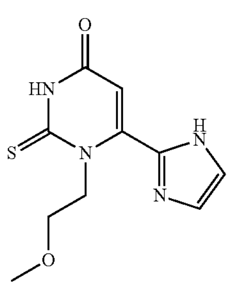 | 6-(1H-imidazol-2-yl)-1-(2-methoxyethyl)-2-thioxo-2,3-dihydropyrimidin-4(1H)-one | 253.1 | 1H NMR (400 MHz, METHANOL-d3) δ ppm 7.26 (br. s., 2 H), 6.04 (s, 1 H), 4.84 (br. s., 2 H), 3.63 (t, J = 5.27 Hz, 2 H), 3.13 (s, 3 H) |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 155 | 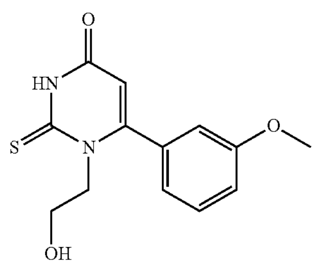 [SMILES: COc1cccc(-c2cc(=O)[nH]c(=S)n2CCO)c1] | 1-(2-hydroxyethyl)-6-(3-methoxyphenyl)-2-thioxo-2,3-dihydropyrimidin-4(1H)-one | 279.1 | 1H NMR (400 MHz, METHANOL-d3) δ ppm 7.43 (dd, J = 7.80, 7.80 Hz, 1 H), 7.08 (ddd, J = 8.47, 2.52, 0.92 Hz, 1 H), 7.04 (dd, J = 2.29, 2.29 Hz, 1 H), 7.00 (ddd, J = 7.80, 2.30, 0.92 Hz, 1 H), 5.79 (s, 1 H), 4.26-4.39 (m, 2 H), 3.84 (s, 3 H), 3.77 (t, J = 6.18 Hz, 2 H) |
| 156 | 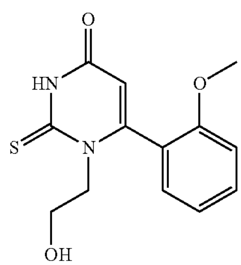 [SMILES: COc1ccccc1-c1cc(=O)[nH]c(=S)n1CCO] | 1-(2-hydroxyethyl)-6-(2-methoxyphenyl)-2-thioxo-2,3-dihydropyrimidin-4(1H)-one | 279.1 | 1H NMR (400 MHz, CHLOROFORM-d) δ ppm 7.51 (ddd, J = 8.24, 7.30, 1.80 Hz, 1 H), 7.25 (dd, J = 7.56, 1.60 Hz, 1 H), 7.08 (ddd, J = 7.60, 7.60, 0.90 Hz, 1 H), 7.00 (d, J = 8.24 Hz, 1 H), 5.86 (s, 1 H), 4.70-4.79 (m, 1 H), 3.83-3.91 (m, 5 H), 3.64-3.72 (m, 1 H) |
| 157 | 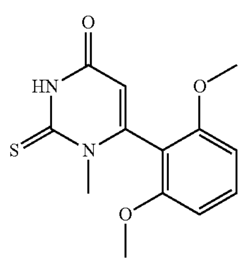 [SMILES: COc1cccc(OC)c1-c1cc(=O)[nH]c(=S)n1C] | 6-(2,6-dimethoxyphenyl)-1-methyl-2-thioxo-2,3-dihydropyrimidin-4(1H)-one | 279.2 | 1H NMR (400 MHz, CHLOROFORM-d) δ ppm 10.00 (br. s., 1 H), 7.40 (t, J = 7.79 Hz, 1 H), 6.62 (d, J = 8.24 Hz, 2 H), 5.85 (s, 1 H), 3.80 (s, 6 H), 3.45 (s, 3 H) |
| 158 | 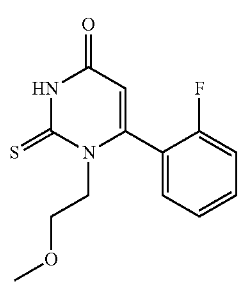 [SMILES: COCCn1c(-c2ccccc2F)cc(=O)[nH]c1=S] | 6-(2-fluorophenyl)-1-(2-methoxyethyl)-2-thioxo-2,3-dihydropyrimidin-4(1H)-one | 281.1 | 1H NMR (400 MHz, METHANOL-d3) δ ppm 7.54-7.63 (m, 1 H), 7.47 (ddd, J = 7.60, 7.60, 1.80 Hz, 1 H), 7.35 (ddd, J = 7.80, 7.80, 1.40 Hz, 1 H), 7.29 (ddd, J = 9.85, 8.47, 0.92 Hz, 1 H), 5.86 (s, 1 H), 4.64 (dt, J = 14.08, 4.64 Hz, 1 H), 3.99-4.12 (m, 1 H), 3.70 (ddd, J = 10.53, 7.33, 5.04 Hz, 1 H), 3.48 (dt, J = 10.42, 5.09 Hz, 1 H), 3.11 (s, 3 H) |
| 159 | 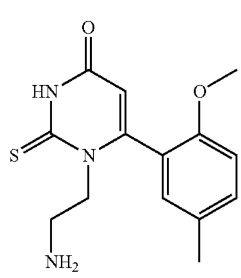 [SMILES: COc1ccc(C)cc1-c1cc(=O)[nH]c(=S)n1CCN] | 1-(2-aminoethyl)-6-(2-methoxy-5-methylphenyl)-2-thioxo-2,3-dihydropyrimidin-4(1H)-one hydrochloride | 292 | 1H NMR (500 MHz, DMSO-d6) δ ppm 12.80-12.90 (m, 1 H) 7.95 (br. s., 3 H) 7.36 (dd, J = 8.42, 1.83 Hz, 1 H) 7.18 (d, J = 1.95 Hz, 1 H) 7.10 (d, J = 8.54 Hz, 1 H) 5.78 (d, J = 2.20 Hz, 1 H) 4.54-4.65 (m, 1 H) 3.86-3.96 (m, 1 H) 3.81 (s, 3 H) 2.82-2.95 (m, 2 H) 2.29 (s, 3 H) |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 160 | 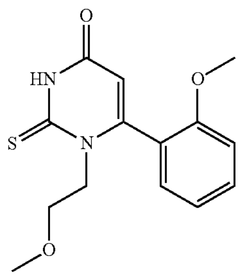 [SMILES: COCCn1c(-c2ccccc2OC)cc(=O)[nH]c1=S] | 1-(2-methoxyethyl)-6-(2-methoxyphenyl)-2-thioxo-2,3-dihydropyrimidin-4(1H)-one | 293.1 | 1H NMR (400 MHz, METHANOL-d3) d ppm 7.53 (ddd, J = 8.00, 8.00, 1.80 Hz, 1 H), 7.32 (dd, J = 7.33, 1.83 Hz, 1 H), 7.14 (d, J = 8.70 Hz, 1 H), 7.09 (ddd, J = 7.60, 7.60, 0.90 Hz, 1 H), 5.75 (s, 1 H), 4.71 (ddd, J = 13.74, 5.95, 4.12 Hz, 1 H), 3.89 (s, 3H), 3.80-3.88 (m, 1 H), 3.68 (ddd, J = 10.53, 7.79, 5.95 Hz, 1 H), 3.43 (ddd, J = 10.42, 6.53, 4.12 Hz, 1 H), 3.08 (s, 3 H) |
| 161 | 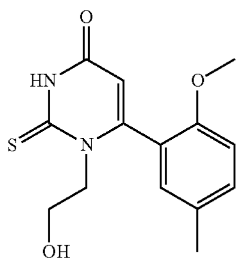 [SMILES: COc1ccc(C)cc1-c1cc(=O)[nH]c(=S)n1CCO] | 1-(2-hydroxyethyl)-6-(2-methoxy-5-methylphenyl)-2-thioxo-2,3-dihydropyrimidin-4(1H)-one | 293.2 | 1H NMR (400 MHz, DMSO-d6) δ ppm 12.71 (br. s, 1 H) 7.32 (ddd, J = 8.39, 2.15, 0.59 Hz, 1 H) 7.14 (d, J = 2.15 Hz, 1 H) 7.06 (d, J = 8.39 Hz, 1 H) 5.72 (d, J = 2.15 Hz, 1 H) 4.70 (t, J = 5.56 Hz, 1 H) 4.43-4.51 (m, 1 H) 3.79 (s, 3 H) 3.55-3.64 (m, 1 H) 3.47-3.55 (m, 1 H) 3.38-3.46 (m, 1 H) 2.28 (s, 3 H) |
| 162 | 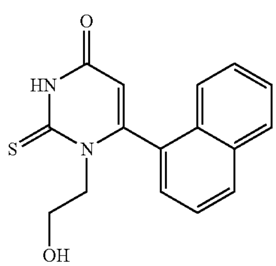 [SMILES: O=c1cc(-c2cccc3ccccc23)n(CCO)c(=S)[nH]1] | 1-(2-hydroxyethyl)-6-(1-naphthyl)-2-thioxo-2,3-dihydropyrimidin-4(1H)-one | 299.1 | 1H NMR (400 MHz, DMSO-d6) δ ppm 12.82 (br. s., 1 H), 7.99-8.13 (m, 2 H), 7.67-7.73 (m, 1 H), 7.52-7.66 (m, 4 H), 5.87 (d, J = 1.76 Hz, 1 H), 4.61 (br. s., 1 H), 4.23-4.37 (m, 1 H), 3.34-3.51 (m, 3 H) |
| 163 | 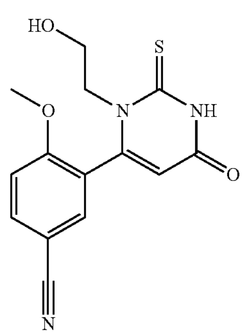 [SMILES: COc1ccc(C#N)cc1-c1cc(=O)[nH]c(=S)n1CCO] | 3-[3-(2-hydroxyethyl)-6-oxo-2-thioxo-1,2,3,6-tetrahydropyrimidin-4-yl]-4-methoxybenzonitrile | 304.2 | 1H NMR (500 MHz, DMSO-d6) δ ppm 12.80 (s, 1 H) 8.03 (dd, J = 8.78, 1.95 Hz, 1 H) 7.82 (d, J = 2.20 Hz, 1 H) 7.36 (d, J = 8.78 Hz, 1 H) 5.87 (d, J = 2.20 Hz, 1 H) 4.46-4.54 (m, 1 H) 3.92 (s, 3 H) 3.57-3.64 (m, 1 H) 3.38-3.49 (m, 2 H) |
| 164 | 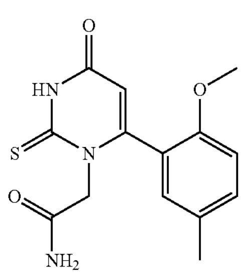 [SMILES: COc1ccc(C)cc1-c1cc(=O)[nH]c(=S)n1CC(N)=O] | 2-[6-(2-methoxy-5-methylphenyl)-4-oxo-2-thioxo-3,4-dihydropyrimidin-1(2H)-yl]acetamide | 306.0 | 1.44 min Waters Atlantis dC18 5 um 4.6 x 50 mm, 95% H2O/5% MeCN linear to 5% H2O/95% MeCN over 4.0 min, HOLD at 5% H2O/95% MeCN to 5.0 min. (0.05% TFA). Flow rate: 2 mL/min |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 165 | 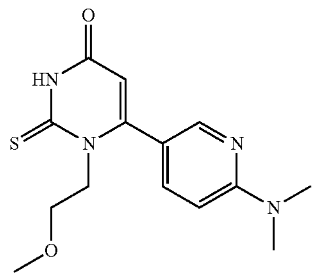 [SMILES: COCCn1c(-c2ccc(N(C)C)nc2)cc(=O)[nH]c1=S] | 6-[6-(dimethylamino)pyridin-3-yl]-1-(2-methoxyethyl)-2-thioxo-2,3-dihydropyrimidin-4(1H)-one | 307.2 | 1H NMR (400 MHz, METHANOL-d3) δ ppm 8.07 (d, J = 1.83 Hz, 1 H), 7.99 (dd, J = 9.62, 2.29 Hz, 1 H), 7.28 (d, J = 9.62 Hz, 1 H), 5.90 (s, 1 H), 4.40 (br. s., 2 H), 3.71 (t, J = 5.04 Hz, 2 H), 3.33 (s, 6 H), 3.26 (s, 3 H) |
| 166 | 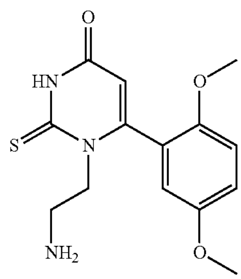 [SMILES: COc1ccc(OC)c(-c2cc(=O)[nH]c(=S)n2CCN)c1] | 1-(2-aminoethyl)-6-(2,5-dimethoxyphenyl)-2-thioxo-2,3-dihydropyrimidin-4(1H)-one hydrochloride | 308.0 | 1H NMR (400 MHz, DMSO-d6) δ ppm 12.87 (s, 1 H) 7.93 (br. s., 3 H) 7.09-7.16 (m, 2 H) 7.03 (d, J = 2.73 Hz, 1 H) 5.82 (d, J = 1.95 Hz, 1 H) 4.54-4.64 (m, 1 H) 3.86-3.98 (m, 1 H) 3.79 (s, 3 H) 3.75 (s, 3 H) 2.85-2.97 (m, 2 H) |
| 167 | 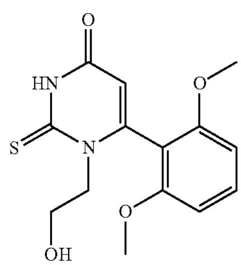 [SMILES: COc1cccc(OC)c1-c1cc(=O)[nH]c(=S)n1CCO] | 6-(2,6-dimethoxyphenyl)-1-(2-hydroxyethyl)-2-thioxo-2,3-dihydropyrimidin-4(1H)-one | 309.0 | 1H NMR (400 MHz, DMSO-d6) δ ppm 12.72 (br. s., 1 H), 7.45 (t, J = 8.36 Hz, 1 H), 6.79 (d, J = 8.47 Hz, 2 H), 5.71 (d, J = 2.06 Hz, 1 H), 3.94 (t, J = 7.21 Hz, 2 H), 3.76 (s, 6 H), 3.35 (t, J = 7.56 Hz, 2 H) |
| 168 | 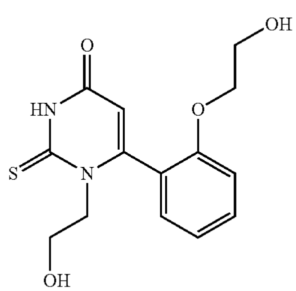 [SMILES: O=c1cc(-c2ccccc2OCCO)n(CCO)c(=S)[nH]1] | 6-[2-(2-hydroxyethoxy)phenyl]-1-(2-hydroxyethyl)-2-thioxo-2,3-dihydropyrimidin-4(1H)-one | 309.1 | 1.57 min Waters Atlantis dC18 5 um 4.6 x 50 mm, 95% H2O/5% MeCN linear to 5% H2O/95% MeCN over 4.0 min, HOLD at 5% H2O/95% MeCN to 5.0 min. (0.05% TFA). Flow rate: 2 mL/min |
| 169 | 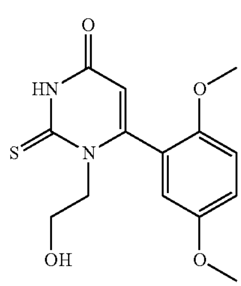 [SMILES: COc1ccc(OC)c(-c2cc(=O)[nH]c(=S)n2CCO)c1] | 6-(2,5-dimethoxyphenyl)-1-(2-hydroxyethyl)-2-thioxo-2,3-dihydropyrimidin-4(1H)-one | 309.2 | 1H NMR (500 MHz, DMSO-d6) δ ppm 12.72 (s, 1 H) 7.06-7.11 (m, 2 H) 6.95 (d, J = 2.44 Hz, 1 H) 5.77 (d, J = 2.20 Hz, 1 H) 4.72 (t, J = 5.61 Hz, 1 H) 4.44-4.50 (m, 1 H) 3.77 (s, 3 H) 3.74 (s, 3 H) 3.51-3.64 (m, 2 H) 3.40-3.46 (m, 1 H) |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 170 | 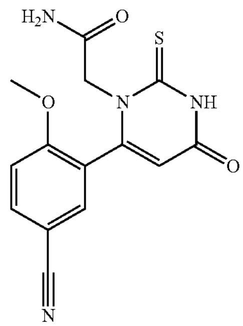 [SMILES: COc1ccc(C#N)cc1-c1cc(=O)[nH]c(=S)n1CC(N)=O] | 2-[6-(5-cyano-2-methoxyphenyl)-4-oxo-2-thioxo-3,4-dihydropyrimidin-1(2H)-yl]acetamide | 317.2 | 1H NMR (500 MHz, DMSO-d6) δ ppm 3.76-3.94 (m, 2 H), 3.93 (s, 3 H), 5.92 (d, J = 1.7 Hz, 1 H), 7.10 (br. s., 1 H), 7.31 (br. s., 1 H), 7.37 (d, J = 8.8 Hz, 1 H), 7.61 (s, 1 H), 8.03 (dd, J = 8.7, 1.6 Hz, 1 H), 12.88 (br. s., 1 H) |
| 171 | 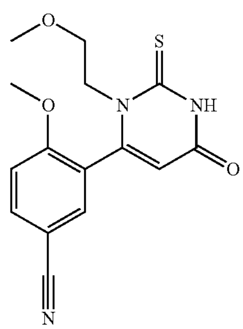 [SMILES: COCCn1c(-c2cc(C#N)ccc2OC)cc(=O)[nH]c1=S] | 4-methoxy-3-[3-(2-methoxyethyl)-6-oxo-2-thioxo-1,2,3,6-tetrahydro-pyrimidin-4-yl]benzonitrile | 318.1 | 2.34 min Waters Atlantis dC18 5 um 4.6 x 50 mm, 95% H2O/5% MeCN linear to 5% H2O/95% MeCN over 4.0 min, HOLD at 5% H2O/95% MeCN to 5.0 min. (0.05% TFA). Flow rate: 2 mL/min |
| 172 | 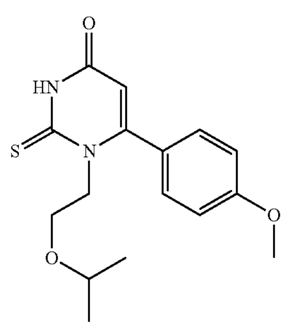 [SMILES: COc1ccc(-c2cc(=O)[nH]c(=S)n2CCOC(C)C)cc1] | 1-(2-isopropoxyethyl)-6-(4-methoxyphenyl)-2-thioxo-2,3-dihydropyrimidin-4(1H)-one | 321.1 | 1H NMR (400 MHz, CHLOROFORM-d) δ ppm 10.19 (br. s, 1 H) 7.29 (d, J = 8.78 Hz, 2 H) 6.97 (d, J = 8.97 Hz, 2 H) 5.84 (d, J = 2.15 Hz, 1 H) 4.37 (t, J = 5.46 Hz, 2 H) 3.87 (s, 3 H) 3.68 (t, J = 5.66 Hz, 2 H) 3.47 (spt, J = 6.08 Hz, 1 H) 1.06 (d, J = 6.05 Hz, 6 H) |
| 173 | 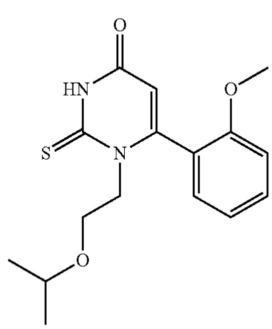 [SMILES: COc1ccccc1-c1cc(=O)[nH]c(=S)n1CCOC(C)C] | 1-(2-isopropoxyethyl)-6-(2-methoxyphenyl)-2-thioxo-2,3-dihydropyrimidin-4(1H)-one | 321.5 | 1H NMR (400 MHz, METHANOL-d4) δ ppm 7.53 (ddd, J = 8.39, 7.61, 1.76 Hz, 1 H) 7.33 (dd, J = 7.41, 1.76 Hz, 1 H) 7.13 (d, J = 8.58 Hz, 1 H) 7.08 (ddd, J = 7.51, 7.51, 0.98 Hz, 1 H) 5.75 (s, 1 H) 4.69 (ddd, J = 13.51, 6.58, 3.90 Hz, 1 H) 3.88 (s, 3 H) 3.78 (dt, J = 13.61, 7.34 Hz, 1 H) 3.64-3.72 (m, 1 H) 3.50 (ddd, J = 9.80, 7.07, 4.00 Hz, 1 H) 3.38 (spt, J = 6.11 Hz, 1 H) 0.99 (dd, J = 6.15, 2.44 Hz, 6 H) |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 174 | 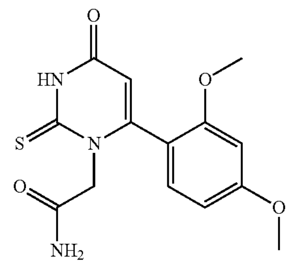 [SMILES: COc1ccc(-c2cc(=O)[nH]c(=S)n2CC(N)=O)c(OC)c1] | 2-[6-(2,4-dimethoxyphenyl)-4-oxo-2-thioxo-3,4-dihydropyrimidin-1(2H)-yl]acetamide | 322.2 | 1H NMR (500 MHz, DMSO-d6) δ ppm 12.75 (s, 1 H) 7.31 (br. s., 1 H) 7.08 (d, J = 8.54 Hz, 1 H) 6.98 (br. s., 1 H) 6.69 (d, J = 2.20 Hz, 1 H) 6.61 (dd, J = 8.54, 2.20 Hz, 1 H) 5.74 (s, 1 H) 5.38 (br. s., 1 H) 3.87 (br. s., 1 H) 3.82 (s, 3 H) 3.81 (s, 3 H) |
| 175 | ABS | 1-[(2R)-2-aminopropyl]-6-(2,4-dimethoxyphenyl)-2-thioxo-2,3-dihydropyrimidin-4(1H)-one hydrochloride | 322.1 | 1H NMR (400 MHz, METHANOL-d3) δ ppm 7.21-7.31 (m, 1 H), 6.71 (d, J = 1.83 Hz, 1 H), 6.68 (dd, J = 8.24, 2.29 Hz, 1 H), 5.77-5.85 (m, 1 H), 5.10-5.24 (m, 1 H), 3.87-3.90 (m, 3 H), 3.83-3.86 (m, 3 H), 3.61-3.73 (m, 1 H), 3.47-3.59 (m, 1 H), 0.90-1.15 (m, 3 H) |
| 176 | ABS | 1-[(2S)-2-aminopropyl]-6-(2,4-dimethoxyphenyl)-2-thioxo-2,3-dihydropyrimidin-4(1H)-one hydrochloride | 322.1 | 1H NMR (400 MHz, METHANOL-d3) δ ppm 7.24-7.33 (m, 1 H), 6.67-6.76 (m, 2 H), 5.80-5.85 (m, 1 H), 5.13-5.25 (m, 1 H), 3.87-3.92 (m, 6 H), 3.51-3.76 (m, 2 H), 0.95-1.16 (m, 3 H) |
| 177 | 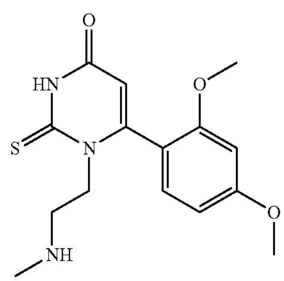 [SMILES: CNCCn1c(-c2ccc(OC)cc2OC)cc(=O)[nH]c1=S] | 6-(2,4-dimethoxyphenyl)-1-[2-(methylamino)ethyl]-2-thioxo-2,3-dihydropyrimidin-4(1H)-one formate | 322.1 | 1H NMR (400 MHz, METHANOL-d3) δ ppm 7.27 (d, J = 8.24 Hz, 1 H), 6.73 (d, J = 2.29 Hz, 1 H), 6.70 (dd, J = 8.47, 2.52 Hz, 1 H), 5.81 (s, 1 H), 4.06-4.17 (m, 2 H), 3.90 (s, 3 H), 3.87 (s, 3 H), 2.99-3.16 (m, 2 H), 2.55 (s, 3 H) |
| 178 | 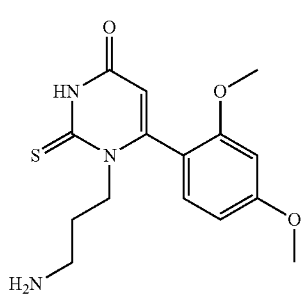 [SMILES: COc1ccc(-c2cc(=O)[nH]c(=S)n2CCCN)c(OC)c1] | 1-(3-aminopropyl)-6-(2,4-dimethoxyphenyl)-2-thioxo-2,3-dihydropyrimidin-4(1H)-one formate | 322.1 | 1H NMR (400 MHz, DMSO-d6) δ ppm 8.29 (s, 1 H), 7.25 (d, J = 8.70 Hz, 1 H), 6.68 (d, J = 2.29 Hz, 1 H), 6.62 (dd, J = 8.24, 2.29 Hz, 1 H), 5.72 (s, 1 H), 4.31-4.45 (m, 2 H), 3.80 (s, 3 H), 3.79 (s, 3 H), 3.16-3.62 (m, 3 H), 2.39-2.44 (m, 2 H), 1.52-1.81 (m, 2 H) |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 179 | 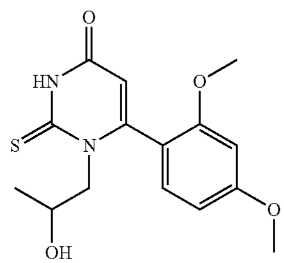 [SMILES: COc1ccc(-c2cc(=O)[nH]c(=S)n2CC(C)O)c(OC)c1] | 6-(2,4-dimethoxyphenyl)-1-(2-hydroxypropyl)-2-thioxo-2,3-dihydropyrimidin-4(1H)-one | 323.1 | 1H NMR (400 MHz, CHLOROFORM-d) δ ppm 9.57-9.72 (m, 1 H), 7.11-7.21 (m, 1 H), 6.45-6.60 (m, 2 H), 5.82 (dd, J = 13.05, 2.52 Hz, 1 H), 4.41-4.93 (m, 1 H), 4.27-4.41 (m, 1 H), 3.86 (s, 3 H), 3.82 (m, 3 H), 3.53-3.69 (m, 1 H), 0.94-1.05 (m, 3 H) |
| 180 | 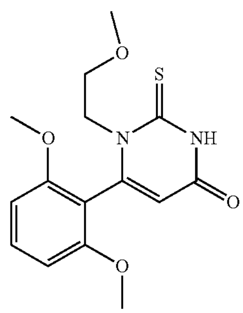 [SMILES: COCCn1c(-c2c(OC)cccc2OC)cc(=O)[nH]c1=S] | 6-(2,6-dimethoxyphenyl)-1-(2-methoxyethyl)-2-thioxo-2,3-dihydropyrimidin-4(1H)-one | 323.1 | 2.50 min Waters Atlantis dC18 5 um 4.6 x 50 mm, 95% H2O/5% MeCN linear to 5% H2O/95% MeCN over 4.0 min, HOLD at 5% H2O/95% MeCN to 5.0 min. (0.05% TFA). Flow rate: 2 mL/min |
| 181 | 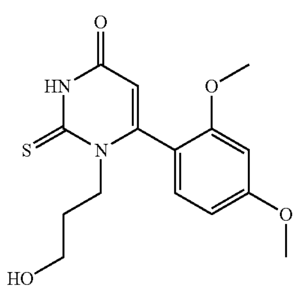 [SMILES: COc1ccc(-c2cc(=O)[nH]c(=S)n2CCCO)c(OC)c1] | 6-(2,4-dimethoxyphenyl)-1-(3-hydroxypropyl)-2-thioxo-2,3-dihydropyrimidin-4(1H)-one | 323.1 | 1H NMR (400 MHz, CHLOROFORM-d) δ ppm 9.46 (br. s., 1 H), 7.11 (d, J = 8.24 Hz, 1 H), 6.56 (dd, J = 8.24, 2.29 Hz, 1 H), 6.52 (d, J = 2.29 Hz, 1 H), 5.82 (d, J = 2.75 Hz, 1 H), 4.64-4.75 (m, 1 H), 3.86 (s, 3 H), 3.82 (s, 3 H), 3.80-3.89 (m, 2H), 3.49 (t, J = 5.72 Hz, 1 H), 1.56-1.83 (m, 2 H) |
| 182 | 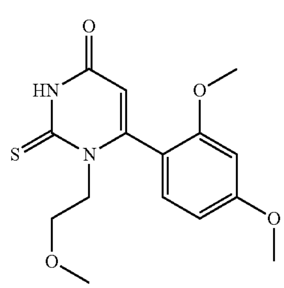 [SMILES: COCCn1c(-c2ccc(OC)cc2OC)cc(=O)[nH]c1=S] | 6-(2,4-dimethoxyphenyl)-1-(2-methoxyethyl)-2-thioxo-2,3-dihydropyrimidin-4(1H)-one | 323.2 | 1H NMR (300 MHz, CDCl3) 9.80 (bs, 1H), 7.13 (d, J = 8.4 Hz, 1H), 6.56 (d, J = 8.4 Hz, 1H), 6.50 (s, 1H), 5.80 (d, J = 2.1 Hz, 1H), 4.70 (dt, J = 13.5, 4.5 Hz, 1H), 3.86 (s, 3H), 3.83-3.91 (m, 1H) 3.82 (s, 3H), 3.66-3.74 (m, 1H), 3.41-3.47 (m, 1H), 3.16 (s, 3H) |
| 183 | 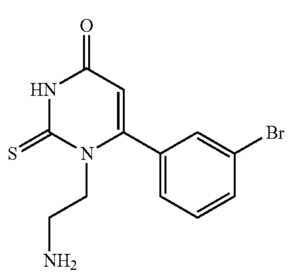 [SMILES: NCCn1c(-c2cccc(Br)c2)cc(=O)[nH]c1=S] | 1-(2-aminoethyl)-6-(3-bromophenyl)-2-thioxo-2,3-dihydropyrimidin-4(1H)-one hydrochloride | M + 1 (—NH2) = 311.0 | 1H NMR (500 MHz, DMSO-d6) = d ppm 12.88 (br. s., 1 H), 7.86 (br. s., 2 H), 7.82 (s, 1 H), 7.77 (d, J = 7.8 Hz, 1 H), 7.56 (m, 1 H), 7.51 (m, 1 H), 5.87 (s, 1 H), 4.26 (br. s., 2 H), 2.94 (m, 2 H) |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 184 | 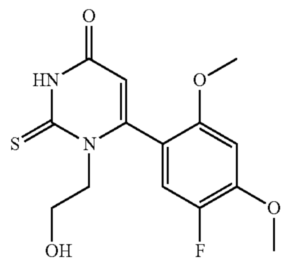 [SMILES: COc1cc(OC)c(-c2cc(=O)[nH]c(=S)n2CCO)cc1F] | 6-(5-fluoro-2,4-dimethoxyphenyl)-1-(2-hydroxyethyl)-2-thioxo-2,3-dihydropyrimidin-4(1H)-one | 326.8 | 1H NMR (400 MHz, CD$_3$OD) d ppm 7.12 (dd, 1 H), 6.85 (d, 1 H), 5.75 (d, 1 H), 4.60-4.73 (m, 1 H), 3.97 (s, 3 H), 3.90 (s, 3 H), 3.76-3.86 (m, 2 H), 3.56-3.65 (m, 1 H) |
| 185 | 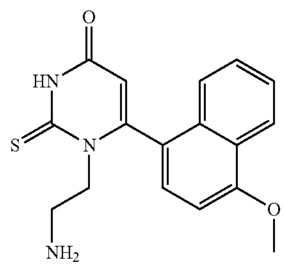 [SMILES: COc1ccc(-c2cc(=O)[nH]c(=S)n2CCN)c2ccccc12] | 1-(2-aminoethyl)-6-(4-methoxy-1-naphthyl)-2-thioxo-2,3-dihydropyrimidin-4(1H)-one hydrochloride | 327.9 | 1H NMR (400 MHz, DMSO-d6) δ ppm 12.92 (br. s, 1 H), 8.24 (dd, J = 7.44, 1.95 Hz, 1 H), 7.73 (d, J = 7.33 Hz, 1 H), 7.49-7.65 (m, 6 H), 7.08 (d, J = 8.01 Hz, 1 H), 5.89 (s, 1 H), 4.47 (ddd, J = 13.91, 8.87, 5.15 Hz, 1 H), 4.01 (s, 3H), 3.66-3.77 (m, 1 H), 2.82-2.91 (m, 1 H), 2.77 (ddd, J = 12.31, 8.87, 6.30 Hz, 1 H) |
| 186 | 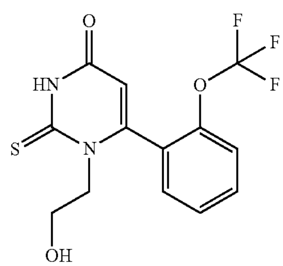 [SMILES: O=c1cc(-c2ccccc2OC(F)(F)F)n(CCO)c(=S)[nH]1] | 1-(2-hydroxyethyl)-2-thioxo-6-[2-(trifluoromethoxy)phenyl]-2,3-dihydropyrimidin-4(1H)-one | 333.0 | 1H NMR (400 MHz, CDCl3): δ 9.89 (br. s., 1H), 7.63-7.58 (m, 1H), 7.45-7.40 (m, 3H), 5.89 (d, 1H), 4.74-4.67 (m, 1H), 4.01-3.95 (m, 1H), 3.82-3.75 (m, 1H), 3.71-3.66 (m, 1H), 1.83 (s, 1H). |
| 187 | 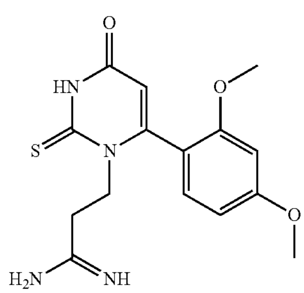 [SMILES: COc1ccc(-c2cc(=O)[nH]c(=S)n2CCC(=N)N)c(OC)c1] | 3-[6-(2,4-dimethoxyphenyl)-4-oxo-2-thioxo-3,4-dihydropyrimidin-1(2H)-yl]propanimidamide trifluoroacetate | 335.1 | 1H NMR (400 MHz, METHANOL-d4) δ ppm 7.23 (d, J = 8.22 Hz, 1 H), 6.71 (d, J = 2.15 Hz, 1 H), 6.68 (dd, J = 8.41, 2.15 Hz, 1 H), 5.78 (s, 1 H), 4.97 (dt, J = 14.57, 5.72 Hz, 1 H), 3.99-4.07 (m, 1 H), 3.89 (s, 3 H), 3.88 (s, 3 H), 2.87 (ddd, J = 14.48, 8.22, 5.50 Hz, 1 H), 2.62-2.72 (m, 1 H) |
| 188 | 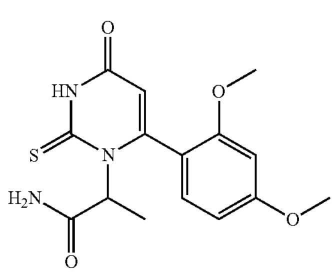 [SMILES: COc1ccc(-c2cc(=O)[nH]c(=S)n2C(C)C(N)=O)c(OC)c1] | 2-[6-(2,4-dimethoxyphenyl)-4-oxo-2-thioxo-3,4-dihydropyrimidin-1(2H)-yl]propanamide | 336.1 | 1H NMR (400 MHz, CHLOROFORM-d) δ ppm 9.79 (br. s., 1 H), 7.11-7.25(m, 1 H), 6.48-6.64 (m, 2 H), 5.85-5.91 (m, 1 H), 5.42-5.75 (m, 2 H), 4.35-4.76 (m, 1 H), 3.85-3.90 (m, 3 H), 3.81-3.85 (m, 3 H), 1.85 (m, J = 6.87 Hz, 3 H) |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 189 | 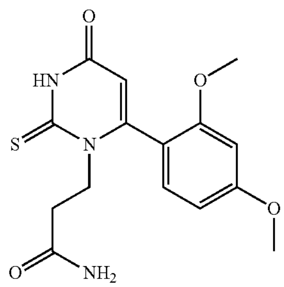 [SMILES: COc1ccc(-c2cc(=O)[nH]c(=S)n2CCC(N)=O)c(OC)c1] | 3-[6-(2,4-dimethoxyphenyl)-4-oxo-2-thioxo-3,4-dihydropyrimidin-1(2H)-yl]propanamide | 336.1 | 1H NMR (400 MHz, DMSO-d6) δ ppm 12.66 (br. s, 1 H), 7.23 (d, J = 8.70 Hz, 1 H), 7.21 (br. s., 1 H), 6.72 (br. s., 1 H), 6.67 (d, J = 2.29 Hz, 1 H), 6.60 (dd, J = 8.24, 2.29 Hz, 1 H), 5.69 (s, 1 H), 4.31-4.44 (m, 2 H), 3.79 (s, 3 H), 3.78 (s, 3 H) |
| 190 | 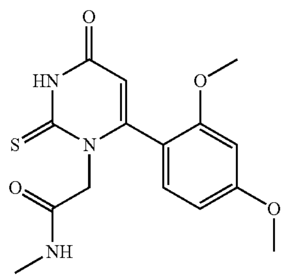 [SMILES: CNC(=O)Cn1c(-c2ccc(OC)cc2OC)cc(=O)[nH]c1=S] | 2-[6-(2,4-dimethoxyphenyl)-4-oxo-2-thioxo-3,4-dihydropyrimidin-1(2H)-yl]-N-methylacetamide | 336.2 | 1H NMR (400 MHz, DMSO-d6) δ ppm 12.77 (br. s, 1 H), 7.75 (d, J = 4.58 Hz, 1 H), 7.07 (d, J = 8.24 Hz, 1 H), 6.67 (d, J = 2.29 Hz, 1 H), 6.60 (dd, J = 8.47, 2.06 Hz, 1 H), 5.75 (s, 1 H), 5.24-5.43 (m, 1 H), 3.87-3.99 (m, 1 H), 3.81 (s, 3 H), 3.78-3.81 (m, 3 H), 2.45 (d, J = 4.58 Hz, 3 H) |
| 191 | 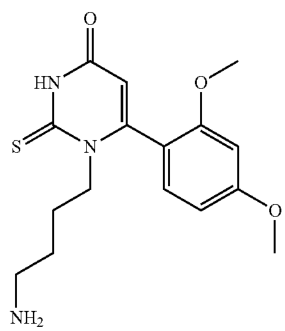 [SMILES: COc1ccc(-c2cc(=O)[nH]c(=S)n2CCCCN)c(OC)c1] | 1-(4-aminobutyl)-6-(2,4-dimethoxyphenyl)-2-thioxo-2,3-dihydropyrimidin-4(1H)-one hydrochloride | 335.9 | 1H NMR (300 MHz, DMSO-d6) δ ppm 12.73 (br. s, 1 H), 7.85 (br. s, 3 H), 7.31 (d, J = 8.36 Hz, 1 H), 6.72 (d, J = 2.09 Hz, 1 H), 6.66 (dd, J = 8.36, 2.79 Hz, 1 H), 5.75 (d, J = 2.09 Hz, 1 H), 4.29-4.48 (m, 1 H), 3.84 (s, 3 H), 3.83 (s, 3 H), 3.45-3.50 (m, 1 H), 2.53-2.62 (m, 2 H), 1.38-1.66 (m, 2 H), 1.21-1.37 (m, 2 H) |
| 192 | 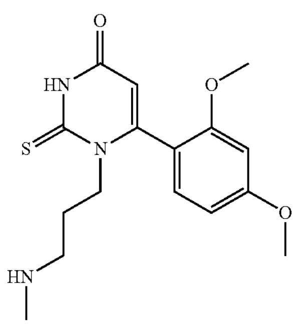 [SMILES: CNCCCn1c(-c2ccc(OC)cc2OC)cc(=O)[nH]c1=S] | 6-(2,4-dimethoxyphenyl)-1-[3-(methylamino)propyl]-2-thioxo-2,3-dihydropyrimidin-4(1H)-one hydrochloride | 336.1 | 1H NMR (400 MHz, DMSO-d6) δ ppm 12.75 (br. s., 1 H), 8.38 (br. s., 2 H), 7.28 (d, J = 8.24 Hz, 1 H), 6.69 (d, J = 2.06 Hz, 1 H), 6.63 (dd, J = 8.47, 2.29 Hz, 1 H), 5.73 (d, J = 2.06 Hz, 1 H), 4.32-4.44 (m, 1 H), 3.80 (s, 6 H), 3.52-3.63 (m, 1 H), 3.28 (s, 3 H), 2.39 (t, J = 4.92 Hz, 2 H), 1.63-1.92 (m, 2 H) |
| 193 | 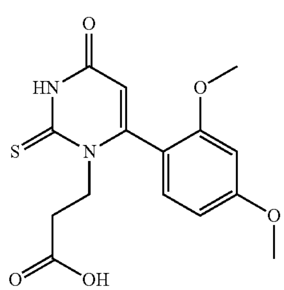 [SMILES: COc1ccc(-c2cc(=O)[nH]c(=S)n2CCC(=O)O)c(OC)c1] | 3-[6-(2,4-dimethoxyphenyl)-4-oxo-2-thioxo-3,4-dihydropyrimidin-1(2H)-yl]propanoic acid | 337.1 | 1H NMR (400 MHz, DMSO-d6) δ ppm 12.76 (br. s., 1 H), 7.30 (d, J = 8.70 Hz, 1 H), 6.70 (d, J = 2.29 Hz, 1 H), 6.65 (dd, J = 8.70, 2.29 Hz, 1 H), 5.74 (s, 1 H), 4.38-4.51 (m, 1 H), 3.82 (s, 3 H), 3.82-3.87 (m, 1 H), 3.82 (s, 3 H), 2.53-2.63 (m, 1 H), 2.40-2.48 (m, 1 H) |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 194 | 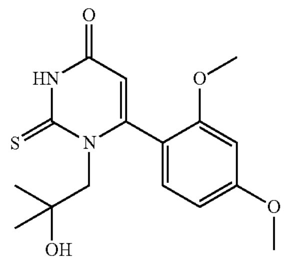 [SMILES: COc1ccc(-c2cc(=O)[nH]c(=S)n2CC(C)(C)O)c(OC)c1] | 6-(2,4-dimethoxyphenyl)-1-(2-hydroxy-2-methylpropyl)-2-thioxo-2,3-dihydropyrimidin-4(1H)-one | 337.1 | 1H NMR (400 MHz, CHLOROFORM-d) δ ppm 9.89 (br. s, 1 H), 7.21 (d, J = 8.24 Hz, 1 H), 6.58 (dd, J = 8.70, 1.83 Hz, 1 H), 6.51 (d, J = 1.83 Hz, 1 H), 5.87 (s, 1 H), 5.11-5.30 (m, 1 H), 3.87 (s, 3 H), 3.84 (s, 3 H), 3.46-3.64 (m, 1 H), 1.11 (br. s., 3 H), 0.96 (br. s., 3 H) |
| 195 | 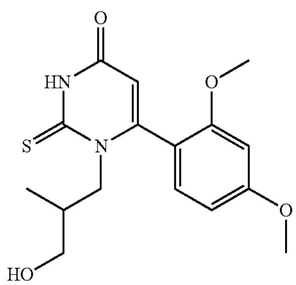 [SMILES: COc1ccc(-c2cc(=O)[nH]c(=S)n2CC(C)CO)c(OC)c1] | 6-(2,4-dimethoxyphenyl)-1-(3-hydroxy-2-methylpropyl)-2-thioxo-2,3-dihydropyrimidin-4(1H)-one | 337.1 | 1H NMR (400 MHz, CHLOROFORM-d) δ ppm 10.07 (br. s., 1 H), 7.13 (d, J = 8.70 Hz, 1 H), 6.57 (dd, J = 8.70, 2.29 Hz, 1 H), 6.52 (d, J = 2.29 Hz, 1 H), 5.87 (s, 1 H), 4.95 (br. s., 2 H), 3.88 (s, 3 H), 3.85 (s, 3 H), 3.54 (dd, J = 11.91, 3.21 Hz, 1 H), 3.34-3.41 (m, 1 H), 1.83 (br. s., 1 H), 0.62 (d, J = 6.87 Hz, 3 H) |
| 196 | 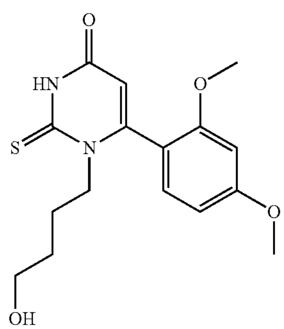 [SMILES: COc1ccc(-c2cc(=O)[nH]c(=S)n2CCCCO)c(OC)c1] | 6-(2,4-dimethoxyphenyl)-1-(4-hydroxybutyl)-2-thioxo-2,3-dihydropyrimidin-4(1H)-one | 337.1 | $^1$H NMR (400 MHz, METHANOL-d4) δ ppm 7.20 (d, J = 8.20 Hz, 1 H), 6.66 (d, J = 2.15 Hz, 1 H), 6.64 (dd, J = 8.20, 2.34 Hz, 1 H), 5.71 (s, 1 H), 4.44-4.56 (m, 1 H), 3.85 (s, 6 H), 3.62-3.75 (m, 1 H), 3.32 (t, J = 6.64 Hz, 2 H), 1.66-1.81 (m, 1 H), 1.40-1.56 (m, 1 H), 1.16-1.32 (m, 2 H) |
| 197 | ABS | 1-[(2R)-3-amino-2-hydroxypropyl]-6-(2,4-dimethoxyphenyl)-2-thioxo-2,3-dihydropyrimidin-4(1H)-one trifluoroacetate | 338.0 | 1H NMR (400 MHz, DMSO-d6) δ ppm 12.72-12.82 (m, 1 H), 7.61-7.74 (m, 3 H), 7.16-7.28 (m, 1 H), 6.59-6.75 (m, 2 H), 5.70-5.79 (m, 1 H), 5.60-5.65 (m, 1 H), 4.53-4.63 (m, 1 H), 4.21-4.31 (m, 1 H), 3.77-3.86 (m, 6 H), 2.72-2.85 (m, 2 H) |
| 198 | 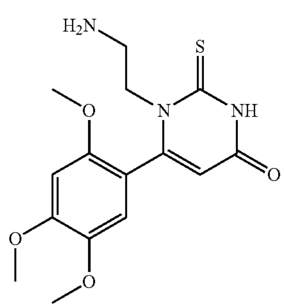 [SMILES: COc1cc(OC)c(-c2cc(=O)[nH]c(=S)n2CCN)cc1OC] | 1-(2-aminoethyl)-2-thioxo-6-(2,4,5-trimethoxyphenyl)-2,3-dihydropyrimidin-4(1H)-one hydrochloride | 338.1 | 1H NMR (400 MHz, DMSO-d6) δ ppm 12.79 (s, 1 H), 7.92 (br. s., 3 H), 6.99 (s, 1 H), 6.80 (s, 1 H), 5.76 (d, J = 1.76 Hz, 1 H), 4.55 (dt, J = 13.96, 6.88 Hz, 1 H), 3.93 (dt, J = 14.06, 7.03 Hz, 1 H), 3.84 (s, 3 H), 3.80 (s, 3 H), 3.70 (s, 3 H), 2.80-2.97 (m, 2 H) |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 199 | 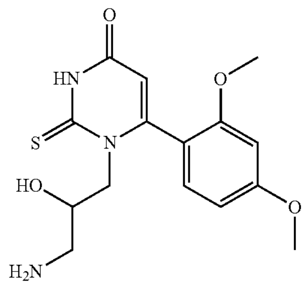 [SMILES: COc1ccc(-c2cc(=O)[nH]c(=S)n2CC(O)CN)c(OC)c1] | 1-(3-amino-2-hydroxypropyl)-6-(2,4-dimethoxyphenyl)-2-thioxo-2,3-dihydropyrimidin-4(1H)-one hydrochloride | 338.1 | 1H NMR (400 MHz, DMSO-d6) δ ppm 12.69-12.76 (m, 1 H), 7.61-8.08 (m, 3 H), 7.13-7.26 (m, 1 H), 6.56-6.71 (m, 2 H), 5.65-5.76 (m, 1 H), 5.60 (m, J = 4.90 Hz, 1 H), 4.55 (s, 1 H), 4.15-4.30 (m, 1 H), 3.74-3.84 (m, 6 H), 3.54-3.63 (m, 1 H), 2.61-2.95 (m, 2 H) |
| 200 | ABS | 1-[(2S)-3-amino-2-hydroxypropyl]-6-(2,4-dimethoxyphenyl)-2-thioxo-2,3-dihydropyrimidin-4(1H)-one trifluoroacetate | 338.2 | 1H NMR (300 MHz, DMSO-d6) δ ppm 12.78 (m, 1 H), 7.63 (br. s, 3 H), 7.18-7.28 (m, 1 H), 6.60-6.75 (m, 2 H), 5.71-5.80 (m, 1H), 5.58-5.66 (m, 1H), 4.54-4.62 (m, 1H), 4.08-4.23 (m, 1H), 3.78-3.85 (m, 6H), 3.23-3.41 (m, 1H), 2.71-2.83 (m, 1H), 2.38-2.45 (m, 1H) |
| 201 | 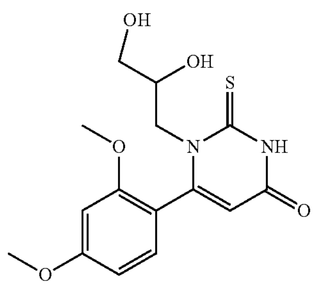 [SMILES: COc1ccc(-c2cc(=O)[nH]c(=S)n2CC(O)CO)c(OC)c1] | 1-(2,3-dihydroxypropyl)-6-(2,4-dimethoxyphenyl)-2-thioxo-2,3-dihydropyrimidin-4(1H)-one | 339.2 | 1H NMR (400 MHz, CHLOROFORM-d) δ ppm 10.33 (br. s., 1 H) 7.17 (br. s., 1 H) 6.58 (br. s., 1 H) 6.52 (d, J = 7.22 Hz, 1 H) 5.88 (d, J = 7.22 Hz, 1 H) 4.80-4.95 (m, 1 H) 4.60-4.73 (m, 1 H) 3.99-4.14 (m, 1 H) 3.87 (s, 3 H) 3.83 (s, 3 H) 3.23-3.68 (m, 4 H) |
| 202 | 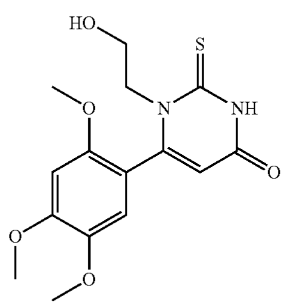 [SMILES: COc1cc(OC)c(-c2cc(=O)[nH]c(=S)n2CCO)cc1OC] | 1-(2-hydroxyethyl)-2-thioxo-6-(2,4,5-trimethoxyphenyl)-2,3-dihydro-pyrimidin-4(1H)-one | 339.2 | 1H NMR (500 MHz, DMSO-d6) δ ppm 12.68 (s, 1 H), 6.95 (s, 1 H), 6.80 (s, 1 H), 5.74 (s, 1 H), 4.43-4.51 (m, 1 H), 3.86 (s, 3 H), 3.82 (s, 3 H), 3.71 (s, 3 H), 3.64-3.70 (m, 1 H), 3.49-3.56 (m, 1 H), 3.40-3.46 (m, 1 H) |
| 203 | ABS | 1-[(2S)-2,3-dihydroxypropyl]-6-(2,4-dimethoxyphenyl)-2-thioxo-2,3-dihydropyrimidin-4(1H)-one | 339.2 | 1H NMR (400 MHz, CHLOROFORM-d) δ ppm 10.33 (br. s., 1 H) 7.17 (br. s., 1 H) 6.58 (br. s., 1 H) 6.52 (d, J = 7.22 Hz, 1 H) 5.88 (d, J = 7.22 Hz, 1 H) 4.80-4.95 (m, 1 H) 4.60-4.73 (m, 1 H) 3.99-4.14 (m, 1 H) 3.87 (s, 3 H) 3.83 (s, 3 H) 3.23-3.68 (m, 4 H) |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 204 | ABS | 1-[(2R)-2,3-dihydroxypropyl]-6-(2,4-dimethoxyphenyl)-2-thioxo-2,3-dihydropyrimidin-4(1H)-one | 339.2 | 1H NMR (400 MHz, CHLOROFORM-d) δ ppm 10.33 (br. s, 1 H) 7.17 (br. s, 1 H) 6.58 (br. s, 1 H) 6.52 (d, J = 7.22 Hz, 1 H) 5.88 (d, J = 7.22 Hz, 1 H) 4.80-4.95 (m, 1 H) 4.60-4.73 (m, 1 H) 3.99-4.14 (m, 1 H) 3.87 (s, 3 H) 3.83 (s, 3 H) 3.23-3.68 (m, 4 H) |
| 205 | 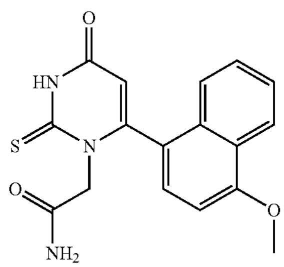 | 2-[6-(4-methoxy-1-naphthyl)-4-oxo-2-thioxo-3,4-dihydropyrimidin-1(2H)-yl]acetamide | 342.2 | 1H NMR (400 MHz, DMSO-d6) δ ppm 12.90 (br. s, 1 H), 8.25 (d, J = 7.33 Hz, 1 H), 7.69-7.77 (m, 1 H), 7.56-7.68 (m, 2 H), 7.38-7.47 (m, 1 H), 7.23 (s, 1 H), 7.06 (d, J = 8.24 Hz, 1 H), 6.98 (br. s., 1 H), 5.92 (d, J = 1.83 Hz, 1 H), 5.10-5.35 (m, 2 H), 4.02 (s, 3 H) |
| 206 | 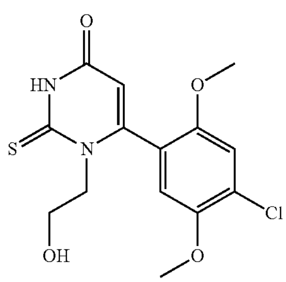 | 6-(4-chloro-2,5-dimethoxyphenyl)-1-(2-hydroxyethyl)-2-thioxo-2,3-dihydropyrimidin-4(1H)-one | 343 | 1H NMR (400 MHz, CHLOROFORM-d) δ ppm 9.88 (br. s., 1 H), 7.03 (s, 1 H), 6.85 (s, 1 H), 5.84 (s, 1 H), 4.73 (dt, J = 14.20, 5.15 Hz, 1 H), 3.91-4.00 (m, 1 H), 3.87-3.90 (m, 1 H), 3.86 (s, 3 H), 3.81 (s, 3 H), 3.59-3.73 (m, 1 H), 1.95 (br. s., 1 H) |
| 207 | 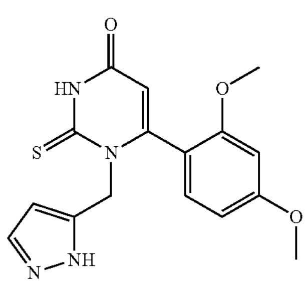 | 6-(2,4-dimethoxyphenyl)-1-(1H-pyrazol-5-ylmethyl)-2-thioxo-2,3-dihydropyrimidin-4(1H)-one | 345.1 | 1H NMR (500 MHz, METHANOL-d4) δ ppm 7.48 (br. s, 1 H), 6.90 (d, J = 8.05 Hz, 1 H), 6.62 (d, J = 2.20 Hz, 1 H), 6.46 (d, J = 5.12 Hz, 1 H), 5.95-6.13 (m, 2 H), 5.77 (s, 1 H), 4.88-5.01 (m, 1 H), 3.82 (s, 3 H), 3.81 (s, 3 H) |
| 208 | 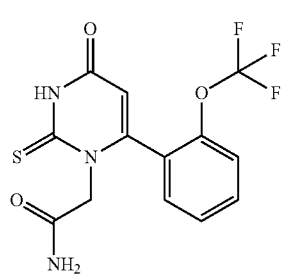 | 2-{4-oxo-2-thioxo-6-[2-(trifluoromethoxy)phenyl]-3,4-dihydropyrimidin-1(2H)-yl}acetamide | 345.9 | 1H NMR (400 MHz, Methoanol-d3) d ppm 7.67 (ddd, J = 7.7, 7.6, 2.0 Hz, 1 H), 7.46-7.52 (m, 3 H), 5.89 (s, 1 H), 5.50 (br. s., 1 H), 4.01 (br. s., 1H) |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 209 | 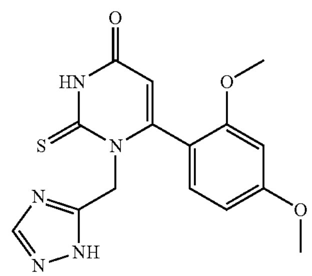 [SMILES: COc1ccc(-c2cc(=O)[nH]c(=S)n2Cc2ncn[nH]2)c(OC)c1] | 6-(2,4-dimethoxyphenyl)-2-thioxo-1-(1H-1,2,4-triazol-5-ylmethyl)-2,3-dihydropyrimidin-4(1H)-one | 346.0 | 1.84 min Waters Atlantis dC18 5 um 4.6 x 50 mm, 95% H2O/5% MeCN linear to 5% H2O/95% MeCN over 4.0 min, HOLD at 5% H2O/95% MeCN to 5.0 min. (0.05% TFA). Flow rate: 2 mL/min |
| 210 | 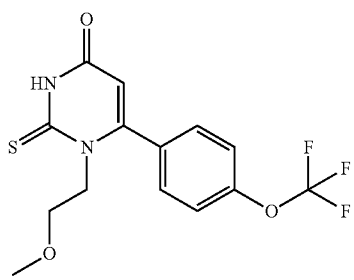 [SMILES: COCCn1c(-c2ccc(OC(F)(F)F)cc2)cc(=O)[nH]c1=S] | 1-(2-methoxyethyl)-2-thioxo-6-[4-(trifluoromethoxy)phenyl]-2,3-dihydropyrimidin-4(1H)-one | 347.1 | 1H NMR (400 MHz, CHLOROFORM-d) δ ppm 9.53 (br. s., 1 H), 7.42 (d, J = 8.70 Hz, 2 H), 7.34 (d, J = 8.24 Hz, 2 H), 5.82 (d, J = 2.29 Hz, 1 H), 4.34 (br. s., 2 H), 3.67 (t, J = 5.27 Hz, 2 H), 3.20 (s, 3 H) |
| 211 | 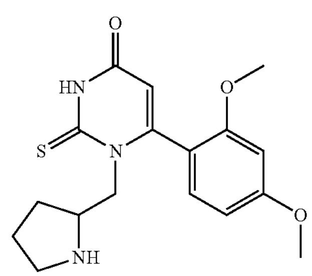 [SMILES: COc1ccc(-c2cc(=O)[nH]c(=S)n2CC2CCCN2)c(OC)c1] | 6-(2,4-dimethoxyphenyl)-1-(pyrrolidin-2-ylmethyl)-2-thioxo-2,3-dihydropyrimidin-4(1H)-one hydrochloride | 348.4 | 1H NMR (400 MHz, DMSO-d6) δ ppm 12.89 (s, 1 H), 9.25 (br. s, 1 H), 8.08-8.71 (br. m., 1 H), 7.24-7.42 (m, 1 H), 6.74 (d, J = 2.33 Hz, 1 H), 6.69 (dd, J = 8.61, 2.09 Hz, 1 H), 5.80 (m, 1 H), 4.97-5.07 (m, 1 H), 3.81-3.88 (m, 6 H), 3.61-3.78 (m, 2 H), 2.96-3.17 (m, 2 H), 1.73-1.90 (m, 1 H), 1.65 (m, 2 H), 1.13-1.26 (m, 1 H) |
| 212 | 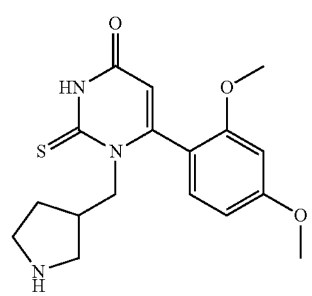 [SMILES: COc1ccc(-c2cc(=O)[nH]c(=S)n2CC2CCNC2)c(OC)c1] | 6-(2,4-dimethoxyphenyl)-1-(pyrrolidin-3-ylmethyl)-2-thioxo-2,3-dihydropyrimidin-4(1H)-one hydrochloride | 348.4 | 1H NMR (300 MHz, DMSO-d6) δ ppm 12.80 (s, 1 H), 8.77 (br. s., 2 H), 7.27-7.38 (m, 1 H), 6.73 (d, J = 2.09 Hz, 1 H), 6.67 (dd, J = 8.36, 2.09 Hz, 1 H), 5.76-5.79 (m, 1 H), 4.60-4.75 (m, 1 H), 3.84 (br. s, 4 H), 3.57 (s, 3 H), 3.13-3.24 (m, 1 H), 3.01-3.13 (m, 1 H), 2.85-2.97 (m, 1 H), 2.70-2.83 (m, 1 H), 2.55-2.69 (m, 1 H), 1.81-1.95 (m, 1 H), 1.62-1.79 (m, 1 H) |
| 213 | ABS | 6-(2,4-dimethoxyphenyl)-1-[(2S)-tetrahydrofuran-2-ylmethyl]-2-thioxo-2,3-dihydropyrimidin-4(1H)-one | 349.1 | 1H NMR (400 MHz, CHLOROFORM-d) δ ppm 9.59 (br. s, 1 H), 7.12-7.24 (m, 1 H), 6.56 (dd, J = 8.24, 1.83 Hz, 1 H), 6.43-6.51 (m, 1 H), 5.75-5.82 (m, 1 H), 4.67 (dd, J = 13.74, 2.29 Hz, 1 H), 4.53-4.62 (m, 1 H), 3.85 (s, 3 H), 3.79-3.83 (m, 3 H), 3.54 (q, J = 7.20 Hz, 1 H), 3.39 (dd, J = 13.28, 10.08 Hz, 1 H), 3.15 (q, J = 7.17 Hz, 1 H), 1.89-2.02 (m, 1 H), 1.64-1.80 (m, 1 H), 1.45-1.54 (m, 1 H), 1.23-1.35 (m, 1 H) |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 214 | ABS | 6-(2,4-dimethoxyphenyl)-1-[(2R)-tetrahydrofuran-2-ylmethyl]-2-thioxo-2,3-dihydropyrimidin-4(1H)-one | 349.1 | 1H NMR (400 MHz, METHANOL-d4) δ ppm 7.20-7.28 (m, 1 H) 6.63-6.68 (m, 2 H) 5.70-5.74 (m, 1 H) 4.71 (dd, J = 14.07, 2.74 Hz, 1 H) 4.56-4.65 (m, 1 H) 3.84-3.88 (m, 6 H) 3.50-3.57 (m, 1 H) 3.43-3.50 (m, 1 H) 3.22 (dt, J = 8.26, 6.72 Hz, 1 H) 1.93 (m, J = 12.46, 7.89, 7.89, 6.16 Hz, 1 H) 1.64-1.77 (m, 1 H) 1.43-1.55 (m, 1 H) 1.31-1.40 (m, 1 H) |
| 215 | 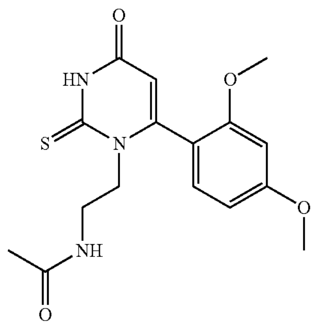 | N-{2-[6-(2,4-dimethoxyphenyl)-4-oxo-2-thioxo-3,4-dihydropyrimidin-1(2H)-yl]ethyl}acetamide | 350.1 | 1H NMR (400 MHz, DMSO-d6) δ ppm 12.70 (br. s., 1 H), 7.77 (t, J = 5.95 Hz, 1 H), 7.20 (d, J = 8.24 Hz, 1 H), 6.61-6.70 (m, 2 H), 5.70 (s, 1 H), 4.50 (dt, J = 13.40, 5.21 Hz, 1 H), 3.82 (s, 3 H), 3.79 (s, 3 H), 3.59 (dt, J = 13.62, 6.70 Hz, 1 H), 3.15-3.28 (m, 2 H), 1.67 (s, 3 H) |
| 216 | 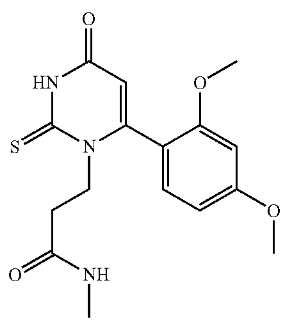 | 3-[6-(2,4-dimethoxyphenyl)-4-oxo-2-thioxo-3,4-dihydropyrimidin-1(2H)-yl]-N-methylpropanamide | 350.1 | 1H NMR (400 MHz, DMSO-d6) δ ppm 12.63 (br. s., 1 H), 7.71 (br. s., 1 H), 7.25 (d, J = 7.79 Hz, 1 H), 6.70 (s, 1 H), 6.64 (d, J = 8.70 Hz, 1 H), 5.72 (s, 1 H), 4.37-4.53 (m, 2 H), 3.83 (s, 3 H), 3.82 (s, 3 H), 3.35-3.44 (m, 2 H), 2.45 (d, J = 4.58 Hz, 3 H) |
| 217 | 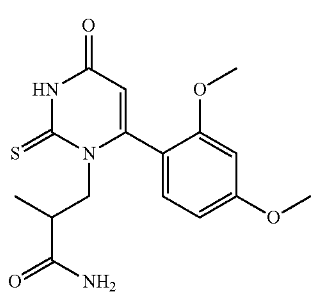 | 3-[6-(2,4-dimethoxyphenyl)-4-oxo-2-thioxo-3,4-dihydropyrimidin-1(2H)-yl]-2-methylpropanamide | 350.2 | 1H NMR (500 MHz, DMSO-d6) δ ppm 12.50-12.85 (m, 1 H) 7.15-7.34 (m, 2 H) 6.55-6.83 (m, 3 H) 5.64-5.77 (m, 1 H) 4.34-4.67 (m, 1 H) 3.75-3.89 (m, 6 H) 3.46-3.71 (m, 1 H) 2.75-3.13 (m, 1 H) 0.66-0.90 (m, 3 H) |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 218 | 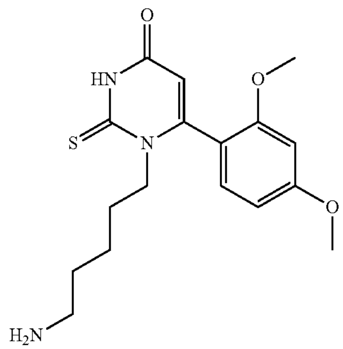 [SMILES: COc1ccc(-c2cc(=O)[nH]c(=S)n2CCCCCN)c(OC)c1] | 1-(5-aminopentyl)-6-(2,4-dimethoxyphenyl)-2-thioxo-2,3-dihydropyrimidin-4(1H)-one hydrochloride | 349.9 | $^1$H NMR (400 MHz, METHANOL-d4) δ ppm 7.24 (d, J = 7.81 Hz, 1 H), 6.69 (s, 1 H), 6.66 (d, J = 8.00 Hz, 1 H), 5.75 (s, 1 H), 4.46-4.60 (m, 1 H), 3.87 (s, 6 H), 3.62-3.75 (m, 1 H), 2.83 (br. s, 2 H), 1.69-1.83 (m, 1 H), 1.41-1.57 (m, 3 H), 1.05-1.24 (m, 2 H) |
| 219 | 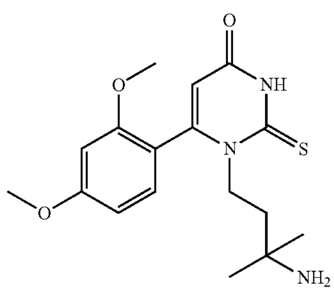 [SMILES: COc1ccc(-c2cc(=O)[nH]c(=S)n2CCC(C)(C)N)c(OC)c1] | 1-(3-amino-3-methylbutyl)-6-(2,4-dimethoxyphenyl)-2-thioxo-2,3-dihydropyrimidin-4(1H)-one hydrochloride | 350.1 | 1H NMR (400 MHz, DMSO-d6): δ 7.28 (d, 1 H), 6.71 (s, 1 H), 6.65 (d, 1 H), 5.76 (s, 1 H), 4.49 (br. s., 1 H), 3.84 (s, 3 H), 3.82 (s, 3 H), 3.50-3.60 (br. s., 1H), 1.82-1.95 (m, 1 H), 1.42-1.55 (m, 1 H), 0.89 (s, 3 H), 0.80 (s, 3 H): |
| 220 | 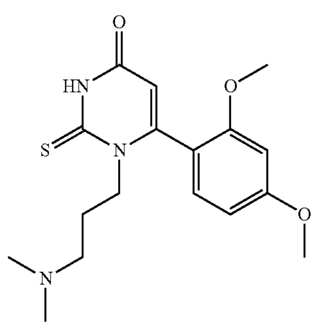 | 6-(2,4-dimethoxyphenyl)-1-[3-(dimethylamino)propyl]-2-thioxo-2,3-dihydropyrimidin-4(1H)-one | 350.2 | 1H NMR (400 MHz, DMSO-d6) δ ppm 12.76 (br. s., 1 H), 7.29 (d, J = 8.47 Hz, 1 H), 6.71 (d, J = 2.06 Hz, 1 H), 6.64 (dd, J = 8.47, 2.06 Hz, 1 H), 5.74 (s, 1 H), 4.29-4.47 (m, 1 H), 3.80 (s, 6 H), 3.50-3.68 (m, 1 H), 3.41-3.51 (m, 1 H), 2.74 (br. s., 1 H), 2.55 (br. s., 6 H), 1.79-1.94 (m, 1 H), 1.63-1.78 (m, 1 H) |
| 221 | 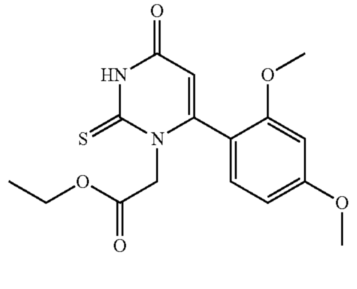 [SMILES: CCOC(=O)Cn1c(-c2ccc(OC)cc2OC)cc(=O)[nH]c1=S] | ethyl [6-(2,4-dimethoxyphenyl)-4-oxo-2-thioxo-3,4-dihydropyrimidin-1(2H)-yl]acetate | 351.2 | 1H NMR (400 MHz, DMSO-d6) δ ppm 12.94 (s, 1 H), 7.11 (d, J = 8.70 Hz, 1 H), 6.70 (d, J = 2.29 Hz, 1 H), 6.63 (dd, J = 8.24, 2.29 Hz, 1 H), 5.83 (s, 1 H), 5.18-5.40 (m, 1 H), 4.16-4.31 (m, 1 H), 4.02 (dtt, J = 10.88, 7.16, 7.16, 3.66, 3.66 Hz, 2 H), 3.82 (s, 6 H), 1.08 (t, J = 7.10 Hz, 3 H) |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 222 | 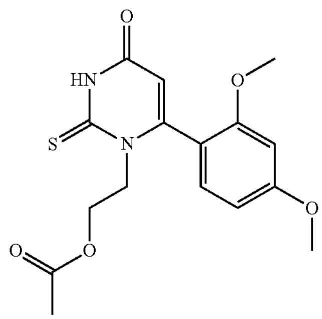 [SMILES: COc1ccc(-c2cc(=O)[nH]c(=S)n2CCOC(C)=O)c(OC)c1] | 2-[6-(2,4-dimethoxyphenyl)-4-oxo-2-thioxo-3,4-dihydropyrimidin-1(2H)-yl]ethyl acetate | 351.2 | 1H NMR (500 MHz, DMSO-d6) δ ppm 12.78 (br. s., 1 H) 7.28 (d, J = 8.54 Hz, 1 H) 6.70 (d, J = 2.20 Hz, 1 H) 6.67 (dd, J = 8.29, 2.20 Hz, 1 H) 5.75 (s, 1 H) 4.70 (dt, J = 14.70, 4.36 Hz, 1 H) 4.29 (ddd, J = 11.95, 7.81, 4.39 Hz, 1 H) 4.02 (dt, J = 11.71, 4.64 Hz, 1 H) 3.83 (s, 3 H) 3.82 (s, 3 H) 3.77-3.81 (m, 1 H) 1.91 (s, 3 H) |
| 223 | 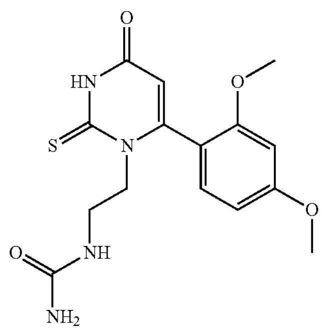 [SMILES: COc1ccc(-c2cc(=O)[nH]c(=S)n2CCNC(N)=O)c(OC)c1] | 1-{2-[6-(2,4-dimethoxyphenyl)-4-oxo-2-thioxo-3,4-dihydropyrimidin-1(2H)-yl]ethyl}urea | 351.2 | 1.80 min Waters Atlantis dC18 5 um 4.6 x 50 mm, 95% H2O/5% MeCN linear to 5% H2O/95% MeCN over 4.0 min, HOLD at 5% H2O/95% MeCN to 5.0 min. (0.05% TFA). Flow rate: 2 mL/min |
| 224 | 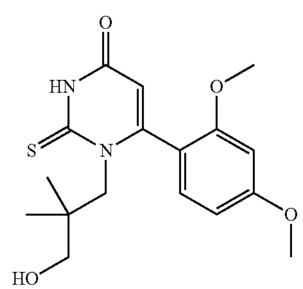 [SMILES: COc1ccc(-c2cc(=O)[nH]c(=S)n2CC(C)(C)CO)c(OC)c1] | 6-(2,4-dimethoxyphenyl)-1-(3-hydroxy-2,2-dimethylpropyl)-2-thioxo-2,3-dihydropyrimidin-4(1H)-one | 351.1 | 1H NMR (400 MHz, METHANOL-d3) δ ppm 7.31 (d, J = 8.24 Hz, 1 H), 6.63-6.69 (m, 2 H), 5.76 (s, 1 H), 5.19 (d, J = 15.11 Hz, 1 H), 3.87 (s, 3 H), 3.87 (s, 3 H), 3.50 (d, J = 14.66 Hz, 1 H), 3.29 (d, J = 10.53 Hz, 1 H), 3.05 (d, J = 10.99 Hz, 1 H), 0.83 (s, 3 H), 0.66 (s, 3 H) |
| 225 | 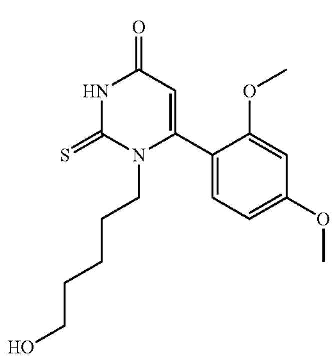 [SMILES: COc1ccc(-c2cc(=O)[nH]c(=S)n2CCCCCO)c(OC)c1] | 6-(2,4-dimethoxyphenyl)-1-(5-hydroxypentyl)-2-thioxo-2,3-dihydropyrimidin-4(1H)-one | 351.1 | $^1$H NMR (500 MHz, METHANOL-d4) δ ppm 7.22 (d, J = 8.29 Hz, 1 H), 6.68 (d, J = 1.95 Hz, 1 H), 6.66 (dd, J = 8.29, 2.20 Hz, 1 H), 5.73 (s, 1 H), 4.44-4.57 (m, 1 H), 3.87 (s, 6 H), 3.61-3.71 (m, 1 H), 3.40 (t, J = 6.46 Hz, 2 H), 1.68-1.79 (m, 1 H), 1.39-1.51 (m, 1 H), 1.25-1.36 (m, 2 H), 1.03-1.20 (m, 2 H) |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 226 | 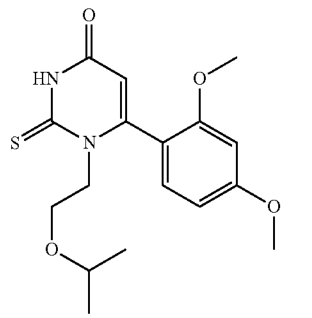 [SMILES: COc1ccc(-c2cc(=O)[nH]c(=S)n2CCOC(C)C)c(OC)c1] | 6-(2,4-dimethoxyphenyl)-1-(2-isopropoxyethyl)-2-thioxo-2,3-dihydropyrimidin-4(1H)-one | 351.1 | 1H NMR (400 MHz, CHLOROFORM-d) δ ppm 9.58 (br. s., 1 H) 7.15 (d, J = 8.40 Hz, 1 H) 6.55 (dd, J = 8.40, 2.35 Hz, 1 H) 6.50 (d, J = 2.35 Hz, 1 H) 5.79 (d, J = 2.35 Hz, 1 H) 4.64-4.71 (m, 1 H) 3.87 (s, 3 H) 3.82 (s, 3 H) 3.69-3.81 (m, 2 H) 3.49 (ddd, J = 9.58, 5.86, 3.13 Hz, 1 H) 3.46 (dt, J = 12.31, 6.25 Hz, 1 H) 1.04 (dd, J = 6.06, 1.37 Hz, 6 H) |
| 227 | 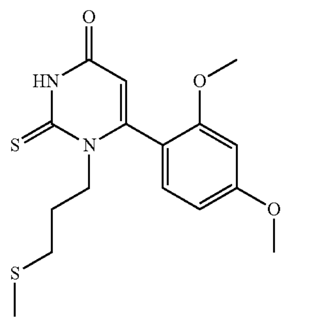 [SMILES: COc1ccc(-c2cc(=O)[nH]c(=S)n2CCCSC)c(OC)c1] | 6-(2,4-dimethoxyphenyl)-1-[3-(methylthio)propyl]-2-thioxo-2,3-dihydropyrimidin-4(1H)-one | 353.1 | 1H NMR (400 MHz, DMSO-d6) δ ppm 7.32 (d, J = 8.4 Hz, 1 H), 6.73 (d, J = 2.0 Hz, 1 H), 6.68 (dd, J = 8.4, 2.0 Hz, 1 H), 5.76 (d, J = 2.0 Hz, 1 H), 4.45 (br. s., 1 H), 3.84 (s, 6H), 3.70 (br. s., 1 H), 2.22 (tt, d = 6.4, 6.4 Hz, 2 H), 1.85-1.91 (m, 1 H), 1.83 (s, 3 H), 1.59-1.65 (m, 1 H) |
| 228 | 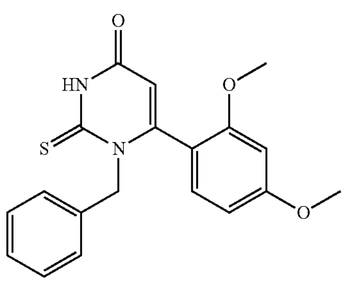 [SMILES: COc1ccc(-c2cc(=O)[nH]c(=S)n2Cc2ccccc2)c(OC)c1] | 1-benzyl-6-(2,4-dimethoxyphenyl)-2-thioxo-2,3-dihydropyrimidin-4(1H)-one | 355.2 | 1H NMR (400 MHz, CHLOROFORM-d) δ ppm 9.84 (br. s., 1 H), 7.14-7.22 (m, 3 H), 6.84-6.93 (m, 2 H), 6.72 (d, J = 8.24 Hz, 1 H), 6.44 (d, J = 1.83 Hz, 1 H), 6.34 (dd, J = 8.47, 2.06 Hz, 1 H), 5.96 (d, J = 16.03 Hz, 1 H), 5.84 (s, 1 H), 4.94 (d, J = 15.11 Hz, 1 H), 3.82 (s, 3 H), 3.70 (s, 3 H) |
| 229 | 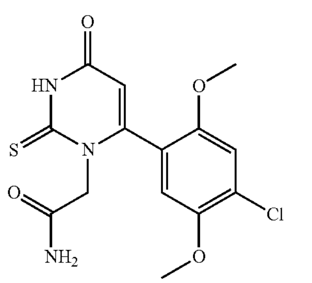 [SMILES: COc1cc(-c2cc(=O)[nH]c(=S)n2CC(N)=O)c(OC)cc1Cl] | 2-[6-(4-chloro-2,5-dimethoxyphenyl)-4-oxo-2-thioxo-3,4-dihydropyrimidin-1(2H)-yl]acetamide | 356.1 | 1H NMR (400 MHz, METHANOL-d3) δ ppm 7.20 (s, 1 H), 6.96 (s, 1 H), 5.84 (s, 1 H), 4.65 (br. s, 2 H), 3.83 (s, 3 H), 3.81 (s, 3 H) |
| 230 | 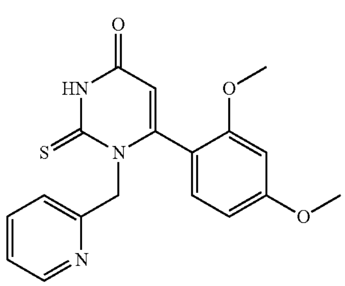 [SMILES: COc1ccc(-c2cc(=O)[nH]c(=S)n2Cc2ccccn2)c(OC)c1] | 6-(2,4-dimethoxyphenyl)-1-(pyridin-2-ylmethyl)-2-thioxo-2,3-dihydropyrimidin-4(1H)-one | 356.1 | 1H NMR (400 MHz, CHLOROFORM-d) δ ppm 9.57 (br. s., 1 H), 8.43 (dd, J = 4.58, 0.90 Hz, 1 H), 7.57 (ddd, J = 7.60, 7.60, 1.80 Hz, 1 H), 7.11 (ddd, J = 7.79, 5.04, 0.92 Hz, 1 H), 7.00 (d, J = 7.79 Hz, 1 H), 6.88 (d, J = 8.24 Hz, 1 H), 6.43 (d, J = 2.29 Hz, 1 H), 6.32 (dd, J = 8.24, 2.29 Hz, 1 H), 6.02 (d, J = 16.03 Hz, 1 H), 5.87 (s, 1 H), 4.95 (d, J = 16.49 Hz, 1 H), 3.79 (s, 3 H), 3.75 (s, 3 H) |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 231 | 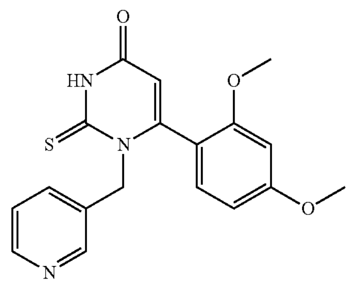 [SMILES: COc1ccc(-c2cc(=O)[nH]c(=S)n2Cc2cccnc2)c(OC)c1] | 6-(2,4-dimethoxyphenyl)-1-(pyridin-3-ylmethyl)-2 thioxo-2,3-dihydropyrimidin-4(1H)-one | 356.1 | 1H NMR (400 MHz, CHLOROFORM-d) δ ppm 9.56 (br. s., 1 H), 8.46 (dd, J = 4.81, 1.60 Hz, 1 H), 7.97 (d, J = 1.83 Hz, 1 H), 7.51 (ddd, J = 8.00, 1.80, 1.80 Hz, 1 H), 7.18 (ddd, J = 8.01, 4.81, 0.92 Hz, 1 H), 6.79 (d, J = 8.24 Hz, 1 H), 6.46 (d, J = 2.29 Hz, 1 H), 6.42 (dd, J = 8.24, 2.29 Hz, 1 H), 5.88 (d, J = 15.11 Hz, 1 H), 5.84 (s, 1 H), 5.06 (d, J = 15.57 Hz, 1 H), 3.84 (s, 3 H), 3.68 (s, 3 H) |
| 232 | 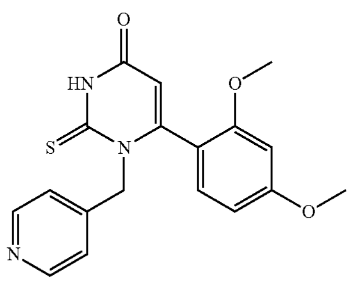 [SMILES: COc1ccc(-c2cc(=O)[nH]c(=S)n2Cc2ccncc2)c(OC)c1] | 6-(2,4-dimethoxyphenyl)-1-(pyridin-4-ylmethyl)-2-thioxo-2,3-dihydropyrimidin-4(1H)-one | 356.1 | 1H NMR (400 MHz, CHLOROFORM-d) δ ppm 11.02 (br. s, 1 H), 8.48 (d, J = 5.95 Hz, 2 H), 6.87 (d, J = 5.95 Hz, 2 H), 6.77 (d, J = 8,24 Hz, 1 H), 6.42 (d, J = 2.29 Hz, 1 H), 6.36 (dd, J = 8.24, 2.29 Hz, 1 H), 5.88-5.90 (m, 1 H), 5.87 (s, 1 H), 4.93-5.08 (m, 1 H), 3.81 (s, 3 H), 3.66 (s, 3 H) |
| 233 | 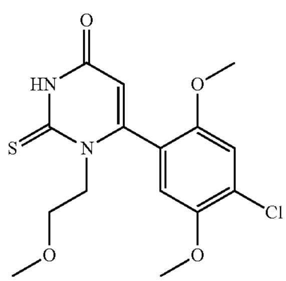 [SMILES: COCCn1c(-c2cc(OC)c(Cl)cc2OC)cc(=O)[nH]c1=S] | 6-(4-chloro-2,5-dimethoxyphenyl)-1-(2-methoxyethyl)-2-thioxo-2,3-dihydropyrimidin-4(1H)-one | 357.1 | 1H NMR (400 MHz, DMSO-d6) δ ppm 12.81 (br. s., 1 H), 7.27 (s, 1 H), 7.16 (s, 1 H), 5.83 (s, 1 H), 4.50 (dt, J = 14.14, 5.41 Hz, 1 H), 3.79 (s, 3 H), 3.77 (s, 3 H), 3.66-3.75 (m, 1 H), 3.52 (dt, J = 9.96, 6.93 Hz, 1 H), 3.33-3.39 (m, 1 H), 3.01 (s, 3 H) |
| 234 | 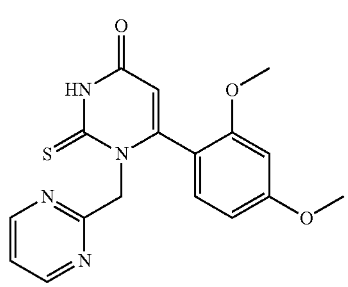 [SMILES: COc1ccc(-c2cc(=O)[nH]c(=S)n2Cc2ncccn2)c(OC)c1] | 6-(2,4-dimethoxyphenyl)-1-(pyrimidin-2-ylmethyl)-2-thioxo-2,3-dihydropyrimidin-4(1H)-one | 357.0 | 1H NMR (400 MHz, CHLOROFORM-d) δ ppm 9.81 (br. s., 1 H), 8.59 (d, J = 4.81 Hz, 2 H), 7.12 (t, J = 4.81 Hz, 1 H), 6.91 (d, J = 8.47 Hz, 1 H), 6.44 (d, J = 1.83 Hz, 1 H), 6.28 (dd, J = 8.36, 1.95 Hz, 1 H), 6.21 (d, J = 17.40 Hz, 1 H), 5.87 (s, 1 H), 4.94 (d, J = 17.17 Hz, 1 H), 3.81 (s, 3 H), 3.76 (s, 3 H) |
| 235 | 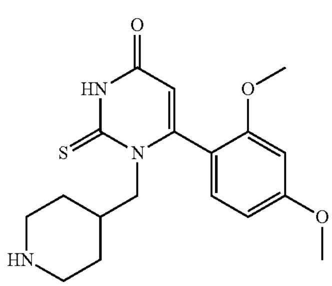 [SMILES: COc1ccc(-c2cc(=O)[nH]c(=S)n2CC2CCNCC2)c(OC)c1] | 6-(2,4-dimethoxyphenyl)-1-(piperidin-4-ylmethyl)-2-thioxo-2,3-dihydropyrimidin-4(1H)-one hydrochloride | 362.1 | 1H NMR (400 MHz, DMSO-d6) δ ppm 12.77 (d, J = 1.86 Hz, 1 H), 8.66-8.77 (m, 1 H), 8.17-8.31 (m, 1 H), 7.32 (d, J = 8.37 Hz, 1 H), 6.71 (d, J = 2.33 Hz, 1 H), 6.67 (dd, J = 8.37, 2.33 Hz, 1 H), 5.76 (d, J = 2.33 Hz, 1 H), 4.51-4.77 (m, 1 H), 3.84 (s, 3 H), 3.83 (s, 3 H), 3.67-3.79 (m, 1 H), 3.03-3.20 (m, 2 H), 2.57-2.80 (m, 2 H), 1.98-2.16 (m, 1 H), 1.56-1.71 (m, 1 H), 1.38-1.52 (m, 1 H), 1.11-1.27 (m, 1 H), 0.78-0.99 (m, 1 H) |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 236 | 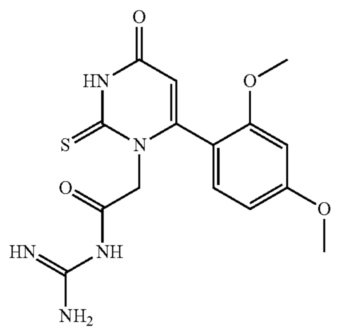 [SMILES: COc1ccc(-c2cc(=O)[nH]c(=S)n2CC(=O)NC(=N)N)c(OC)c1] | N-[amino(imino)methyl]-2-[6-(2,4-dimethoxyphenyl)-4-oxo-2-thioxo-3,4-dihydropyrimidin-1(2H)-yl]acetamide trifluoroacetate | 364.0 | 1H NMR (400 MHz, METHANOL-d4) δ ppm 7.19 (d, J = 8.41 Hz, 1 H), 6.68 (d, J = 2.15 Hz, 1 H), 6.63 (dd, J = 8.41, 2.35 Hz, 1 H), 5.84 (s, 1 H), 5.44 (br. d, J = 15.10 Hz, 1 H), 4.55 (br. d, J = 17.40 Hz, 1 H), 3.88 (s, 3 H), 3.85 (s, 3 H) |
| 237 | 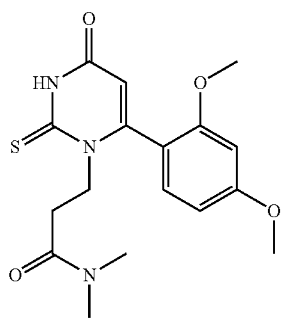 [SMILES: COc1ccc(-c2cc(=O)[nH]c(=S)n2CCC(=O)N(C)C)c(OC)c1] | 3-[6-(2,4-dimethoxyphenyl)-4-oxo-2-thioxo-3,4-dihydropyrimidin-1(2H)-yl]-N,N-dimethylpropanamide | 364.1 | 1H NMR (400 MHz, DMSO-d6) δ ppm 12.71 (br. s, 1 H), 7.30 (d, J = 8.24 Hz, 1 H), 6.70 (d, J = 1.83 Hz, 1 H), 6.65 (dd, J = 8.24, 2.29 Hz, 1 H), 5.74 (s, 1 H), 4.39-4.55 (m, 2 H), 3.82 (s, 6 H), 2.81 (s, 3 H), 2.69 (s, 3 H) |
| 238 | 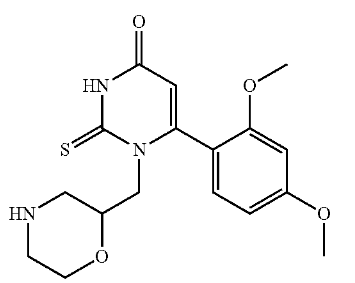 [SMILES: COc1ccc(-c2cc(=O)[nH]c(=S)n2CC2CNCCO2)c(OC)c1] | 6-(2,4-dimethoxyphenyl)-1-(morpholin-2-ylmethyl)-2-thioxo-2,3-dihydropyrimidin-4(1H)-one hydrochloride | 364.2 | 1H NMR (400 MHz, METHANOL-d4) δ ppm 7.19 (d, J = 8.39 Hz, 1 H), 6.57-6.69 (m, 2 H), 5.73 (s, 1 H), 4.74 (dd, J = 14.45, 2.15 Hz, 1 H), 4.33 (ddt, J = 11.18, 8.44, 2.39 Hz, 1 H), 3.93 (dd, J = 12.98, 3.61 Hz, 1 H), 3.84 (d, J = 1.17 Hz, 6 H), 3.54-3.68 (m, 3 H), 3.13 (d, J = 12.69 Hz, 1 H), 2.95 (td, J = 12.69, 3.90 Hz, 1 H), 2.67 (t, J = 11.91 Hz, 1 H) |
| 239 | 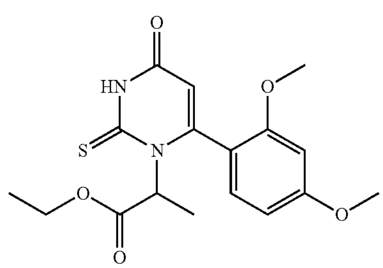 [SMILES: CCOC(=O)C(C)n1c(-c2ccc(OC)cc2OC)cc(=O)[nH]c1=S] | ethyl 2-[6-(2,4-dimethoxyphenyl)-4-oxo-2-thioxo-3,4-dihydropyrimidin-1(2H)-yl]propanoate | 365.1 | 1H NMR (400 MHz, DMSO-d6) δ ppm 12.69-12.78 (m, 1 H), 7.09-7.31 (m, 1 H), 6.61-6.73 (m, 2 H), 5.75-5.83 (m, 1 H), 4.44-4.57 (m, 1 H), 3.91-4.18 (m, 2 H), 3.75-3.85 (m, 6 H), 1.67 (d, J = 6.90 Hz, 3 H), 1.09-1.24 (m, 3 H) |
| 240 | 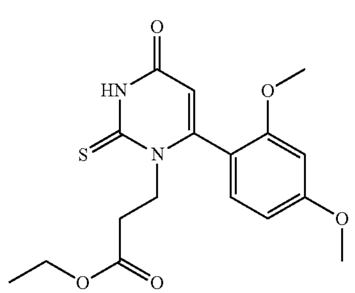 [SMILES: CCOC(=O)CCn1c(-c2ccc(OC)cc2OC)cc(=O)[nH]c1=S] | ethyl 3-[6-(2,4-dimethoxyphenyl)-4-oxo-2-thioxo-3,4-dihydropyrimidin-1(2H)-yl]propanoate | 365.1 | 1H NMR (400 MHz, DMSO-d6) δ ppm 12.78 (s, 1 H), 7.29 (d, J = 8.24 Hz, 1 H), 6.71 (d, J = 1.83 Hz, 1 H), 6.66 (dd, J = 8.24, 2.29 Hz, 1 H), 5.75 (d, J = 2.29 Hz, 1 H), 4.43-4.58 (m, 1 H), 3.94 (q, J = 6.87 Hz, 2 H), 3.83-3.89 (m, 1 H), 3.82 (s, 3 H), 3.82 (s, 3 H), 2.59 (td, J = 10.19, 6.18 Hz, 2 H), 1.08 (t, J = 7.10 Hz, 3 H) |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 241 | 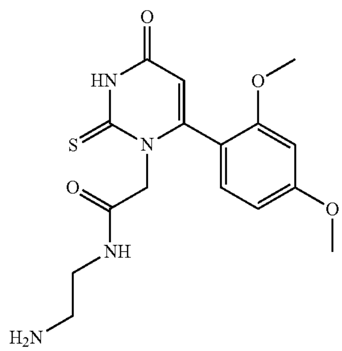 [SMILES: COc1ccc(-c2cc(=O)[nH]c(=S)n2CC(=O)NCCN)c(OC)c1] | N-(2-aminoethyl)-2-[6-(2,4-dimethoxyphenyl)-4-oxo-2-thioxo-3,4-dihydropyrimidin-1(2H)-yl]acetamide hydrochloride | 364.8 | 1H NMR (400 MHz, METHANOL-d4): δ 8.28 (m, 1H), 7.15 (d, 1H), 6.66 (d, 1H), 6.62 (dd, 1H), 5.79 (s, 1H), 5.42-5.40 (m, 1H), 4.37-4.23 (m, 1H), 3.90 (s, 3H), 3.80 (s, 3H), 3.20-3.15 (m, 1H), 3.05-3.12 (m, 1H), 2.95-2.85 (m, 2H). |
| 242 | 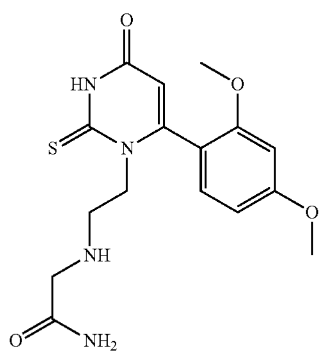 [SMILES: COc1ccc(-c2cc(=O)[nH]c(=S)n2CCNCC(N)=O)c(OC)c1] | N~2~-{2-[6-(2,4-dimethoxyphenyl)-4-oxo-2-thioxo-3,4-dihydropyrimidin-1(2H)-yl]ethyl}glycinamide | 365.1 | 1H NMR (400 MHz, METHANOL-d4): δ 7.14 (d, 1H), 6.55-6.60 (m, 2H), 5.65 (s, 1H), 4.55-4.62 (m, 1H), 4.51 (s, 1H), 3.77 (s, 6H), 3.00 (s, 2H), 2.64-2.79 (m, 2H). |
| 243 | 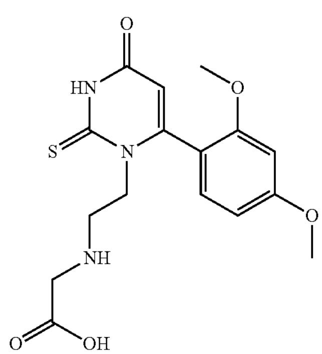 [SMILES: COc1ccc(-c2cc(=O)[nH]c(=S)n2CCNCC(=O)O)c(OC)c1] | N-{2-[6-(2,4-dimethoxyphenyl)-4-oxo-2-thioxo-3,4-dihydropyrimidin-1(2H)-yl]ethyl}glycine hydrochloride | 365.9 | 1H NMR (400 MHz, DMSO-d6): δ 12.88 (br, 1H), 7.26 (d, 1H), 6.66-6.74 (m, 2H), 5.78 (s, 1H), 4.76 (m, 1H), 3.92 (m, 1H), 3.83 (s, 6H), 3.70 (s, 2H), 3.02 (m, 2H). |
| 244 | 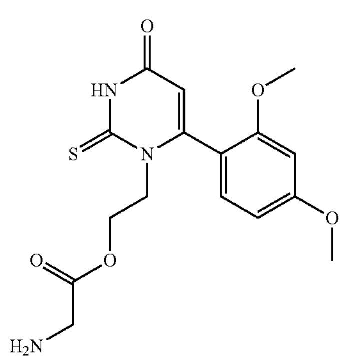 [SMILES: COc1ccc(-c2cc(=O)[nH]c(=S)n2CCOC(=O)CN)c(OC)c1] | 2-[6-(2,4-dimethoxyphenyl)-4-oxo-2-thioxo-3,4-dihydropyrimidin-1(2H)-yl]ethyl glycinate tosylate | 366.2 | 1H NMR (400 MHz, CD$_3$OD) δ 2.37 (s, 3 H), 3.71 (d, J = 17.2 Hz, 1 H), 3.79 (d, J = 17.2 Hz, 1 H), 3.87 (s, 3 H), 3.88 (s, 3 H), 4.04 (ddd, J = 14.8, 6.8, 5.5 Hz, 1 H), 4.28 (dt, J = 11.7, 5.3 Hz, 1 H), 4.51 (ddd, J = 11.6, 6.7, 5.1 Hz, 1 H), 4.97 (dt, J = 14.5, 5.0 Hz, 1 H), 5.78 (s, 1 H), 6.65-6.72 (m, 2 H), 7.23 (d, J = 8.0 Hz, 2 H), 7.27 (d, J = 8.0 Hz, 1 H), 7.71 (d, J = 8.2 Hz, 2 H) |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 245 | 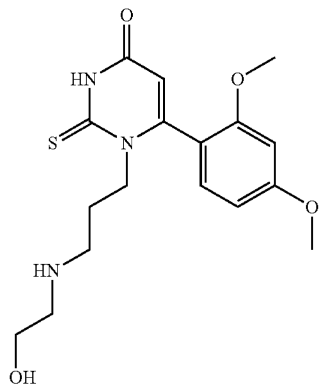 [SMILES: COc1ccc(-c2cc(=O)[nH]c(=S)n2CCCNCCO)c(OC)c1] | 6-(2,4-dimethoxyphenyl)-1-{3-[(2-hydroxyethyl)amino]propyl}-2-thioxo-2,3-dihydropyrimidin-4(1H)-one | 365.9 | 1.58 min Waters Atlantis dC18 5 um 4.6 x 50 mm, 95% H2O/5% MeCN linear to 5% H2O/95% MeCN over 4.0 min, HOLD at 5% H2O/95% MeCN to 5.0 min. (0.05% TFA). Flow rate: 2 mL/min |
| 246 | 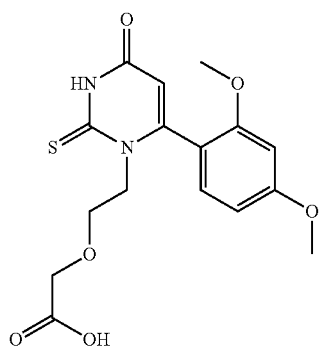 [SMILES: COc1ccc(-c2cc(=O)[nH]c(=S)n2CCOCC(=O)O)c(OC)c1] | {2-[6-(2,4-dimethoxyphenyl)-4-oxo-2-thioxo-3,4-dihydropyrimidin-1(2H)-yl]ethoxy}acetic acid | 388.9 [M + Na]+ | 1H NMR (400 MHz, METHANOL-d4): δ 7.25 (d, 1H), 6.64 (m, 2H), 5.73 (s, 1H), 4.74 (m, 1H), 3.92 (m, 1H), 3.87 (s, 3H), 3.86 (s, 3H), 3.75 (m, 3H), 3.61 (m, 1H). |
| 247 | 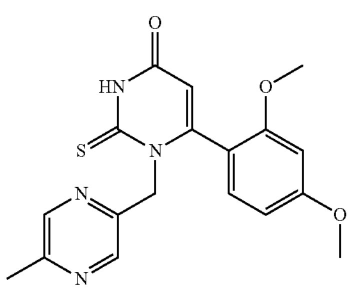 | 6-(2,4-dimethoxyphenyl)-1-[(5-methylpyrazin-2-yl)methyl]-2-thioxo-2,3-dihydropyrimidin-4(1H)-one | 371.1 | 1H NMR (400 MHz, DMSO-d6) δ ppm 12.81 (br. s., 1 H), 8.34 (s, 1 H), 8.19 (s, 1 H), 6.98 (d, J = 8.24 Hz, 1 H), 6.58 (d, J = 2.06 Hz, 1 H), 6.42 (dd, J = 8.36, 2.18 Hz, 1 H), 5.81 (d, J = 16.26 Hz, 1 H), 5.78 (s, 1 H), 4.88 (d, J = 16.72 Hz, 1 H), 3.72 (s, 3 H), 3.71 (br. s., 3 H), 2.39 (s, 3 H) |
| 248 | 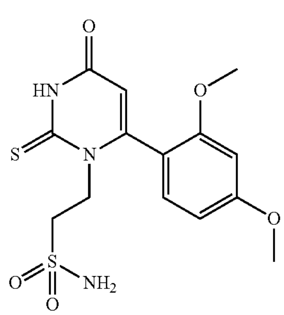 [SMILES: COc1ccc(-c2cc(=O)[nH]c(=S)n2CCS(N)(=O)=O)c(OC)c1] | 2-[6-(2,4-dimethoxyphenyl)-4-oxo-2-thioxo-3,4-dihydropyrimidin-1(2H)-yl]ethanesulfonamide | 372.0 | 1H NMR (400 MHz, DMSO-d6) δ ppm 12.76 (br. s., 1 H), 7.26 (d, J = 8.24 Hz, 1 H), 6.92 (s, 2 H), 6.66 (d, J = 2.06 Hz, 1 H), 6.61 (dd, J = 8.47, 2.06 Hz, 1 H), 5.72 (d, J = 1.60 Hz, 1 H), 4.57 (br. s., 1 H), 3.92-4.06 (m, 1 H), 3.79 (s, 3 H), 3.78 (s, 3 H), 3.08-3.29 (m, 2 H) |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 249 | 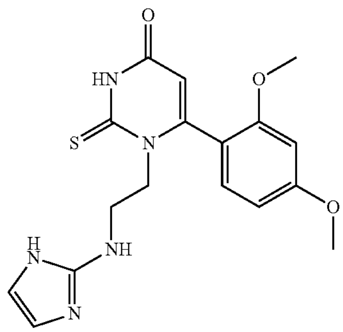 [SMILES: COc1ccc(-c2cc(=O)[nH]c(=S)n2CCNc2ncc[nH]2)c(OC)c1] | 6-(2,4-dimethoxyphenyl)-1-[2-(1H-imidazol-2-ylamino)ethyl]-2-thioxo-2,3-dihydropyrimidin-4(1H)-one | 374.0 | 1H NMR (500 MHz, METHANOL-d4) δ ppm 7.05 (d, J = 8.29 Hz, 1 H) 6.71 (s, 2 H) 6.62 (d, J = 2.20 Hz, 1 H) 6.43 (dd, J = 8.42, 2.07 Hz, 1 H) 5.77 (s, 1 H) 4.84 (br. s., 1 H) 3.90-3.93 (m, 1 H) 3.88 (s, 3 H) 3.84 (s, 3 H) 3.26-3.33 (m, 2 H) |
| 250 | 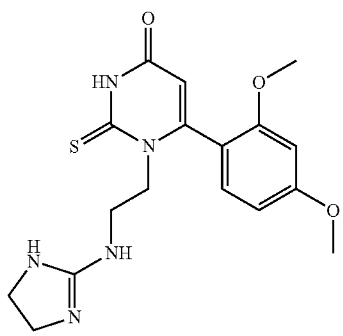 [SMILES: COc1ccc(-c2cc(=O)[nH]c(=S)n2CCNC2=NCCN2)c(OC)c1] | 1-[2-(4,5-dihydro-1H-imidazol-2-ylamino)ethyl]-6-(2,4-dimethoxyphenyl)-2-thioxo-2,3-dihydropyrimidin-4(1H)-one | 376.1 | 1H NMR (400 MHz, METHANOL-d4) δ ppm 7.21 (d, J = 8.00 Hz, 1 H), 6.68-6.73 (m, 2 H), 5.79 (s, 1 H), 4.72-4.84 (m, 2 H), 3.89 (s, 6 H), 3.69-3.81 (m, 1 H), 3.57-3.67 (m, 2 H), 3.43-3.57 (m, 2 H), 3.23 (d, J = 15.23 Hz, 1 H) |
| 251 | 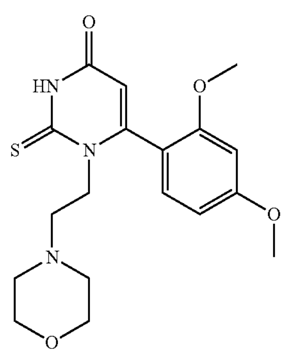 [SMILES: COc1ccc(-c2cc(=O)[nH]c(=S)n2CCN2CCOCC2)c(OC)c1] | 6-(2,4-dimethoxyphenyl)-1-(2-morpholin-4-ylethyl)-2-thioxo-2,3-dihydropyrimidin-4(1H)-one | 377.8 | 1H NMR (400 MHz, CDCl3): δ 9.89 (br. s., 1H), 7.13 (d, 1H), 6.56 (dd, 1H), 6.53 (s, 1H), 5.80 (s, 1H), 4.68 (br. s., 1H), 3.81-3.85 (m, 1H), 3.84 (s, 3H), 3.80 (s, 3H), 3.58-3.65 (m, 4H), 2.52-2.66 (m, 2H), 2.28-2.38 (m, 4H). |
| 252 | 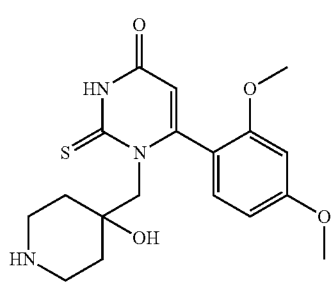 [SMILES: COc1ccc(-c2cc(=O)[nH]c(=S)n2CC2(O)CCNCC2)c(OC)c1] | 6-(2,4-dimethoxyphenyl)-1-[(4-hydroxypiperidin-4-yl)methyl]-2-thioxo-2,3-dihydropyrimidin-4(1H)-one hydrochloride | 378.1 | 1H NMR (500 MHz, DMSO-d6) δ ppm 12.73 (br. s., 1 H), 8.63 (d, J = 8.78 Hz, 1 H), 8.26 (d, J = 10.00 Hz, 1 H), 7.25 (d, J = 8.29 Hz, 1 H), 6.66 (s, 1 H), 6.63 (d, J = 8.29 Hz, 1 H), 5.74 (d, J = 1.46 Hz, 1 H), 5.24 (d, J = 14.64 Hz, 1 H), 4.82 (br. s., 1 H), 3.82 (s, 3 H), 3.81 (s, 3 H), 3.47-3.53 (m, 1 H), 3.05 (d, J = 11.95 Hz, 1 H), 2.97 (d, J = 11.22 Hz, 1 H), 2.86 (q, J = 11.63 Hz, 2 H), 1.88 (td, J = 13.54, 3.90 Hz, 1 H), 1.55 (d, J = 13.91 Hz, 1 H), 1.48 (td, J = 13.42, 4.15 Hz, 1 H), 1.29 (d, J = 13.42 Hz, 1 H) |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 253 | 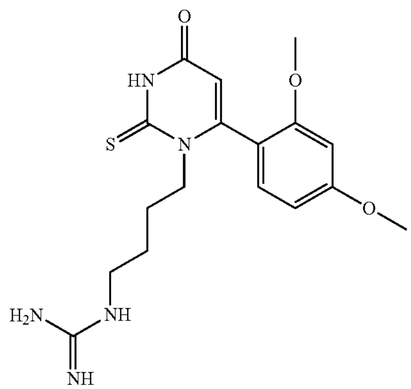 [SMILES: COc1ccc(-c2cc(=O)[nH]c(=S)n2CCCCNC(=N)N)c(OC)c1] | 1-{4-[6-(2,4-dimethoxyphenyl)-4-oxo-2-thioxo-3,4-dihydropyrimidin-1(2H)-yl]butyl}guanidine | 378.0 | 1H NMR (400 MHz, METHANOL-d4): δ 8.57 (br, 1H), 7.25 (d, 1H), 6.71 (d, 1H), 6.68 (dd, 1H), 5.77 (s, 1H), 4.58-4.61 (m, 1H), 3.70-3.72 (m, 1H), 3.02-3.06 (t, 2H), 1.76-1.78 (m, 1H), 1.52-1.55 (m, 1H), 1.33-1.40 (m, 2H). |
| 254 | 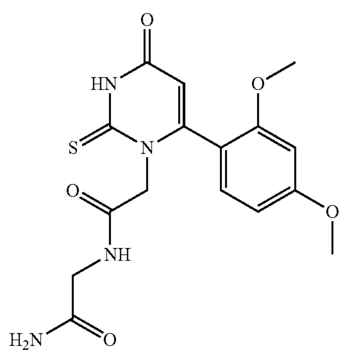 [SMILES: COc1ccc(-c2cc(=O)[nH]c(=S)n2CC(=O)NCC(N)=O)c(OC)c1] | N~2~-{[6-(2,4-dimethoxyphenyl)-4-oxo-2-thioxo-3,4-dihydropyrimidin-1(2H)-yl]acetyl}glycinamide | 305.1 [M − NHCH2CO NH2]+ | 1H NMR (400 MHz, CD3OD) δ 3.69 (d, J = 17.0 Hz, 1 H), 3.79 (d, J = 17.0Hz, 1 H), 3.85 (s, 3 H), 3.86 (s, 3 H), 4.34 (br. d, J = 16.2 Hz, 1 H), 5.33 (br. d, J = 14.9 Hz, 1 H), 5.81 (s, 1 H), 6.61 (dd, J = 8.5, 2.2 Hz, 1 H), 6.66 (d, J = 2.3 Hz, 1 H), 7.18 (d, J = 8.4 Hz, 1 H) |
| 255 | ABS | N-{2-[6-(2,4-dimethoxyphenyl)-4-oxo-2-thioxo-3,4-dihydropyrimidin-1(2H)-yl]ethyl}-D-alaninamide trifluoroacetate | 379.2 | 7.51 min Chiralcel OD-H 4.6 mm x 25 cm, 75% CO2/25% MeOH (0.2% iPrNH2). Flow rate: 2.5 mL/min |
| 256 | ABS | N-{2-[6-(2,4-dimethoxyphenyl)-4-oxo-2-thioxo-3,4-dihydropyrimidin-1(2H)-yl]ethyl}-L-alaninamide trifluoroacetate | 379.2 | 6.32 min Chiralcel OD-H 4.6 mm x 25 cm, 75% CO2/25% MeOH (0.2% iPrNH2). Flow rate: 2.5 mL/min |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 257 | 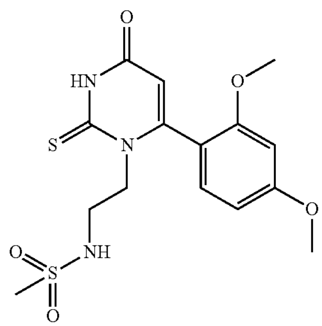 [SMILES: COc1ccc(-c2cc(=O)[nH]c(=S)n2CCNS(C)(=O)=O)c(OC)c1] | N-{2-[6-(2,4-dimethoxyphenyl)-4-oxo-2-thioxo-3,4-dihydropyrimidin-1(2H)-yl]ethyl}methane sulfonamide | 386.1 | 1H NMR (400 MHz, CHLOROFORM-d) δ ppm 9.48 (br. s., 1 H), 7.21 (d, J = 8.70 Hz, 1 H), 6.61 (dd, J = 8.24, 2.29 Hz, 1 H), 6.54 (d, J = 2.29 Hz, 1 H), 5.85 (d, J = 2.29 Hz, 1 H), 4.62 (t, J = 6.64 Hz, 2 H), 3.88 (s, 3 H), 3.85 (s, 3 H), 3.27-3.47 (m, 2 H), 2.86 (s, 3 H) |
| 258 | 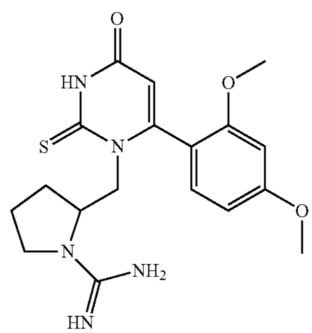 [SMILES: COc1ccc(-c2cc(=O)[nH]c(=S)n2CC2CCCN2C(=N)N)c(OC)c1] | 2-{[6-(2,4-dimethoxyphenyl)-4-oxo-2-thioxo-3,4-dihydropyrimidin-1(2H)-yl]methyl}pyrrolidine-1-carboximidamide trifluoroacetate | 390.1 | 1.72 min Waters Atlantis dC18 5 um 4.6 x 50 mm, 95% H2O/5% MeCN linear to 5% H2O/95% MeCN over 4.0 min, HOLD at 5% H2O/95% MeCN to 5.0 min. (0.05% TFA). Flow rate: 2 mL/min |
| 259 | 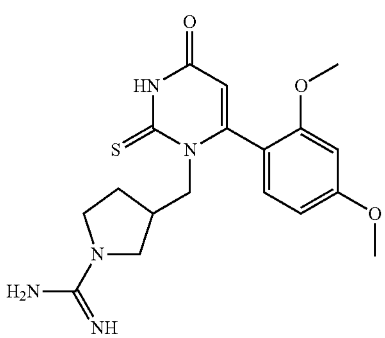 [SMILES: COc1ccc(-c2cc(=O)[nH]c(=S)n2CC2CCN(C(=N)N)C2)c(OC)c1] | 3-{[6-(2,4-dimethoxyphenyl)-4-oxo-2-thioxo-3,4-dihydropyrimidin-1(2H)-yl]methyl}pyrrolidine-1-carboximidamide trifluoroacetate | 390.1 | 1.69 min Waters Atlantis dC18 5 um 4.6 x 50 mm, 95% H2O/5% MeCN linear to 5% H2O/95% MeCN over 4.0 min, HOLD at 5% H2O/95% MeCN to 5.0 min. (0.05% TFA). Flow rate: 2 mL/min |
| 260 | 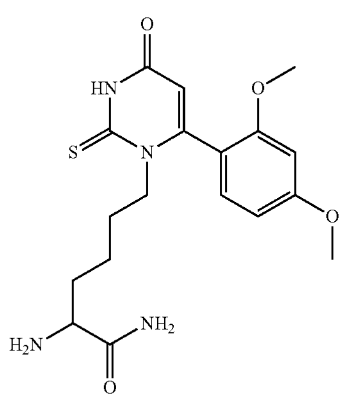 [SMILES: COc1ccc(-c2cc(=O)[nH]c(=S)n2CCCCC(N)C(N)=O)c(OC)c1] | 6-[6-(2,4-dimethoxyphenyl)-4-oxo-2-thioxo-3,4-dihydropyrimidin-1(2H)-yl]norleucinamide hydrochloride | 393.1 | 1H NMR (400 MHz, METHANOL-d4) δ ppm 7.23 (d, J = 8.20 Hz, 1 H), 6.68 (d, J = 2.15 Hz, 1 H), 6.66 (dd, J = 8.39, 2.54 Hz, 1 H), 5.75 (s, 1 H), 4.48-4.59 (m, 1 H), 3.87 (s, 6 H), 3.75-3.81 (m, 1 H), 3.65-3.74 (m, 1 H), 1.73-1.83 (m, 1 H), 1.63-1.73 (m, 2 H), 1.45-1.57 (m, 1 H), 1.14-1.25 (m, 2 H) |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 261 | 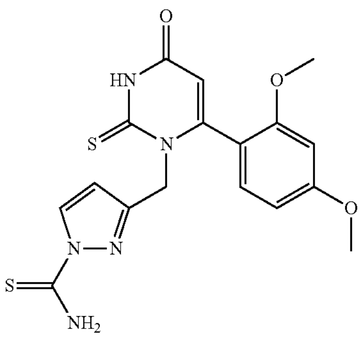 [SMILES: COc1ccc(-c2cc(=O)[nH]c(=S)n2Cc2ccn(C(N)=S)n2)c(OC)c1] | 3-{[6-(2,4-dimethoxyphenyl)-4-oxo-2-thioxo-3,4-dihydropyrimidin-1(2H)-yl]methyl}-1H-pyrazole-1-carbothioamide | 404.2 | 1H NMR (500 MHz, DMSO-d6) δ ppm 12.81 (d, J = 1.71 Hz, 1 H), 9.86 (s, 1 H), 9.11 (s, 1 H), 8.47 (d, J = 2.93 Hz, 1 H), 7.20 (d, J = 8.54 Hz, 1 H), 6.63 (d, J = 2.20 Hz, 1 H), 6.51 (dd, J = 8.29, 2.20 Hz, 1 H), 6.32 (d, J = 2.93 Hz, 1 H), 5.80 (d, J = 2.20 Hz, 1 H), 5.77 (d, J = 17.08 Hz, 1 H), 4.78 (d, J = 16.34 Hz, 1 H), 3.77 (s, 3 H), 3.75 (s, 3 H) |
| 262 | 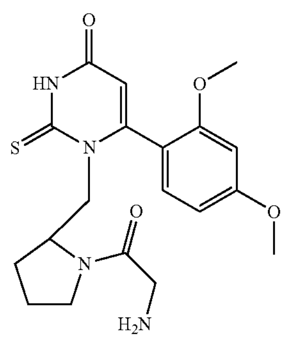 [SMILES: COc1ccc(-c2cc(=O)[nH]c(=S)n2CC2CCCN2C(=O)CN)c(OC)c1] | 6-(2,4-dimethoxyphenyl)-1-[(1-glycylpyrrolidin-2-yl)methyl]-2-thioxo-2,3-dihydropyrimidin-4(1H)-one hydrochloride | 405.1 | 0.83 min Column: Xtimate C18, 2.1 x 30 mm, 3 µm; Mobile phase: from 10% MeCN (0.06% TFA) in water (0.06% TFA) to 80% MeCN (0.06% TFA) in water (0.06% TFA); wavelength; 220 nm |
| 263 | ABS | N-{2-[6-(2,4-dimethoxyphenyl)-4-oxo-2-thioxo-3,4-dihydropyrimidin-1(2H)-yl]ethyl}-L-valinamide trifluoroacetate | 407.3 | 5.74 min Column: XBRIDGE-C18 4.6 mm X 150 mm 5 µm Mobile phase- A = 0.1% TFA IN MeCN, B = 0.1% TFA IN WATER: Phase A = 5% to 1.5 min, linear to 100% to 10 min. Flow rate = 1.5 mL/min. |
| 264 | 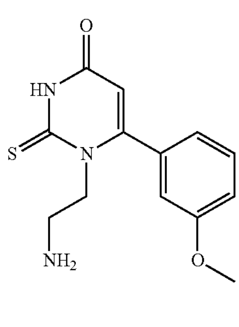 [SMILES: COc1cccc(-c2cc(=O)[nH]c(=S)n2CCN)c1] | 1-(2-aminoethyl)-6-(3-methoxyphenyl)-2-thioxo-2,3-dihydropyrimidin-4(1H)-one hydrochloride | 278.1 | 1H NMR (300 MHz, DMSO-d6) δ ppm 12.87 (br. s., 1 H), 7.81 (br. s., 3 H), 7.46 (t, J = 7.67 Hz, 1 H), 7.10-7.17 (m, 2 H), 7.07 (d, J = 7.67 Hz, 1 H), 5.82 (s, 1 H), 4.31 (t, J = 6.62 Hz, 2 H), 3.81 (s, 3 H), 2.90-3.01 (m, 2 H) |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 265 | 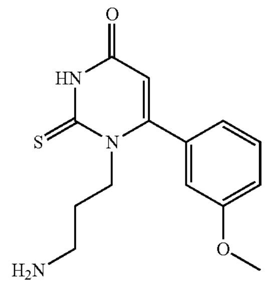 [SMILES: COc1cccc(-c2cc(=O)[nH]c(=S)n2CCCN)c1] | 1-(3-aminopropyl)-6-(3-methoxyphenyl)-2-thioxo-2,3-dihydropyrimidin-4(1H)-one hydrochloride | 292.0 | 1H NMR (400 MHz, DMSO-d6) δ ppm 12.80 (s, 1 H), 7.73 (br. s, 3 H), 7.45 (dd, J = 9.05, 7.58 Hz, 1 H), 7.09-7.13 (m, 2 H), 7.07 (d, J = 7.83 Hz, 1 H), 5.82 (d, J = 1.96 Hz, 1 H), 4.02-4.14 (m, 2 H), 3.81 (s, 3 H), 2.53-2.59 (m, 2 H), 1.79-1.90 (m, 2 H) |
| 266 | 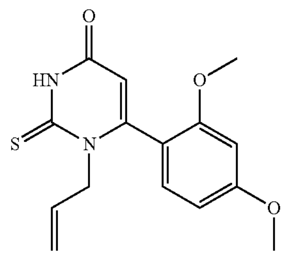 [SMILES: C=CCn1c(-c2ccc(OC)cc2OC)cc(=O)[nH]c1=S] | 1-allyl-6-(2,4-dimethoxyphenyl)-2-thioxo-2,3-dihydropyrimidin-4(1H)-one | 305.1 | 1H NMR (400 MHz, CHLOROFORM-d) δ ppm 10.35 (br. s., 1 H), 7.04 (d, J = 8.19 Hz, 1 H), 6.52 (d, J = 2.34 Hz, 1 H), 6.47-6.50 (m, 1 H), 5.82 (d, J = 2.15 Hz, 1 H), 5.72 (ddt, J = 16.78, 10.93, 5.46, 5.46 Hz, 1 H), 5.21 (dd, J = 15.80, 5.07 Hz, 1 H), 5.04 (dd, J = 10.34, 0.98 Hz, 1 H), 4.77 (dd, J = 17.27, 0.88 Hz, 1 H), 4.24 (dd, J = 15.80, 6.05 Hz, 1 H), 3.84 (s, 3 H), 3.79 (s, 3 H) |
| 267 | ABS | 6-(2,4-dimethoxyphenyl)-1-[(2R)-pyrrolidin-2-ylmethyl]-2-thioxo-2,3-dihydropyrimidin-4(1H)-one hydrochloride | 348.1 | 1H NMR (500 MHz, DMSO-d6) δ ppm 12.89 (br. s., 1 H), 9.25-9.43 (m, 1 H), 8.74 (br. s., 1 H), 7.25-7.43 (m, 1 H), 6.73 (d, J = 1.46 Hz, 1 H), 6.68 (dd, J = 8.42, 1.83 Hz, 1 H), 5.73-5.85 (m, 1 H), 4.96-5.08 (m, 1 H), 3.80-3.88 (m, 6 H), 3.61-3.77 (m, 1 H), 3.42-3.53 (m, 1 H), 2.93-3.15 (m, 2 H), 1.73-1.90 (m, 1 H), 1.50-1.73 (m, 2 H), 1.14-1.25 (m, 1 H) |
| 268 | ABS | 6-(2,4-dimethoxyphenyl)-1-[(2S)-pyrrolidin-2-ylmethyl]-2-thioxo-2,3-dihydropyrimidin-4(1H)-one hydrochloride hydrochloride | 348.1 | 1H NMR (500 MHz, DMSO-d6) δ ppm 12.89 (br. s., 1 H), 9.25-9.43 (m, 1 H), 8.74 (br. s., 1 H), 7.25-7.43 (m, 1 H), 6.73 (d, J = 1.46 Hz, 1 H), 6.68 (dd, J = 8.42, 1.83 Hz, 1 H), 5.73-5.85 (m, 1 H), 4.96-5.08 (m, 1 H), 3.80-3.88 (m, 6 H), 3.61-3.77 (m, 1 H), 3.42-3.53 (m, 1 H), 2.93-3.15 (m, 2 H), 1.73-1.90 (m, 1 H), 1.50-1.73 (m, 2 H), 1.14-1.25 (m, 1 H) |
| 269 | 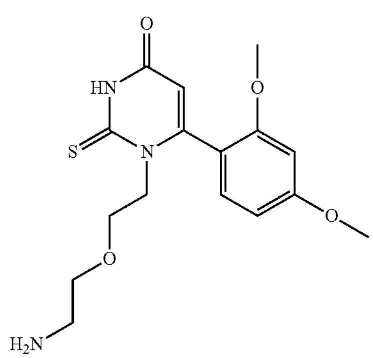 [SMILES: COc1ccc(-c2cc(=O)[nH]c(=S)n2CCOCCN)c(OC)c1] | 1-[2-(2-aminoethoxy)ethyl]-6-(2,4-dimethoxyphenyl)-2-thioxo-2,3-dihydropyrimidin-4(1H)-one hydrochloride | 352.3 | 1H NMR (300 MHz, DMSO-d6) δ ppm 12.78 (br. s, 1 H), 7.73 (br. s, 3 H), 7.29 (d, J = 8.36 Hz, 1 H), 6.72 (s, 1 H), 6.66 (dd, J = 8.36, 2.09 Hz, 1 H), 5.76 (d, J = 2.09 Hz, 1 H), 4.55-4.68 (m, 1 H), 3.83 (s, 6 H), 3.70-3.79 (m, 1 H), 3.47-3.56 (m, 2 H), 3.34-3.41 (m, 2 H), 2.80-2.90 (m, 2 H) |

TABLE 3-continued

Examples from Methyl Ketone Route

| Example # | Structure | Compound Name | Obs Mass | 1H NMR Spectral Data or HPLC Retention Time and Conditions |
|---|---|---|---|---|
| 270 | 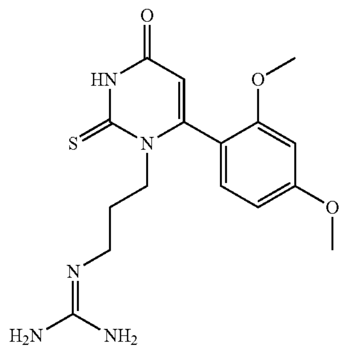 [SMILES: COc1ccc(-c2cc(=O)[nH]c(=S)n2CCCN=C(N)N)c(OC)c1] | 2-{3-[6-(2,4-dimethoxyphenyl)-4-oxo-2-thioxo-3,4-dihydropyrimidin-1(2H)-yl]propyl}guanidine trifluoroacetate | 364.1 | 1H NMR (400 MHz, METHANOL-d4) δ ppm 7.22 (d, J = 8.41 Hz, 1 H), 6.68 (d, J = 1.96 Hz, 1 H), 6.65 (dd, J = 8.41, 2.15 Hz, 1 H), 5.76 (s, 1 H), 4.51-4.63 (m, 1 H), 3.86 (s, 6 H), 3.75-3.83 (m, 1 H), 2.98-3.09 (m, 2 H), 1.86-2.00 (m, 1 H), 1.67-1.79 (m, 1 H) |

The following Examples of Table 4 were prepared from the corresponding aryl halide to afford the intermediate beta-keto-ester as described above for the Preparations in the Aryl Halide Route section followed by employing the methods described in the I. Beta Keto Ester Route Section as well as standard methods and techniques known to those skilled in the art.

TABLE 4

Examples from Aryl Halide Route

| Example # | Structure | Compound Name | Obs Mass | 1H NMR Spectral Data or HPLC Retention Time and Conditions |
|---|---|---|---|---|
| 271 | 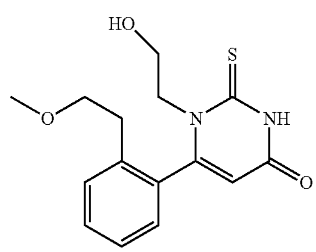 [SMILES: COCCc1ccccc1-c1cc(=O)[nH]c(=S)n1CCO] | 1-(2-hydoxyethyl)-6-[2-(2-methoxyethyl)phenyl]-2-thioxo-2,3-dihydropyrimidin-4(1H)-one | 306.9 | 1H NMR (500 MHz, CHLOROFORM-d) δ ppm 10.31 (br. s., 1 H), 7.48 (dd, J = 7.80 , 7.80 Hz, 1 H), 7.42 (d, J = 7.81 Hz, 1 H), 7.35 (dd, J = 7.60 Hz, 1 H), 7.25 (d, J = 7.81 Hz, 1 H), 5.88 (s, 1 H), 4.57 (dt, J = 13.80, 5.80 Hz, 1 H), 3.92 (dt, J = 14.00, 5.90 Hz, 1 H), 3.75-3.85 (m, 2 H), 3.61 (t, J = 6.46 Hz, 2 H), 3.31 (s, 3 H), 2.88 (dt, J = 14.45, 7.04 Hz, 1 H), 2.73 (dt, J = 14.45, 5.95 Hz, 1 H) |
| 272 | 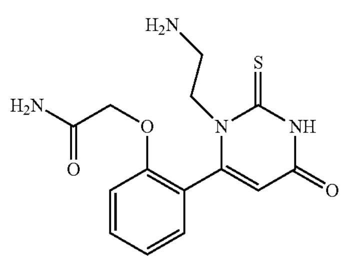 [SMILES: NCCn1c(-c2ccccc2OCC(N)=O)cc(=O)[nH]c1=S] | 2-{2-[3-(2-aminoethyl)-6-oxo-2-thioxo-1,2,3,6-tetrahydropyrimidin-4-yl]phenoxy}acetamide trifluoroacetate | 320.9 | 1H NMR (500 MHz, METHANOL-d4) δ ppm 3.11-3.20 (m, 1 H) 3.26-3.33 (m, 1 H) 4.46 (dt, J = 13.72, 6.92 Hz, 1 H) 4.65 (d, J = 6.10 Hz, 1 H) 4.70-4.81 (m, 2H) 5.89 (s, 1 H) 7.08 (d, J = 8.54 Hz, 1 H) 7.19 (t, J = 7.56 Hz, 1 H) 7.40 (dd, J = 7.32, 1.22 Hz, 1 H) 7.54-7.60 (m, 1 H) |

TABLE 4-continued

Examples from Aryl Halide Route

| Example # | Structure | Compound Name | Obs Mass | 1H NMR Spectral Data or HPLC Retention Time and Conditions |
|---|---|---|---|---|
| 273 | 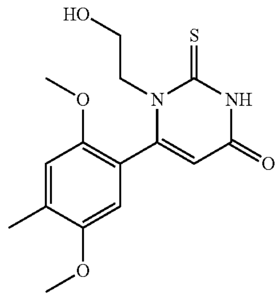 [SMILES: COc1cc(-c2cc(=O)[nH]c(=S)n2CCO)c(OC)cc1C] | 6-(2,5-dimethoxy-4-methylphenyl)-1-(2-hydroxyethyl)-2-thioxo-2,3-dihydropyrimidin-4(1H)-one | 323.2 | 1H NMR (500 MHz, METHANOL-d4) δ ppm 6.97 (s, 1 H), 6.88 (s, 1 H), 5.78 (s, 1 H), 4.61-4.71 (m, 1 H), 3.85-3.91 (m, 1 H), 3.84 (s, 3 H), 3.82 (s, 3 H), 3.79-3.81 (m, 1 H), 3.59-3.67 (m, 1 H), 2.28 (s, 3 H) |
| 274 | 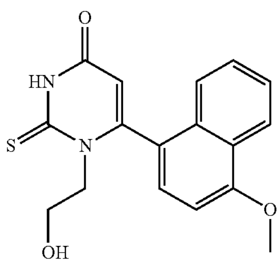 [SMILES: COc1ccc(-c2cc(=O)[nH]c(=S)n2CCO)c2ccccc12] | 1-(2-hydroxyethyl)-6-(4-methoxy-1-naphthyl)-2-thioxo-2,3-dihydropyrimidin-4(1H)-one | 329.0 | 2.53 min Waters Atlantis dC 18 5 um 4.6 × 50 mm, 95% H2O/5% MeCN linear to 5% H2O/95% MeCN over 4.0 min, HOLD at 5% H2O/95% MeCN to 5.0 min. (0.05% TFA). Flow rate: 2 mL/min |
| 275 | 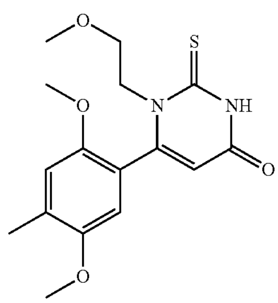 [SMILES: COCCn1c(-c2cc(OC)c(C)cc2OC)cc(=O)[nH]c1=S] | 6-(2,5-dimethoxy-4-methylphenyl)-1-(2-methoxyethyl)-2-thioxo-2,3-dihydropyrimidin-4(1H)-one | 337.1 | 2.79 min Waters Atlantis dC18 5 um 4.6 × 50 mm, 95% H2O/5% MeCN linear to 5% H2O/95% MeCN over 4.0 min. HOLD at 5% H2O/95% MeCN to 5.0 min. (0.05% TFA). Flow rate: 2 mL/min |

The following Examples of Table 5 were prepared from 6-iodo-1-(2-methoxyethyl)-2-(methylthio)pyrimidin-4(1H)-one and the appropriate aryl boronate as described above for the Preparations and procedures in the Suzuki Route section as well as standard methods and techniques known to those skilled in the art.

TABLE 5

Examples from Suzuki Route

| Example # | Structure | Compound Name | Obs Mass | 1H NMR Spectral Data or HPLC Retention Time and Conditions |
|---|---|---|---|---|
| 276 | 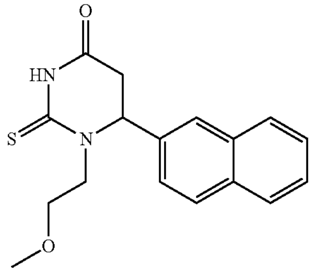 [SMILES: COCCN1C(=S)NC(=O)CC1c1ccc2ccccc2c1] | 1-(2-methoxyethyl)-6-(2-naphthyl)-2-thioxo-2,3-dihydropyrimidin-4(1H)-one | 313.1 | 1H NMR (400 MHz, METHANOL-d3) δ ppm 7.93-8.05 (m, 4 H), 7.58-7.65 (m, 2 H), 7.52 (dd, J = 8.24, 1.83 Hz, 1 H), 5.90 (s, 1 H), 4.40-4.52 (m, 2H), 3.59-3.68 (m, 2 H), 3.07 (s, 3 H) |

TABLE 5-continued

Examples from Suzuki Route

| Example # | Structure | Compound Name | Obs Mass | 1H NMR Spectral Data or HPLC Retention Time and Conditions |
|---|---|---|---|---|
| 277 | 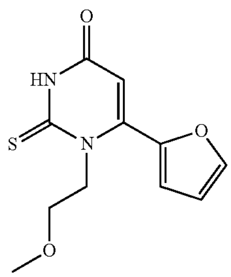 [SMILES: COCCn1c(-c2ccco2)cc(=O)[nH]c1=S] | 6-(2-furyl)-1-(2-methoxyethyl)-2-thioxo-2,3-dihydropyrimidin-4(1H)-one | 253.1 | 1H NMR (400 MHz, METHANOL-d3) δ ppm 7.80 (dd, J = 1.83, 0.92 Hz, 1 H), 7.06 (dd, J = 3.66, 0.92 Hz, 1 H), 6.66 (dd, J = 3.21, 1.83 Hz, 1 H), 6.10 (s, 1 H), 4.66 (t, J = 5.04 Hz, 2 H), 3.73 (t, J = 6.18 Hz, 2H), 3.25 (s, 3 H) |
| 278 | 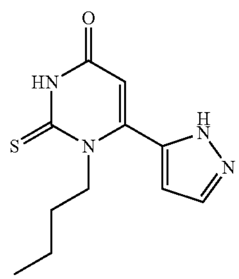 [SMILES: CCCCn1c(-c2ccn[nH]2)cc(=O)[nH]c1=S] | 1-(2-methoxyethyl)-6-(1H-pyrazol-5-yl)-2-thioxo-2,3-dihydropyrimidin-4(1H)-one | 253.1 | 1H NMR (400 MHz, METHANOL-d3) δ ppm 7.81 (br. s., 1 H), 6.66 (d, J = 2.29 Hz, 1 H), 5.99 (s, 1 H), 4.76 (br. s., 2 H), 3.66 (t, J = 6.18 Hz, 2 H), 3.17 (s, 3 H) |
| 279 | 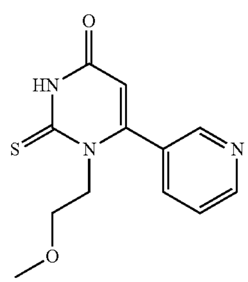 [SMILES: COCCn1c(-c2cccnc2)cc(=O)[nH]c1=S] | 1-(2-methoxyethyl)-6-pyridin-3-yl-2-thioxo-2,3-dihydropyrimidin-4(1H)-one | 264.1 | 1H NMR (400 MHz, CHLOROFORM-d) δ ppm 9.76 (br. s., 1 H), 8.76 (dd, J = 4.81, 1.60 Hz, 1 H), 8.64 (d, J = 1.83 Hz. 1 H), 7.72 (ddd, J = 7.80, 2.10, 2.10 Hz, 1 H), 7.45 (ddd, J = 7.79, 4.58, 0.92 Hz, 1 H), 5.85 (s, 1 H), 4.34 (br. s., 2 H), 3.67 (t, J = 5.04 Hz, 2 H), 3.21 (s, 3 H) |
| 280 | 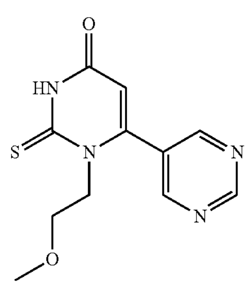 [SMILES: COCCn1c(-c2cncnc2)cc(=O)[nH]c1=S] | 3-(2-methoxyethyl)-2-thioxo-2,3-dihydro-4,5'-bipyrimidin-6(1H)-one | 265.1 | 1H NMR (400 MHz, METHANOL-d3) δ ppm 9.26 (s, 1 H), 8.90 (s, 2H), 5.94 (s, 1 H), 4.35 (br. s., 2 H), 3.67 (t, J = 4.81 Hz, 2 H), 3.20 (s, 3 H) |
| 281 | 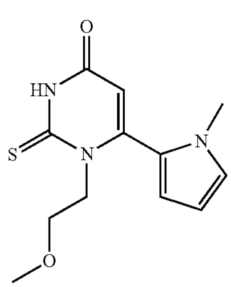 [SMILES: COCCn1c(-c2cccn2C)cc(=O)[nH]c1=S] | 1-(2-methoxyethyl)-6-(1-methyl-1H-pyrrol-2-yl)-2-thioxo-2,3-dihydropyrimidin-4(1H)-one | 266.1 | 1H NMR (400 MHz. METHANOL-d3) δ ppm 6.87 (dd, J = 2.70, 1.80 Hz, 1 H), 6.32 (dd, J = 3.66, 1.83 Hz, 1 H), 6.19 (dd, J = 3.66, 2.75 Hz, 1 H), 5.86 (s, 1 H), 4.50 (br. s., 2 H), 3.62 (t, J = 5.27 Hz, 2 H), 3.58 (s, 3 H), 3.12 (s, 3H) |

TABLE 5-continued

Examples from Suzuki Route

| Example # | Structure | Compound Name | Obs Mass | 1H NMR Spectral Data or HPLC Retention Time and Conditions |
|---|---|---|---|---|
| 282 | 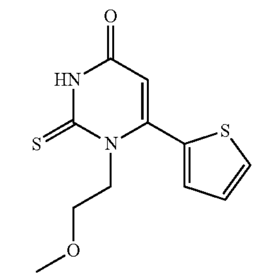 [SMILES: COCCn1c(-c2cccs2)cc(=O)[nH]c1=S] | 1-(2-methoxyethyl)-6-(2-thienyl)-2-thioxo-2,3-dihydropyrimidin-4(1H)-one | 269.1 | 1H NMR (400 MHz, CHLOROFORM-d) δ ppm 9.54 (br. s., 1 H), 7.53 (dd, J = 5.04, 1.37 Hz, 1 H), 7.33 (dd, J = 3.66, 0.92 Hz, 1 H), 7.13 (dd, J = 5.04, 3.66 Hz, 1 H), 6.02 (d, J = 2.29 Hz, 1 H), 4.53 (t, J = 5.72 Hz, 2 H), 3.74 (t, J = 5.72 Hz, 2 H), 3.28 (s, 3 H) |
| 283 | 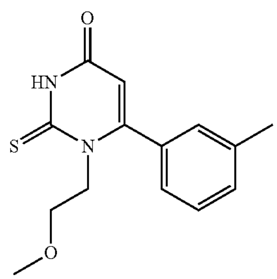 [SMILES: COCCn1c(-c2cccc(C)c2)cc(=O)[nH]c1=S] | 1-(2-methoxyethyl)-6-(3-methylphenyl)-2-thioxo-2,3-dihydropyrimidin-4(1H)-one | 277.1 | 1H NMR (400 MHz, CHLOROFORM-d) δ ppm 9.55 (br. s., 1 H), 7.29-7.41 (m, 2 H), 7.12-7.16 (m, 2 H), 5.83 (d, J = 2.75 Hz, 1 H), 4.38 (t, J = 5.27 Hz, 2 H), 3.63 (t, J = 5.50 Hz, 2H), 3.18 (s, 3 H), 2.42 (s, 3H) |
| 284 | 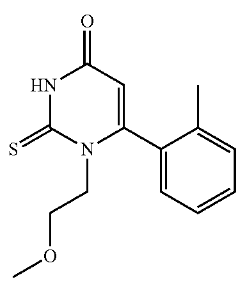 [SMILES: COCCn1c(-c2ccccc2C)cc(=O)[nH]c1=S] | 1-(2-methoxyethyl)-6-(2-methylphenyl)-2-thioxo-2,3-dihydropyrimidin-4(1H)-one | 277.2 | 1H NMR (400 MHz, CHLOROFORM-d) δ ppm 9.65 (br. s., 1 H), 7.41 (ddd, J = 7.80, 7.80, 1.80 Hz, 1 H), 7.28-7.34 (m, 2H), 7.23 (dd, J = 6.87, 1.83 Hz, 1 H), 5.82 (d, J = 2.29 Hz, 1 H), 4.57 (dt, J = 13.74, 5.04 Hz, 1 H), 3.89 (dt, J = 13.28, 6.87 Hz, 1 H), 3.67 (ddd, J = 10.53, 7.33, 5.04 Hz, 1 H), 3.56 (dt, J = 10.53, 5.04 Hz, 1 H), 3.16 (s, 3H), 2.25 (s, 3 H) |
| 285 | 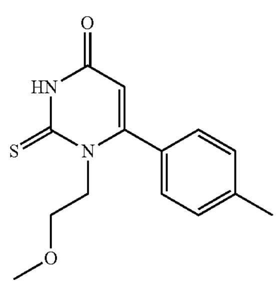 [SMILES: COCCn1c(-c2ccc(C)cc2)cc(=O)[nH]c1=S] | 1-(2-methoxyethyl)-6-(4-methylphenyl)-2-thioxo-2,3-dihydropyrimidin-4(1H)-one | 277.2 | 1H NMR (400 MHz, CHLOROFORM-d) δ ppm 9.71 (br. s., 1 H), 7.29 (d, J = 7.79 Hz, 2 H), 7.23 (d, J = 8.24 Hz, 2 H), 5.83 (s, 1 H), 4.39 (t, J = 5.04 Hz, 2 H), 3.63 (t, J = 5.72 Hz, 2 H), 3.19 (s, 3 H), 2.43 (s, 3 H) |
| 286 | 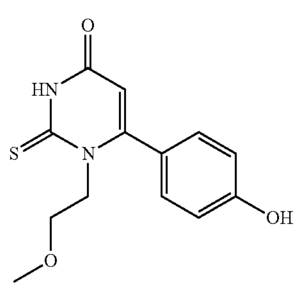 [SMILES: COCCn1c(-c2ccc(O)cc2)cc(=O)[nH]c1=S] | 6-(4-hydroxyphenyl)-1-(2-methoxyethyl)-2-thioxo-2,3-dihydropyrimidin-4(1H)-one | 279.1 | 1H NMR (400 MHz, DMSO-d6) d ppm 12.73 (br. s., 1 H), 9.97 (s, 1 H), 7.29 (d, J = 8.24 Hz, 2 H), 6.85 (d, J = 8.24 Hz, 2 H), 5.72 (s, 1 H), 4.29 (t, J = 5.95 Hz, 2 H), 3.46 (t, J = 6.41 Hz, 2 H), 3.02 (s, 3 H) |

TABLE 5-continued

Examples from Suzuki Route

| Example # | Structure | Compound Name | Obs Mass | 1H NMR Spectral Data or HPLC Retention Time and Conditions |
|---|---|---|---|---|
| 287 | 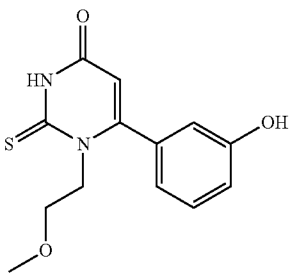 [SMILES: COCCn1c(-c2cccc(O)c2)cc(=O)[nH]c1=S] | 6-(3-hydroxyphenyl)-1-(2-methoxyethyl)-2-thioxo-2,3-dihydropyrimidin-4(1H)-one | 279.1 | 1H NMR (301 MHz DMSO-d6) δ ppm 12.75 (br. s., 1 H), 9.85 (s, 1 H), 7.27 (dd, J = 7.80, 7.80 Hz, 1 H), 6.82-6.90 (m, 2 H), 6.79 (br. s., 1 H), 5.72 (s, 1 H), 4.20 (t, J = 6.54 Hz, 1 H), 3.45 (t, J = 6.08 Hz, 2 H), 3.00 (s, 3 H) |
| 288 | 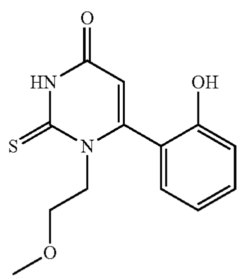 [SMILES: COCCn1c(-c2ccccc2O)cc(=O)[nH]c1=S] | 6-(2-hydroxyphenyl)-1-(2-methoxyethyl)-2-thioxo-2,3-dihydropyrimidin-4(1H)-one | 279.1 | 1H NMR (400 MHz, METHANOL-d3) δ ppm 7.34 (td, J = 7.90, 1.60 Hz, 1 H), 7.23 (dd, J = 7.67, 1.49 Hz, 1 H), 6.94 (t, J = 7.44 Hz, 1 H), 6.90 (d, J = 8.24 Hz, 1 H), 5.73 (s, 1 H), 4.76 (ddd, J = 13.51, 5.72, 4.58 Hz, 1 H), 3.97 (dt, J = 13.91, 7.13 Hz, 1 H), 3.65 (ddd, J = 10.25, 7.38, 6.64 Hz, 1 H), 3.45 (ddd, J = 10.42, 6.41, 4.24 Hz, 1 H), 3.06 (s, 3 H) |
| 289 | 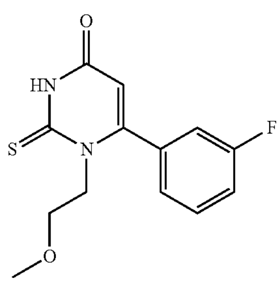 [SMILES: COCCn1c(-c2cccc(F)c2)cc(=O)[nH]c1=S] | 6-(3-fluorophenyl)-1-(2-methoxyethyl)-2-thioxo-2,3-dihydropyrimidin-4(1H)-one | 281.1 | 1H NMR (400 MHz, CHLOROFORM-d) δ ppm 10.00 (br. s., 1 H), 7.47 (ddd, J = 8.10, 8.10, 5.70 Hz, 1 H), 7.22 (ddd, J = 8.10, 8.10, 2.10 Hz, 1 H), 7.07-7.16 (m, 2 H), 5.85 (d, J = 1.37 Hz, 1 H), 4.36 (br. s., 2 H), 3.66 (br. s., 2 H), 3.21 (s, 3 H) |
| 290 | 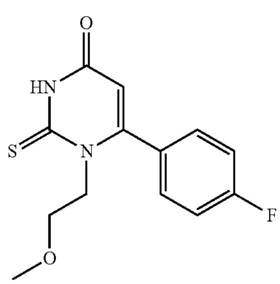 [SMILES: COCCn1c(-c2ccc(F)cc2)cc(=O)[nH]c1=S] | 6-(4-fluorophenyl)-1-(2-methoxyethyl)-2-thioxo-2,3-dihydropyrimidin-4(1H)-one | 281.1 | 1H NMR (400 MHz, CHLOROFORM-d) δ ppm 9.57 (br. s, 1 H), 7.35 (dd, J = 8.93, 5.27 Hz, 2 H), 7.18 (dd, J = 8.20 Hz, 2 H), 5.82 (s, 1 H), 4.35 (t, J = 5.04 Hz, 2 H), 3.65 (t, J = 5.50 Hz, 2 H), 3.20 (s, 3 H) |
| 291 | 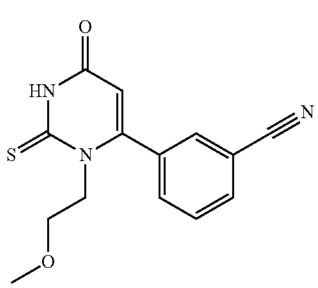 [SMILES: COCCn1c(-c2cccc(C#N)c2)cc(=O)[nH]c1=S] | 3-[3-(2-methoxyethyl)-6-oxo-2-thioxo-1,2,3,6-tetrahydropyrimidin-4-yl]benzonitrile | 288.1 | 1H NMR (400 MHz, CHLOROFORM-d) δ ppm 9.70 (br. s., 1 H), 7.81 (d, J = 7.33 Hz, 1 H), 7.71 (s, 1 H), 7.55-7.66 (m, 2H), 5.82 (d, J = 1.83 Hz, 1 H), 4.29 (br. s., 2H), 3.67 (br. s., 2H), 3.23 (s, 3H) |

TABLE 5-continued

Examples from Suzuki Route

| Example # | Structure | Compound Name | Obs Mass | 1H NMR Spectral Data or HPLC Retention Time and Conditions |
|---|---|---|---|---|
| 292 | 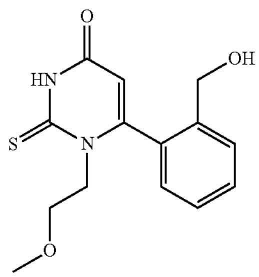 [SMILES: COCCn1c(-c2ccccc2CO)cc(=O)[nH]c1=S] | 6-[2-(hydroxymethyl)phenyl]-1-(2-methoxyethyl)-2-thioxo-2,3-dihydropyrimidin-4(1H)-one | 293.0 | 1H NMR (400 MHz. DMSO-d6) δ ppm 12.77 (br. s., 1 H), 7.43-7.56 (m, 2 H), 7.30-7.41 (m, 2 H), 5.76 (s, 1 H), 5.27 (t, J = 5.38 Hz, 1 H), 4.38 (d, J = 5.27 Hz, 2 H), 4.26-4.35 (m, 1 H), 3.69-3.82 (m, 1 H), 3.45-3.55 (m, 1 H), 3.39 (dt, J = 9.85, 6.75 Hz, 1 H), 2.97 (s, 3 H) |
| 293 | 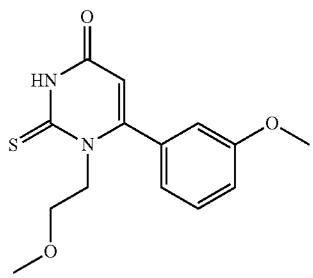 [SMILES: COCCn1c(-c2cccc(OC)c2)cc(=O)[nH]c1=S] | 1-(2-methoxyethyl)-6-(3-methoxyphenyl)-2-thioxo-2,3-dihydropyrimidin-4(1H)-one | 293.2 | 1H NMR (400 MHz, METHANOL-d3) δ ppm 7.42 (t, J = 8.24, 8.24 Hz, 1 H), 7.08 (ddd, J = 8.24, 2.75, 0.92 Hz, 1 H), 7.03 (dd, J = 2.75, 1.37 Hz, 1 H), 6.99 (ddd, J = 7.79, 1.83, 0.92 Hz, 2 H), 5.79 (s, 1 H), 4.39 (t, J = 5.50 Hz, 2 H), 3.84 (s, 3 H), 3.64 (t, J = 5.72 Hz, 2 H), 3.15 (s, 3 H) |
| 294 | 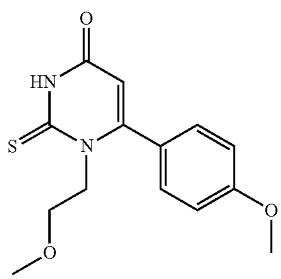 [SMILES: COCCn1c(-c2ccc(OC)cc2)cc(=O)[nH]c1=S] | 1-(2-methoxyethyl)-6-(4-methoxyphenyl)-2-thioxo-2,3-dihydropyrimidin-4(1H)-one | 293.2 | 1H NMR (400 MHz, CHLOROFORM-d) δ ppm 9.62 (br. s., 1 H), 7.28 (d, J = 8.70 Hz, 2 H), 6.99 (d, J = 8.70 Hz, 2 H), 5.83 (d, J = 1.37 Hz, 1 H), 4.41 (t, J = 5.50 Hz, 2 H), 3.87 (s, 3 H), 3.64 (t, J = 5.72 Hz, 2 H), 3.20 (s, 3 H) |
| 295 | 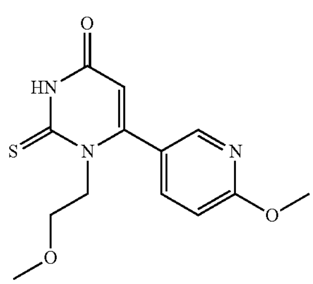 [SMILES: COCCn1c(-c2ccc(OC)nc2)cc(=O)[nH]c1=S] | 1-(2-methoxyethyl)-6-(6-methoxypyridin-3-yl)-2-thioxo-2,3-dihydropyrimidin-4(1H)-one | 294.1 | 1H NMR (400 MHz, CHLOROFORM-d) δ ppm 9.53 (br. s., 1 H), 8.16 (d, J = 1.83 Hz, 1 H), 7.58 (dd, J = 8.70, 2.29 Hz, 1 H), 6.85 (dd, J = 8.70, 0.92 Hz, 1 H), 5.84 (d, J = 2.29 Hz, 1 H), 4.37 (br. s., 2 H), 4.01 (s, 3 H), 3.68 (t, J = 5.27 Hz, 3 H), 3.23 (s, 3 H) |
| 296 | 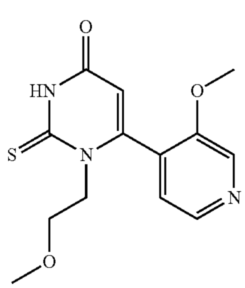 [SMILES: COCCn1c(-c2ccncc2OC)cc(=O)[nH]c1=S] | 1-(2-methoxyethyl)-6-(3-methoxypyridin-4-yl)-2-thioxo-2,3-dihydropyrimidin-4(1H)-one | 294.1 | 1H NMR (400 MHz, CHLOROFORM-d) δ ppm 9.61 (br. s., 1 H), 8.42 (s, 1 H), 8.40 (d, J = 4.81 Hz, 1 H), 7.18 (d, J = 4.81 Hz, 1 H), 5.77 (d, J = 2.29 Hz, 1 H), 4.73 (dt, J = 13.97, 3.43 Hz, 1 H), 3.97 (s, 3 H), 3.80 (td, J = 9.62, 3.89 Hz, 1 H), 3.68 (ddd, J = 13.80, 9.33, 4.58 Hz, 1 H), 3.36 (dt, J = 10.08, 3.89 Hz, 1 H), 3.14 (s, 3H) |

TABLE 5-continued

Examples from Suzuki Route

| Example # | Structure | Compound Name | Obs Mass | 1H NMR Spectral Data or HPLC Retention Time and Conditions |
|---|---|---|---|---|
| 297 | 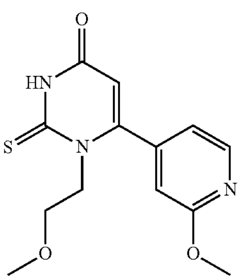 [SMILES: COCCn1c(-c2ccnc(OC)c2)cc(=O)[nH]c1=S] | 1-(2-methoxyethyl)-6-(2-methoxypyridin-4-yl)-2-thioxo-2,3-dihydropyrimidin-4(1H)-one | 294.2 | 1H NMR (400 MHz, CHLOROFORM-d) δ ppm 9.59 (br. s., 1 H), 8.29 (dd, J = 5.04, 0.92 Hz, 1 H), 6.85 (dd, J = 5.27, 1.60 Hz, 1 H), 6.74 (d, J = 1.37 Hz. 1 H), 5.81 (d, J = 2.29 Hz, 1 H), 4.35 (br. s., 2 H), 4.00 (s, 3 H), 3.66 (t, J = 5.27 Hz, 2 H), 3.22 (s, 3 H) |
| 298 | 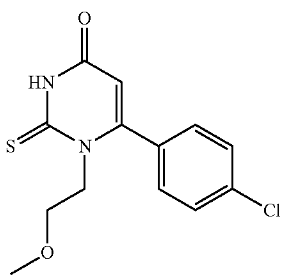 [SMILES: COCCn1c(-c2ccc(Cl)cc2)cc(=O)[nH]c1=S] | 6-(4-chlorophenyl)-1-(2-methoxyethyl)-2-thioxo-2,3-dihydropyrimidin-4(1H)-one | 297.1 | 1H NMR (400 MHz, METHANOL-d3) δ ppm 7.53 (d, J = 7.79 Hz, 2 H), 7.45 (d, J = 8.24 Hz, 2H), 5.79 (s, 1 H), 4.38 (t, J = 5.04 Hz, 2 H), 3.62 (t, J = 5.72 Hz, 2 H), 3.16 (s, 3 H) |
| 299 | 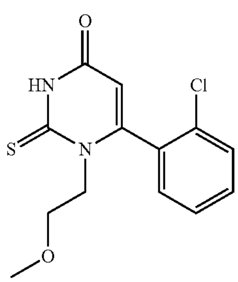 [SMILES: COCCn1c(-c2ccccc2Cl)cc(=O)[nH]c1=S] | 6-(2-chlorophenyl)-1-(2-methoxyethyl)-2-thioxo-2,3-dihydropyrimidin-4(1H)-one | 297.1 | 1H NMR (400 MHz, CHLOROFORM-d) δ ppm 9.57 (br. s., 1 H), 7.44-7.52 (m, 2 H), 7.39-7.44 (m, 1 H), 7.34-7.39 (m, 1 H), 5.83 (d, J = 1.37 Hz, 1 H), 4.66-4.76 (m, 1 H), 3.73-3.86 (m, 2 H), 3.41-3.47 (m, 1 H), 3.17 (s, 3H) |
| 300 | 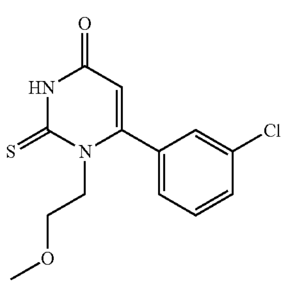 [SMILES: COCCn1c(-c2cccc(Cl)c2)cc(=O)[nH]c1=S] | chlorophenyl)-1-(2-methoxyethyl)-2-thioxo-2,3-dihydropyrimidin-4(1H)-one | 297.1 | 1H NMR (400 MHz, METHANOL-d3) δ ppm 7.47-7.57 (m, 3 H), 7.39 (ddd, J = 7.30, 1.40 Hz, 1 H), 5.80 (s, 1 H), 4.36 (br. s., 2H), 3.64 (t, J = 5.50 Hz, 2 H), 3.16 (s, 3 H) |
| 301 | 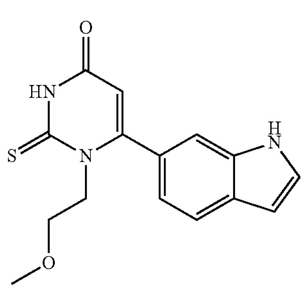 [SMILES: COCCn1c(-c2ccc3cc[nH]c3c2)cc(=O)[nH]c1=S] | 6-(1H-indol-6-yl)-1-(2-methoxyethyl)-2-thioxo-2,3-dihydropyrimidin-4(1H)-one | 302.1 | 1H NMR (400 MHz, CHLOROFORM-d) δ ppm 9.55 (br. s., 1 H), 8.44 (br. s., 1 H), 7.73 (d, J = 8.24 Hz, 1 H), 7.41 (s, 1 H), 7.38 (dd, J = 3.43, 2.52 Hz, 1 H), 7.05 (dd, J = 8.24, 1.37 Hz, 1 H), 6.65 (ddd, J = 3.09, 1.95, 0.92 Hz, 1 H), 5.91 (s, 1 H), 4.46 (br. s., 2 H), 3.63 (br. s., 2H), 3.15 (s, 3 H) |

TABLE 5-continued

Examples from Suzuki Route

| Example # | Structure | Compound Name | Obs Mass | 1H NMR Spectral Data or HPLC Retention Time and Conditions |
|---|---|---|---|---|
| 302 | 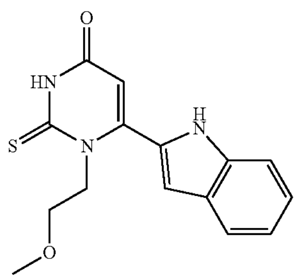 [SMILES: COCCn1c(-c2cc3ccccc3[nH]2)cc(=O)[nH]c1=S] | 6-(1H-indol-2-yl)-1-(2-methoxyethyl)-2-thioxo-2,3-dihydropyrimidin-4(1H)-one | 302.1 | 1H NMR (400 MHz, DMSO-d6) d ppm 12.81 (s, 1 H), 11.66 (br. s., 1 H), 7.59 (d, J = 7.79 Hz, 1 H), 7.41 (d, J = 8.24 Hz, 1 H), 7.18 (t, J = 7.67 Hz, 1 H), 7.05 (t, J = 7.44 Hz, 1 H), 6.84 (s, 1 H), 6.03 (s, 1 H), 4.55 (t, J = 5.84 Hz, 2 H), 3.52 (t, J = 5.84 Hz, 2 H), 3.01 (s, 3 H) |
| 303 | 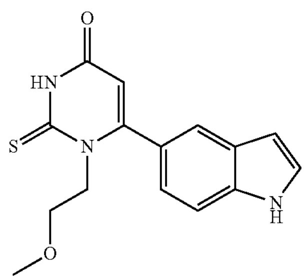 [SMILES: COCCn1c(-c2ccc3[nH]ccc3c2)cc(=O)[nH]c1=S] | 6-(1H-indol-5-yl)-1-(2-methoxyethyl)-2-thioxo-2,3-dihydropyrimidin-4(1H)-one | 302.1 | 1H NMR (400 MHz, CHLOROFORM-d) δ ppm 9.54 (br. s., 1 H), 8.39 (br. s., 1 H), 7.61 (s, 1 H), 7.48 (d, J = 8.24 Hz, 1 H), 7.34 (t, J = 2.75 Hz, 1 H), 7.12 (dd, J = 8.36, 1.49 Hz, 1 H), 6.63 (d, J = 2.06 Hz, 1 H), 5.90 (d, J = 2.52 Hz, 1 H), 4.45 (br. s., 2H), 3.60 (t, J = 5.84 Hz, 2H), 3.08-3.18 (m, 3 H) |
| 304 | 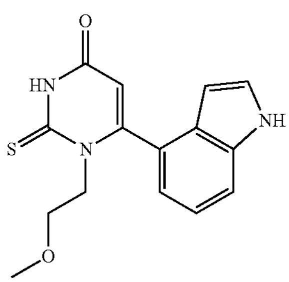 [SMILES: COCCn1c(-c2cccc3[nH]ccc23)cc(=O)[nH]c1=S] | 6-(1H-indol-4-yl)-1-(2-methoxyethyl)-2-thioxo-2,3-dihydropyrimidin-4(1H)-one | 302.1 | 1H NMR (400 MHz, METHANOL-d3) δ ppm 7.55 (d, J = 8.01 Hz, 1 H), 7.39 (d, J = 3.21 Hz, 1 H), 7.23 (t, J = 7.79 Hz, 1 H), 7.09 (d, J = 7.10 Hz, 1 H), 6.31 (d, J = 2.98 Hz, 1 H), 5.86 (s, 1 H), 4.57-4.70 (m, 1 H), 4.15 (dt, J = 13.34, 6.50 Hz, 1 H), 3.56 (dt, J = 10.19, 6.58 Hz, 1 H), 3.42 (ddd, J = 10.76, 6.18, 5.04 Hz, 1 H), 2.93 (s, 3 H) |
| 305 | 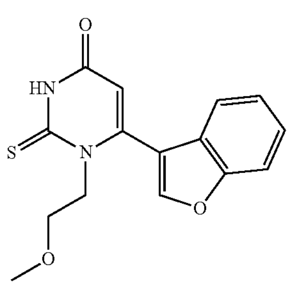 [SMILES: COCCn1c(-c2coc3ccccc23)cc(=O)[nH]c1=S] | 6-(1-benzofuran-3-yl)-1-(2-methoxyethyl)-2-thioxo-2,3-dihydropyrimidin-4(1H)-one | 303.0 | 1H NMR (400 MHz, CHLOROFORM-d) δ ppm 9.69 (br. s., 1 H), 7.94 (s, 1 H), 7.59 (d, J = 8.24 Hz, 1 H), 7.47 (d, J = 7.79 Hz, 1 H), 7.42 (td, J = 7.67, 1.14 Hz, 1 H), 7.36 (t, J = 6.87 Hz, 1 H), 6.02 (d, J = 2.52 Hz, 1 H), 4.49 (br. s., 2 H), 3.63-3.72 (m, 2 H), 3.19 (s, 3 H) |
| 306 | 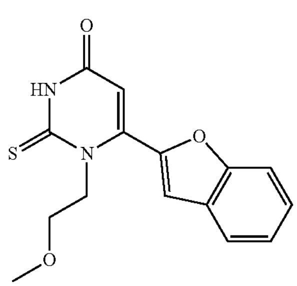 [SMILES: COCCn1c(-c2cc3ccccc3o2)cc(=O)[nH]c1=S] | 6-(1-benzofuran-2-yl)-1-(2-methoxyethyl)-2-thioxo-2,3-dihydropyrimidin-4(1H)-one | 303.1 | 1H NMR (400 MHz, CHLOROFORM-d) δ ppm 9.54 (br. s., 1 H), 7.68 (d, J = 7.56 Hz, 1 H), 7.55 (d, J = 8.24 Hz, 1 H), 7.44 (t, J = 7.67 Hz, 1 H), 7.34 (t, J = 7.44 Hz, 1 H), 7.23 (s, 1 H), 6.25 (d, J = 2.29 Hz, 1 H), 4.66 (br. s., 2 H), 3.78 (t, J = 5.84 Hz, 2 H), 3.25 (s, 3 H) |

TABLE 5-continued

Examples from Suzuki Route

| Example # | Structure | Compound Name | Obs Mass | 1H NMR Spectral Data or HPLC Retention Time and Conditions |
|---|---|---|---|---|
| 307 | 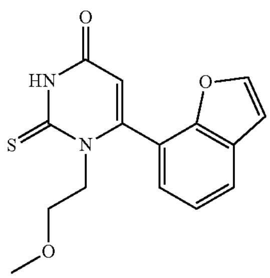 [SMILES: COCCn1c(-c2cccc3ccoc23)cc(=O)[nH]c1=S] | 6-(1-benzofuran-7-yl)-1-(2-methoxyethyl)-2-thioxo-2,3-dihydropyrimidin-4(1H)-one | 303.4 | 1H NMR (400 MHz, CHLOROFORM-d) δ ppm 10.48 (br. s., 1 H), 7.75 (dd, J = 7.79, 1.37 Hz, 1 H), 7.67 (d, J = 2.29 Hz, 1 H), 7.35 (dd, J = 7.30, 7.30 Hz, 1 H), 7.27 (dd, J = 7.56, 1.15 Hz, 1 H), 6.87 (d, J = 2.29 Hz, 1 H), 5.98 (s, 1 H), 4.57-4.76 (m, 1 H), 3.93-4.10 (m, 1 H), 3.59-3.75 (m, 1 H), 3.33-3.50 (m, 1 H), 3.03 (s, 3 H) |
| 308 | 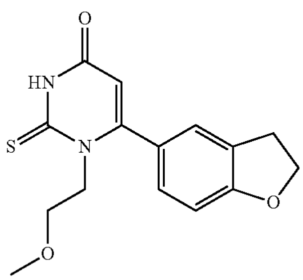 [SMILES: COCCn1c(-c2ccc3c(c2)CCO3)cc(=O)[nH]c1=S] | 6-(2,3-dihydro-1-benzofuran-5-yl)-1-(2-methoxyethyl)-2-thioxo-2,3-dihydropyrimidin-4(1H)-one | 305.1 | 1H NMR (400 MHz, CHLOROFORM-d) δ ppm 9.97 (br. s., 1 H), 7.15 (d, J = 1.37 Hz, 1 H), 7.08 (dd, J = 8.01, 2.06 Hz, 1 H), 6.85 (d, J = 8.24 Hz, 1 H), 5.84 (d, J = 2.75 Hz, 1 H), 4.67 (t, J = 8.70 Hz, 2 H), 4.43 (t, J = 5.50 Hz, 1 H), 3.64 (t, J = 5.50 Hz, 2 H), 3.28 (t, J = 8.93 Hz, 2 H), 3.20 (s, 3 H) |
| 309 | 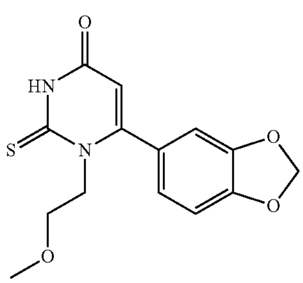 [SMILES: COCCn1c(-c2ccc3c(c2)OCO3)cc(=O)[nH]c1=S] | 6-(1,3-benzodioxol-5-yl)-1-(2-methoxyethyl)-2-thioxo-2,3-dihydropyrimidin-4(1H)-one | 307.1 | 1H NMR (400 MHz, METHANOL-d3) δ ppm 6.96 (d, J = 1.83 Hz, 1 H), 6.94 (s, 1 H), 6.92 (d, J = 1.83 Hz, 1 H), 6.05 (s, 2 H), 5.78 (s, 1 H), 4.43 (t, J = 5.72 Hz, 2 H), 3.63 (t, J = 5.72 Hz, 2H), 3.17 (s, 3 H) |
| 310 | 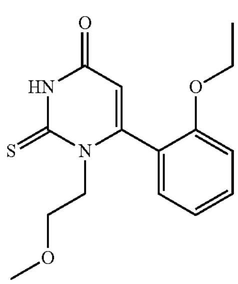 [SMILES: CCOc1ccccc1-c1cc(=O)[nH]c(=S)n1CCOC] | 6-(2-ethoxyphenyl)-1-(2-methoxyethyl)-2-thioxo-2,3-dihydropyrimidin-4(1H)-one | 307.1 | 1H NMR (400 MHz, METHANOL-d3) δ ppm 7.51 (ddd, J = 8 36, 7.44, 1.60 Hz, 1 H), 7.32 (dd, J = 7.56, 1.60 Hz, 1 H), 7.11 (d, J = 8.70 Hz, 1 H), 7.08 (t, J = 7.30 Hz, 1 H), 5.75 (s, 1 H), 4.70-4.79 (m, 1 H), 4.15 (q, J = 7.20 Hz, 2 H), 3.82-3.92 (m, 1 H), 3.69 (ddd, J = 10.08, 7.79, 5.95 Hz, 1 H), 3.43 (ddd, J = 10.19, 6.30, 4.12 Hz, 1 H), 3.08 (s, 3H), 1.36 (t, J = 7.10 Hz, 3H) |
| 311 | 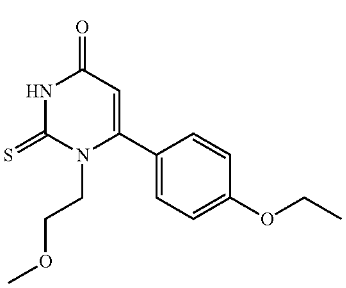 [SMILES: CCOc1ccc(-c2cc(=O)[nH]c(=S)n2CCOC)cc1] | 6-(4-ethoxyphenyl)-1-(2-methoxyethyl)-2-thioxo-2,3-dihydropyrimidin-4(1H)-one | 307.2 | 1H NMR (400 MHz, METHANOL-d3) δ ppm 7.36 (d, J = 8.70 Hz, 2 H), 7.03 (d, J = 8.70 Hz, 2 H), 5.76 (s, 1 H), 4.44 (t, J = 5.50 Hz, 2 H), 4.10 (q, J = 6.87 Hz, 2 H), 3.61 (t, J = 5.95 Hz, 2 H), 3.14 (s, 3 H), 1.42 (t, J = 7.10 Hz, 3H) |

TABLE 5-continued

Examples from Suzuki Route

| Example # | Structure | Compound Name | Obs Mass | 1H NMR Spectral Data or HPLC Retention Time and Conditions |
|---|---|---|---|---|
| 312 | 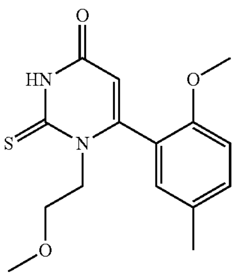 | 1-(2-methoxyethyl)-6-(2-methoxy-5-methylphenyl)-2-thioxo-2,3-dihydropyrimidin-4(1H)-one | 307.2 | 1H NMR (400 MHz, CHLOROFORM-d) δ ppm 9.46 (br. s, 1 H), 7.27-7.31 (m, 1 H), 7.03 (d, J = 1.83 Hz, 1 H), 6.86 (d, J = 8.20 Hz, 1 H), 5.81 (d, J = 2.29 Hz, 1 H), 4.62-4.72 (m, 1 H), 3.84-3.93 (m, 1 H), 3.82 (s, 3 H), 3.72 (ddd, J = 10.19, 7.90, 5.72 Hz, 1 H), 3.44 (ddd, J = 10.19, 6.30, 4.12 Hz, 1 H), 3.14 (s, 3 H), 2.34 (s, 3 H) |
| 313 | 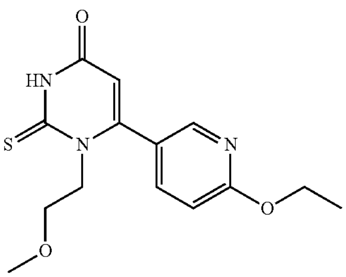 [SMILES: CCOc1ccc(-c2cc(=O)[nH]c(=S)n2CCOC)cn1] | 6-(6-ethoxypyridin-3-yl)-1-(2-methoxyethyl)-2-thioxo-2,3-dihydropyrimidin-4(1H)-one | 308.1 | 1H NMR (400 MHz, CHLOROFORM-d) δ ppm 9.60 (br. s., 1 H), 8.13 (d, J = 2.29 Hz, 1 H), 7.57 (dd, J = 8.47, 2.06 Hz, 1 H), 6.82 (d, J = 8.70 Hz, 1 H), 5.84 (s, 1 H), 4.42 (q, J = 7.02 Hz, 2H), 4.37 (br. s, 2 H), 3.68 (t, J = 5.04 Hz, 2 H), 3.23 (s, 3 H), 1.43 (t, J = 6.87 Hz, 3 H) |
| 314 | 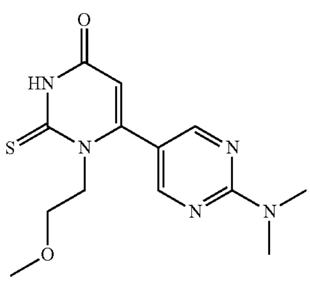 | 2'-(dimethylamino)-3-(2-methoxyethyl)-2-thioxo-2,3-dihydro-4,5'-bipyrimidin-6(1H)-one | 308.1 | 1H NMR (400 MHz, CHLOROFORM-d) δ ppm 9.83 (br. s., 1 H), 8.30 (s, 2 H), 5.83 (d, J = 2.75 Hz, 1 H), 4.43 (br. s., 2H), 3.72 (t, J = 5.04 Hz, 2 H), 3.26 (s, 3H), 3.26 (s, 6 H) |
| 315 | 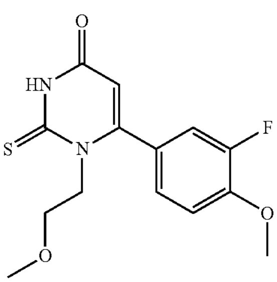 | 6-(3-fluoro-4-methoxyphenyl)-1-(2-methoxyethyl)-2-thioxo-2,3-dihydropyrimidin-4(1H)-one | 311.1 | 1H NMR (400 MHz. CHLOROFORM-d) δ ppm 9.58 (br. s., 1 H), 7.13 (dd, J = 11.22, 2.06 Hz, 1 H), 7.07 (dd, J = 8.70, 1.83 Hz, 1 H), 7.03 (dd, J = 7.80, 7.80 Hz, 1 H), 5.81 (d, J = 2.29 Hz, 1 H), 4.37 (br. s., 2 H), 3.95 (s, 3 H), 3.65 (t, J = 5.27 Hz, 1 H), 3.21 (s, 3 H) |
| 316 | 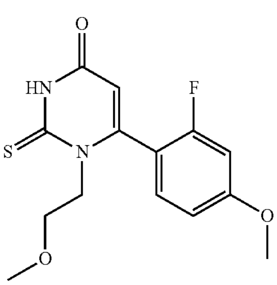 | 6-(2-fluoro-4-methoxyphenyl)-1-(2-methoxyethyl)-2-thioxo-2,3-dihydropyrimidin-4(1H)-one | 311.1 | 1H NMR (400 MHz, CHLOROFORM-d) δ ppm 9.49 (br. s., 1 H), 7.22 (t, J = 8.47 Hz, 1 H), 6.81 (dd, J = 8.24, 2 29 Hz, 1 H), 6.72 (dd, J = 11.68, 2.06 Hz, 1 H), 5.86 (d, J = 2.75 Hz, 1 H), 4.60-4.70 (m, 1 H), 4.02-4.12 (m, 1 H), 3.87 (s, 3 H), 3.71-3.81 (m, 1 H), 3.48 (dd, J = 9.85, 4.81 Hz, 1 H), 3.18 (s, 3H) |

TABLE 5-continued

Examples from Suzuki Route

| Example # | Structure | Compound Name | Obs Mass | 1H NMR Spectral Data or HPLC Retention Time and Conditions |
|---|---|---|---|---|
| 317 | 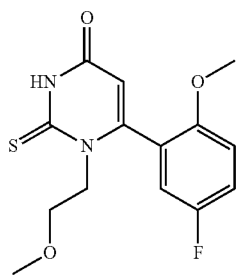 | 6-(5-fluoro-2-methoxyphenyl)-1-(2-methoxyethyl)-2-thioxo-2,3-dihydropyrimidin-4(1H)-one | 311.1 | 1H NMR (400 MHz, CHLOROFORM-d) δ ppm 9.58 (br. s, 1 H), 7.17 (ddd, J = 9.05, 7.90, 3.21 Hz, 1 H), 6.98 (dd, J = 7.79, 3.21 Hz, 1 H), 6.89 (dd, J = 9.16, 4.12 Hz, 1 H), 5.79 (d, J = 2.29 Hz, 1 H), 4.65-4.75 (m, 1 H), 3.82 (s, 3 H), 3.72-3.80 (m, 2 H), 3.37-3.43 (m, 1 H), 3.16 (s, 3 H) |
| 318 | 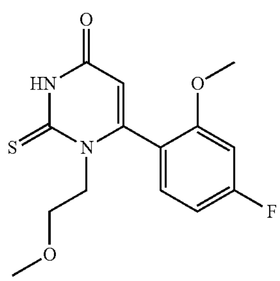 [SMILES: COCCn1c(-c2ccc(F)cc2OC)cc(=O)[nH]c1=S] | 6-(4-fluoro-2-methoxyphenyl)-1-(2-methoxyethyl)-2-thioxo-2,3-dihydropyrimidin-4(1H)-one | 311.2 | 1H NMR (400 MHz, CHLOROFORM-d) δ ppm 9.58 (br. s., 1 H), 7.21 (dd, J = 8.24, 6.41 Hz, 1 H), 6.78 (ddd, J = 8.20, 8.20, 2.30 Hz, 1 H), 6.71 (dd, J = 10.53, 2.29 Hz, 1 H), 5.79 (s, 1 H), 4.65-4.75 (m, 1 H), 3.85 (s, 3 H), 3.69-3.83 (m, 2 H), 3.38-3.47 (m, 1 H), 3.16 (s, 2 H) |
| 319 | 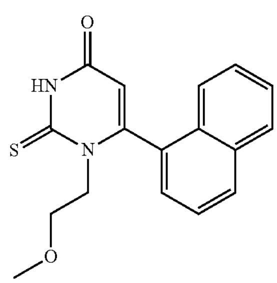 [SMILES: COCCn1c(-c2cccc3ccccc23)cc(=O)[nH]c1=S] | 1-(2-methoxyethyl)-6-(1-naphthyl)-2-thioxo-2,3-dihydropyrimidin-4(1H)-one | 313.1 | 1H NMR (400 MHz, METHANOL-d3) δ ppm 8.07 (dd, J = 6.87, 2.75 Hz, 1 H), 7.98-8.04 (m, 1 H), 7.66-7.71 (m, 1 H), 7.58-7.66 (m, 4 H), 5.92 (s, 1 H), 4.50-4.60 (m, 1 H), 3.70-3.80 (m, 1 H), 3.59-3.67 (m, 1 H), 3.43 (ddd, J = 10.42, 6.07, 4.58 Hz, 1 H), 2.98 (s, 3 H) |
| 320 | 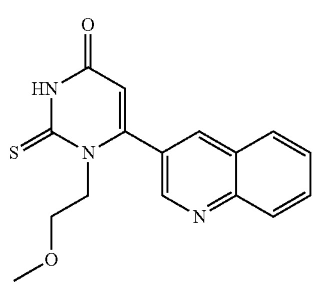 [SMILES: COCCn1c(-c2cnc3ccccc3c2)cc(=O)[nH]c1=S] | 1-(2-methoxyethyl)-6-quinolin-3-yl-2-thioxo-2,3-dihydropyrimidin-4(1H)-one | 314.1 | 1H NMR (400 MHz, CHLOROFORM-d) δ ppm 9.99 (br. s., 1 H), 8.89 (d, J = 2.29 Hz, 1 H), 8.17-8.23 (m, 2 H), 7.91 (dd, J = 8.01, 1.14 Hz, 1 H), 7.87 (ddd, J = 8.59, 6.98, 1.37 Hz, 1 H), 7.69 (ddd, J = 8.24, 6.87, 1.37 Hz, 1 H), 5.95 (d, J = 0.92 Hz, 1 H), 4.36-4.46 (m, 2 H), 3.68 (t, J = 4.81 Hz, 2H), 3.21 (s, 3 H) |
| 321 | 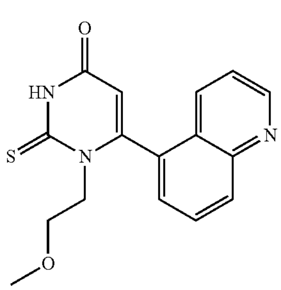 [SMILES: COCCn1c(-c2cccc3ncccc23)cc(=O)[nH]c1=S] | 1-(2-methoxyethyl)-6-quinolin-5-yl-2-thioxo-2,3-dihydropyrimidin-4(1H)-one | 314.1 | 1H NMR (400 MHz, CHLOROFORM-d) δ ppm 10.50 (br. s., 1 H), 9.02 (dd, J = 4.12, 1.60 Hz, 1 H), 8.28 (d, J = 8.47 Hz, 1 H), 8.02 (d, J = 8.47 Hz, 1 H), 7.81 (dd, J = 8.47, 7.33 Hz, 1 H), 7.56 (dd, J = 7.10, 0.69 Hz, 1 H), 7.51 (dd, J = 8.59, 4.24 Hz, 1 H), 5.96 (d, J = 1.37 Hz, 1 H), 4.45 (dt, J = 14.14, 4.84 Hz, 1 H), 3.83-3.98 (m, 1 H), 3.60 (ddd, J = 10.48, 6.35, 4.69 Hz, 1 H), 3.49 (dt, J = 10.30, 4.92 Hz, 1 H), 3.02 (s, 3H) |

TABLE 5-continued

Examples from Suzuki Route

| Example # | Structure | Compound Name | Obs Mass | 1H NMR Spectral Data or HPLC Retention Time and Conditions |
|---|---|---|---|---|
| 322 | 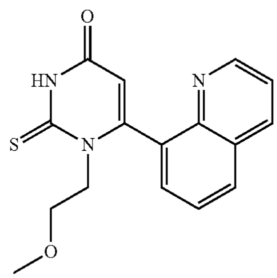 [SMILES: COCCn1c(-c2cccc3cccnc23)cc(=O)[nH]c1=S] | 1-(2-methoxyethyl)-6-quinolin-8-yl-2-thioxo-2,3-dihydropyrimidin-4(1H)-one | 314.1 | 1H NMR (400 MHz, CHLOROFORM-d) δ ppm 9.82 (br. s., 1 H), 8.95 (dd, J = 4.12, 1.83 Hz, 1 H), 8.25 (dd, J = 8.47, 1.60 Hz, 1 H), 8.01 (dd, J = 8.24, 1.37 Hz, 1 H), 7.74 (dd, J = 6.87, 1.37 Hz, 1 H), 7.66 (dd, J = 8.24, 6.87 Hz, 1 H), 7.52 (dd, J = 8 24, 4.12 Hz, 1 H), 5.93 (d, J = 2.29 Hz, 1 H), 4.65 (ddd, J = 13.74, 5.04, 3.66 Hz, 1 H), 3.75 (ddd, J = 10.30, 8.24, 5.50 Hz, 1 H), 3.65 (ddd, J = 13.97, 8.24, 5.72 Hz, 1 H), 3.36 (ddd, J = 10.30, 5.50, 3.66 Hz, 1 H), 3.07 (s, 3 H) |
| 323 | 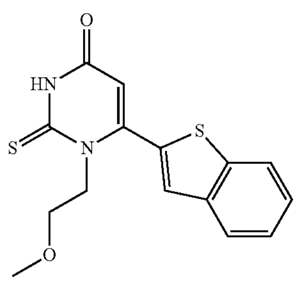 [SMILES: COCCn1c(-c2cc3ccccc3s2)cc(=O)[nH]c1=S] | 6-(1-benzothien-2-yl)-1-(2-methoxyethyl)-2-thioxo-2,3-dihydropyrimidin-4(1H)-one | 319.4 | 1H NMR (400 MHz, CHLOROFORM-d) δ ppm 9.81 (br. s., 1 H), 7.80-7.92 (m, 2 H), 7.51 (s, 1 H), 7.42-7.48 (m, 2H), 6.10 (d, J = 2.29 Hz, 1 H), 4.57 (t, J = 5.50 Hz, 2 H), 3.74 (t, J = 5.50 Hz, 2 H), 3.26 (s, 3 H) |
| 324 | 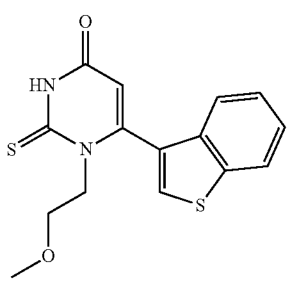 [SMILES: COCCn1c(-c2csc3ccccc23)cc(=O)[nH]c1=S] | 6-(1-benzothien-3-yl)-1-(2-methoxyethyl)-2-thioxo-2,3-dihydropyrimidin-4(1H)-one | 319.4 | 1H NMR (400 MHz, CHLOROFORM-d) δ ppm 9.88 (br. s., 1 H), 7.87-7.98 (m, 1 H), 7.67 (s, 1 H), 7.52-7.60 (m, 1 H), 7.41-7.51 (m, 2 H), 5.98 (d, J = 2.29 Hz, 1 H), 4.66 (dt, J = 13.97, 4.10 Hz, 1 H), 3.92-4.07 (m, 1 H), 3.69-3.82 (m, 1 H), 3.41-3.50 (m, 1 H), 3.11 (s, 3H) |
| 325 | 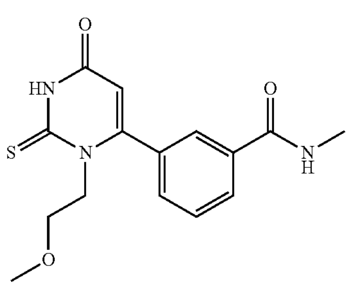 | 3-[3-(2-methoxyethyl)-6-oxo-2-thioxo-1,2,3,6-tetrahydropyrimidin-4-yl]-N-methylbenzamide | 320.1 | 1H NMR (400 MHz, METHANOL-d3) δ ppm 7.89-7.99 (m, 1 H), 7.86 (s, 1 H), 7.54-7.65 (m, 2 H), 5.81 (s, 1 H), 4.36 (br. s., 2 H), 3.60 (t, J = 5.50 Hz, 2 H), 3.11 (s, 3 H), 2.92 (s, 3 H) |
| 326 | 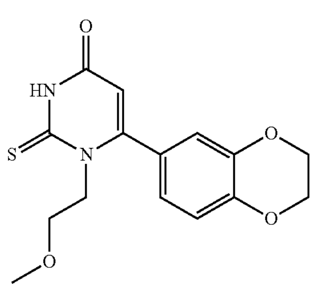 [SMILES: COCCn1c(-c2ccc3c(c2)OCCO3)cc(=O)[nH]c1=S] | 6-(2,3-dihydro-1,4-benzodioxin-6-yl)-1-(2-methoxyethyl)-2-thioxo-2,3-dihydropyrimidin-4(1H)-one | 321.1 | 1H NMR (400 MHz, CHLOROFORM-d) δ ppm 9.49 (br. s., 1 H), 6.94 (d, J = 8.24 Hz, 1 H), 6.87 (d, J = 2.29 Hz, 1 H), 6.80 (dd, J = 8.24, 2.29 Hz, 1 H), 5.82 (d, J = 2.29 Hz, 1 H), 4.42 (t, J = 5.27 Hz, 2 H), 4.27-4.35 (m, 4H), 3.65 (t, J = 5.72 Hz, 2 H), 3.22 (s, 3 H) |

TABLE 5-continued

Examples from Suzuki Route

| Example # | Structure | Compound Name | Obs Mass | 1H NMR Spectral Data or HPLC Retention Time and Conditions |
|---|---|---|---|---|
| 327 | 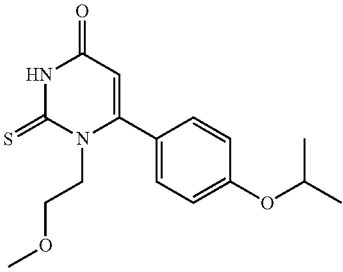 [SMILES: COCCn1c(-c2ccc(OC(C)C)cc2)cc(=O)[nH]c1=S] | 6-(4-isopropoxyphenyl)-1-(2-methoxyethyl)-2-thioxo-2,3-dihydropyrimidin-4(1H)-one | 321.2 | 1H NMR (400 MHz, CHLOROFORM-d) δ ppm 9.59 (br. s., 1 H), 7.25 (d, J = 9.16 Hz, 2H), 6.95 (d, J = 8.70 Hz, 2 H), 5.83 (d, J = 2.29 Hz, 1 H), 4.62 (spt, J = 6.00 Hz, 1 H), 4.42 (t, J = 5.50 Hz, 2 H), 3.64 (t, J = 5.72 Hz, 2H), 3.18-3.21 (m, 3 H), 1.38 (d, J = 6.41 Hz, 6H) |
| 328 | 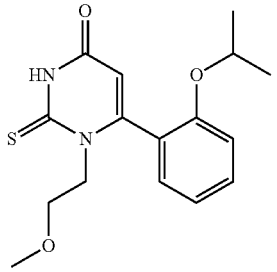 [SMILES: COCCn1c(-c2ccccc2OC(C)C)cc(=O)[nH]c1=S] | 6-(2-isopropoxyphenyl)-1-(2-methoxyethyl)-2-thioxo-2,3-dihydropyrimidin-4(1H)-one | 321.2 | 1H NMR (400 MHz, CHLOROFORM-d) δ ppm 10.13 (br. s., 1 H), 7.45 (ddd, J = 8.00, 7.80, 1.60 Hz, 1 H), 7.23 (dd, J = 7.56, 1.60 Hz, 1 H), 7.02 (ddd, J = 7.80, 7.70, 0.92 Hz, 1 H), 6.95 (d, J = 8.24 Hz, 1 H), 5.82 (s, 1 H), 4.74 (ddd, J = 13.74, 5.04, 3.66 Hz, 1 H), 4.62 (spt, J = 6.00 Hz, 1 H), 3.86 (ddd, J = 13.85, 7.90, 6.18 Hz, 1 H), 3.71 (ddd, J = 10.08, 8.24, 5.50 Hz, 1 H), 3.45 (ddd, J = 10.08, 6.18, 3.89 Hz, 1 H), 3.13 (s, 3H), 1.35 (d, J = 5.95 Hz, 3H), 1.28 (d, J = 5.95 Hz, 3 H) |
| 329 | 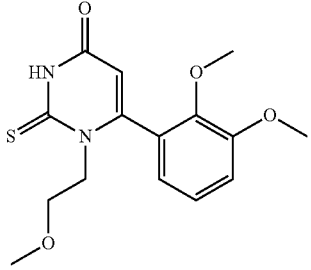 | 6-(2,3-dimethoxyphenyl)-1-(2-methoxyethyl)-2-thioxo-2,3-dihydropyrimidin-4(1H)-one | 323.1 | 1H NMR (400 MHz, CHLOROFORM-d) δ ppm 9.48 (br. s., 1 H), 7.15 (dd, J = 8.20 Hz, 1 H), 7.06 (dd, J = 8.24, 1.37 Hz, 1 H), 6.83 (dd, J = 7.79, 1.37 Hz, 1 H), 5.85 (d, J = 2.75 Hz, 1 H), 4.67 (dt, J = 13.74, 4.58 Hz, 1 H), 3.92 (s, 3 H), 3.86-4.00 (m, 1 H), 3.82 (s, 3H), 3.72 (ddd, J = 10.30, 8.01, 5.95 Hz, 1 H), 3.44 (ddd, J = 10.30, 6.18, 4.12 Hz, 1 H), 3.14 (s, 3 H) |
| 330 | 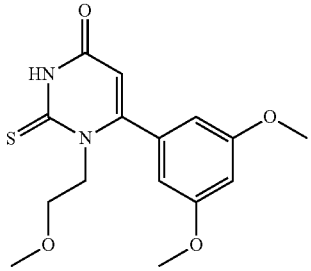 | 6-(3,5-dimethoxyphenyl)-1-(2-methoxyethyl)-2-thioxo-2,3-dihydropyrimidin-4(1H)-one | 323. | 1H NMR (300 MHz, CHLOROFORM-d) δ ppm 10.17 (br. s., 1 H), 6.55 (t, J = 2.30 Hz, 1 H), 6.48 (d, J = 2.30 Hz, 2H), 5.88 (d, J = 1.84 Hz, 1 H), 4.39 (t, J = 5.51 Hz, 2 H), 3.82 (s, 6 H), 3.68 (t, J = 5.51 Hz, 2 H), 3.22 (s, 3 H) |
| 331 | 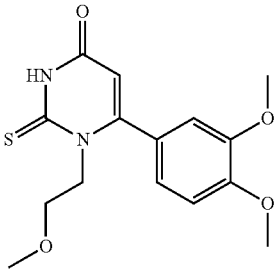 | 6-(3,4-dimethoxyphenyl)-1-(2-methoxyethyl)-2-thioxo-2,3-dihydropyrimidin-4(1H)-one | 323.1 | 1H NMR (400 MHz, CHLOROFORM-d) δ ppm 10.27 (br. s., 1 H), 6.85-6.98 (m, 3H), 5.88 (s, 1 H), 4.33-4.49 (m, 2 H), 3.94 (s, 3 H), 3.91 (s, 3 H), 3.63-3.75 (m, 2 H), 3.22 (s, 3 H) |

TABLE 5-continued

Examples from Suzuki Route

| Example # | Structure | Compound Name | Obs Mass | 1H NMR Spectral Data or HPLC Retention Time and Conditions |
|---|---|---|---|---|
| 332 | 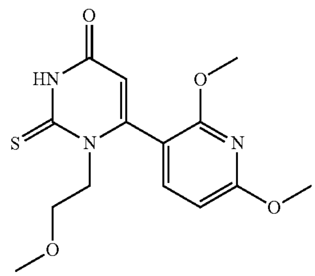 | 6-(2,6-dimethoxypyridin-3-yl)-1-(2-methoxyethyl)-2-thioxo-2,3-dihydropyrimidin-4(1H)-one | 324.1 | 1H NMR (400 MHz, CHLOROFORM-d) d ppm 9.77 (br. s., 1 H), 7.43 (d, J = 7.79 Hz, 1 H), 6.42 (d, J = 8.24 Hz, 1 H), 5.79 (s, 1 H), 4.75 (ddd, J = 13.60, 3.50, 3.50 Hz, 1 H), 3.98 (s, 3H), 3.97 (s, 3 H), 3.85 (ddd, J = 13.74, 8.70, 5.50 Hz, 1 H), 3.77 (ddd, J = 9.20, 9.20, 4.10 Hz, 1 H), 3.43 (ddd, J = 9.60, 4.60, 4.60 Hz, 1 H), 3.18 (s, 3 H) |
| 333 | 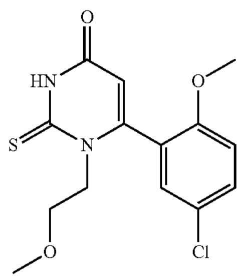 | 6-(5-chloro-2-methoxyphenyl)-1-(2-methoxyethyl)-2-thioxo-2,3-dihydropyrimidin-4(1H)-one | 327.1 | 1H NMR (400 MHz, METHANOL-d3) δ ppm 7.51 (dd, J = 8.70, 2.75 Hz, 1 H), 7.35 (d, J = 2.75 Hz, 1 H), 7.13 (d, J = 9.16 Hz, 1 H), 5.77 (s, 1 H), 4.67-4.76 (m, 1 H), 3.89 (s, 3 H), 3.73-3.81 (m, 2H), 3.38-3.45 (m, 1 H), 3.12 (s, 3 H) |
| 334 | 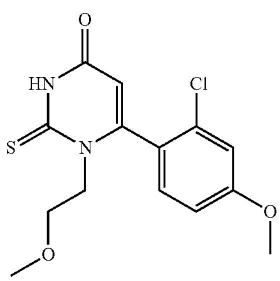 | 6-(2-chloro-4-methoxyphenyl)-1-(2-methoxyethyl)-2-thioxo-2,3-dihydropyrimidin-4(1H)-one | 327.1 | 1H NMR (400 MHz, CHLOROFORM-d) δ ppm 10.18 (br. s., 1 H), 7.26 (d, J = 8.70 Hz, 1 H), 7.00 (d, J = 2.29 Hz, 1 H), 6 92 (dd, J = 8.93, 2.06 Hz, 1 H), 5.84 (s, 1 H), 4.64-4.78 (m, 1 H), 3.87 (s, 3 H), 3.76-3.85 (m, 2 H), 3.39-3.52 (m, 1 H), 3.19 (s, 3 H) |
| 335 | 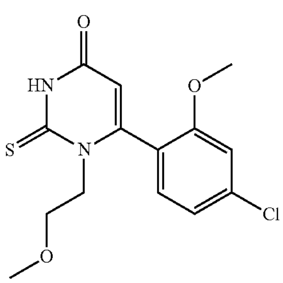 [SMILES: COCCn1c(-c2ccc(Cl)cc2OC)cc(=O)[nH]c1=S] | 6-(4-chloro-2-methoxyphenyl)-1-(2-methoxyethyl)-2-thioxo-2,3-dihydropyrimidin-4(1H)-one | 327.1 | 1H NMR (400 MHz, CHLOROFORM-d) δ ppm 9.96 (br. s., 1 H), 7.17 (d, J = 7.79 Hz, 1 H), 7.06 (dd, J = 8.24, 1.83 Hz, 1 H), 6.97 (d, J = 1.37 Hz, 1 H), 5.79 (s, 1 H), 4.64-4.77 (m, 1 H), 3.86 (s, 3 H), 3.72-3.82 (m, 2H), 3.36-3.47 (m, 1 H), 3.16 (s, 3 H) |
| 336 | 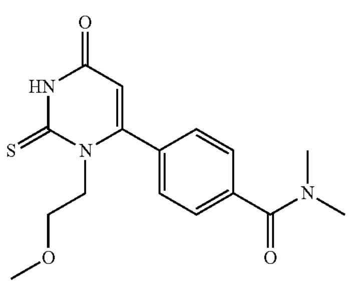 | 4-[3-(2-methoxyethyl)-6-oxo-2-thioxo-1,2,3,6-tetrahydropyrimidin-4-yl]-N,N-dimethylbenzamide | 334.2 | 1H NMR (400 MHz, METHANOL-d3) δ ppm 7.53-7.60 (m, 4 H), 5.82 (s, 1 H), 4.40 (t, J = 5.27 Hz, 2 H), 3.62 (t, J = 5.50 Hz, 2H), 3.14 (s, 3 H), 3.13 (s, 3 H), 3.03 (s, 3 H) |

TABLE 5-continued

Examples from Suzuki Route

| Example # | Structure | Compound Name | Obs Mass | 1H NMR Spectral Data or HPLC Retention Time and Conditions |
|---|---|---|---|---|
| 337 | 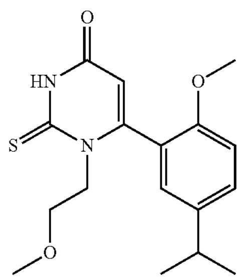 [SMILES: COCCn1c(-c2cc(C(C)C)ccc2OC)cc(=O)[nH]c1=S] | 6-(5-isopropyl-2-methoxyphenyl)-1-(2-methoxyethyl)-2-thioxo-2,3-dihydropyrimidin-4(1H)-one | 335.2 | 1H NMR (400 MHz, METHANOL-d3) δ ppm 7.37 (dd, J = 8.59, 2.18 Hz, 1 H), 7.16 (d, J = 2.29 Hz, 1 H), 7.03 (d, J = 8.70 Hz, 1 H), 5.72 (s, 1 H), 4.69 (dt, J = 13.80, 4.89 Hz, 1 H), 3.83 (s, 3 H), 3.76-3.82 (m, 1 H), 3.66 (ddd, J = 10.19, 7.79, 6.07 Hz, 1 H), 3.41 (ddd, J = 10.25, 6.24, 4.12 Hz 1 H), 3.06 (s, 3H), 2.90 (spt, J = 7.10 Hz, 1 H), 1.24 (dd, J = 6.87, 2.98 Hz, 6 H) |
| 338 | 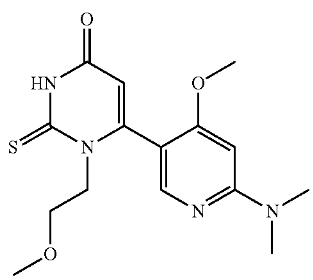 | 6-[6-(dimethylamino)-4-methoxypyridin-3-yl]-1-(2-methoxyethyl)-2-thioxo-2,3-dihydropyrimidin-4(1H)-one | 337.2 | 1H NMR (400 MHz, CHLOROFORM-d) δ ppm 9.61 (br. s., 1 H), 7.90 (s, 1 H), 7.27 (s, 1 H), 5.91 (s, 1 H), 4.78 (dt, J = 14.08, 3.72 Hz, 1 H), 3.87 (s, 3H), 3.82 (dt, J = 13.74, 6.41 Hz, 1 H), 3.67-3.76 (m, 1 H), 3.42-3.51 (m, 1 H), 3.21 (s, 3 H), 3.16 (s, 6 H) |
| 339 | 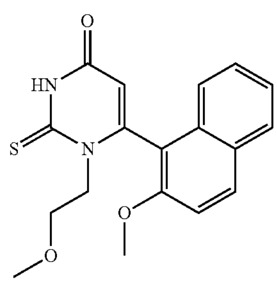 [SMILES: COCCn1c(-c2c(OC)ccc3ccccc23)cc(=O)[nH]c1=S] | 1-(2-methoxyethyl)-6-(2-methoxy-1-naphthyl)-2-thioxo-2,3-dihydropyrimidin-4(1H)-one | 343.4 | 1H NMR (400 MHz, CHLOROFORM-d) 9.58 (s, 1H), 8.02 (d, 1H), 7.82 (d, 1H), 7.50-7.58 (m, 2H), 7.39-7.43 (dd, 1H), 7.31 (d, 1H), 5.89 (s, 1H), 4.26-4.33 (m, 1H), 4.02-4.11 (m, 1H), 3.97 (s, 3H), 3.51- 3.57 (m, 1H), 3.31-3.39 (m, 1H), 2.88 (s, 3H) |
| 340 | 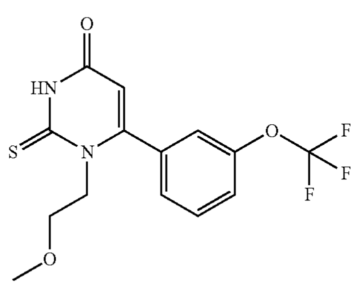 [SMILES: COCCn1c(-c2cccc(OC(F)(F)F)c2)cc(=O)[nH]c1=S] | 1-(2-methoxyethyl)-2-thioxo-6-[3-(trifluoromethoxy)phenyl]-2,3-dihydropyrimidin-4(1H)-one | 347.1 | 1H NMR (400 MHz, CHLOROFORM-d) δ ppm 9.56 (br. s., 0 H), 7.53 (dd, J = 7.80, 7.80 Hz, 1 H), 7.37 (d, J = 9.16 Hz, 1 H), 7.25-7.31 (m, 2 H), 5.84 (d, J = 2.29 Hz, 1 H) 4.34 (br. s, 2 H), 3.66 (br. s, 2 H), 3.20 (s, 3 H) |
| 341 | 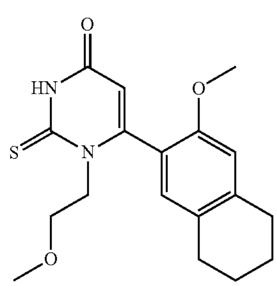 [SMILES: COCCn1c(-c2cc3c(cc2OC)CCCC3)cc(=O)[nH]c1=S] | 1-(2-methoxyethyl)-6-(3-methoxy-5,6,7,8-tetrahydronaphthalen-2-yl)-2-thioxo-2,3-dihydropyrimidin-4(1H)-one | 347.5 | 1H NMR (400 MHz, METHANOL-d3) δ ppm 6.96 (s, 1 H), 6.78 (s, 1 H), 5.70 (s, 1 H), 4.60-4.72 (m, 1 H), 3.86 (dt, J = 14.03, 7.30 Hz, 1 H), 3.81 (s, 3 H), 3.67 (ddd, J = 10.30, 7.56, 6.41 Hz, 1 H), 3.41 (ddd, J = 10.36, 6.35, 4.12 Hz, 1 H), 3.07 (s, 3 H), 2.82 (br. s., 2 H), 272 (br. s, 2H), 1.75-1.86 (m, 4H) |

TABLE 5-continued

Examples from Suzuki Route

| Example # | Structure | Compound Name | Obs Mass | 1H NMR Spectral Data or HPLC Retention Time and Conditions |
|---|---|---|---|---|
| 342 | 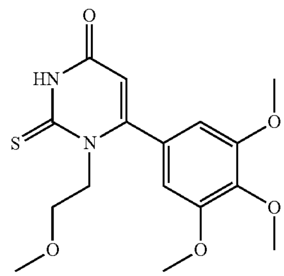 | 1-(2-methoxyethyl)-2-thioxo-6-(3,4,5-trimethoxyphenyl)-2,3-dihydropyrimidin-4(1H)-one | 353.1 | 1H NMR (400 MHz, CHLOROFORM-d) δ ppm 9.91 (br. s., 1 H), 6.59 (s, 2 H), 5.88 (d, J = 2.29 Hz, 1 H), 4.39 (t, J = 5.50 Hz, 2H), 3.92 (s, 3 H), 3.88 (s, 6 H), 3.73 (t, J = 5.27 Hz, 2 H), 3.24 (s, 3 H) |
| 343 | 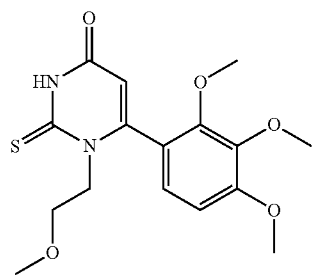 | 1-(2-methoxyethyl)-2-thioxo-6-(2,3,4-trimethoxyphenyl)-2,3-dihydropyrimidin-4(1H)-one | 353.1 | 1H NMR (400 MHz. CHLOROFORM-d) δ ppm 9.49 (br. s., 1 H), 6.92 (d, J = 8.70 Hz, 1 H), 6.73 (d, J = 8.70 Hz, 1 H), 5.83 (d, J = 2.29 Hz, 1 H), 4.62-4.71 (m, 1 H), 3.93-3.98 (m, 1 H), 3.92 (s, 3 H), 3.90 (s, 3 H), 3.89 (s, 3 H), 3.73 (ddd, J = 10.08, 8.01, 5.72 Hz, 1 H), 3.46 (ddd, J = 10.08, 6.18, 3.89 Hz, 1 H), 3.17 (s, 3H) |
| 344 | 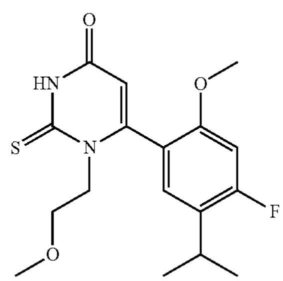 [SMILES: COCCn1c(-c2cc(C(C)C)c(F)cc2OC)cc(=O)[nH]c1=S] | 6-(4-fluoro-5-isopropyl-2-methoxyphenyl)-1-(2-methoxyethyl)-2-thioxo-2,3-dihydropyrimidin-4(1H)-one | 353.1 | 1H NMR (400 MHz, METHANOL-d3) δ ppm 7.23 (d, J = 8.24 Hz, 1 H), 6.87 (d, J = 12.14 Hz, 1 H), 5.72 (s, 1 H), 4.69 (dt, J = 13.45, 4.15 Hz, 1 H), 3.84 (s, 3 H), 3.64-3.81 (m, 2 H), 3.40 (ddd, J = 9.79, 5.55, 3.66 Hz, 1 H), 3.19 (spt, J = 7.10 Hz. 1 H), 3.10 (s, 3 H), 1.24 (d, J = 6.87 Hz, 6 H) |
| 345 | 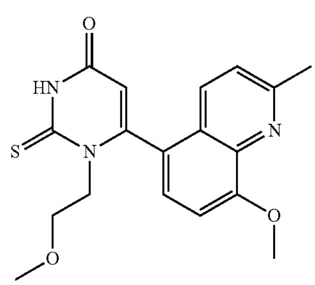 | 1-(2-methoxyethyl)-6-(8-methoxy-2-methylquinolin-5-yl)-2-thioxo-2,3-dihydropyrimidin-4(1H)-one | 358.2 | 1H NMR (400 MHz CHLOROFORM-d) δ ppm 9.86 (br. s., 1 H), 7.84 (d, J = 8.70 Hz, 1 H), 7.42 (d, J = 8.70 Hz, 2 H), 7.10 (d, J = 8.24 Hz, 1 H), 5.95 (d, J = 2.29 Hz, 1 H), 4.49 (dt, J = 14.08, 5.09 Hz, 1 H), 4.15 (s, 3H), 3.85-4.00 (m, 1 H), 3.61 (ddd, J = 10.99, 6.87, 4.58 Hz, 1 H), 3.49 (dt, J = 10.30, 5.38 Hz, 1 H), 3.04 (s, 3 H), 2.84 (s, 3 H) |
| 346 | 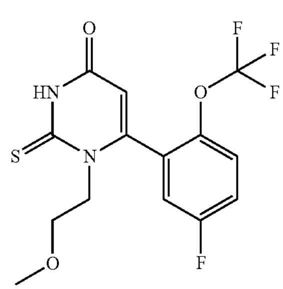 [SMILES: COCCn1c(-c2cc(F)ccc2OC(F)(F)F)cc(=O)[nH]c1=S] | 6-[5-fluoro-2-(trifluoromethoxy)phenyl]-1-(2-methoxyethyl)-2-thioxo-2,3-dihydropyrimidin-4(1H)-one | 365.1 | 1H NMR (400 MHz, CHLOROFORM-d) δ ppm 9.58 (br. s., 1 H), 7.31-7.39 (m, 1 H), 7.26-7.29 (m, 1 H), 7.15 (dd, J = 7.90, 3.09 Hz, 1 H), 5.83 (d, J = 2.52 Hz, 1 H), 4.68 (dt, J = 14.20, 3.32 Hz, 1 H), 3.88 (td, J = 9.85, 3.66 Hz, 1 H), 3.72 (ddd, J = 13.91, 9.45, 3.89 Hz, 1 H), 3.39 (dt, J = 10.36, 3.75 Hz, 1 H), 3.19 (s, 3 H) |

TABLE 5-continued

Examples from Suzuki Route

| Example # | Structure | Compound Name | Obs Mass | 1H NMR Spectral Data or HPLC Retention Time and Conditions |
|---|---|---|---|---|
| 347 | 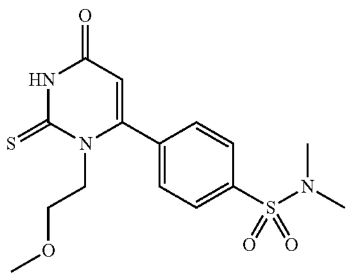 | 4-[3-(2-methoxyethyl)-6-oxo-2-thioxo-1,2,3,6-tetrahydropyrimidin-4-yl]-N,N-dimethylbenzenesulfonamide | 370.1 | 1H NMR (400 MHz, CHLOROFORM-d) δ ppm 9.84 (br. s., 1 H), 7.90 (d, J = 6.87 Hz, 2H), 7.56 (d, J = 6.87 Hz, 2 H), 5.84 (s, 1 H), 4.32 (br. s., 2H), 3.66 (t, J = 4.35 Hz, 2 H), 3.20 (s, 3 H), 2.81 (s, 6 H) |
| 348 | 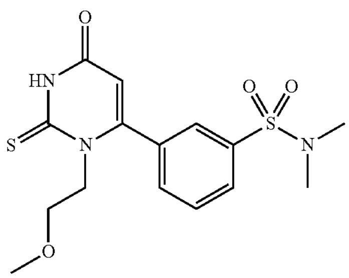 | 3-[3-(2-methoxyethyl)-6-oxo-2-thioxo-1,2,3,6-tetrahydropyrimidin-4-yl]-N,N-dimethylbenzenesulfonamide | 370.1 | 1H NMR (400 MHz, CHLOROFORM-d) δ ppm 10.14 (br. s., 1 H), 7.91 (ddd, J = 8.24, 1.80, 1.50 Hz, 1 H), 7.84 (dd, J = 1.60, 1.60 Hz, 1 H), 7.69 (dd, J = 7.80, 7.80 Hz, 1 H), 7.59 (ddd, J = 7.80, 1.40, 1.40 Hz, 1 H), 5.85 (d, J = 1.83 Hz, 1 H), 4.31 (br. s, 2H), 3.67 (br. s., 2H), 3.21 (s, 3H), 2.77 (s, 6 H) |

Additions to I. Beta Keto Ester Route Section

E. Ester Route Section

Preparation 19

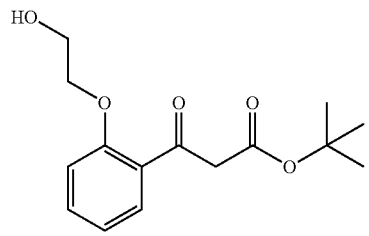 [SMILES: CC(C)(C)OC(=O)CC(=O)c1ccccc1OCCO]

tert-Butyl 3-(2-(2-hydroxyethoxy)phenyl)-3-oxopropanoate

To a solution of tert-butyl acetate (7.96 g, 68.5 mmol) in anhydrous THF (100 mL) was added freshly prepared lithium diisopropyl amine (37 mL, 1.85 M in THF) dropwise over 15 min at −78° C., and the mixture was stirred at −78° C. for 30 min. 2H-benzo[e][1,4]dioxepin-5(3H)-one (10.2 g, 62.3 mmol) was added dropwise as a solution in THF (50 mL) at −78 C, and stirring was continued for 30 min. Saturated NaHCO3 solution was added and the mixture was extracted with EtOAc. The organic layer was dried (Na$_2$SO$_4$), and concentrated under reduced pressure to give the title compound (6.0 g, 77.9%) as a yellow oil, which was used directly in the next step without further purification.

MS (ES+) 303.2 [M+Na]$^+$. $^1$H NMR (500 MHz, CDCl$_3$) δ 7.85 (dd, J=7.8, 1.8 Hz, 1H) 7.50 (ddd, J=8.5, 7.1, 1.8 Hz, 1H) 7.05 (td, J=7.5, 1.0 Hz, 1H) 6.97 (d, J=8.4 Hz, 1H) 4.16-4.20 (m, 2H) 4.01 (d, J=4.3 Hz, 2H) 3.90 (s, 2H) 2.79 (br. s, 1H) 1.33 (s, 9H).

Preparation 20

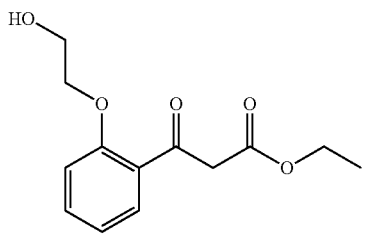 [SMILES: CCOC(=O)CC(=O)c1ccccc1OCCO]

Ethyl 3-(2-(2-hydroxyethoxy)phenyl)-3-oxopropanoate tert-Butyl 3-(2-(2-hydroxyethoxy)phenyl)-3-oxopropanoate (2.0 g, 7.14 mmol) in ethanol (20 mL) was heated in a microwave reactor at 120° C. for 90 min. The mixture was cooled to room temperature and the solvent was concentrated under reduced pressure to give a yellow oil. The crude product was purified by flash chromatography (30-40% EtOAc: petroleum ether) to give the title compound as a yellow solid.

Preparation 21

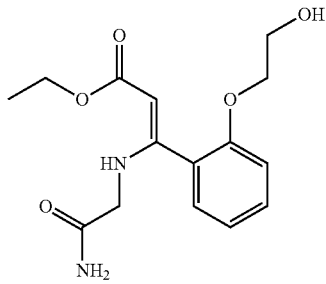 [SMILES: CCOC(=O)/C=C(\NCC(N)=O)c1ccccc1OCCO]

(Z)-Ethyl 3-((2-amino-2-oxoethyl)amino)-3-(2-(2-hydroxyethoxy)phenyl)acrylate

To a solution of ethyl 3-(2-(2-hydroxyethoxy)phenyl)-3-oxopropanoate (2 g, 7.94 mmol) and glycinamide hydrochloride (3.5 g, 31.7 mmol) in methanol (20 mL) was added triethylamine (3.21 g, 31.7 mmol) at room temperature. The mixture was stirred at 40° C. for 20 min. Acetic acid (1.9 g, 31.7 mmol) was added, and the mixture was stirred at 80° C. for 18 hours. The reaction mixture was cooled to room temperature and saturated sodium bicarbonate (200 mL) was added. The organic layer was separated, dried ($Na_2SO_4$) and concentrated to give a yellow solid. The solid was washed with EtOAc (20 mL), and the residue was dried under reduced pressure to give the title compound as a white solid. This material was used without further purification.

Example 349

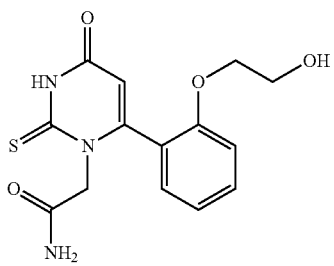

2-(6-(2-(2-Hydroxyethoxy)phenyl)-4-oxo-2-thioxo-3, 4-dihydropyrimidin-1 (2H)-acetamide To a solution of (Z)-ethyl 3-((2-amino-2-oxoethyl)amino)-3-(2-(2-hydroxyethoxy)phenyl)acrylate (1.0 g, 3.25 mmol) in tetrahydrofuran (15 mL) was added trimethylsilyl isothiocyanate (1.7 g, 12.9 mmol), and the mixture was stirred at 80° C. for 18 hours. The reaction mixture was cooled to room temperature, poured into a flask containing water and extracted with $CH_2Cl_2$ (3×100 mL). The combined organic layers were dried and concentrated under reduced pressure to give a yellow solid, which was purified by flash chromatography (2-5% MeOH:$CH_2Cl_2$) to give the title compound (330 mg, 31.7%) as a yellow solid.

MS (ES+) 343.9 [M+Na]. $^1$H NMR (DMSO-d6) d: 12.77 (s, 1H), 7.44-7.53 (m, 1H), 7.31 (5, 1H), 7.14-7.22 (m, 2H), 7.02 (t, J=7.5 Hz, 1H), 6.98 (br. s., 1H), 5.74-5.82 (m, 1H), 5.34 (br. s., 1H), 4.84 (br. s., 1H), 4.00-4.16 (m, 2H), 3.93 (br. s., 1H), 3.65 (q, J=4.4 Hz, 2H)

III. Amide Coupling Route Section

Preparation 22

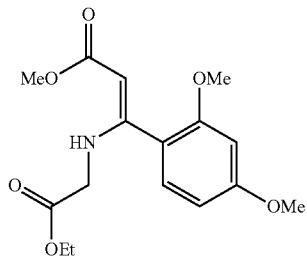 [SMILES: CCOC(=O)CN/C(=C\C(=O)OC)c1ccc(OC)cc1OC]

(Z)-Methyl 3-(2, 4-dimethoxyphenyl)-3-((2-ethoxy-2-oxoethyl)amino)acrylate

To a solution of methyl 3-(2,4-dimethoxyphenyl)-3-oxopropanoate (5.0 g, 21 mmol) in EtOH (30 mL) was added glycine methyl ester hydrochloride (10.5 g, 83.9 mmol) followed by acetic acid (1.20 mL, 21 mmol) and triethylamine (8.5 g, 83.9 mmol) and the reaction mixture was heated at 100° C. for 18 hours. After cooling to room temperature, the residue was partitioned between EtOAc and saturated aqueous ammonium chloride. The organic layer was washed with brine, dried over sodium sulfate and concentrated in vacuo. The crude product was dissolved in $CH_2Cl_2$ (10 mL) filtered through a plug of silica gel, eluting with 15-35% EtOAc in heptanes and dried under vacuum to give the title compound (4.7 g, 69%) as a yellow solid. This material was used in the next step without further purification.

MS (ES+) 324.3 [M+1]$^+$. $^1$H NMR (500 MHz, CDCl$_3$) δ 8.95 (br. s., 1H) 7.14 (d, J=10.57 Hz, 1H) 6.49 (dd, J=8.28, 2.07 Hz, 1H) 6.46 (d, J=2.07, 1 H) 4.60 (s, 1H) 4.16 (q, J=7.80 Hz, 2H) 3.83 (s, 3H) 3.80 (s, 3H), 3.69 (s, 3H), 1.24 (t, J=7.80 Hz, 3H).

Preparation 23

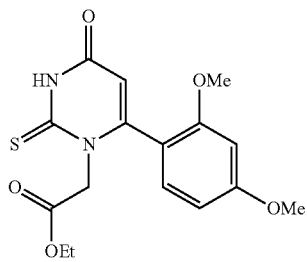 [SMILES: CCOC(=O)Cn1c(-c2ccc(OC)cc2OC)cc(=O)[nH]c1=S]

Ethyl 2-(6-(2, 4-dimethoxyphenyl)-4-oxo-2-thioxo-3, 4-dihydropyrimidin-1 (2H)-yl)acetate To a solution of (Z)-methyl 3-(2,4-dimethoxyphenyl)-3-((2-ethoxy-2-oxoethyl)amino)acrylate (4.68 g, 15.1 mmol) in 2-methyltetrahydrofuran (38 mL) was added (trimethylsilyl)isothiocyanate (12.9 mL, 90.8 mmol). The resulting solution was purged with nitrogen gas for 3 times, and the mixture was heated at 110° C. for 18 hours. The mixture was cooled down to room temperature and the solvent was removed under reduced pressure to give a red solid. This residue was suspended in a mixture of 3:1 heptane/EtOAc (200 mL), and it was stirred at room temperature for 1 hour. The solid was filtered, and triturated with CH$_2$Cl$_2$ (100 mL), concentrated under reduced pressure and dried under vacuum the title compound (4.42 g, 87%) as a pink solid. This material was used without further purification in the next step.

MS (ES+) 351.5 [M+1]$^+$. $^1$H NMR (500 MHz, CDCl$_3$) δ 9.91 (br s, 1H) 7.13 (d, J=6.12 Hz, 1H) 6.54 (s, 1H) 6.51 (d, J=6.12 Hz, 1H) 5.86 (s, 1H) 5.44-5.40 (m, 1H) 4.25-4.20 (m, 1H) 4.16-4.06 (m, 2H), 3.86 (s, 3H) 3.83 (s, 3H), 1.20 (t, J=6.12 Hz, 3H).

Preparation 24

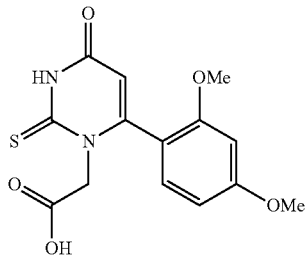 [SMILES: COc1ccc(-c2cc(=O)[nH]c(=S)n2CC(=O)O)c(OC)c1]

2-(6-(2,4-dimethoxyphenyl)-4-oxo-2-thioxo-3,4-dihydropyrimidin-1(2H)-yl)acetic acid To a solution of ethyl 2-(6-(2,4-dimethoxyphenyl)-4-oxo-2-thioxo-3,4-dihydropyrimidin-1(2H)-yl)acetate (6.8 g, 20.3 mmol) in methanol (34 mL) was added 6N aqueous NaOH (16.9 mL), and the solution was stirred at 35° C. for 3 hours. The mixture was concentrated under reduced pressure, and water (100 mL) was added. The aqueous layer was washed with ethyl acetate (2×200 mL), and acidified with concentrated HCl to pH~2. The resultant acidic aqueous solution was extracted with EtOAc (3×200 mL), and the combined organic layers were dried with sodium sulfate, and concentrated under reduced pressure to give the title compound 6.53 g (99%) as a white solid.

MS (ES+) 323.2 [M+1]$^+$. $^1$H NMR (500 MHz, CD$_3$OD) δ 7.16 (d, J=8.86 Hz, 1H) 6.67 (s, 1H) 6.64 (d, J=8.86 Hz, 1H) 5.79 (s, 1H) 5.52-5.40 (m, 1H) 4.34-4.19 (m, 1H) 3.87 (s, 3H) 3.86 (s, 3H).

Preparation 25

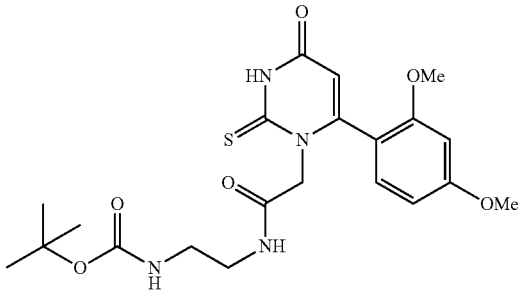 [SMILES: COc1ccc(-c2cc(=O)[nH]c(=S)n2CC(=O)NCCNC(=O)OC(C)(C)C)c(OC)c1]

tert-Butyl (2-(2-(6-(2, 4-dimethoxyphenyl)-4-oxo-2-thioxo-3,4-dihydropyrimidin-1(2H)-yl)acetamido)ethyl)carbamate To a solution of 2-(6-(2,4-dimethoxyphenyl)-4-oxo-2-thioxo-3,4-dihydropyrimidin-1(2H)-yl)acetic acid (40 g, 124 mmol) in DMF (300 mL) was added tert-butyl (2-aminoethyl)carbamate (40 g, 250 mmol) and pyridine (30 mL), and the mixture was stirred at room temperature for 15 minutes. The solution was cooled to 0° C. and it was purged with nitrogen gas for 3 times. After 10 minutes, a 50% solution of T3P in DMF (109 mL) was added drop-wise at 0° C., and stirring was continued for 1 hour, whereupon the water/ice bath was removed and stirring was continued for 4 hours. The reaction solution was slowly poured into a stirring solution of aqueous HCl solution (2500 mL, 0.5 M), and the suspension was stirred at room temperature for 1 hour. The formed solid was filtered, and the filter cake was washed with 0.5M HCl solution (500 mL) followed by water (500 mL). The solid was dried in the vacuum oven at 50° C. for 20 hours to give 54.6 g of light beige powder. This solid was suspended in EtOAc (500 mL), heated to 70° C. under a stream of nitrogen gas with stirring for 1 hour, and then at room temperature for 18 h. The suspension was cooled down to 0° C., and the solid was filtered, the filter cake washed with cold (0° C.) EtOAc (100 mL) and dried in the vacuum oven at 50° C. for 9 hours to give 49.0 g of off-white solid. This solid was suspended in acetonitrile (300 mL), and stirred at 70° C. under a stream of nitrogen for 18 h. The mixture was cooled to 0° C., and the resultant solid was filtered, washed with cold acetonitrile (50 mL) and dried in the vacuum oven at 50° C. for 8 hours to give 46.5 g of off-white solid. This solid was suspended in EtOAc (350 mL), heated to 70° C. under a stream of nitrogen gas with stirring for 1 hour, and then at room temperature for 18 h. The suspension was cooled down to 0° C., and the solid was filtered, the filter cake washed with cold (0° C.) EtOAc (50 mL) and dried in the vacuum oven at 50° C. for 9 hours to give the title compound (45.4 g, 78.8%) as an off-white powder.

MS (ES+) 465.3 [M+1]$^+$. $^1$H NMR (500 MHz, CD$_3$OD) δ 8.99 (br. s., 1H) 7.16 (d, J=7.65 Hz, 1H) 6.65 (s, 1H) 6.62 (d, J=7.65 Hz, 1H) 5.78 (s, 1H) 5.51-5.41 (m, 1H) 4.22-4.14 (m, 1H) 3.87 (s, 3H) 3.85 (s, 3H) 3.19-3.11 (m, 2H) 3.06-3.00 (m, 2H) 1.42 (s, 9H).

Example 241

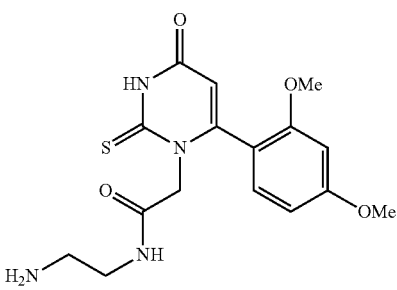 [SMILES: COc1ccc(-c2cc(=O)[nH]c(=S)n2CC(=O)NCCN)c(OC)c1]

N-(2-aminoethyl)-2-(6-(2, 4-dimethoxyphenyl)-4-oxo-2-thioxo-3, 4-dihydropyrimidin-1(2H)-yl)acetamide hydrochloride To cold (0° C.) ethanol (21.5 mL) under nitrogen was added acetyl chloride (1.55 mL) dropwise over 5 minutes, and the reaction mixture was then heated at 50° C. for 30 minutes. The reaction mixture was cooled to room temperature and tert-butyl (2-(2-(6-(2,4-dimethoxyphenyl)-4-oxo-2-thioxo-3,4-dihydropyrimidin-1(2H)-yl)acetamido)ethyl)carbamate was added (1.0 g, 2.15 mmol), followed by heating to 50° C. for 1 hour. The mixture was cooled to room temperature and concentrated under reduced pressure. The residue was suspended in ethanol (10 mL), heated to 75° C. for 20 minutes, and EtOAc (20 mL) was added and heating was continued for another 20 minutes. The mixture was allowed to slowly cool to down to room temperature with stirring during 18 hours. The resultant precipitate was filtered and dried in a vacuum oven at 70° C. for 20 hours to give the title compound (751 mg, 87%) as a white solid.

MS (ES+) 365.2 [M+1]+. 1H NMR (500 MHz, DMSO-D6) δ 12.81 (br. s., 1H) 8.26 (br. s., 1H) 8.01 (br. s., 2H) 7.08 (d, J=7.91 Hz, 1H) 6.70 (s, 1H) 6.62 (d, J=7.91 Hz, 1H) 5.78 (s, 1H) 5.41-5.35 (m, 1H) 4.07-4.02 (m, 1H) 3.84 (s, 3H) 3.83 (s, 3H) 3.20-3.16 (m, 2H) 2.74-2.64 (m, 2H).

IV. Guanidine Route Section

Example 350

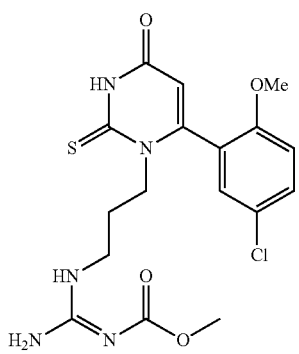 [SMILES: COC(=O)/N=C(/N)NCCCn1c(-c2cc(Cl)ccc2OC)cc(=O)[nH]c1=S]

Methyl [amino({3-[6-(5-chloro-2-methoxyphenyl)-4-oxo-2-thioxo-3, 4-dihydropyrimidin-1(2H)-yl]propyl}amino)methylidene]carbamate To a solution of 1-(3-aminopropyl)-6-(5-chloro-2-methoxyphenyl)-2-thioxo-2,3-dihydropyrimidin-4(1H)-one (prepared in an analogous manner to Example 6; 50 mg, 0.14 mmol) and methyl [amino(1H-pyrazol-1-yl)methylidene]carbamate (28 mg, 0.16 mmol) in DMF (0.46 mL) was added N,N-diisopropylethylamine (0.024 mL, 0.14 mmol) at room temperature, and the mixture was stirred for 72 hours. The solvent was removed under reduced pressure, the residue was dissolved in DMSO (0.9 mL) and purified using mass-triggered automatic purification to give the title compound (4.9 mg)

MS (ES+) 425.9 [M+H]+. Retention time: 1.54 min; Method: XBridge C18 5 um 4.6×50 mm, 95% H2O/5% MeCN linear to 5% H2O/95% MeCN over 4.0 min, HOLD at 5% H2O/95% MeCN to 5.0 min. (0.03% NH4OH). Flow rate: 2 mL/min.

Preparation 26

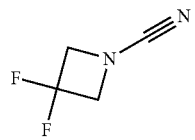

3,3-Difluoroazetidine-1-carbonitrile

A suspension of 3,3-difluoroazetidine hydrochloride (600 mg, 4.63 mmol) in DCM (15.4 mL) was treated with triethylamine (1.48 mL). The reaction mixture was cooled to 0° C., treated with cyanogen bromide (3M in DCM, 2.01 mL, 6.02 mmol) and the reaction mixture was stirred at 0° C. for 2 hours. The reaction mixture was diluted with water (10 mL) and saturated sodium bicarbonate (5 mL), and extracted with ethyl acetate (3×50 mL) and DCM (2×50 mL). The combined organics were dried over sodium sulfate, filtered and concentrated in vacuo. The crude product was dissolved in dichlormethane (30 mL) and washed with saturated aqueous ammonium chloride (2×15 mL). The organic layer was dried over sodium sulfate, filtered and concentrated in vacuo to give the title compound as a light brown solid (490 mg, 89%).

1H NMR (500 MHz, CDCl3) δ 4.52 (t, 4H).

Preparation 27

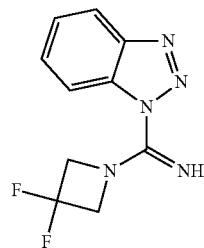 [SMILES: N=C(N1CC(F)(F)C1)n1nnc2ccccc21]

1-(1H-Benzotriazol-1-yl)-1-(3,3-difluoroazetidin-1-yl)methanimine

A mixture of 3,3-difluoroazetidine-1-carbonitrile (135 mg, 1.14 mmol) and benzotriazole (136 mg, 1.14 mmol) in 1,2-dichloroethane (0.2 mL) was heated to 80° C. under nitrogen for 30 min. A needle was inserted to facilitate evaporation of the solvent and the mixture was heated at 80° C. for 45 min. The resulting solids were washed with ether (2×3 mL) and dried under reduced pressure to give the title compound as an off-white solid (160 mg, 51%).

1H NMR (500 MHz, DMSO-d6) δ 8.35 (d, 1H, J=8.4 Hz), 8.15 (d, 1H, J=8.4 Hz), 7.92 (s, 1H), 7.67 (t, 1H, J=8.4 Hz), 7.52 (t, 1H, J=8.4 Hz), 4.64 (t, 4H, J=12.8 Hz).

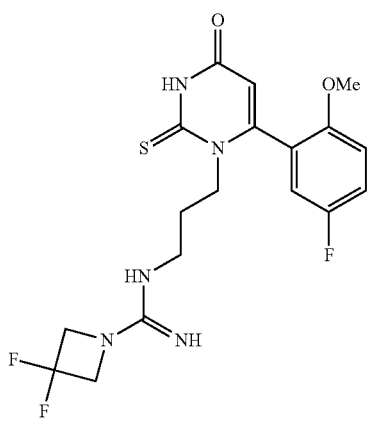 [SMILES: COc1ccc(F)cc1-c1cc(=O)[nH]c(=S)n1CCCNC(=N)N1CC(F)(F)C1]

Example 351

3,3-Difluoro-N-{3-[6-(5-fluoro-2-methoxyphenyl)-4-oxo-2-thioxo-3,4-dihydropyrimidin-1(2H)-yl]propyl}azetidine-1-carboximidamide To a mixture of 1-(3-aminopropyl)-6-(5-fluoro-2-methoxyphenyl)-2-thioxo-2,3-dihydropyrimidin-4(1H)-one (prepared in an analogous manner to Example 6; 50 mg, 0.14 mmol) and 1-(1H-benzotriazol-1-yl)-1-(3,3-difluoroazetidin-1-yl)methanimine (47.5 mg, 0.174 mmol) in DMF (0.46 mL) was added N,N-diisopropylethylamine (0.061 mL, 0.35 mmol) under nitrogen and heated at 60° C. under nitrogen for 1 h. The reaction mixture was cooled to room temperature, and treated with 4N HCl in dioxane (0.25 mL). The mixture was stirred at room temperature for 10 min, then concentrated in vacuo and azeotroped with heptanes (3×10 mL). The residue was dissolved in water (1 mL) and purified using medium pressure reverse-phase (C18) chromatography (100:0 to 70:30 water/acetonitrile) to give the title compound as a white solid (22 mg, 33%).

MS(ES+) 428.2 [M+H]$^+$. $^1$H NMR (500 MHz, CD3OD) δ 7.36 (ddd, 1H, J=9.1, 8.2, 3.2 Hz), 7.21-7.24 (m, 2H), 5.85 (s, 1H), 4.6 (br s, 1H), 4.45 (td, 4H, J=11.4, 4.7 Hz), 3.92 (s, 3H), 3.80 (br s, 1H), 3.12 (td, 2H, J=6.0, 2.4 Hz), 2.00-2.05 (m, 1H), 1.72-1.82 (m, 1H).

The following Examples of Table 6 (additions to Table 2) were prepared from the corresponding carboxylic acid to afford the intermediate beta-keto-ester as described above for the Preparations in the Carboxylic Acid Route section followed by employing other the methods described in the I. Beta Keto Ester Route Section as well as standard methods and techniques known to those skilled in the art.

TABLE 6

Examples from Carboxylic Acid Route

| Example # | Structure | Compound Name | Obs Mass | 1H NMR Spectral Data or HPLC Retention Time and Conditions |
|---|---|---|---|---|
| 352 | 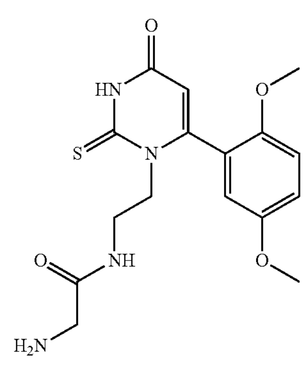 [SMILES: COc1ccc(OC)c(-c2cc(=O)[nH]c(=S)n2CCNC(=O)CN)c1] | N-{2-[6-(2,5-dimethoxyphenyl)-4-oxo-2-thioxo-3,4-dihydropyrimidin-1(2H)-yl]ethyl}glycinamide | 365.2 | 0.31 min Waters Acqity HSS T3, 2.1 × 50 mm, C18, 1.7 μm; A: 0.1% formic acid in water; Mobile phase B: 0.1% formic acid in MeCN A: 0.1% ammonia in water; Mobile phase B: 0.1% ammonia in MeCN Flow 1.25 ml/min |
| 353 | 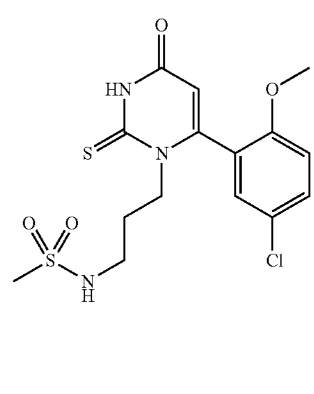 | N-{3-[6-(5-chloro-2-methoxyphenyl)-4-oxo-2-thioxo-3,4-dihydropyrimidin-1(2H)-yl]propyl}methanesulfonamide | 404.0 | 1H NMR (400 MHz, CHLOROFORM-d) δ ppm 7.59 (dd, J = 8.8, 2.7 Hz, 1H) 7.54 (d, J = 2.7 Hz, 1H) 7.22 (d, J = 9.0 Hz, 1H) 6.86 (t, J = 6.2 Hz, 1H), 5.86 (d, J = 2.2 Hz, 1H) 4.28 (br. s., 1H) 3.84 (s, 3H) 3.65 (br. s., 1H) 2.75-2.78 (m, 3H) 2.71 (tt, J = 12.7, 6.3 Hz, 2H) 1.71-1.81 (m, 1H) 1.56-1.66 (m, 1H) |

TABLE 6-continued

Examples from Carboxylic Acid Route

| Example # | Structure | Compound Name | Obs Mass | 1H NMR Spectral Data or HPLC Retention Time and Conditions |
|---|---|---|---|---|
| 354 | 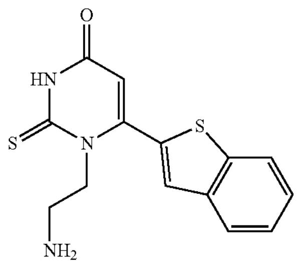 [SMILES: NCCn1c(-c2cc3ccccc3s2)cc(=O)[nH]c1=S] | 1-(2-amino ethyl)-6-(1-benzothiophen-2-yl)-2-thioxo-2,3-dihydro pyrimidin-4(1H)-one | 305.0 | 1H NMR (400 MHz, DMSO-d6) δ ppm 8.09 (br. s., 1H), 8.01 (br. s., 3H), 7.98 (br. s., 1H), 7.79 (s, 1H), 7.49 (br. s., 2H), 6.12 (s, 1H), 4.50 (br. s., 2H), 3.12 (br. s., 2H) |
| 355 | 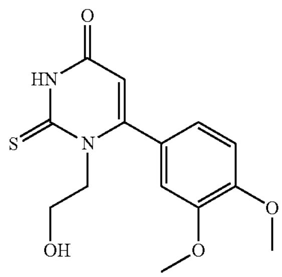 [SMILES: COc1ccc(-c2cc(=O)[nH]c(=S)n2CCO)cc1OC] | 6-(3,4-dimethoxy phenyl)-1-(2-hydroxyethyl)-2-thioxo-2,3-dihydropyrimidin-4(1H)-one | 309.1 | 1H NMR (400 MHz, DMSO-d6) δ ppm 7.12 (d, J = 1.8 Hz, 1H), 7.05 (d, J = 8.3 Hz, 1H), 7.01 (dd, J = 8.1, 1.9 Hz, 1H), 5.74 (s, 1H), 4.72 (t, J = 5.7 Hz, 1H), 4.19 (t, J = 6.4 Hz, 2H), 3.81 (s, 3H), 3.78 (s, 3H), 3.57 (q, J = 6.1 Hz, 2H) |
| 356 | 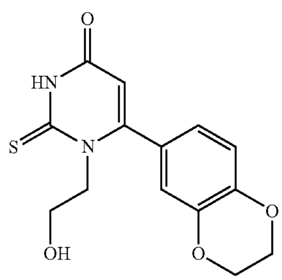 [SMILES: O=c1cc(-c2ccc3c(c2)OCCO3)n(CCO)c(=S)[nH]1] | 6-(2,3-dihydro-1,4-benzo dioxin-6-yl)-1-(2-hydroxyethyl)-2-thioxo-2,3-dihydro pyrimidin-4(1H)-one | 307.1 | 1H NMR (400 MHz, DMSO-d6) δ ppm 7.02 (d, J = 1.8 Hz, 1H), 6.94-6.97 (m, 1H), 6.92 (dd, J = 8.3, 1.8 Hz, 1H), 5.70 (s, 1H), 4.72 (t, J = 5.7 Hz, 1H), 4.25-4.33 (m, 4H), 4.17 (t, J = 6.4 Hz, 2H), 3.55 (q, J = 6.1 Hz, 2H) |
| 357 | 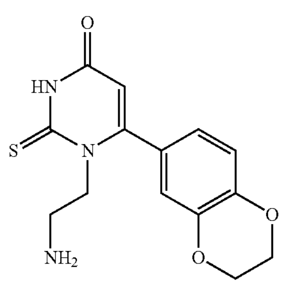 [SMILES: NCCn1c(-c2ccc3c(c2)OCCO3)cc(=O)[nH]c1=S] | 1-(2-aminoethyl)-6-(2,3-dihydro-1,4-benzo dioxin-6-yl)-2-thioxo-2,3-dihydropyrimidin-4(1H)-one | 306.0 | 1H NMR (400 MHz, DMSO-d6) δ ppm 7.89-8.01 (m, 3H), 7.07 (d, J = 1.8 Hz, 1H), 6.92-7.02 (m, 2H), 5.75 (s, 1H), 4.34 (br. s., 2H), 4.30 (br. s., 4H), 2.91-2.98 (m, 2H) |
| 358 | 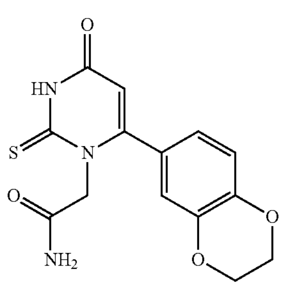 [SMILES: NC(=O)Cn1c(-c2ccc3c(c2)OCCO3)cc(=O)[nH]c1=S] | 2-[6-(2,3-dihydro-1,4-benzodioxin-6-yl)-4-oxo-2-thioxo-3,4-dihydropyrimidin-1(2H)-yl]acetamide | 320.0 | 2.039 min Symmetry-C18 2.1 × 50 mm 3.5 μm Mobile phase-A = 0.1 % FA in MeCN, B = 0.1% FA IN water; Time(min)/% B = 0/90, 0.5/90, 2/55, 3/55, 3.5/10, 6.5/10, 7/90; Flow: 0.5 mL/min, Column Temp = 40° C.; Diluent: ACN |

TABLE 6-continued

Examples from Carboxylic Acid Route

| Example # | Structure | Compound Name | Obs Mass | 1H NMR Spectral Data or HPLC Retention Time and Conditions |
|---|---|---|---|---|
| 359 | ABS | 6-(5-chloro-2-methoxyphenyl)-1-[(2S)-2,3-dihydroxypropyl]-2-thioxo-2,3-dihydropyrimidin-4(1H)-one | 343.0 | 2.018 min AQUITY BEH C-18, 2.1 × 50 mm, 1.7 μm Mobile Phase:A-0.1% FA IN MeCN, B-0.1% FA IN water T/% B(min): 0/90, 0.7/90, 2/55, 3/55, 3.8/5, 5.8/5, 6/90 Flow: 0.5 mL/min, Diluent: ACN, Temp - 40° C. |
| 360 | 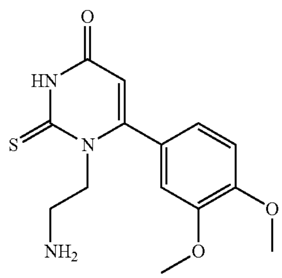 | 1-(2-amino ethyl)-6-(3,4-dimethoxy phenyl)-2-thioxo-2,3-dihydropyrimidin-4(1H)-one | 308.1 | 1H NMR (600 MHz, DMSO-d6) δ ppm 8.44 (br. s., 4H), 7.17 (d, J = 1.3 Hz, 1H), 7.09-7.05 (m, 1H), 7.05-6.96 (m, 1H), 5.78 (s, 1H), 4.36 (br. s., 2H), 3.81 (s, 3H), 3.79 (s, 3H), 2 97 (t, J = 7.2 Hz, 2H) |
| 361 | ABS | 1-[(2S)-2-aminopropyl]-6-(5-chloro-2-methoxyphenyl)-2-thioxo-2.3-dihydropyrimidin-4(1H)-one | 326.1 | 4.82 min × Bridge C-18 4.6 × 150 mm, 3.5 um M phase: A = MeCN; B = 5 mM ammonium acetate in water; TIME (min) % OF B: 0/95, 1/95, 3/5, 10/5, 10.05/95 flow: 0.8 ml/min, Diluent: ACN |
| 362 | 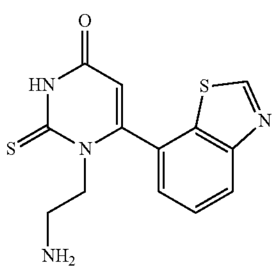 | 1-(2-aminoethyl)-6-(1,3-benzo thiazol-7-yl)-2-thioxo-2,3-dihydropyrimidin-4(1H)-one | 305.1 | 1H NMR (DMSO-d6) δ ppm 9.53 (s, 1H), 8.28 (dd, J = 7.5, 1.3 Hz, 1H), 7.80-8.10 (m, 3H), 7.68-7.77 (m, 2H), 6.07 (s, 1H), 4.44-4.54 (m, 1H), 4.02 (br. s., 1H), 2.92-2.98 (m, 1H), 2.83-2.91 (m, 1H) |
| 363 | 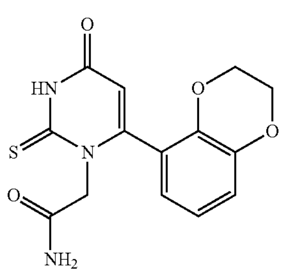 | 2-[6-(2,3-dihydro-1,4-benzodioxin-5-yl)-4-oxo-2-thioxo-3,4-dihydropyrimidin-1(2H)-yl] acetamide | 319.8 | 1H NMR (400 MHz, DMSO-d6) δ ppm 12.84 (br. s, 1H), 7.32 (s, 1H), 7.02 (dd, J = 8.5, 1.5 Hz, 2H), 6.91 (t, J = 7.8 Hz, 1H), 6.70-6.76 (m, J = 1.5 Hz, 1H), 5.83 (s, 1H), 5.42 (br. s, 1H), 4.26-4.38 (m, 4H), 3.93-4.07 (m, J = 7.0 Hz, 1H) |

TABLE 6-continued

Examples from Carboxylic Acid Route

| Example # | Structure | Compound Name | Obs Mass | 1H NMR Spectral Data or HPLC Retention Time and Conditions |
|---|---|---|---|---|
| 364 | 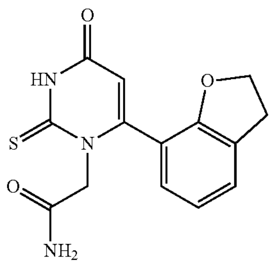 [SMILES: NC(=O)Cn1c(-c2cccc3c2OCC3)cc(=O)[nH]c1=S] | 2-[6-(2,3-dihydro-1-benzofuran-7-yl)-4-oxo-2-thioxo-3,4-dihydropyrimidin-1(2H)-yl) acetamide | 304.1 | 1H NMR (400 MHz, DMSO-d6) δ ppm 12.80 (br. s., 1H), 7.38 (d, J = 7.5 Hz, 2H), 7.00 (d, J = 8.5 Hz, 2H), 6.87-6.95 (m, 1H), 5.81 (s, 1H), 5.38-5.53 (m, 1H), 4.61 (t, J = 8.8 Hz, 2H), 3.98-4.11 (m, 1H), 3.24 (t, J = 9.0 Hz, 3H) |
| 365 | 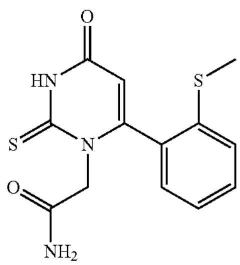 | 2-{6-[2-(methyl sulfanyl)phenyl]-4-oxo-2-thioxo-3,4-dihydro pyrimidin-1(2H) yl}acetamide | 307.8 | 1H NMR (400 MHz, METHANOL-d4) δ ppm 7.48-7.55 (m, 1H), 7.43 (d, J = 8.0 Hz, 1H), 7.22-7.32 (m, 2H), 5.81 (s, 1H), 5.54 (d, J = 17.1 Hz, 1H), 3.97 (d, J = 18.1 Hz, 1H), 2.54 (s, 3H) |
| 366 | 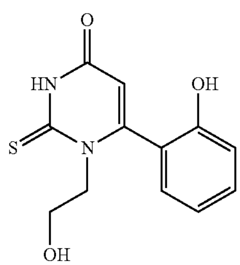 [SMILES: O=c1cc(-c2ccccc2O)n(CCO)c(=S)[nH]1] | 1-{2-hydroxy ethyl)-6-(2-hydroxyphenyl)-2-thioxo-2,3-dihydropyrimidin-4(1H)-one | 264.7 | 1H NMR (400 MHz, DMSO-d6) δ ppm 12.71 (br. s., 1H), 10.25 (s, 1H), 7.30-7.42 (m, 1H), 7.25 (d, J = 7.5 Hz, 1H), 6.86-7.00 (m, 2H), 5.71 (s, 1H), 4.72 (t, J = 5.5 Hz, 1H), 4.51-4.63 (m, 1H), 3.60-3.74 (m, 1H), 3.43-3.55 (m, J = 6.0 Hz, 2H) |
| 367 | 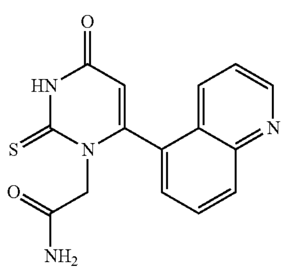 [SMILES: NC(=O)Cn1c(-c2cccc3ncccc23)cc(=O)[nH]c1=S] | 2-[4-oxo-6-(quinolin-5-yl)-2-thioxo-3,4-dihydropyrimidin-1(2H)-yl]acetamide | 313.1 | 1H NMR (400 MHz, DMSO-d6) δ ppm 12.75-13.08 (m, 1H), 9.00 (d, J = 2.5 Hz, 1H), 8.35 (d, J = 8.0 Hz, 1H), 8.18 (d, J = 8.5 Hz, 1H), 7.82-7.91 (m, 1H), 7.62 (br. s., 2H), 7.22 (s, 1H), 6.98 (br. s., 1H), 6.00 (s, 1H) |
| 368 | 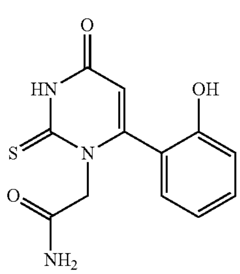 [SMILES: NC(=O)Cn1c(-c2ccccc2O)cc(=O)[nH]c1=S] | 2-[6-(2-hydroxyphenyl)-4-oxo-2-thioxo-3,4-dihydropyrimidin-1(2H)-yl]acetamide | 277.8 | 1H NMR (400 MHz, DMSO-d6) δ ppm 10.37 (br. s., 1H), 7.37 (br. s., 1H), 7.30-7.36 (m, J = 7.8, 7.8 Hz, 1H), 7.09 (dd, J = 7.8, 1.8 Hz, 1H), 6.98 (br. s., 1H), 6.96 (d, J = 8.5 Hz, 1H), 6.84-6.90 (m, 1H), 5.76 (s, 1H), 5.43 (br. s., 1H), 3.94 (br. s., 1H), 3.16 (d, J = 5.0 Hz, 1H) |

TABLE 6-continued

Examples from Carboxylic Acid Route

| Example # | Structure | Compound Name | Obs Mass | 1H NMR Spectral Data or HPLC Retention Time and Conditions |
|---|---|---|---|---|
| 369 | 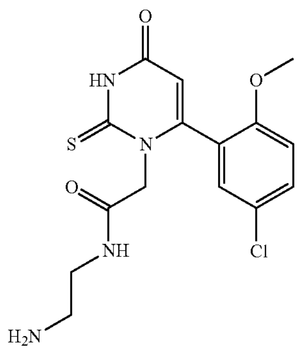 [SMILES: COc1ccc(Cl)cc1-c1cc(=O)[nH]c(=S)n1CC(=O)NCCN] | N-(2-aminoethyl)-2-[6-(5-chloro-2-methoxyphenyl)-4-oxo-2-thioxo-3,4-dihydropyrimidin-1(2H)-yl]acetamide | 369.2 | 1H NMR (400 MHz, DMSO-d6) δ ppm 12.93 (br. s., 1H), 8.24 (br. s., 1H), 7.88 (br. s., 3H), 7.57 (d, J = 9.0 Hz, 1H), 7.28-7.10 (m, 2H), 5.93 (s, 1H), 5.43 (d, J = 14.1 Hz, 1H), 4.05-3.92 (m, 1H), 3.85 (s, 3H), 3.16 (d, J = 4.5 Hz, 2H), 2.76-2.61 (m, 2H) |
| 370 | 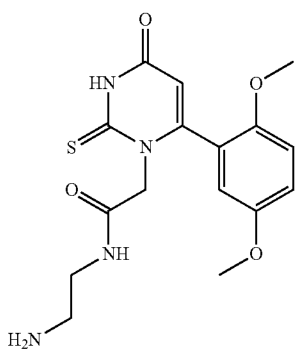 [SMILES: COc1ccc(OC)c(-c2cc(=O)[nH]c(=S)n2CC(=O)NCCN)c1] | N-(2-aminoethyl)-2-[6-(2,5-dimethoxyphenyl)-4-oxo-2-thioxo-3,4-dihydropyrimidin-1(2H)-yl]acetamide | 365.2 | 1H NMR (400 MHz, DMSO-d6) δ ppm 12.89 (s, 1H), 8.18 (t, J = 5.5Hz, 1H), 7.82 (br. s., 3H), 7.01-7.16 (m, 2H), 6.75 (s, 1H), 5.86 (d, J = 2.0 Hz, 1H), 5.25-5.53 (m, 1H), 4.02 (d, J = 17.1 Hz, 1H), 3.78 (s, 3H), 3.73 (br. s., 3H), 3.10-3.20 (m, 2H), 2.59-2.75 (m, 2H) |
| 371 | 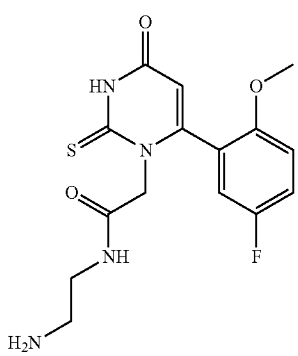 [SMILES: COc1ccc(F)cc1-c1cc(=O)[nH]c(=S)n1CC(=O)NCCN] | N-(2-aminoethyl)-2-[6-(5-fluoro-2-methoxyphenyl)-4-oxo-2-thioxo-3,4-dihydropyrimidin-1(2H)-yl]acetamide | 353.1 | 0.849 min LCMS-C(4#-302) Ultimate XB-C18 2.1 ×30 mm Mobile phase: from 0 MeCN (0.1% TFA) in water (0.1% TFA) to 60% MeCN (0.1% TFA) in water (0.1% TFA) |
| 372 | 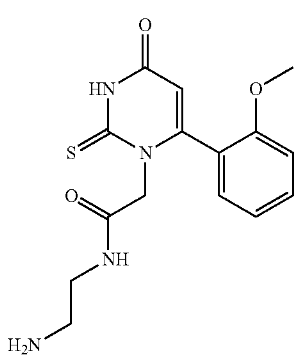 [SMILES: COc1ccccc1-c1cc(=O)[nH]c(=S)n1CC(=O)NCCN] | N-(2-aminoethyl)-2-[6-(2-methoxyphenyl)-4-oxo-2-thioxo-3,4-dihydropyrimidin-1(2H)-yl]acetamide | 335.1 | $^1$H NMR (400 MHz, METHANOL-d4) δ ppm 8.28 (t, J = 5.5 Hz, 1H), 7.51-7.59 (m, 1H), 7.27 (dd, J = 7.5, 1.5 Hz, 1H), 7.16 (d, J = 8.5 Hz, 1H), 7.01-7.10 (m, 1H), 5.84 (s, 1H), 5.45 (d, J = 15.1 Hz, 1H), 4.23 (d, J = 16.1 Hz, 1H), 3.90 (s, 3H), 3.35-3.45 (m, 1H), 3.23-3.29 (m, 1H), 2.87-3.00 (m, 2H) |

TABLE 6-continued

Examples from Carboxylic Acid Route

| Example # | Structure | Compound Name | Obs Mass | 1H NMR Spectral Data or HPLC Retention Time and Conditions |
|---|---|---|---|---|
| 373 | 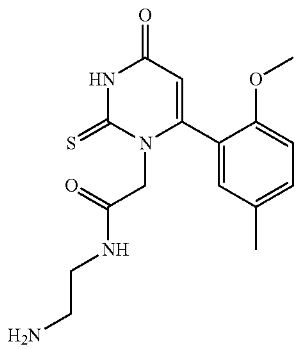 [SMILES: COc1ccc(C)cc1-c1cc(=O)[nH]c(=S)n1CC(=O)NCCN] | N-(2-aminoethyl)-2-[6-(2-methoxy-5-methyl phenyl)-4-oxo-2-thioxo-3,4-dihydropyrimidin-1(2H)-yl]acetamide | 349.1 | 1H NMR (400 MHz, METHANOL-d4) δ ppm 7.34 (dd, J = 8.5, 1.5 Hz, 1H), 7.07 (d, J = 2.0 Hz, 1H), 7.03 (d, J = 8.5 Hz, 1H), 5.81 (s, 1H), 5.44 (d, J = 14.1 Hz, 1H), 4.26 (d, J = 17.1 Hz, 1H), 3.86 (s, 3H), 3.33-3.43 (m, 1H), 3.24-3.29 (m, 1H), 2.85-3.00 (m, 2H), 2.30 (s, 3H) |
| 374 | 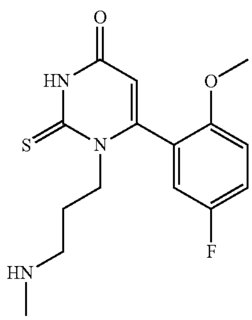 [SMILES: CNCCCn1c(-c2cc(F)ccc2OC)cc(=O)[nH]c1=S] | 6-(5-fluoro-2-methoxyphenyl)-1-[3-(methyl amino)propyl]-2-thioxo-2,3-dihydropyrimidin-4(1H)-one | 324.1 | 1H NMR (400 MHz, methanol-d3): δ ppm 7.33 (td, J = 8.03, 3.01 Hz, 1H), 7.26-7.17 (m, 2H), 5.84 (s, 1H), 4.66-4.50 (br s, 1H), 3.89 (s, 3H), 3.85-3.73 (br m, 1H), 2.86 (t, J = 7.53 Hz, 2H), 2.62 (s, 3H), 2.15-2.00 (m, 1H), 1.96-1.81 (m, 1H) |
| 375 | 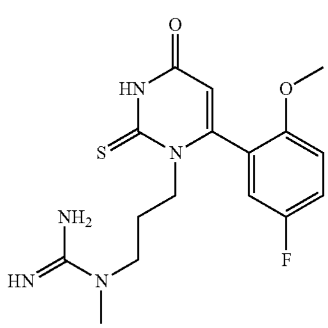 [SMILES: COc1ccc(F)cc1-c1cc(=O)[nH]c(=S)n1CCCN(C)C(=N)N] | 1-{3-[6-(5-fluoro-2-methoxyphenyl)-4-oxo-2-thioxo-3,4-dihydro pyrimidin-1(2H)-yl]propyl}-1-methylguanidine | 366.1 | 1H NMR (400 MHz, DMSO-d6): δ ppm 12.82 (s, 1H), 7.43-7.35 (m, 2H), 7.23-7.17 (m, 1H), 7.17-7.06 (br m, 4H), 5.86 (d, J = 2.01 Hz, 1H), 4.45-4.31 (brs, 1H), 3.82 (s, 3H), 3.67-3.54 (br m, 1H), 3.19-3.12 (br m, 2H), 2.75-2.65 (m 3H), 1.91-1.73 (m, 1H), 1.72-1.56 (m, 1H) |
| 376 | 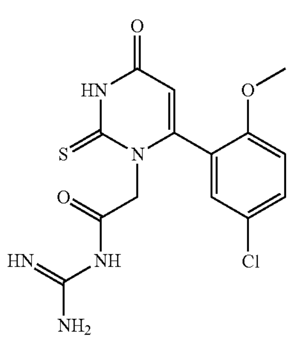 [SMILES: COc1ccc(Cl)cc1-c1cc(=O)[nH]c(=S)n1CC(=O)NC(=N)N] | N-carbamimidoyl-2-[6-(5-chloro-2-methoxy phenyl)-4-oxo-2-thioxo-3,4-dihydropyrimidin-1(2H)-yl] acetamide | 367.9 | 1H NMR (400 MHz, DMSO-d6) δ ppm 13.08 (s, 1 H), 11.64 (brs, 1 H), 8.19 (br s, 4H), 7.61 (dd, J = 9.03, 2.51 Hz, 1 H), 7.34-7.30 (m, 1 H), 7.22 (d, J = 9.03 Hz, 1H), 6.00 (s, 1 H), 5.15 (br s, 1 H), 4.45 (br s, 1 H), 3.83 (s, 3 H) |

TABLE 6-continued

Examples from Carboxylic Acid Route

| Example # | Structure | Compound Name | Obs Mass | 1H NMR Spectral Data or HPLC Retention Time and Conditions |
|---|---|---|---|---|
| 377 | 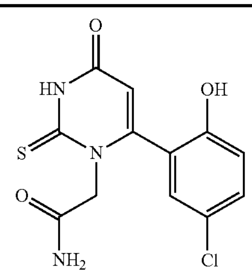 | 2-[6-(5-chloro-2-hydroxy phenyl)-4-oxo-2-thioxo-3,4-dihydropyrimidin-1(2H)-yl]acetamide | 312.0 | 1H NMR (400 MHz, DMSO-d6) δ ppm 12.80 (br. s., 1H), 10.64 (br. s., 1H), 7.34-7.42 (m, 2H), 7.10 (d, J = 9.5 Hz, 2H), 6.95 (d, J = 8.5 Hz, 1H), 5.86 (s, 1H), 5.47 (br. s., 1H), 3.92 (br. s., 1H) |

The following Examples of Table 7 (additions to Table 3) were prepared from the corresponding methyl ketone to afford the intermediate beta-keto-ester as described above for the Preparations in the Methyl Ketone Route section followed by employing other methods described in the I. Beta Ketone Ester Route Section as well as standard methods and techniques known to those skilled in the art.

TABLE 7

Examples from Methyl Ketone Route

| Example # | Structure | Compound Name | Obs Mass | 1H NMR Spectral Data or HPLC Retention Time and Conditions |
|---|---|---|---|---|
| 378 | 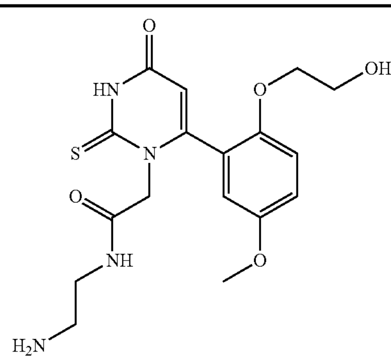 | N-(2-amino ethyl)-2-{6-[2-(2-hydroxy ethoxy)-5-methoxyphenyl]-4-oxo-2-thioxo-3,4-dihydropyrimidin-1(2H)-yl}acetamide | 395.1 | 1.10 min Xtimate C18, 2.1*30 mm Mobile phase: from 0% MeCN in water (0.1% TFA in water) to 30% MeCN in water (0.1% TFA in water) |
| 379 | 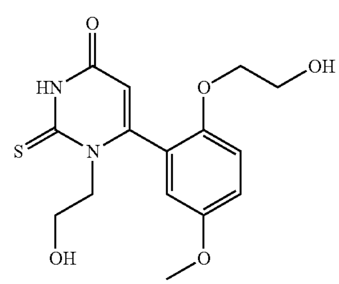 [SMILES: COc1ccc(OCCO)c(-c2cc(=O)[nH]c(=S)n2CCO)c1] | 6-[2-(2-hydroxyethoxy)-5-methoxy phenyl]-1-(2-hydroxyethyl)-2-thioxo-2,3-dihydropyrimidin-4(1H)-one | 339.2 | 1H NMR (400 MHz, methanol-d4): δ ppm 7.11-7.04 (m, 2H), 6.94-6.91 (m, 1H), 5.79 (s, 1H), 4.74-4.59 (m, 2H), 4.12-4.06 (m, 2H), 3.95-3.83 (m, 1H), 3.83-3.76 (m, 6H), 3.68-3.60 (m, 1H) |
| 380 | 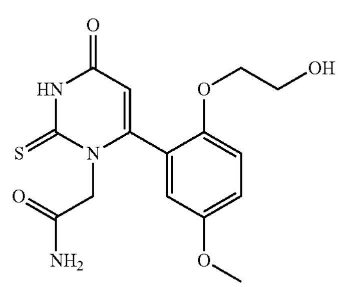 [SMILES: COc1ccc(OCCO)c(-c2cc(=O)[nH]c(=S)n2CC(N)=O)c1] | 2-{6-[2-(2-hydroxyethoxy)-5-methoxy phenyl]-4-oxo-2-thioxo-3,4-dihydropyrimidin-1(2H)-yl}acetamide | 374.1 | 1H NMR (400 MHz, DMSO-d6) δ ppm 12.79 (s, 1H), 7.35 (br. s., 1H), 6.99-7.15 (m, 3H), 6.76 (br. s., 1H), 5.81 (s, 1H), 5.24-5.43 (m, 1H), 4.73-4.92 (m, 1H), 4.01 (d, J = 5.5 Hz, 2H), 3.84-3.95 (m, 1H), 3.70 (s, 3H), 3.62 (t, J = 5.0 Hz, 2H) |

TABLE 7-continued

Examples from Methyl Ketone Route

| Example # | Structure | Compound Name | Obs Mass | 1H NMR Spectral Data or HPLC Retention Time and Conditions |
|---|---|---|---|---|
| 381 | 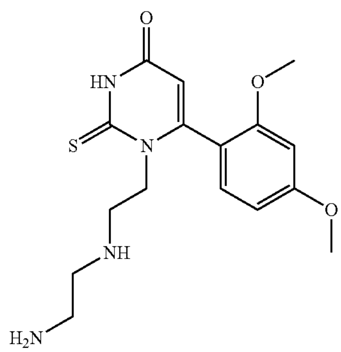 [SMILES: COc1ccc(-c2cc(=O)[nH]c(=S)n2CCNCCN)c(OC)c1] | 1-{2-[(2-aminoethyl)amino]ethyl}-6-(2,4-dimethoxyphenyl)-2-thioxo-2,3-dihydropyrimidin-4(1H)-one | 351.1 | 0.77 min Waters Acqity HSS T3, 2.1 × 50 mm, C18, 1.7 μm; A: 0.1% formic acid in water; Mobile phase B: 0.1% formic acid in MeCN A: 0.1% ammonia in water; Mobile phase B: 0.1% ammonia in MeCN Flow 1.25 ml/min |
| 382 | 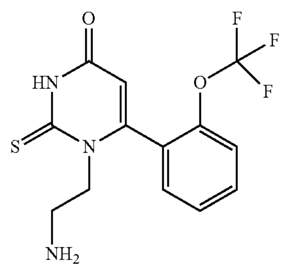 [SMILES: NCCn1c(-c2ccccc2OC(F)(F)F)cc(=O)[nH]c1=S] | 1-(2-aminoethyl)-2-thioxo-6-[2-(trifluoromethoxy)phenyl]-2,3-dihydropyrimidin-4(1H)-one | 331.9 | 3.41 min Waters symmetry 2.1 × 50 mm 5 um Mobile phase: from 0% MeCN in water (0.1% TFA) to 30% MeCN in water (0.1% TFA) |
| 383 | 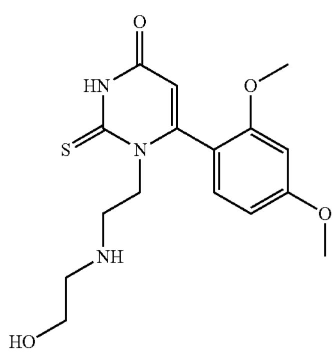 [SMILES: COc1ccc(-c2cc(=O)[nH]c(=S)n2CCNCCO)c(OC)c1] | 6-(2,4-dimethoxyphenyl)-1-{2-[(2-hydroxyethyl)amino]ethyl}-2-thioxo-2,3-dihydropyrimidin-4(1H)-one | 351.9 | 1H NMR (400 MHz, DMSO-d6) δ ppm 8.68 (br. s., 2H), 7.30 (d, J = 8.8 Hz, 1H), 7.10-7.21 (m, 1H), 6.70-6.75 (m, 1H), 6.63-6.69 (m, 1H), 5.76 (s, 1H), 5.18 (br. s., 1H), 4.69 (br. s., 1H), 3.99 (br. s., 1H), 3.85-3.81 (m, 6H), 3.70-3.78 (m, 1H), 3.55 (t, J = 5.0 Hz, 1H), 3.06 (br. s., 1H), 2.97-3.01 (m, 1H) 2.84 (br. s., 2H) |
| 384 | 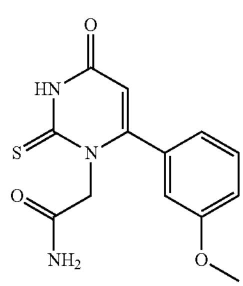 [SMILES: COc1cccc(-c2cc(=O)[nH]c(=S)n2CC(N)=O)c1] | 2-[6-(3-methoxyphenyl)-4-oxo-2-thioxo-3,4-dihydropyrimidin-1(2H)-yl]acetamide | 292.0 | 3.661 min XBRIDGE-C18 4.6 × 75 mm 3.5 μm Mobile phase-A = 0.1% FA IN MeCN, B = 0.1% FA IN water Time(min)/% B = 0/90, 1.8/55, 3/5, 6.5/5 ,7/90 Flow: 0.8 mL/min, Column Temp = 40° C.; Diluent: ACN |

TABLE 7-continued

Examples from Methyl Ketone Route

| Example # | Structure | Compound Name | Obs Mass | 1H NMR Spectral Data or HPLC Retention Time and Conditions |
|---|---|---|---|---|
| 385 | 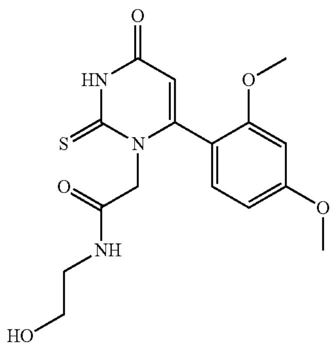 [SMILES: COc1ccc(-c2cc(=O)[nH]c(=S)n2CC(=O)NCCO)c(OC)c1] | 2-[6-(2,4-dimethoxyphenyl)-4-oxo-2-thioxo-3,4-dihydropyrimidin-1(2H)-yl]-N-(2-hydroxyethyl)acetamide | 365.4 | 1H NMR (400 MHz, METHANOL-d4) δ ppm 7.98 (br. s., 1H) 7.15 (d, J = 8.5 Hz, 1H) 6.65 (d, J = 2.0 Hz, 1H) 6.60 (dd, J = 8.5, 2.0 Hz, 1H) 5.77 (s, 1H) 5.50 (br. s., 1H) 4.20 (d, J = 15.1 Hz, 1H) 3.87 (s, 3H) 3.85 (s, 3H) 3.41-3.53 (m, 2H) 3.14-3.22 (m, 2H) |
| 386 | 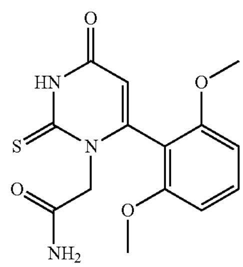 [SMILES: COc1cccc(OC)c1-c1cc(=O)[nH]c(=S)n1CC(N)=O] | 2-[6-(2,6-dimethoxyphenyl)-4-oxo-2-thioxo-3,4-dihydropyrimidin-1(2H)-yl]acetamide | 321.8 | 1H NMR (400 MHz, DMSO-d6) δ ppm 12.75 (br. s., 1H) 7.45 (t, J = 8.5 Hz, 1H) 7.13 (br. s., 1H) 6.92 (s, 1H) 6.77 (d, J = 8.0 Hz, 2H) 5.76 (s, 1H) 4.33-4.80 (m, 2H) 3.74 (s, 1H) |
| 387 | 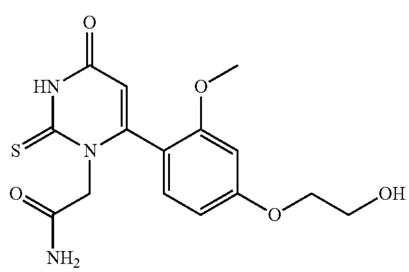 [SMILES: COc1cc(OCCO)ccc1-c1cc(=O)[nH]c(=S)n1CC(N)=O] | 2-{6-[4-(2-hydroxyethoxy)-2-methoxyphenyl]-4-oxo-2-thioxo-3,4-dihydropyrimidin-1(2H)-yl}acetamide | 352.1 | 1H NMR (400 MHz, DMSO-d6) δ ppm 12.76 (s, 1H), 7.31 (br. s., 1H), 7.06 (d, J = 8.5 Hz, 1H), 6.98 (s, 1H), 6.68 (d, J = 2.0 Hz, 1H), 6.60 (dd, J = 8.5, 2.0 Hz, 1H), 5.74 (d, J = 2.5 Hz, 1H), 5.37 (br. s., 1H), 4.04 (t, J = 5.0 Hz, 2H), 3.89 (br. s., 1H), 3.82 (s, 3H), 3.72 (t, J = 4.8 Hz, 2H) |
| 388 | ABS | 2-[6-(2,4-dimethoxyphenyl)-4-oxo-2-thioxo-3,4-dihydropyrimidin-1(2H)-yl]-N-[(3R)-pyrrolidin-3-yl]acetamide | 391.2 | 0.965 min LCMS-AI (4#-302) Ultimate XB-C18 2.1 × 30 mm Mobile phase: from 0 MeCN (0.1% TFA) in water (0.1% TFA) to 60% MeCN (0.1% TFA) in water (0.1% TFA) |

TABLE 7-continued

Examples from Methyl Ketone Route

| Example # | Structure | Compound Name | Obs Mass | 1H NMR Spectral Data or HPLC Retention Time and Conditions |
|---|---|---|---|---|
| 389 | 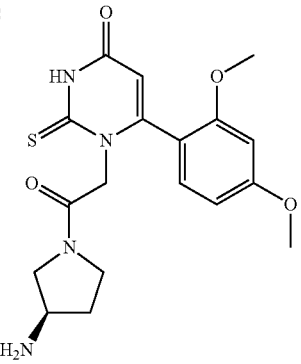 ABS | 1-{2-[(3R)-3-aminopyrrolidin-1-yl]-2-oxoethyl}-6-(2,4-dimethoxyphenyl)-2-thioxo-2,3-dihydropyrimidin-4(1H)-one | 413.2 | 0.972 min LCMS-AI (4#-302) Ultimate XB-C18 2.1 × 30 mm Mobile phase: from 0 MeCN (0.1% TFA) in water (0.1% TFA) to 60% MeCN (0.1% TFA) in water (0.1% TFA) |
| 390 | 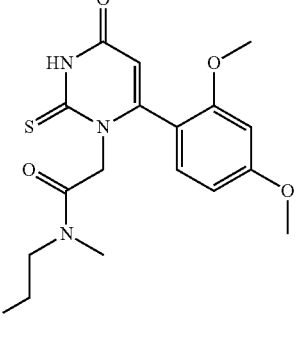 | N-(2-aminoethyl)-2-[6-(2,4-dimethoxyphenyl)-4-oxo-2-thioxo-3,4-dihydropyrimidin-1(2H)-yl]-N-methyl acetamide | 379.0 | 1H NMR (400 MHz, METHANOL-d4) δ ppm 7.17 (d, J = 8.5 Hz, 1H), 6.68 (s, 1H), 6.60 (d, J = 7.5 Hz, 1H), 5.80 (s, 1H), 5.65 (d, J = 17.1 Hz, 1H), 4.33 (d, J = 16.6 Hz, 1H), 3.88 (s, 3H), 3.85 (s, 3H), 3.59-3.70 (m, 1H), 3.36-3.49 (m, 1H), 3.02 (br. s., 2H), 2.97 (s, 3H) |
| 391 | 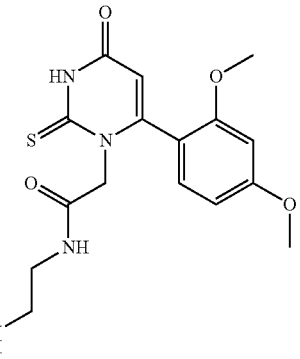 | 2-[6-(2,4-dimethoxyphenyl)-4-oxo-2-thioxo-3,4-dihydropyrimidin-1(2H)-yl]-N-[2-(methylamino)ethyl]acetamide | 379.2 | $^1$H NMR (400 MHz, METHANOL-d$_4$) δ ppm 8.34 (t, J = 5.8 Hz, 1H), 7.17 (d, J = 8.5 Hz, 1H), 6.67 (d, J = 2.0 Hz, 1H), 6.62 (dd, J = 8.5, 2.0 Hz, 1H), 5.81 (s, 1H), 5.42 (d, J = 16.6 Hz, 1H), 4.28 (d, J = 16.6 Hz, 1H), 3.88 (s, 3H), 3.85 (s, 3H), 3.40-3.48 (m, 1H), 3.33-3.38 (m, 1H), 3.00-3.07 (m, 2H), 2.69 (s, 3H) |
| 392 | 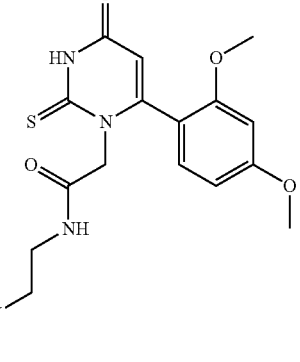 | 2-[6-(2,4-dimethoxyphenyl)-4-oxo-2-thioxo-3,4-dihydropyrimidin-1(2H)-yl]-N-[2-(dimethylamino)ethyl]acetamide | 393.2 | $^1$H NMR (400 MHz, DMSO-d$_6$) δ ppm 12.82 (s, 1H), 10.19 (br. s., 1H), 8.28 (br. s., 1H), 7.09 (d, J = 8.0 Hz, 1H), 6.69 (d, J = 2.0 Hz, 1H), 6.62 (dd, J = 8.5, 2.0 Hz, 1H), 5.79 (d, J = 2.0 Hz, 1H), 5.37 (d, J = 12.5 Hz, 1H), 4.02 (d, J = 16.6 Hz, 1H), 3.83 (s, 3H), 3.81 (s, 3H), 2.95 (d, J = 18.1 Hz, 2H), 2.70 (br. s., 6H) |

TABLE 7-continued

Examples from Methyl Ketone Route

| Example # | Structure | Compound Name | Obs Mass | 1H NMR Spectral Data or HPLC Retention Time and Conditions |
|---|---|---|---|---|
| 393 | ABS 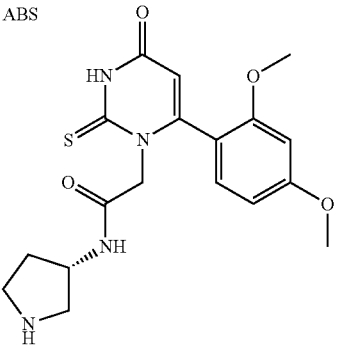 | 2-[6-(2,4-dimethoxyphenyl)-4-oxo-2-thioxo-3,4-dihydropyrimidin-1(2H)-yl]-N-[(3S)-pyrrolidin-3-yl]acetamide | 391.2 | $^1$H NMR (400 MHz, METHANOL-d$_4$) δ ppm 7.16 (dd, J = 8.3, 5.3 Hz, 1H), 6.67 (s, 1H), 6.61 (dt, J = 8.5, 2.3 Hz, 1H), 5.79 (s, 1H), 5.39-5.62 (m, 1H), 4.16-4.34 (m, 2H), 3.88 (d, J = 3.5 Hz, 3H), 3.85 (s, 3H), 3.49-3.37 (m, 2H), 3.09-3.17 (m, 1H), 2.95-3.02 (m, 1H), 2.14-2.32 (m, 1H), 1.80-1.98 (m, 1H) |
| 394 | ABS 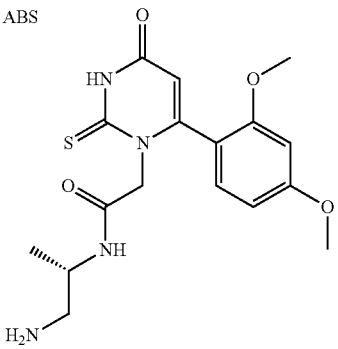 | N-[(2S)-1-aminopropan-2-yl]-2-[6-(2,4-dimethoxyphenyl)-4-oxo-2-thioxo-3,4-dihydropyrimidin-1(2H)-yl]acetamide | 379.2 | $^1$H NMR (400 MHz, METHANOL-d$_4$, rotameric mixture) δ ppm 7.20 (d, J = 8.0 Hz, 0.4H) 7.14 (d, J = 8.5 Hz, 0.6H) 6.67 (d, J = 2.0 Hz, 1H) 6.61 (td, J = 2.3, 8.5 Hz, 1H) 5.81 (s, 0.6H), 5.79 (s, 0.4H) 5.63 (d, J = 15.6 Hz, 1H) 5.35-5.27 (m, 1H) 4.35-4.27 (m, 0.4H) 4.20 (d, J = 16.6 Hz, 0.6H) 4.05-3.94 (m, 1H) 3.89 (s, 2H), 3.87 (s, 1H) 3.85 (d, J = 1.5 Hz, 3H) 3.04-2.92 (m, 0.7H) 2.89-2.77 (m, 1.3H) 1.19 (d, J = 6.5 Hz, 1H) 1.05 (d, J = 7.0 Hz, 2H) |
| 395 | ABS 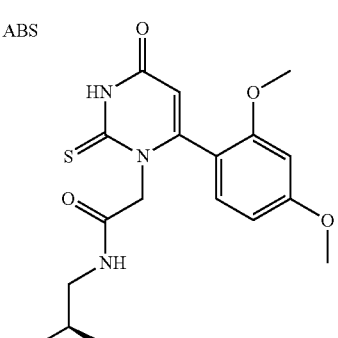 | N-[(2R)-2-aminopropyl]-2-[6-(2,4-dimethoxyphenyl)-4-oxo-2-thioxo-3,4-dihydropyrimidin-1(2H)-yl]acetamide | 379.2 | 1H NMR (400 MHz, METHANOL-d4) δ ppm 7.22 (t, J = 8.3 Hz, 1H), 6.72 (s, 1H), 6.66 (d, J = 8.5 Hz, 1H), 5.86 (s, 1H), 5.37-5.64 (m, 1H), 4.35 (d, J = 15.1 Hz, 1H), 3.93 (d, J = 2.5 Hz, 3H), 3.90 (s, 3H), 3.34-3.47 (m, 3H), 1.25 (dd, J = 13.3, 5.8 Hz, 3H) |
| 396 | ABS 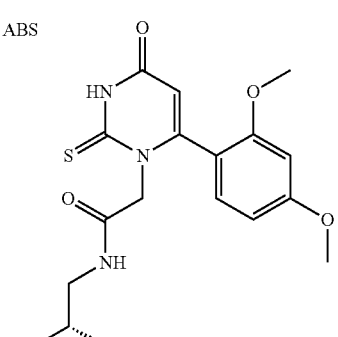 | N-[(2S)-2-aminopropyl]-2-[6-(2,4-dimethoxyphenyl)-4-oxo-2-thioxo-3,4-dihydropyrimidin-1(2H)-yl]acetamide | 379.2 | $^1$H NMR (400 MHz, DMSO-d$_6$) δ ppm 12.81 (br. s., 1H), 8.24 (d, J = 3.0 Hz, 1H), 7.97 (br. s., 3H), 7.07 (dd, J = 11.8, 8.3 Hz, 1H), 6.65-6.73 (m, 1H), 6.59 (ddd, J = 8.4, 4.1, 2.0 Hz, 1H), 5.78 (d, J = 2.0 Hz, 1H), 5.28-5.50 (m, 1H), 4.06 (d, J = 15.6 Hz, 1H), 3.83 (d, J = 2.5 Hz, 3H), 3.81 (s, 2H), 3.21 (d, J = 6.5 Hz, 1H), 2.93-3.09 (m, 2H), 0.93-1.06 (m, 3H) |

TABLE 7-continued

Examples from Methyl Ketone Route

| Example # | Structure | Compound Name | Obs Mass | 1H NMR Spectral Data or HPLC Retention Time and Conditions |
|---|---|---|---|---|
| 397 | 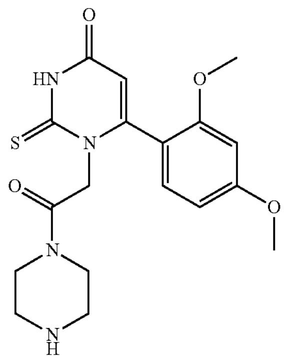 [SMILES: COc1ccc(-c2cc(=O)[nH]c(=S)n2CC(=O)N2CCNCC2)c(OC)c1] | 6-(2,4-dimethoxyphenyl)-1-[2-oxo-2-(piperazin-1-yl)ethyl]-2-thioxo-2,3-dihydropyrimidin-4(1H)-one | 391.2 | 0.879 min Xtimate C18, 2.1 × 30 mm, 3 um Mobile phase: from 0% MeCN in water (0.0685% TFA in water) to 60% MeCN in water (0.0685% TFA in water) |
| 398 | ABS | 1-{2-[(3S)-3-aminopyrrolidin-1-yl]-2-oxoethyl}-6-(2,4-dimethoxyphenyl)-2-thioxo-2,3-dihydropyrimidin-4(1H)-one | 413.0 | 0.988 min LCMS-AI (4#-302) Xtimate C18, 2.1 × 30 mm, 3 um Mobile phase: from 0% MeCN (0.1% TFA) in water (0.1% TFA) to 60% MeCN (0.1% TFA) in water (0.1% TFA) |
| 399 | ABS | N-[2-({[6-(2,4-dimethoxyphenyl)-4-oxo-2-thioxo-3,4-dihydropyrimidin-1(2H)-yl]acetyl}amino)ethyl]-L-alaninamide | 436.0 | 1H NMR (400 MHz, DMSO-d6) δ ppm 8.33 (s, 1H) 8.12 (br. s., 1H) 8.06 (br. s., 1H) 7.07 (d, J = 8.5 Hz, 1H) 6.68 (d, J = 2.5 Hz, 1H) 6.56-6.63 (m, 1H) 5.77 (s, 1H), 5.38 (br. s., 1H) 4.22 (br., 3H) 3.97 (d, J = 13.6 Hz, 1H) 3.82-3.88 (m, 3H) 3.81 (s, 3H) 3.37-3.48 (m, 1H) 2.99 (br. s., 4H) 1.17 (d, J = 7.0 Hz, 3H) |

TABLE 7-continued

Examples from Methyl Ketone Route

| Example # | Structure | Compound Name | Obs Mass | 1H NMR Spectral Data or HPLC Retention Time and Conditions |
|---|---|---|---|---|
| 400 | 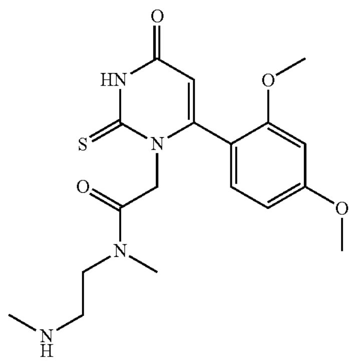 | 2-[6-(2,4-dimethoxyphenyl)-4-oxo-2-thioxo-3,4-dihydropyrimidin-1(2H)-yl]-N-methyl-N-[2-(methylamino)ethyl]acetamide | 393.2 | $^1$H NMR (METHANOL-$d_4$, rotameric mixture) δ ppm 7.18 (d, J = 8.5 Hz, 0.6H) 7.13 (d, J = 8.5 Hz, 0.4H) 6.67 (d, J = 2.0 Hz, 1H) 6.56-6.63 (m, 1H) 5.74-5.81 (m, 1H) 5.66 (d, J = 16.6 Hz, 1H) 4.23-4.38 (m, 1H) 3.87-4.00 (m, 3H) 3.80 (s, 3H) 3.53 (dt, J = 13.6, 6.8 Hz, 0.6H) 3.34-3.40 (m, 0.4H) 3.14-3.27 (m, 1H) 2.93 (s, 2H) 2.84 (s, 1H) 2.57-2.73 (m, 2H) 2.38 (s, 2H) 2.33 (s, 1H) |
| 401 | ABS | N-[(2R)-1-aminopropan-2-yl]-2-[6-(2,4-dimethoxyphenyl)-4-oxo-2-thioxo-3,4-dihydropyrimidin-1(2H)-yl]acetamide | 379.1 | $^1$H NMR (400 MHz, METHANOL-$d_4$, rotameric mixture) δ ppm 7.20 (d, J = 8.0 Hz, 0.4H) 7.14 (d, J = 8.5 Hz, 0.6H) 6.67 (d, J = 2.0 Hz, 1H) 6.61 (td, J = 2.3, 8.5 Hz, 1H) 5.81 (s, 0.6H) 5.79 (s, 0.4H) 5.63 (d, J = 15.6 Hz, 1H) 5.35-5.27 (m, 1H) 4.35-4.27 (m, 0.4H) 4.20 (d, J = 16.6 Hz, 0.6H) 4.05-3.94 (m, 1H) 3.89 (s, 2H) 3.87 (s, 1H) 3.85 (d, J = 1.5 Hz, 3H) 3.04-2.92 (m, 0.7H) 2.89-2.77 (m, 1.3H) 1.19 (d, J = 6.5 Hz, 1H) 1.05 (d, J = 7.0 Hz, 2H) |
| 402 | 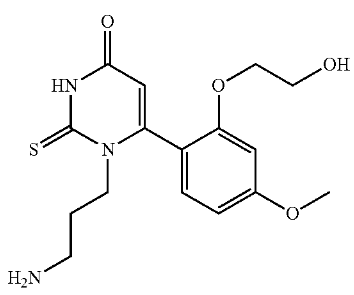 [SMILES: COc1ccc(-c2cc(=O)[nH]c(=S)n2CCCN)c(OCCO)c1] | 1-(3-aminopropyl)-6-[2-(2-hydroxyethoxy)-4-methoxyphenyl]-2-thioxo-2,3-dihydropyrimidin-4(1H)-one | 352.2 | 1H NMR (400 MHz, DMSO-d6) δ ppm 12.75 (s, 1H), 7.73 (br s, 3 H), 7.28 (d, J = 8.03 Hz, 1H), 6.72 (d, J = 2.51 Hz, 1H), 6.64 (dd, J = 8.53, 2.51 Hz, 1H), 5.77-5.73 (m, 1H), 4.40 (br s, 1H), 4.10 (t, J = 5.02 Hz, 2H), 3.82 (s, 3H), 3.75-3.66 (br s, 1H), 3.64 (t, J = 5.02 Hz, 2H), 2.50-2.51 (m, 2H), 1.90-1.78 (m, 1H), 1.78-1.66 (m, 1H) |
| 403 | 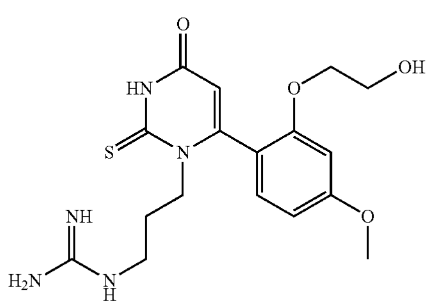 [SMILES: COc1ccc(-c2cc(=O)[nH]c(=S)n2CCCNC(=N)N)c(OCCO)c1] | 1-(3-{6-[2-(2-hydroxyethoxy)-4-methoxyphenyl]-4-oxo-2-thioxo-3,4-dihydropyrimidin-1(2H)-yl}propyl)guanidine | 394.1 | 1H NMR (400 MHz, DMSO-d6) δ ppm 12.70 (s, 1H), 7.35 (t, J = 6.02 Hz, 1H), 7.25 (d, J = 8.53 Hz, 1H), 7.22-6.74 (br s, 4H), 6.71 (d, J = 2.51 Hz, 1H), 6.62 (dd, J = 8.03, 2.51 Hz, 1H), 5.73 (d, J = 2.01 Hz, 1H), 4.87 (br s, 1H), 4.39 (br s, 1H), 4.15-4.02 (m, 2H), 3.82 (s, 3H), 3.60-3.74 (m, 3H), 2.98-2.93 (m, 2H), 1.85-1.68 (m, 1H), 1.66-1.51 (m, 1H) |

TABLE 7-continued

Examples from Methyl Ketone Route

| Example # | Structure | Compound Name | Obs Mass | 1H NMR Spectral Data or HPLC Retention Time and Conditions |
|---|---|---|---|---|
| 404 | 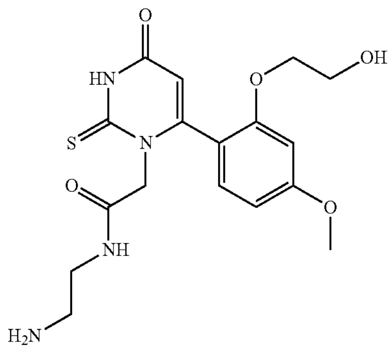 [SMILES: COc1ccc(-c2cc(=O)[nH]c(=S)n2CC(=O)NCCN)c(OCCO)c1] | N-(2-aminoethyl)-2-{6-[2-(2-hydroxyethoxy)-4-methoxyphenyl]-4-oxo-2-thioxo-3,4-dihydropyrimidin-1(2H)-yl}acetamide | 395.12 | 1H NMR (400 MHz, Methanol-d4) δ ppm 8.35-8.26 (m, 0.3H), 7.18 (d, J = 8.53 Hz, 1H), 6.68 (d, J = 2.01 Hz, 1H), 6.62 (dd, J = 8.53, 2.01 Hz, 1H), 5.82 (s, 1H), 5.52-5.37 (br m, 1H), 4.42-4.29 (br m, 1H), 4.20-4.09 (m, 2H), 3.90-3.79 (m, 5H), 3.43-3.33 (m, 2H), 3.00-2.90 (m, 2H) |
| 405 | 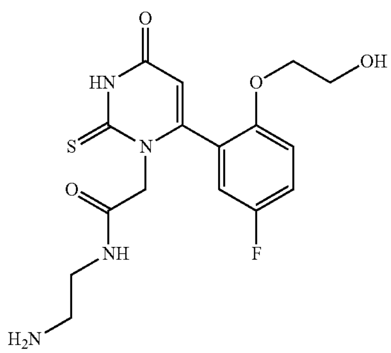 | N-(2-aminoethyl)-2-{6-[5-fluoro-2-(2-hydroxyethoxy)phenyl]-4-oxo-2-thioxo-3,4-dihydropyrimidin-1(2H)-yl}acetamide | 383.1 | 1H NMR (400 MHz, Methanol-d4) δ ppm 7.27 (td, J = 9.03, 3.01 Hz, 1H), 7.16 (dd, J = 9.03, 4.02 Hz, 1H), 7.08 (dd, J = 8.03, 2.51 Hz, 1H), 5.88 (s, 1H), 5.50-5.38 (br m, 1H), 4.36-4.26 (br m, 1H), 4.20-4.10 (m, 2H), 3.84 (t, J = 4.02 Hz, 2H), 3.44-3.33 (m, 2H), 3.00-2.93 (m, 2H) |
| 406 | 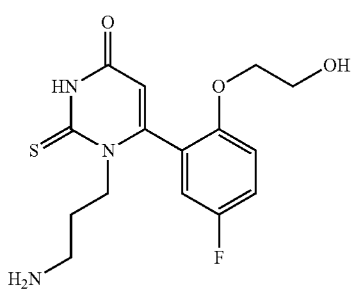 [SMILES: NCCCn1c(-c2cc(F)ccc2OCCO)cc(=O)[nH]c1=S] | 1-(3-aminopropyl)-6-[5-fluoro-2-(2-hydroxyethoxy)phenyl]-2-thioxo-2,3-dihydropyrimidin-4(1H)-one | 340.1 | 1H NMR (400 MHz, Methanol-d4) δ ppm 7.31 (td, J = 9.03, 3.01 Hz, 1H), 7.25-7.18 (m, 2H), 5.85 (s, 1 H), 4.57-4.44 (br s, 1H), 4.03-3.90 (br m, 2H), 3.97-3.96 (m, 1H), 3.84 (t, J = 4.02 Hz, 2H), 2.79 (t, J = 8.03 Hz, 2H), 2.13-2.00 (m, 1H), 1.95-1.82 (m, 1H) |
| 407 | 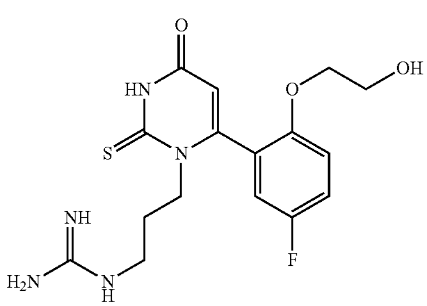 [SMILES: N=C(N)NCCCn1c(-c2cc(F)ccc2OCCO)cc(=O)[nH]c1=S] | 1-(3-{6-[5-fluoro-2-(2-hydroxyethoxy)phenyl]-4-oxo-2-thioxo-3,4-dihydropyrimidin-1(2H)-yl}propyl)guanidine | 382.1 | 1H NMR (400 MHz, Methanol-d4) δ ppm 7.30 (td, J = 9.03, 3.01 Hz, 1H), 7.25-7.15 (m, 2H), 5.84 (s, 1H), 4.60-4.46 (br m, 1H), 4.19-4.10 (m, 2H), 3.96-3.79 (m, 3H), 3.10-3.01 (m, 2H), 2.06-1.93 (m, 1H), 1.83-1.68 (m, 1H) |

TABLE 7-continued

Examples from Methyl Ketone Route

| Example # | Structure | Compound Name | Obs Mass | 1H NMR Spectral Data or HPLC Retention Time and Conditions |
|---|---|---|---|---|
| 408 | 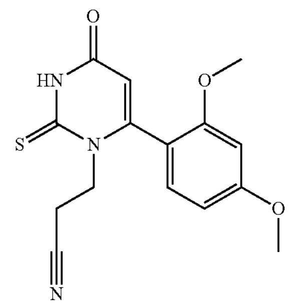 [SMILES: COc1ccc(-c2cc(=O)[nH]c(=S)n2CCC#N)c(OC)c1] | 3-[6-(2,4-dimethoxyphenyl)-4-oxo-2-thioxo-3,4-dihydropyrimidin-1(2H)-yl]propanenitrile | 318.1 | 1H NMR (400 MHz, chloroform-d) δ ppm δ 9.57 (br s, 1H), 7.22 (d, J = 8.53 Hz, 1H), 6.62 (dd, J = 8.53, 2.51 Hz, 1H), 6.55 (d, J = 2.51 Hz, 1H), 5.85 (d, J = 2.51 Hz, 1H), 4.67-4.53 (br m, 1H), 4.19-4.05 (br m, 1H), 3.89 (s, 3H), 3.86 (s, 3H), 3.19-3.06 (m, 1H) 2.71-2.63 (m, 1H) |
| 409 | 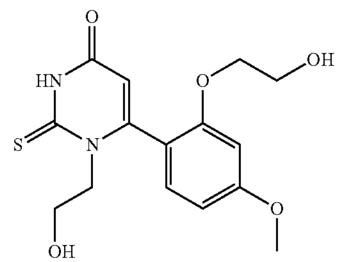 [SMILES: COc1ccc(-c2cc(=O)[nH]c(=S)n2CCO)c(OCCO)c1] | 6-[2-(2-hydroxyethoxy)-4-methoxyphenyl]-1-(2-hydroxyethyl)-2-thioxo-2,3-dihydropyrimidin-4(1H)-one | 338.9 | 1H NMR (400 MHz, DMSO-d6) δ ppm 12.65 (s, 1 H), 7.22 (br s, 1 H), 6.78-6.53 (br m, 2 H), 5.68 (br s, 1H), 4.90-4.78 (br m, 1H), 4.72-4.62 (br m, 1H), 4.59-4.42 (br m, 1H), 4.19-3.97 (br m, 2H), 3.81 (br s, 3H), 3.64 (br s, 3H) |
| 410 | 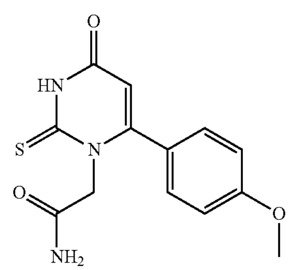 [SMILES: COc1ccc(-c2cc(=O)[nH]c(=S)n2CC(N)=O)cc1] | 2-[6-(4-methoxyphenyl)-4-oxo-2-thioxo-3,4-dihydropyrimidin-1(2H)-yl]acetamide | 314.1 | 0.905 min LCMS-C (4#-302) Ultimate XB-C18 2.1 × 30 mm Mobile phase: from 0 MeCN (0.1% TFA) in water (0.1% TFA) to 60% MeCN (0.1% TFA) in water (0.1% TFA) |
| 411 | 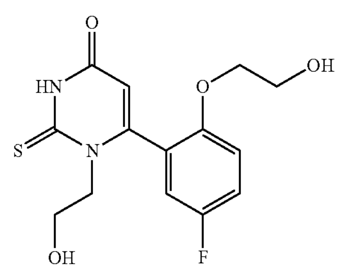 [SMILES: O=c1cc(-c2cc(F)ccc2OCCO)n(CCO)c(=S)[nH]1] | 6-[5-fluoro-2-(2-hydroxyethoxy)phenyl]-1-(2-hydroxyethyl)-2-thioxo-2,3-dihydropyrimidin-4(1H)-one | 326.8 | 1H NMR (400 MHz, methanol-d4) δ ppm 7.25 (td, J = 9.03, 3.01 Hz, 1H), 7.19-7.13 (m, 2H), 5.80 (s, 1H), 4.76-4.65 (m, 1H), 4.61 (br s, 1H), 4.16-4.09 (m, 2H), 3.88-3.78 (m, 3H), 3.66-3.60 (m, 1H) |
| 412 | 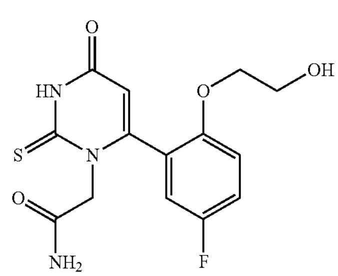 [SMILES: NC(=O)Cn1c(-c2cc(F)ccc2OCCO)cc(=O)[nH]c1=S] | 2-{6-[5-fluoro-2-(2-hydroxyethoxy)phenyl]-4-oxo-2-thioxo-3,4-dihydropyrimidin-1(2H)-yl}acetamide | 362.1 | 1H NMR (400 MHz, methanol-d4) δ ppm 7.25 (td, J = 9.03, 3.01, 1H), 7.15 (dd, J = 9.03, 4.02 Hz, 1H), 7.06 (dd, J = 8.03, 3.01 Hz, 1H), 5.84 (s, 3H), 5.67-5.42 (br s, 1H), 4.37-4.18 (br s, 1H), 4.14 (t, J = 4.52 Hz, 2H), 3.83 (t, J = 4.02 Hz, 2H) |

TABLE 7-continued

Examples from Methyl Ketone Route

| Example # | Structure | Compound Name | Obs Mass | 1H NMR Spectral Data or HPLC Retention Time and Conditions |
|---|---|---|---|---|
| 413 | 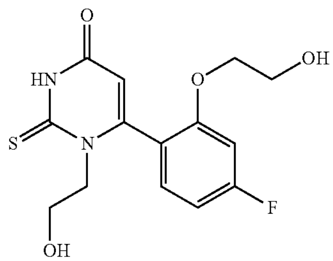 [SMILES: O=c1cc(-c2ccc(F)cc2OCCO)n(CCO)c(=S)[nH]1] | 6-[4-fluoro-2-(2-hydroxyethoxy)phenyl]-1-(2-hydroxyethyl)-2-thioxo-2,3-dihydropyrimidin-4(1H)-one | 327.2 | 1H NMR (400 MHz, DMSO-d6) δ ppm 12.71 (s, 1H), 7.39-7.33 (m, 1H), 7.12 (dd, J = 11.54, 2.01 Hz, 1H), 6.90 (td, J = 8.53, 2.51 Hz, 1H), 5.75 (s, 1H), 5.73 (d, J = 2.01 Hz, 1H), 4.97-4.79 (br s, 1H), 4.77-4.62 (br s, 1H), 4.53-4.43 (m, 1H), 4.16-4.04 (m, 2H), 3.64 (br t, J = 4.52 Hz, 2H), 3.61-3.49 (m, 2H) |
| 414 | 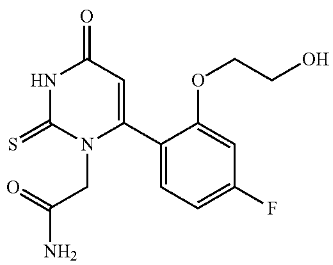 [SMILES: NC(=O)Cn1c(-c2ccc(F)cc2OCCO)cc(=O)[nH]c1=S] | 2-{6-[4-fluoro-2-(2-hydroxyethoxy)phenyl]-4-oxo-2-thioxo-3,4-dihydropyrimidin-1(2H)-yl}acetamide | 362.2 | 1H NMR (400 MHz, DMSO-d6) δ ppm 12.80 (s, 1H), 7.33 (br s, 1H), 7.24-7.17 (m, 1H), 7.12 (d, J = 11.54 Hz, 1H), 7.01 (br s, 1H), 6.91-6.83 (m, 1H), 5.79 (s, 1H), 5.52-5.22 (br s, 1H), 4.97-4.81 (br m, 1H), 4.17-4.05 (br m, 2H), 4.02-3.85 (br s, 1H), 3.69-3.60 (br m, 2H) |
| 415 | 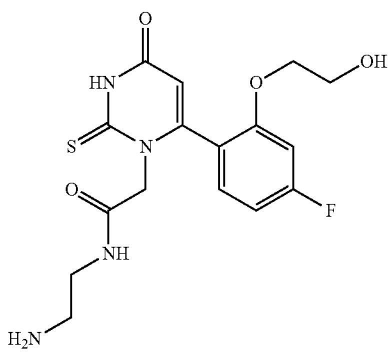 [SMILES: NCCNC(=O)Cn1c(-c2ccc(F)cc2OCCO)cc(=O)[nH]c1=S] | N-(2-aminoethyl)-2-{6-[4-fluoro-2-(2-hydroxyethoxy)phenyl]-4-oxo-2-thioxo-3,4-dihydropyrimidin-1(2H)-yl}acetamide | 383.2 | 1H NMR (400 MHz, methanol-d4) δ ppm 8.33-8.24 (m, 1H), 7.33-7.27 (m, 1H), 7.00 (dd, J = 10.90, 1.71 Hz, 1H), 6.81 (td, J = 8.03, 2.01 Hz, 1H), 5.85 (s, 1H), 5.52-5.39 (br m, 1H), 4.37-4.26 (br m, 1H), 4.23-4.12 (m, 2H), 3.85 (br t, J = 4.02 Hz, 2H), 3.47-3.35 (m, 2H), 3.00-2.91 (m, 2H) |
| 416 | 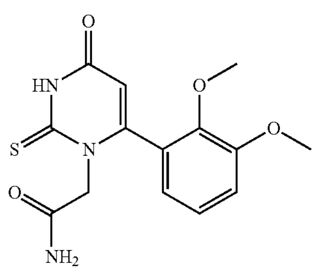 [SMILES: COc1cccc(-c2cc(=O)[nH]c(=S)n2CC(N)=O)c1OC] | 2-[6-(2,3-dimethoxyphenyl)-4-oxo-2-thioxo-3,4-dihydropyrimidin-1(2H)-yl]acetamide | 322.1 | 1H NMR (400 MHz, DMSO-d6) δ ppm 12.77 (br. s., 1H), 7.26 (br. s., 1H), 7.17-7.23 (m, 1H), 7.08-7.17 (m, 1H), 6.93 (br. s., 1H), 6.75 (d, J = 7.5 Hz, 1H), 5.75 (br. s., 1H), 5.42 (br. s., 1H), 4.11 (br. s., 1H), 3.85 (s, 3H), 3.72 (s, 3H) |
| 417 | 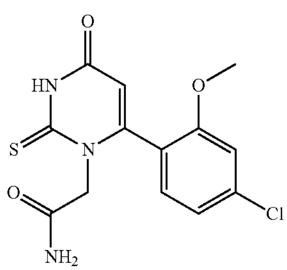 [SMILES: COc1cc(Cl)ccc1-c1cc(=O)[nH]c(=S)n1CC(N)=O] | 2-[6-(4-chloro-2-methoxyphenyl)-4-oxo-2-thioxo-3,4-dihydropyrimidin-1(2H)-yl]acetamide | 326.2 | 1H NMR (400 MHz, DMSO-d6) δ ppm 12.81 (br. s., 1H), 7.34 (br. s., 1H), 7.28 (s, 1H), 7.15-7.20 (m, 1H), 7.10-7.14 (m, 1H), 7.04 (br. s., 1H), 5.83 (s, 1H), 5.43 (br. s., 1H), 3.86 (s, 4H) |

TABLE 7-continued

Examples from Methyl Ketone Route

| Example # | Structure | Compound Name | Obs Mass | 1H NMR Spectral Data or HPLC Retention Time and Conditions |
|---|---|---|---|---|
| 418 | 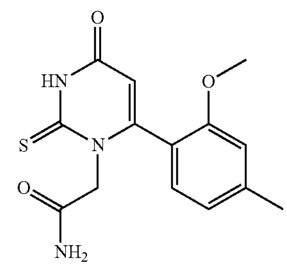 [SMILES: COc1cc(C)ccc1-c1cc(=O)[nH]c(=S)n1CC(N)=O] | 2-[6-(2-methoxy-4-methylphenyl)-4-oxo-2-thioxo-3,4-dihydropyrimidin-1(2H)-yl]acetamide | 306.0 | 1H NMR (400 MHz, DMSO-d6) δ ppm 12.78 (br. s., 1H), 7.04 (d, J = 7.5 Hz, 1H), 7.00 (s, 2H), 6.85 (d, J = 7.5 Hz, 1H), 5.75 (s, 1H), 5.35 (br. s., 1H), 3.86-3.94 (m, 1H), 3.82 (s, 3H), 2.36 (s, 3H) |
| 419 | 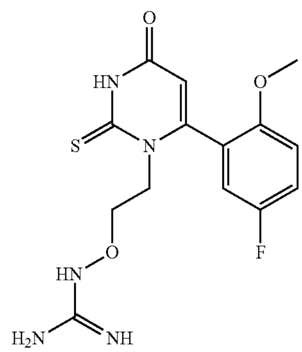 [SMILES: COc1ccc(F)cc1-c1cc(=O)[nH]c(=S)n1CCONC(=N)N] | 1-{2-[6-(5-fluoro-2-methoxyphenyl)-4-oxo-2-thioxo-3,4-dihydropyrimidin-1(2H)-yl]ethoxy}guanidine | 354.2 | 1H NMR (400 MHz, METHANOL-d4) δ ppm 8.45 (br. s., 1H), 7.30 (td, J = 8.5, 3.0 Hz, 1H), 7.10-7.24 (m, 2H), 5.83 (s, 1H), 4.73-4.83 (m, 1H), 3.97-4.16 (m, 3H), 3.89 (s, 3H) |
| 420 | 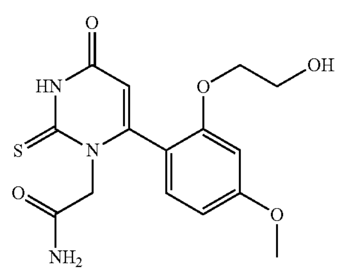 [SMILES: COc1ccc(-c2cc(=O)[nH]c(=S)n2CC(N)=O)c(OCCO)c1] | 2-{6-[2-(2-hydroxyethoxy)-4-methoxyphenyl]-4-oxo-2-thioxo-3,4-dihydropyrimidin-1(2H)-yl}acetamide | 374.0 | 1H NMR (400 MHz, DMSO-d6) δ ppm 12.72 (br. s., 1H), 7.32 (br. s., 1H), 7.09 (d, J = 8.0 Hz, 1H), 6.97 (br. s., 1H), 6.69 (br. s., 1H), 6.60 (d, J = 9.0 Hz, 1H), 5.74 (d, J = 11.0 Hz, 1H), 5.32 (br. s., 1H), 4.84 (br. s., 1H), 4.08 (d, J = 4.0 Hz, 2H), 3.97 (br. s., 1H), 3.80 (s, 3H), 3.64 (br. s., 2H) |
| 421 | 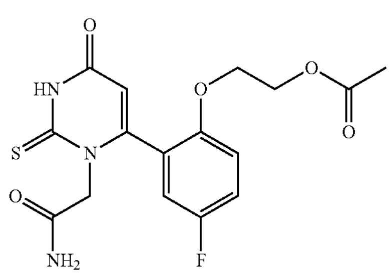 [SMILES: CC(=O)OCCOc1ccc(F)cc1-c1cc(=O)[nH]c(=S)n1CC(N)=O] | 2-{2-[3-(2-amino-2-oxoethyl)-6-oxo-2-thioxo-1,2,3,6-tetrahydropyrimidin-4-yl]-4-fluorophenoxy}ethyl acetate | 404.1 | 1H NMR (400 MHz, METHANOL-d4) δ ppm 8.09 (s, 0.6H), 7.57 (br. s., 0.2H), 7.27 (td, J = 8.5, 3.0 Hz, 1H), 7.14 (dd, J = 9.0, 4.5 Hz, 1H), 7.07 (dd, J = 8.3, 3.3 Hz, 1H), 6.99 (br. s., 0.2H), 5.83 (s, 1H), 5.67 (d, J = 14.1 Hz, 1H), 4.30-4.46 (m, 2H), 4.22-4.30 (m, 2H), 4.12 (d, J = 17.1 Hz, 1H), 2.06 (s, 3H) |

The following Examples of Table 8 (additions to Table 4) were prepared from the corresponding aryl halide to afford the intermediate beta-keto-ester as described above for the Preparations in the Aryl Halide Route section followed by employing the methods described in the I. Beta Keto Ester Route Section as well as standard methods and techniques known to those skilled in the art.

TABLE 8

Examples from Aryl Halide Route

| Example # | Structure | Compound Name | Obs Mass | 1H NMR Spectral Data or HPLC Retention Time and Conditions |
|---|---|---|---|---|
| 422 | 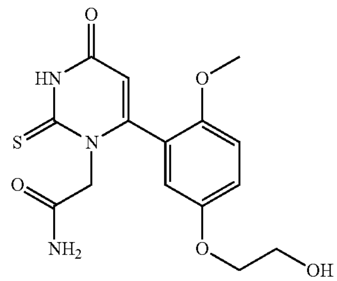 [SMILES: COc1ccc(OCCO)cc1-c1cc(=O)[nH]c(=S)n1CC(N)=O] | 2-{6-[5-(2-hydroxyethoxy)-2-methoxy phenyl]-4-oxo-2-thioxo-3,4-dihydropyrimidin-1(2H)-yl}acetamide | 352.0 | 1H NMR (400 MHz, METHANOL-d4) δ ppm 7.09-7.18 (m, 1H), 7.03-7.09 (m, 1H), 6.88 (d, J = 3.0 Hz, 1H), 5.81 (s, 1H), 5.46-5.63 (m, 1H), 4.17 (br. s., 1H), 4.00 (d, J = 3.5 Hz, 2H), 3.84 (s, 5H) |
| 423 | 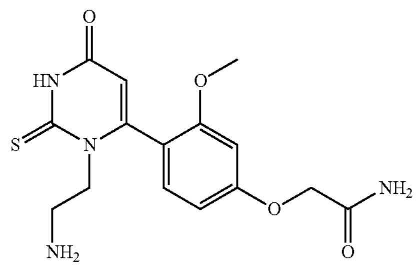 [SMILES: COc1cc(OCC(N)=O)ccc1-c1cc(=O)[nH]c(=S)n1CCN] | 2-{4-[3-(2-aminoethyl)-6-oxo-2-thioxo-1,2,3,6-tetrahydropyrimidin-4-yl]-3-methoxyphenoxy}acetamide | 351.2 | 1H NMR (400 MHz, DMSO-d6) δ ppm 12.85 (s, 1H) 8.06 (br s, 3H) 7.69 (s, 1H) 7.48 (s, 1H) 7.30 (d, J = 8.53 Hz, 1H) 6.82 (d, J = 2.01 Hz) 1H) 6.67 (dd, J = 8.53, 2.01 Hz, 1H) 5.75 (s, 1H) 4.71-4.60 (br s, 1H) 4.51 (s, 2H) 3.94-3.81 (m, 4H) 2.95-2.80 (m, 2H) |

The following Examples of Table 9 were prepared from the corresponding aryl ester or lactone to afford the intermediate beta-keto-ester as described above for the Preparations in the Ester Route section followed by employing the methods described in the I. Beta Keto Ester Route Section as well as standard methods and techniques known to those skilled in the art.

TABLE 9

Examples from Ester Route

| Example # | Structure | Compound Name | Obs Mass | 1H NMR Spectral Data or HPLC Retention Time and Conditions |
|---|---|---|---|---|
| 424 | 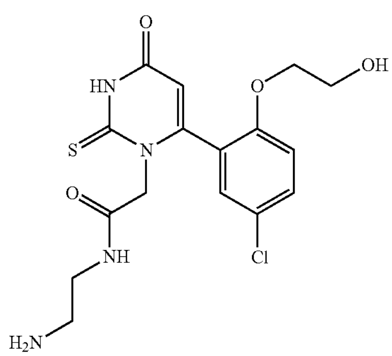 [SMILES: NCCNC(=O)Cn1c(-c2cc(Cl)ccc2OCCO)cc(=O)[nH]c1=S] | N-(2-aminoethyl)-2-{6-[5-chloro-2-(2-hydroxy ethoxy)phenyl]-4-oxo-2-thioxo-3,4-dihydropyrimidin-1(2H)-yl}acetamide | 398.9 | 1H NMR (400 MHz, Methanol-d4) δ ppm 7.50 (dd, J = 9.03, 3.01 Hz, 1 H), 7.30 (d, J = 2.51 Hz, 1 H), 7.17 (d, J = 9.03 Hz, 1 H), 5.88 (s, 1H), 5.56-5.43 (br m, 1H), 4.31-4.06 (m, 4H), 3.84 (t, J = 4.52 Hz, 2H), 3.44-3.33 (m, 2H), 3.03-2.89 (m, 2H) |

TABLE 9-continued

Examples from Ester Route

| Example # | Structure | Compound Name | Obs Mass | 1H NMR Spectral Data or HPLC Retention Time and Conditions |
|---|---|---|---|---|
| 425 | 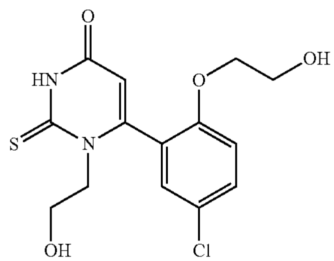 [SMILES: O=c1cc(-c2cc(Cl)ccc2OCCO)n(CCO)c(=S)[nH]1] | 6-[5-chloro-2-(2-hydroxyethoxy)phenyl]-1-(2-hydroxyethyl)-2-thioxo-2,3-dihydropyrimidin-4(1H)-one | 342.7 | 1H NMR (400 MHz, DMSO-d6) δ ppm 12.73 (br s, 1H), 7.52 (br s, 1H), 7.40 (br s, 1H), 7.28-7.15 (br m, 1H), 5.88-5.72 (br m, 1H), 4.92 (br s, 1H), 4.78 (br s, 1H), 4.48 (br s, 1H), 4.08 (br s, 2H), 3.73-3.52 (br m, 4H) |
| 426 | 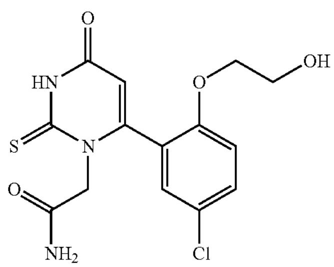 [SMILES: NC(=O)Cn1c(-c2cc(Cl)ccc2OCCO)cc(=O)[nH]c1=S] | 2-{6-[5-chloro-2-(2-hydroxyethoxy)phenyl]-4-oxo-2-thioxo-3,4-dihydropyrimidin-1(2H)-yl}acetamide | 378.1 | 1H NMR (400 MHz, DMSO-d6) δ ppm 12.84 (br. s, 1H), 7.54 (dd, J = 9.0, 3.0 Hz, 1H), 7.35 (s, 1H), 7.21 (d, J = 8.5 Hz, 2H), 7.09 (s, 1H), 5.87 (s, 1H), 5.37 (br. s., 1H), 4.86 (t, J = 5.3 Hz, 1H), 4.04-4.13 (m, 2H), 3.95 (br. s., 1H), 3.58-3.70 (m, 2H) |
| 427 | 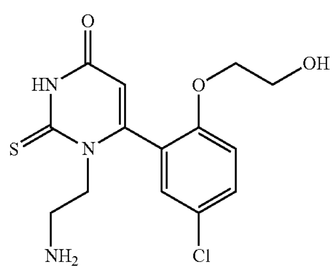 [SMILES: NCCn1c(-c2cc(Cl)ccc2OCCO)cc(=O)[nH]c1=S] | 1-(2-aminoethyl)-6-[5-chloro-2-(2-hydroxyethoxy)phenyl]-2-thioxo-2,3-dihydropyrimidin-4(1H)-one | 341.9 | 1H NMR (400 MHz, METHANOL-d4) δ ppm 8.49 (br. s., 1H) 7.56 (dd, J = 9.3, 2.3 Hz, 1H) 7.45 (d, J = 2.5 Hz, 1H) 7.22 (d, J = 9.0 Hz, 1H) 5.87 (s, 1H) 4.62 (br. s., 2H) 4.12-4.30 (m, 3H) 3.85 (br. s., 2H) 3.14-3.25 (m, 1H) 3.04-3.13 (m, J = 8.0 Hz, 1H) |
| 428 | 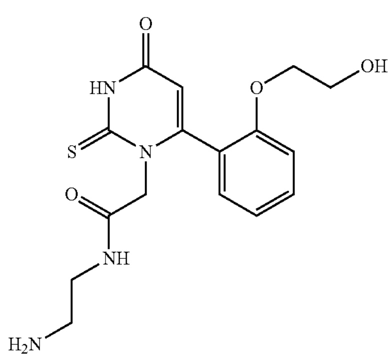 [SMILES: NCCNC(=O)Cn1c(-c2ccccc2OCCO)cc(=O)[nH]c1=S] | N-(2-aminoethyl)-2-{6-[2-(2-hydroxyethoxy)phenyl]-4-oxo-2-thioxo-3,4-dihydropyrimidin-1(2H)-yl}acetamide | 365.1 | $^1$H NMR (400 MHz, METHANOL-$d_4$) δ ppm 8.28 (t, J = 5.8 Hz, 1H) 7.48-7.55 (m, 1H) 7.27 (dd, J = 7.5, 1.5 Hz, 1H) 7.16 (d, J = 8.0 Hz, 1H) 7.06 (td, J = 7.5, 1.0 Hz, 1H) 5.85 (s, 1H) 5.44 (br. s., 1H) 4.31 (d, J = 15.1 Hz, 1H) 4.13-4.20 (m, 2H) 3.85 (ddd, J = 5.4, 3.9, 2.3 Hz, 2H) 3.33-3.40 (m, 2H) 2.92 (t, J = 5.8 Hz, 2H) |

The following Examples of Table 10 were prepared from the corresponding thiouracil carboxylic acid as described above for the Preparations in the III. Amide Coupling Route section and by employing the methods described in the I. Beta Keto Ester Route Section as well as standard methods and techniques known to those skilled in the art.

TABLE 10

Examples from Amide Coupling Route

| Example # | Structure | Compound Name | Obs Mass | 1H NMR Spectral Data or HPLC Retention Time and Conditions |
|---|---|---|---|---|
| 429 | 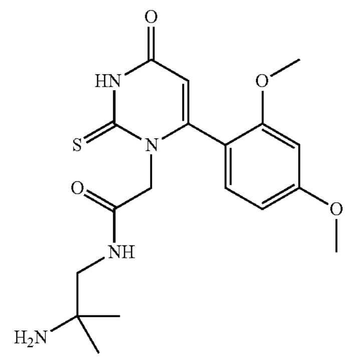 [SMILES: COc1ccc(-c2cc(=O)[nH]c(=S)n2CC(=O)NCC(C)(C)N)c(OC)c1] | N-(2-amino-2-methylpropyl)-2-[6-(2,4-dimethoxyphenyl)-4-oxo-2-thioxo-3,4-dihydropyrimidin-1(2H)-yl]acetamide | 392.2 | $^1$H NMR (400 MHz, METHANOL-d$_4$) δ ppm 8.42 (t, J = 6.3 Hz, 1H), 7.17 (d, J = 8.0 Hz, 1H), 6.68 (d, J = 2.0 Hz, 1H), 6.62 (d, J = 2.0 Hz, 1H), 5.82 (s, 1H), 5.41 (d, J = 13.6 Hz, 1H), 4.31 (d, J = 15.6 Hz, 1H), 3.88 (s, 3H), 3.85 (s, 3H), 3.34-3.40 (m, 1H), 3.09-3.17 (m, 1H), 1.22-1.29 (m, 5H), 1.26 (d, J = 5.5 Hz, 6H) |
| 430 | 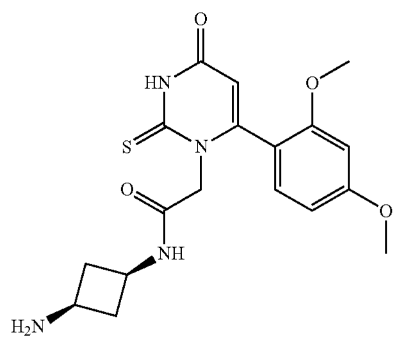 [SMILES: COc1ccc(-c2cc(=O)[nH]c(=S)n2CC(=O)N[C@H]2C[C@@H](N)C2)c(OC)c1] | N-(cis-3-aminocyclobutyl)-2-[6-(2,4-dimethoxyphenyl)-4-oxo-2-thioxo-3,4-dihydropyrimidin-1(2H)-yl]acetamide | 391.2 | $^1$H NMR (400 MHz, METHANOL-d$_4$) δ ppm 8.31 (d, J = 6.5 Hz, 1H), 7.15 (d, J = 8.5 Hz, 1H), 6.67 (d, J = 2.0 Hz, 1H), 6.60 (dd, J = 8.3, 2.3 Hz, 1H), 5.79 (s, 1H), 5.53 (br. s., 1H), 4.20 (br. s., 1H), 3.90-3.98 (m, 1H), 3.88 (s, 3H), 3.86 (s, 3H), 3.43-3.52 (m, 1H), 2.57-2.76 (m, 2H), 1.93-2.14 (m, 2H) |
| 431 | 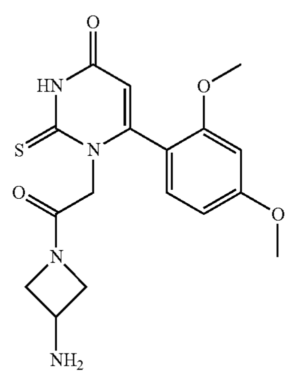 [SMILES: COc1ccc(-c2cc(=O)[nH]c(=S)n2CC(=O)N2CC(N)C2)c(OC)c1] | 1-[2-(3-aminoazetidin-1-yl)-2-oxoethyl]-6-(2,4-dimethoxyphenyl)-2-thioxo-2,3-dihydropyrimidin-4(1H)-one | 377.1 | 1H NMR (400 MHz, METHANOL-d4) δ ppm 7.21 (dd, J = 14.05, 8.53 Hz, 1 H), 6.70-6.58 (m, 2 H), 5.80 (s, 1 H), 5.38-5.28 (br m, 1H), 5.18-5.09 (br m, 1H), 4.44-4.25 (m, 5H), 4.23-4.11 (m, 2H), 4.11-3.92 (m, 1H), 3.86 (s, 6H) |
| 432 | 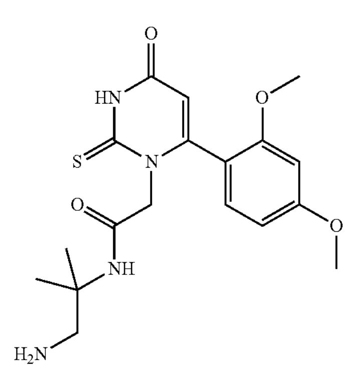 [SMILES: COc1ccc(-c2cc(=O)[nH]c(=S)n2CC(=O)NC(C)(C)CN)c(OC)c1] | N-(1-amino-2-methylpropan-2-yl)-2-[6-(2,4-dimethoxyphenyl)-4-oxo-2-thioxo-3,4-dihydropyrimidin-1(2H)-yl]acetamide | 392.9 | 1H NMR (400 MHz, DMSO-d6) δ ppm 12.81 (br s, 1H), 7.81 (s, 1H), 7.79-7.63 (br s, 3H), 7.08 (d, J = 8.03 Hz, 1H), 6.70 (s, 1H), 6.61 (d, J = 8.50 Hz, 1H), 5.77 (s, 1H), 5.42 (br s, 1H), 4.05 (br s, 1H), 3.83 (s, 3H), 3.81 (s, 3H), 2.94 (s, 2H), 1.13 (s, 3H), 1.09 (s, 3H) |

TABLE 10-continued

Examples from Amide Coupling Route

| Example # | Structure | Compound Name | Obs Mass | 1H NMR Spectral Data or HPLC Retention Time and Conditions |
|---|---|---|---|---|
| 433 | ABS | N-[(2R,3R)-3-aminobutan-2-yl]-2-[6-(2,4-dimethoxyphenyl)-4-oxo-2-thioxo-3,4-dihydropyrimidin-1(2H)-yl]acetamide | 393.1 | 0.931 min Xtimate C18 2.1 × 30 mm 3 um Mobile phase: from 0% MeCN (0.1% TFA) in water (0.1% TFA) to 60% MeCN (0.1% TFA) in water (0.1% TFA) |
| 434 | 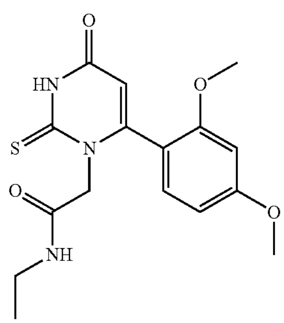 | 2-[6-(2,4-dimethoxyphenyl)-4-oxo-2-thioxo-3,4-dihydropyrimidin-1(2H)-yl]-N-ethylacetamide | 349.9 | 1H NMR (400 MHz, CHLOROFORM-d) δ ppm 9.75 (br, 1H), 7.20 (d, J = 8.53 Hz, 1H), 6.55 (dd, J = 8.53, 2.51 Hz, 1H) 6.49 (d, J = 2.51 Hz, 1H), 5.87 (s, 1H), 5.62 (br, 1H), 5.12 (br, 1H), 4.25 (br, 1H), 3.85 (s, 3 H), 3.81 (s, 3H), 3.36-3.24 (m, 1 H), 3.24-3.14 (m, 1H), 1.10 (t, J = 7.53 Hz, 3H) |
| 435 | 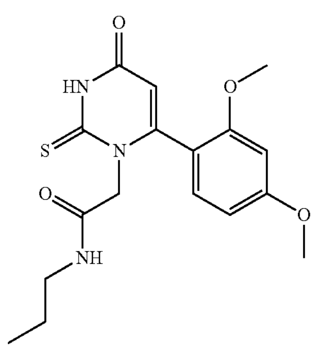 | 2-[6-(2,4-dimethoxyphenyl)-4-oxo-2-thioxo-3,4-dihydropyrimidin-1(2H)-yl]-N-propylacetamide | 364.1 | 1H NMR (400 MHz, CHLOROFORM-d) δ ppm 9.61 (br, 1H), 7.21 (d, J = 8.53 Hz, 1H), 6.54 (dd, J = 8.53, 2.51 Hz, 1 H), 6.49 (d, J = 2.51 Hz, 1H), 5.87 (s, 1H), 5.64 (br, 1H), 5.15 (br, 1H), 4.26 (br, 1H), 3.85 (s, 3 H), 3.81 (s, 3H), 3.30-3.18 (m, 1 H), 3.15-3.04 (m, 1H), 1.48 (q, J = 7.03, 2 H), 0.88 (t, J = 7.03 Hz, 3 H) |
| 436 | 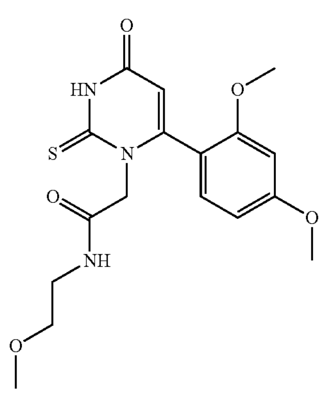 | 2-[6-(2,4-dimethoxyphenyl)-4-oxo-2-thioxo-3,4-dihydropyrimidin-1(2H)-yl]-N-(2-methoxyethyl)acetamide | 402.1 | 1H NMR (400 MHz, CHLOROFORM-d) δ ppm 9.59 (br, 1H), 7.22 (d, J = 8.53 Hz, 1H), 6.54 (dd, J = 8.53, 2.51 Hz, 1H), 6.49 (d, J = 2.51 Hz, 1H), 5.99 (br s, 1H), 5.86 (s, 1H), 5.18 (br s, 1H), 4.22 (br s, 1H), 3.85 (s, 3H), 3.82 (s, 3H) 3.51-3.38 (m, 3 H), 3.36-3.28 (m, 4H) |

TABLE 10-continued

Examples from Amide Coupling Route

| Example # | Structure | Compound Name | Obs Mass | 1H NMR Spectral Data or HPLC Retention Time and Conditions |
|---|---|---|---|---|
| 437 | 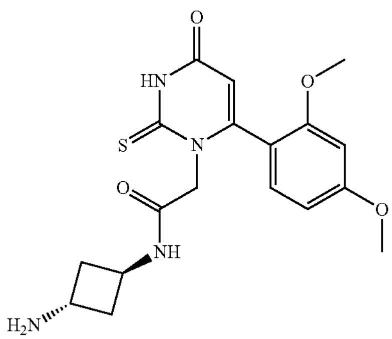 [SMILES: COc1ccc(-c2cc(=O)[nH]c(=S)n2CC(=O)N[C@H]2C[C@H](N)C2)c(OC)c1] | N-(trans-3-aminocyclobutyl)-2-[6-(2,4-dimethoxyphenyl)-4-oxo-2-thioxo-3,4-dihydropyrimidin-1(2H)-yl]acetamide | 391.2 | 1H NMR (400 MHz, METHANOL-d4) δ ppm 7.13 (d, J = 8.53 Hz, 1H), 6.67 (d, J = 2.01 Hz, 1H), 6.59 (dd, J = 8.53, 2.01 Hz, 1H), 5.78 (s, 1H), 5.68-5.43 (br s, 1H), 4.38-4.27 (m, 1H), 4.27-4.13 (br m, 1H), 3.88 (s, 3H), 3.85 (s, 3H), 3.83-3.73 (m, 1H), 2.50-2.33 (m, 3H), 2.32-2.22 (m, 1H). |
| 438 | 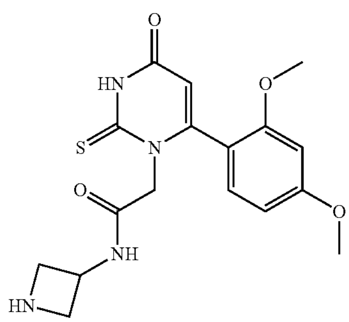 [SMILES: COc1ccc(-c2cc(=O)[nH]c(=S)n2CC(=O)NC2CNC2)c(OC)c1] | N-(azetidin-3-yl)-2-[6-(2,4-dimethoxyphenyl)-4-oxo-2-thioxo-3,4-dihydropyrimidin-1(2H)-yl]acetamide | 377.1 | 1H NMR (400 MHz, METHANOL-d4) δ ppm 8.71 (d, J = 6.02 Hz, 1H), 7.15 (d, J = 8.53 Hz, 1H), 6.69-6.65 (m, 1H), 6.60 (dd, J = 8.53, 2.01 Hz, 1H), 5.80 (s, 1H), 5.54 (br s, 1H), 4.59-4.48 (m, 1H), 4.27-4.15 (m, 3H), 4.13-3.98 (m, 2H), 3.88 (s, 3H), 3.85 (s, 3H). |
| 439 | ABS | N-[(1S,2S)-2-aminocyclobutyl]-2-[6-(2,4-dimethoxyphenyl)-4-oxo-2-thioxo-3,4-dihydropyrimidin-1(2H)-yl]acetamide | 391.1 | 0.903 min Xtimate C18 2.1 × 30 mm 3 um Mobile phase: from 0% MeCN in water (0.0685% TFA in water) to 60% MeCN in water (0.0685% TFA in water) |
| 440 | 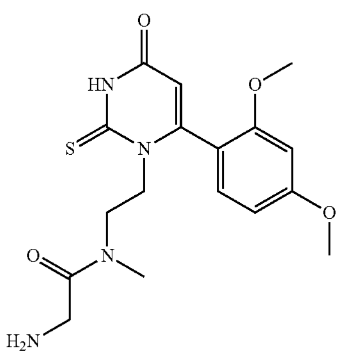 [SMILES: COc1ccc(-c2cc(=O)[nH]c(=S)n2CCN(C)C(=O)CN)c(OC)c1] | N-{2-[6-(2,4-dimethoxyphenyl)-4-oxo-2-thioxo-3,4-dihydropyrimidin-1(2H)-yl]ethyl}-N-methylglycinamide | 378.9 | 1H NMR (400 MHz, DMSO-d6) δ ppm 12.90 (s, 0.33H), 12.75 (s, 0.66H), 8.02 (br s, 3H), 7.33 (d, J = 8.53 Hz, 0.33H), 7.30 (d, J = 8.53 Hz, 0.66H), 6.72-6.66 (m, 2H), 5.83 (s, 0.33H), 5.73 (s, 0.66H), 4.66-4.44 (br m, 1H), 3.86-3.81 (m, 6H), 3.79-3.64 (m, 3H), 3.62-3.51 (m, 1H), 2.62 (s, 2H), 2.40 (s, 1H) |

TABLE 10-continued

Examples from Amide Coupling Route

| Example # | Structure | Compound Name | Obs Mass | 1H NMR Spectral Data or HPLC Retention Time and Conditions |
|---|---|---|---|---|
| 441 | ABS | N-[(1R,2R)-2-aminocyclobutyl]-2-[6-(2,4-dimethoxyphenyl)-4-oxo-2-thioxo-3,4-dihydropyrimidin-1(2H)-yl]acetamide | 391.2 | 0.897 min Xtimate C18, 2.1 × 30 mm 3 um Mobile phase: from 0% MeCN (0.1% TFA) in water (0.1% TFA) to 60% MeCN (0.1% TFA) in water (0.1% TFA) |
| 442 | 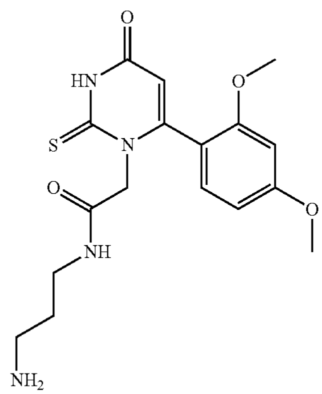 | N-(3-aminopropyl)-2-[6-(2,4-dimethoxyphenyl)-4-oxo-2-thioxo-3,4-dihydropyrimidin-1(2H)-yl]acetamide | 379.1 | 1H NMR (400 MHz, METHANOL-d4) δ ppm 8.25 (t, 0.5H), 7.17 (d, J = 8.53 Hz, 1 H), 6.66 (d, J = 2.01 Hz, 1 H), 6.61 (dd, J = 8.53, 2.01 Hz, 1H), 5.80 (s, 1H), 5.36 (br s, 1H), 4.19-4.35 (m, 1H), 3.89 (s, 3H), 3.87 (s, 3H), 3.21-3.05 (m, 2H), 2.98-2.90 (m, 2H), 1.85-1.75 (m, 2H). |
| 443 | 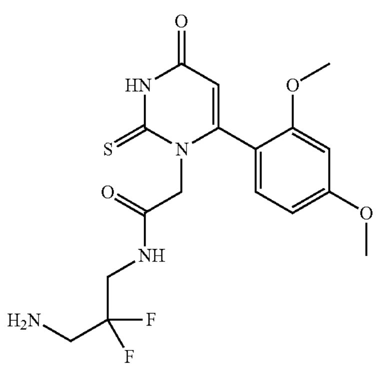 | N-(3-amino-2,2-difluoropropyl)-2-[6-(2,4-dimethoxyphenyl)-4-oxo-2-thioxo-3,4-dihydropyrimidin-1(2H)-yl]acetamide | 437.1 | 0.888 min Xtimate C18 2.1 × 30 mm 3 um Mobile phase: from 0% MeCN in water (0.1% TFA in water) to 60% MeCN in water (0.1% TFA in water) |
| 444 | 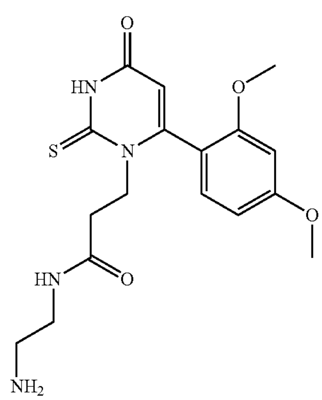 | N-(2-aminoethyl)-3-[6-(2,4-dimethoxyphenyl)-4-oxo-2-thioxo-3,4-dihydropyrimidin-1(2H)-yl]propanamide | 379.1 | 1H NMR (400 MHz, METHANOL-d4) δ ppm 7.23 (d, J = 8.53 Hz, 1H), 6.68 (d, J = 2.01 Hz, 1H), 6.65 (dd, J = 8.53, 2.01 Hz, 1H), 5.75 (s, 1H), 4.81-4.70 (br s, 1H), 4.07-3.95 (br m, 1H), 3.88 (s, 3H), 3.87 (s, 1H), 3.93-3.32 (m, 2H), 3.01-2.95 (m, 2H), 2.70-2.48 (m, 2H), 1.40-1.35 (m, 2H). |

TABLE 10-continued

Examples from Amide Coupling Route

| Example # | Structure | Compound Name | Obs Mass | 1H NMR Spectral Data or HPLC Retention Time and Conditions |
|---|---|---|---|---|
| 445 | 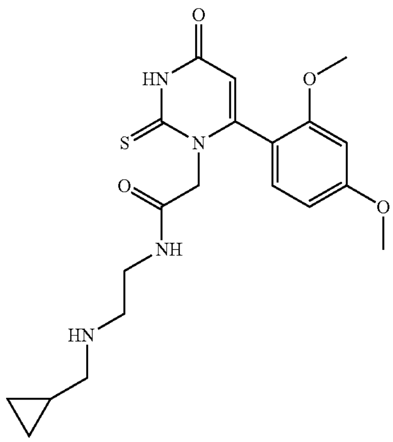 [SMILES: COc1ccc(-c2cc(=O)[nH]c(=S)n2CC(=O)NCCNCC2CC2)c(OC)c1] | N-{2-[(cyclopropylmethyl)amino]ethyl}-2-[6-(2,4-dimethoxyphenyl)-4-oxo-2-thioxo-3,4-dihydropyrimidin-1(2H)-yl]acetamide | 419.1 | 1H NMR (400 MHz, METHANOL-d4) δ ppm 8.42-8.35 (m, 1H), 7.52-7.45 (m, 0.5 H), 7.30-7.33 (m, 0.5H), 7.18 (d, J = 8.53 Hz, 1H), 6.69-6.66 (m, 1H), 6.64-6.60 (m, 1H), 5.82 (s, 1H), 5.49 (s, 1H), 5.44-5.28 (br s, 1H), 4.35-4.22 (br m, 1H), 3.88 (s, 3H), 3.85 (s, 1H), 3.54-3.42 (m, 1H), 3.15-2.99 (m, 2H), 2.95-2.86 (m, 2H), 1.12-1.01 (m, 1H), 0.73-0.66 (m, 2H), 0.43-0.37 (m, 2H). |
| 446 | 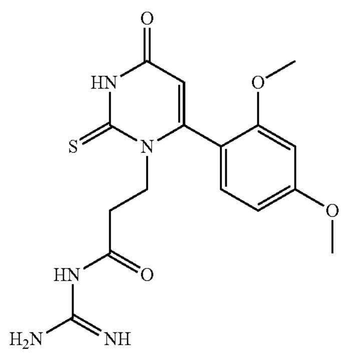 [SMILES: COc1ccc(-c2cc(=O)[nH]c(=S)n2CCC(=O)NC(=N)N)c(OC)c1] | N-carbamimidoyl-3-[6-(2,4-dimethoxyphenyl)-4-oxo-2-thioxo-3,4-dihydropyrimidin-1(2H)-yl]propanamide | 377.9 | 1H NMR (400 MHz, DMSO-d6) δ ppm 12.81 (s, 1H), 11.82 (br s, 1H) 8.51-7.95 (br m, 4H) 7.27 (d, J = 8.53 Hz, 1H) 6.69 (d, J = 2.01 Hz, 1H) 6.63 (dd, J = 8.53, 2.01 Hz, 1H) 5.76 (d, J = 2.01 Hz, 1H) 4.57-4.41 (br m, 1H) 4.03-3.90 (br m, 1H) 3.86-3.78 (m, 6H) 2.82-2.71 (m, 2H). |

The following Examples of Table 11 were prepared from the corresponding thiouracil amines as described above for the Preparations in the IV. Guanidine Route section and by employing the methods described in the I. Beta Keto Ester Route Section as well as standard methods and techniques known to those skilled in the art.

TABLE 11

Examples from Guanidine Route

| Example # | Structure | Compound Name | Obs Mass | 1H NMR Spectral Data or HPLC Retention Time and Conditions |
|---|---|---|---|---|
| 447 | 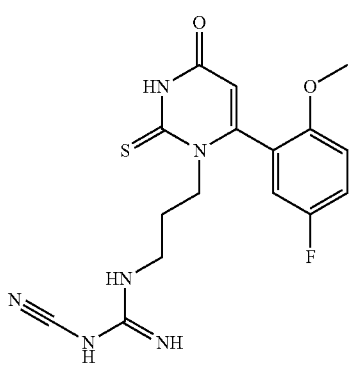 [SMILES: COc1ccc(F)cc1-c1cc(=O)[nH]c(=S)n1CCCNC(=N)NC#N] | 1-cyano-3-{3-[6-(5-fluoro-2-methoxyphenyl)-4-oxo-2-thioxo-3,4-dihydropyrimidin-1(2H)-yl]propyl}guanidine | 377.2 | 1H NMR (400 MHz, DMSO-d6) δ ppm 12.78 (s, 1H), 7.41-7.34 (m, 2H), 7.16 (dd, J = 9.03,4.02 Hz, 1H), 6.94-6.31 (brs, 3H), 5.85 (s, 1H), 4.26 (br s, 1H), 3.82 (s, 3H), 3.72-3.58 (br m, 1H), 2.91-2.75 (m, 2H), 1.77-1.66 (br m, 1H), 1.61-1.46 (br m, 1H). |

TABLE 11-continued

Examples from Guanidine Route

| Example # | Structure | Compound Name | Obs Mass | 1H NMR Spectral Data or HPLC Retention Time and Conditions |
|---|---|---|---|---|
| 448 | 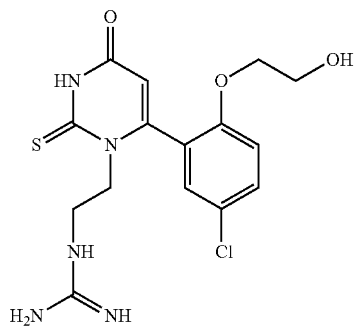 [SMILES: N=C(N)NCCn1c(-c2cc(Cl)ccc2OCCO)cc(=O)[nH]c1=S] | 1-(2-{6-[5-chloro-2-(2-hydroxyethoxy)phenyl]-4-oxo-2-thioxo-3,4-dihydropyrimidin-1(2H)-yl}ethyl)guanidine | 383.9 | 1.31 min Atlantis dC18 5 um 4.6 × 50 mm, 95% H2O/5% MeCN linear to 5% H2O/95% MeCN over 4.0 min, HOLD at 5% H2O/95% MeCN to 5.0 min. (0.05% formic acid). Flow rate: 2 mL/min. |
| 449 | 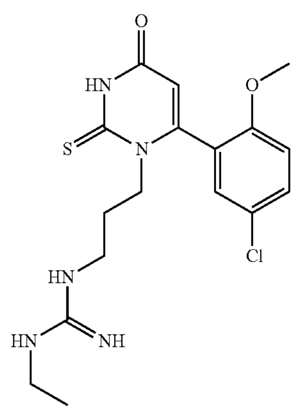 [SMILES: CCNC(=N)NCCCn1c(-c2cc(Cl)ccc2OC)cc(=O)[nH]c1=S] | 1-{3-[6-(5-chloro-2-methoxyphenyl)-4-oxo-2-thioxo-3,4-dihydropyrimidin-1(2H)-yl]propyl}-2-ethylguanidine | 395.9 | 1.62 min Atlantis dC18 5 um 4.6 × 50 mm, 95% H2O/5% MeCN linear to 5% H2O/95% MeCN over 4.0 min, HOLD at 5% H2O/95% MeCN to 5.0 min. (0.05% trifluoroacetic acid). Flow rate: 2 mL/min. |
| 450 | 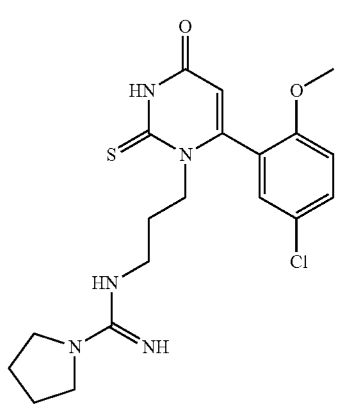 [SMILES: COc1ccc(Cl)cc1-c1cc(=O)[nH]c(=S)n1CCCNC(=N)N1CCCC1] | N-{3-[6-(5-chloro-2-methoxyphenyl)-4-oxo-2-thioxo-3,4-dihydropyrimidin-1(2H)-yl]propyl}pyrrolidine-1-carboximidamide | 422.0 | 2.02 min Atlantis dC18 5 um 4.6 × 50 mm, 95% H2O/5% MeCN linear to 5% H2O/95% MeCN over 4.0 min, HOLD at 5% H2O/95% MeCN to 5.0 min. (0.05% trifluoroacetic acid). Flow rate: 2 mL/min. |

TABLE 11-continued

Examples from Guanidine Route

| Example # | Structure | Compound Name | Obs Mass | 1H NMR Spectral Data or HPLC Retention Time and Conditions |
|---|---|---|---|---|
| 451 | 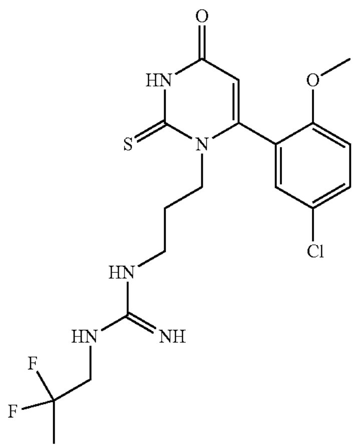 [SMILES: COc1ccc(Cl)cc1-c1cc(=O)[nH]c(=S)n1CCCNC(=N)NCC(C)(F)F] | 1-{3-[6-(5-chloro-2-methoxyphenyl)-4-oxo-2-thioxo-3,4-dihydropyrimidin-1(2H)-yl]propyl}-3-(2,2-difluoropropyl)guanidine | 446.2 | 1H NMR (500 MHz, METHANOL-d4) δ ppm 7.58 (m, 2H), 7.43 (m, 2H), 7.31 (br s, 1H), 7.20 (d, J = 8.8 Hz, 1H), 5.84 (s, 2H), 4.56 (br s, 1H), 3.92 (s, 3H), 3.81 (br s, 1H), 3.62 (td, J = 14.0, 6.4 Hz, 2H), 3.15 (q, J = 6.8 Hz, 2H), 1.95-2.03 (m, 1H), 1.75-1.85 (m, 1H), 1.67 (t, J = 18.2 Hz, 3H). |
| 452 | 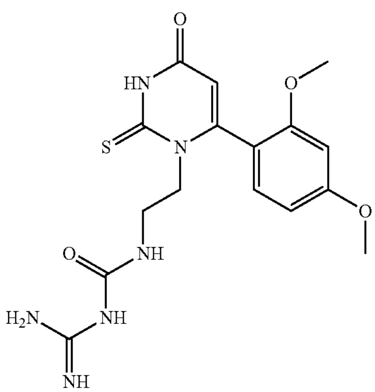 [SMILES: COc1ccc(-c2cc(=O)[nH]c(=S)n2CCNC(=O)NC(=N)N)c(OC)c1] | 1-carbamimidoyl-3-{2-[6-(2,4-dimethoxyphenyl)-4-oxo-2-thioxo-3,4-dihydropyrimidin-1(2H)-yl]ethyl}urea | 393.1 | 1.002 min Xtimate C18 2.1 × 30 mm, 3 um Mobile phase: from 0% MeCN (0.1% TFA) in water (0.1% TFA) to 60% MeCN (0.1% TFA) in water (0.1% TFA) |
| 453 | 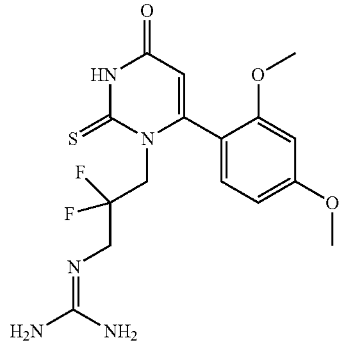 [SMILES: COc1ccc(-c2cc(=O)[nH]c(=S)n2CC(F)(F)CN=C(N)N)c(OC)c1] | 2-{3-[6-(2,4-dimethoxyphenyl)-4-oxo-2-thioxo-3,4-dihydropyrimidin-1(2H)-yl]-2,2-difluoropropyl}guanidine | 400.1 | 1H NMR (400 MHz, DMSO-d6) δ ppm 12.96 (s, 1 H), 7.81-7.72 (m, 1 H), 7.59-7.24 (br s, 4H), 7.23-7.16 (m, 2H), 6.70-6.67 (m, 1 H), 6.64 (dd, J = 8.53, 2.01 Hz, 1H), 5.82 (d, J = 1.51 Hz, 1 H), 5.79-5.61 (m, 1 H), 3.89-3.80 (m, 6 H), 3.75-3.62 (m, 2 H) |

All publications, including but not limited to, issued patents, patent applications, and journal articles, cited in this application are each herein incorporated by reference in their entirety.

Although the invention has been described above with reference to the disclosed embodiments, those skilled in the art will readily appreciate that the specific experiments detailed are only illustrative of the invention. It should be understood that various modifications can be made without departing from the spirit of the invention.

What is claimed:

1. A compound having Formula I

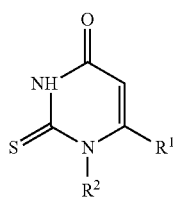

Formula I or a pharmaceutically acceptable salt thereof
wherein
$R^1$ is a five to six membered aromatic ring optionally having one to three heteroatoms selected independently from nitrogen, sulfur and oxygen or a bicyclic ring consisting of two fused partially saturated, fully saturated or fully unsaturated five to six membered rings, taken independently, optionally having one to four heteroatoms selected independently from nitrogen, sulfur and oxygen; and said $R^1$ is optionally mono-, di-, or tri-substituted independently with cyano, halo, hydroxyl, amino, $(C_1-C_4)$alkyl, $(C_1-C_4)$alkoxy, $(C_1-C_4)$alkoxy$(C_1-C_4)$alkyl, hydroxy$(C_2-C_4)$alkoxy, carbamoyl$(C_1-C_4)$alkoxy, amino$(C_2-C_4)$alkoxy, cyano$(C_1-C_4)$alkyl, mono-N— or di-N,N—$(C_1-C_4)$alkylamino, aminocarbonyl, mono-N— or di-N,N$(C_1-C_4)$alkylaminocarbonyl, $(C_1-C_4)$alkylthio, aminosulfonyl, $(C_1-C_4)$alkylsulfinyl, $(C_1-C_4)$alkylsulfonyl, or mono-N— or di-N,N$(C_1-C_4)$alkylaminosulfonyl, wherein any of the $(C_1-C_4)$alkyl or $(C_1-C_4)$alkoxy may be optionally mono-, di- or tri-substituted with fluoro; or wherein $R^1$ is optionally substituted with a five to six membered aromatic ring optionally having one to three heteroatoms selected independently from nitrogen, sulfur and oxygen;

$R^2$ is a fully saturated, partially unsaturated or fully unsaturated one to fourteen membered straight carbon chain wherein the carbons, other than the connecting carbon,
a. may be branched
b. may optionally be replaced with one or two heteroatoms selected independently from oxygen, sulfur and nitrogen, wherein said sulfur is optionally mono- or di-substituted with oxo,
c. may optionally be mono-, di- or tri-substituted independently with halo,
d. may optionally be mono-substituted with hydroxy, and
e. may optionally be mono-substituted with oxo,
and wherein the carbon chain is optionally mono-substituted with Z;
wherein Z is a partially saturated, fully saturated or fully unsaturated three to seven membered ring optionally having one to three heteroatoms selected independently from oxygen, sulfur and nitrogen, or a bicyclic ring consisting of two fused partially saturated, fully saturated or fully unsaturated five to six membered rings, taken independently, optionally having one to four heteroatoms selected independently from nitrogen, sulfur and oxygen;
wherein said Z is optionally mono-, di- or tri-substituted independently with halo, $(C_1-C_6)$alkyl, $(C_1-C_6)$alkylcarbonyl, aminothioxo, amino$(C_1-C_6)$alkylcarbonyl, hydroxyl, diaminomethylene, carbamoyl or $(C_1-C_6)$alkoxy and wherein said $(C_1-C_6)$alkyl or $(C_1-C_6)$alkoxy substituent is also optionally substituted with one to three halo, and wherein said $(C_1-C_6)$alkyl or $(C_2-C_6)$alkoxy substituent is also optionally substituted with one to three hydroxy;

with the proviso that $R^1$ is not phenyl, and $R^2$ is not $(C_1-C_6)$alkyl; and with the proviso that when
$R^1$ is phenyl and said $R^1$ is mono-, di-, or tri-substituted independently with hydroxyethoxy, methyl, methoxy, fluoro or chloro; and $R^2$ is diaminomethyleneamino$(C_2-C_4)$alkyl, carbamoyl $(C_1-C_4)$alkyl, hydroxy$(C_2-C_4)$alkyl, amino$(C_2-C_4)$alkylcarbamoyl$(C_1-C_4)$alkyl, $(C_1-C_4)$alkylcarbonylamino$(C_2-C_4)$alkyl, amino$(C_r-C_4)$alkylcarbonylamino$(C_2-C_4)$alkyl, amino$(C_3-C_4)$hydroxyalkyl or amino$(C_2-C_4)$alkyl, said compounds are not included; and with the proviso that 2-(6-(5-chloro-2-methoxyphenyl)-4-oxo-2-thioxo-3,4-dihydropyrimidin-1(2H)-yl)acetamide and N-(2-aminoethyl)-2-[6-(2,4-dimethoxyphenyl)-4-oxo-2-thioxo-3,4-dihydropyrimidin-1(2H)-yl] acetamide or a pharmaceutically acceptable salt of said proviso's compounds are not included.

2. The compound of claim 1 wherein $R^1$ is phenyl, naphthyl, furanyl, pyridinyl, pyrimidinyl, pyridazinyl, pyrazinyl, quinolinyl, isoquinolinyl, pyrazolyl, imidazolinyl, cyclopentyl, cyclohexyl, pyrrolyl, indolyl, benzo[b]thiophenyl, benzothiazolyl, benzo[b]furanyl or thiophenyl; and wherein said $R^1$ is mono-, di-, or tri-substituted independently with cyano, $(C_1-C_4)$alkyl, $(C_1-C_4)$alkoxy, hydroxy$(C_2-C_4)$alkoxy, trifluoro$(C_1-C_4)$alkyl, trifluoro$(C_1-C_4)$alkoxy or halo.

3. The compound of claim 2 wherein $R^2$ is a fully saturated, partially unsaturated or fully unsaturated one to fourteen membered straight carbon chain wherein the carbons, other than the connecting carbon,
a. may be branched
b. may optionally be replaced with one or two heteroatoms selected independently from oxygen, sulfur and nitrogen, wherein said sulfur is optionally mono- or di-substituted with oxo,
c. may optionally be mono-, di- or tri-substituted independently with halo,
d. may optionally be mono-substituted with hydroxy, and
e. may optionally be mono-substituted with oxo; or
$R^2$ is furanyl$(C_1-C_4)$alkyl, triazolyl$(C_1-C_4)$alkyl, pyridinyl $(C_1-C_4)$alkyl, pyrizinyl$(C_1-C_4)$alkyl, pyridazinyl$(C_1-C_4)$alkyl, pyrimidinyl$(C_1-C_4)$alkyl, imidazolyl$(C_1-C_4)$alkyl or pyrrolidinyl$(C_1-C_4)$alkyl, said $R^2$ rings optionally mono-, di- or tri-substituted independently with $(C_1-C_4)$alkyl, $(C_1-C_4)$alkoxy or halo.

4. The compound of claim 3 wherein
$R^1$ is phenyl, naphthyl, pyridinyl, quinolinyl, isoquinolinyl, pyrazolyl, pyrimidinyl, pyridazinyl, pyrazinyl, imidazolinyl, furanyl, cyclopentyl, cyclohexyl, pyrrolyl, indolyl, benzo[b]thiophenyl, benzothiazolyl, benzo[b]furanyl or thiophenyl; wherein said $R^1$ is mono-, di-, or tri-substituted independently with $(C_1$-$C_4)$alkyl, $(C_1$-$C_4)$alkoxy, hydroxy$(C_2$-$C_4)$alkoxy, cyano, trifluoromethyl, trifluoromethoxy or halo; and $R^2$ is $(C_1$-$C_4)$alkoxy$(C_1$-$C_4)$alkyl, carboxy$(C_1$-$C_4)$alkyl, mono- or di-hydroxy$(C_2$-$C_6)$alkyl, amino$(C_2$-$C_4)$alkyl, diaminomethyleneamino$(C_2$-$C_4)$alkyl, mono-N— or di-N,N$(C_1$-$C_4)$alkylamino$(C_2$-$C_4)$alkyl, $(C_1$-$C_4)$alkylcarbonyloxy$(C_1$-$C_4)$alkyl, $(C_1$-$C_4)$alkoxycarbonyl$(C_1$-$C_4)$alkyl, carbamoyl$(C_1$-$C_4)$alkyl, carbamoylamino$(C_2$-$C_4)$alkyl, mono-N— or di-N,N$(C_1$-$C_4)$alkylcarbamoyl$(C_1$-$C_4)$alkyl, amino$(C_2$-$C_4)$alkylcarbamoyl$(C_1$-$C_4)$alkyl, $(C_1$-$C_4)$alkylcarbonylamino$(C_2$-$C_4)$alkyl, amino$(C_1$-$C_4)$alkylcarbonylamino$(C_2$-$C_4)$alkyl, $(C_1$-$C_4)$alkoxycarbonylamino$(C_2$-$C_4)$alkyl, $(C_1$-$C_4)$alkylsulfonylamino$(C_2$-$C_4)$alkyl, $(C_1$-$C_4)$alkylaminosulfonyl$(C_1$-$C_4)$alkyl, aminosulfonyl$(C_1$-$C_4)$alkyl, amino$(C_3$-$C_4)$hydroxyalkyl or $(C_1$-$C_4)$alkylthioalkyl$(C_1$-$C_4)$.

5. The compound of claim 3 wherein $R^1$ is phenyl, naphthyl, pyridinyl, quinolinyl, isoquinolinyl, pyrazolyl, pyrimidinyl, pyridazinyl, pyrazinyl, imidazolinyl, furanyl, cyclopentyl, cyclohexyl, pyrrolyl, indolyl, benzo[b]thiophenyl, benzothiazolyl, benzo[b]furanyl or thiophenyl; wherein said $R^1$ is mono-, di-, or tri-substituted independently with $(C_1$-$C_4)$alkyl, $(C_1$-$C_4)$alkoxy, hydroxy$(C_2$-$C_4)$alkoxy, cyano, trifluoromethyl, trifluoromethoxy or halo; and $R^2$ is triazolyl$(C_1$-$C_4)$alkyl, pyridinyl$(C_1$-$C_4)$alkyl, pyrizinyl$(C_1$-$C_4)$alkyl, pyridazinyl$(C_1$-$C_4)$alkyl, pyrimidinyl$(C_1$-$C_4)$alkyl, imidazolyl$(C_1$-$C_4)$alkyl or pyrrolidinyl$(C_1$-$C_4)$alkyl, said $R^2$ rings optionally mono-, di- or tri-substituted independently with $(C_1$-$C_4)$alkyl, $(C_1$-$C_4)$alkoxy or halo.

6. The compound of claim 1 wherein $R^1$ is phenyl and said $R^1$ is mono-, di-, tri-substituted independently with hydroxyethoxy, methyl, methoxy, fluoro or chloro.

7. The compound of claim 1 wherein $R^2$ is hydroxy$(C_2$-$C_4)$alkyl, diaminomethyleneamino$(C_2$-$C_4)$alkyl, carbamoyl$(C_1$-$C_4)$alkyl, amino$(C_3$-$C_4)$hydroxyalkyl, amino$(C_2$-$C_4)$alkylcarbamoyl$(C_1$-$C_4)$alkyl, $(C_1$-$C_4)$alkylcarbonylamino$(C_2$-$C_4)$alkyl, amino$(C_1$-$C_4)$alkylcarbonylamino$(C_2$-$C_4)$alkyl or amino$(C_2$-$C_4)$alkyl.

8. The compound of claim 1 wherein $R^2$ is $(C_1$-$C_4)$alkyl mono- or di-substituted independently with amino, carbamoyl, hydroxyl, $(C_1$-$C_4)$alkoxy, amino$(C_1$-$C_4)$alkylcarbonylamino, amino$(C_2$-$C_4)$alkylcarbamoyl, $(C_1$-$C_4)$alkylcarbonylamino or diaminomethyleneamino.

9. A method of treating cardiovascular conditions comprising administering to a mammal in need of such treatment a therapeutically effective amount of a compound of claim 1 or a pharmaceutically acceptable salt of said compound wherein the cardiovascular condition is stroke, primary or secondary myocardial infarction, heart failure, congestive heart failure, peripheral arterial disease, pulmonary hypertension, vasculitis or unstable angina or the mammal has experienced myocardial infarction.

10. A pharmaceutical composition which comprises a therapeutically effective amount of a compound of claim 1 or a pharmaceutically acceptable salt of said compound and a pharmaceutically acceptable carrier, vehicle or diluent.

11. A pharmaceutical combination composition comprising: a therapeutically effective amount of a composition comprising:

a first compound, said first compound being a compound of claim 1, or a pharmaceutically acceptable salt of said compound or;

a second compound, said second compound being an angiotensin converting enzyme inhibitor, a HMG-CoA reductase inhibitor, a non-steroidal anti-inflammatory agent, a Factor Xa inhibitor or warfarin; and a pharmaceutical carrier, vehicle or diluents.

* * * * *